(12) United States Patent
Schnell

(10) Patent No.: US 12,139,709 B2
(45) Date of Patent: *Nov. 12, 2024

(54) ANTISENSE OLIGOMERS AND METHODS OF USING THE SAME FOR TREATING DISEASES ASSOCIATED WITH THE ACID ALPHA-GLUCOSIDASE GENE

(71) Applicant: Sarepta Therapeutics, Inc., Cambridge, MA (US)

(72) Inventor: Frederick Joseph Schnell, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/343,447

(22) Filed: Jun. 9, 2021

(65) Prior Publication Data

US 2022/0364085 A1 Nov. 17, 2022

Related U.S. Application Data

(63) Continuation of application No. 16/094,858, filed as application No. PCT/US2017/028002 on Apr. 17, 2017, now Pat. No. 11,060,089.

(60) Provisional application No. 62/324,185, filed on Apr. 18, 2016.

(51) Int. Cl.
| | |
|---|---|
| *C07H 21/02* | (2006.01) |
| *A61K 9/00* | (2006.01) |
| *A61K 31/7105* | (2006.01) |
| *A61P 3/00* | (2006.01) |
| *C07H 21/04* | (2006.01) |
| *C12N 15/113* | (2010.01) |

(52) U.S. Cl.
CPC .......... *C12N 15/113* (2013.01); *A61K 9/0019* (2013.01); *A61K 9/0053* (2013.01); *A61K 31/7105* (2013.01); *A61P 3/00* (2018.01); *C07H 21/02* (2013.01); *C07H 21/04* (2013.01); *C12N 15/1137* (2013.01); *C12N 2310/11* (2013.01); *C12N 2310/3145* (2013.01); *C12N 2310/3233* (2013.01); *C12N 2310/351* (2013.01); *C12N 2310/3513* (2013.01); *C12N 2320/33* (2013.01); *C12Y 302/0102* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 4,426,330 A | 1/1984 | Sears | |
| 4,534,899 A | 8/1985 | Sears | |
| 5,013,556 A | 5/1991 | Woodle et al. | |
| 5,034,506 A | 7/1991 | Summerton et al. | |
| 5,108,921 A | 4/1992 | Low et al. | |
| 5,142,047 A | 8/1992 | Summerton et al. | |
| 5,166,315 A | 11/1992 | Summerton et al. | |
| 5,185,444 A | 2/1993 | Summerton et al. | |
| 5,213,804 A | 5/1993 | Martin et al. | |
| 5,217,866 A | 6/1993 | Summerton et al. | |
| 5,227,170 A | 7/1993 | Sullivan | |
| 5,264,221 A | 11/1993 | Tagawa et al. | |
| 5,354,884 A | 10/1994 | Grosser et al. | |
| 5,356,633 A | 10/1994 | Woodle et al. | |
| 5,395,619 A | 3/1995 | Zalipsky et al. | |
| 5,416,016 A | 5/1995 | Low et al. | |
| 5,417,978 A | 5/1995 | Tari et al. | |
| 5,459,127 A | 10/1995 | Feigner et al. | |
| 5,462,854 A | 10/1995 | Coassin et al. | |
| 5,469,854 A | 11/1995 | Unger et al. | |
| 5,506,337 A | 4/1996 | Summerton et al. | |
| 5,512,295 A | 4/1996 | Kornberg et al. | |
| 5,521,063 A | 5/1996 | Summerton et al. | |
| 5,521,291 A | 5/1996 | Curiel et al. | |
| 5,527,528 A | 6/1996 | Allen et al. | |
| 5,534,259 A | 7/1996 | Zalipsky et al. | |
| 5,539,082 A | 7/1996 | Nielsen et al. | |
| 5,543,152 A | 8/1996 | Webb et al. | |
| 5,543,158 A | 8/1996 | Gref et al. | |
| 5,547,932 A | 8/1996 | Curiel et al. | |
| 5,556,948 A | 9/1996 | Tagawa et al. | |
| 5,580,575 A | 12/1996 | Unger et al. | |
| 5,583,020 A | 12/1996 | Sullivan | |

(Continued)

FOREIGN PATENT DOCUMENTS

| | | |
|---|---|---|
| EP | 3445405 | 2/2019 |
| JP | 2012-506698 | 3/2012 |

(Continued)

OTHER PUBLICATIONS

Fragall et al., "Mismatched single stranded antisense oligonucleotides can induce efficient dystrophin splice switching", *BMC Medical Genetics* 12:141 (2011).

(Continued)

*Primary Examiner* — Amy Rose Hudson

(74) *Attorney, Agent, or Firm* — Sterne, Kessler, Goldstein & Fox P.L.L.C.

(57) ABSTRACT

The present disclosure relates to modified antisense oligonucleotides. The nucleotides described herein are of 10 to 40 nucleobases and include a targeting sequence complementary to a target region within intron 1 of a pre-mRNA of the human alpha glucosidase (GAA) gene. The target region includes at least one additional nucleobase compared to the targeting sequence, wherein the at least one additional nucleobase has no complementary nucleobase in the targeting sequence, and wherein the at least one additional nucleobase is internal to the target region.

16 Claims, 29 Drawing Sheets

Specification includes a Sequence Listing.

(56) References Cited

U.S. PATENT DOCUMENTS

| | | |
|---|---|---|
| 5,591,721 A | 1/1997 | Agrawal et al. |
| 5,595,756 A | 1/1997 | Bally et al. |
| 5,698,685 A | 12/1997 | Summerton et al. |
| 5,714,331 A | 2/1998 | Buchardt et al. |
| 5,719,262 A | 2/1998 | Buchardt et al. |
| 5,770,713 A | 6/1998 | Imbach et al. |
| 6,245,747 B1 | 6/2001 | Porter et al. |
| 6,287,860 B1 | 9/2001 | Monia et al. |
| 6,670,461 B1 | 12/2003 | Wengel et al. |
| 6,794,499 B2 | 9/2004 | Wengel et al. |
| 6,965,025 B2 | 11/2005 | Gaarde et al. |
| 6,969,400 B2 | 11/2005 | Rhee et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,084,125 B2 | 8/2006 | Wengel |
| 7,125,994 B2 | 10/2006 | Kim et al. |
| 7,145,006 B2 | 12/2006 | Kim et al. |
| 7,179,896 B2 | 2/2007 | Kim et al. |
| 7,211,668 B2 | 5/2007 | Kim et al. |
| 7,422,874 B2 | 9/2008 | Kim |
| 7,569,575 B2 | 8/2009 | Sorensen et al. |
| 7,572,582 B2 | 8/2009 | Wengel et al. |
| 7,838,657 B2 | 11/2010 | Singh et al. |
| 7,935,816 B2 | 5/2011 | Li |
| 7,943,762 B2 | 5/2011 | Weller et al. |
| 8,084,598 B1 | 12/2011 | Bentwich |
| 2003/0166588 A1 | 9/2003 | Iversen et al. |
| 2004/0049022 A1 | 3/2004 | Nyce et al. |
| 2005/0255487 A1 | 11/2005 | Khvorova |
| 2006/0003322 A1 | 1/2006 | Bentwich |
| 2010/0016215 A1 | 1/2010 | Moulton et al. |
| 2011/0269820 A1 | 11/2011 | Singh et al. |
| 2012/0058946 A1 | 3/2012 | Moulton et al. |
| 2012/0065169 A1 | 3/2012 | Hanson et al. |
| 2012/0289457 A1 | 11/2012 | Hanson |
| 2013/0131312 A1 | 5/2013 | Iversen et al. |
| 2014/0017212 A1 | 1/2014 | Rebar |
| 2014/0330006 A1 | 11/2014 | Hanson et al. |
| 2015/0133529 A1 | 5/2015 | Krieg |
| 2015/0141320 A1 | 5/2015 | Krieg |
| 2015/0197534 A1 | 7/2015 | Wilton |
| 2015/0361425 A1 | 12/2015 | Geller et al. |
| 2016/0208264 A1 | 7/2016 | Wilton |
| 2017/0182189 A1 | 6/2017 | Nelson |
| 2017/0247704 A1 | 8/2017 | Bergsma et al. |
| 2018/0216111 A1 | 8/2018 | Wilton |

FOREIGN PATENT DOCUMENTS

| | | |
|---|---|---|
| JP | 2013-049714 | 3/2013 |
| JP | 2013-515504 | 5/2013 |
| JP | 2013-532965 | 8/2013 |
| JP | 2014-515762 A | 7/2014 |
| JP | 2016-533761 | 11/2016 |
| JP | 2019-050828 | 4/2019 |
| TW | 201605881 A | 2/2016 |
| TW | 2017041459 | 12/2017 |
| WO | WO 1993/001286 | 1/1993 |
| WO | WO 1993/024510 | 12/1993 |
| WO | WO 1994/026764 | 11/1994 |
| WO | WO 2004/043977 | 5/2004 |
| WO | WO 2004/097017 | 11/2004 |
| WO | WO 2005/078077 | 8/2005 |
| WO | WO 2007/002390 | 1/2007 |
| WO | WO 2008/036127 | 3/2008 |
| WO | WO 2009/005793 | 1/2009 |
| WO | WO 2009/008725 | 1/2009 |
| WO | WO 2009/064471 | 5/2009 |
| WO | WO 2010/064146 | 6/2010 |
| WO | WO 2010/115993 | 10/2010 |
| WO | WO 2010/120820 | 10/2010 |
| WO | WO 2010/148249 | 12/2010 |
| WO | WO 2011/005761 | 1/2011 |
| WO | WO 2011/028941 | 3/2011 |
| WO | WO 2011/034072 | 3/2011 |
| WO | WO 2011/107611 | 9/2011 |
| WO | WO 2012/039448 | 3/2012 |
| WO | WO 2012/043730 | 4/2012 |
| WO | WO 2012/150960 | 11/2012 |
| WO | WO 2013/053928 | 4/2013 |
| WO | WO 2013/082551 | 6/2013 |
| WO | WO 2013/086207 | 6/2013 |
| WO | WO 2013/112053 | 8/2013 |
| WO | WO 2013/127858 | 9/2013 |
| WO | WO 2014/010250 | 1/2014 |
| WO | WO 2014/012081 | 1/2014 |
| WO | WO 2013/074834 | 5/2014 |
| WO | WO 2014/153220 | 9/2014 |
| WO | WO 2015/035231 | 3/2015 |
| WO | WO 2015/107425 | 7/2015 |
| WO | WO 2015/108046 | 7/2015 |
| WO | WO 2015/108047 | 7/2015 |
| WO | WO 2015/108048 | 7/2015 |
| WO | WO 2015/179741 | 11/2015 |
| WO | WO 2015/190921 | 12/2015 |
| WO | WO 2015/190922 | 12/2015 |
| WO | WO 2016/138534 | 9/2016 |
| WO | WO 2017/184529 | 10/2017 |

OTHER PUBLICATIONS

Maimaiti et al., "Silent exonic mutation in the acid-α-glycosidase gene that causes glycogen storage disease type II by affecting mRNA splicing", Journal of Human Genetics 54:493-496 (2009).
Accession No. AC009890, genomic sequence for Homo sapiens clone H-NH0262L04 from chromosome 18, deposited on (Apr. 29, 2000).
Accession No. JR118655, TSA: Capra hircus cuffB11 Gene ID 65169 mRNA sequence, deposited on (Oct. 29, 2012).
Accession No. MIMAT0021051, mature sequence gma-miR1523b, accessed and retrieved from www.mirbase.org on (Apr. 12, 2016).
Accession No. MIMAT0025174, mature sequence mmu-miR-6418-3p, accessed and retrieved from www.mirbase.org on (Apr. 12, 2016).
Accession No. MIMAT0029917, mature sequence cbr-miR-2231, accessed and retrieved from www.mirbase.org on (Apr. 12, 2016).
Altschul et al., "Gapped BLAST and PSI-BLAST: A New Generation of Protein Database Search Programs," Nucleic Acids Research, vol. 25(17), p. 3389-3402, (1997).
AU; First Examination Report dated Jun. 18, 2019, in the Application No. 2016224976.
Benner et al., "Synthetic Biology," Nature Reviews Genetics, vol. 6(7), pp. 553-543, (Jul. 2005).
Bergsma Atze et al., "Identification and Characterization of Aberrant GAA Pre-mRNA Splicing in Pompe Disease Using a Generic Approach," Human Mutation, pp. 1-12, (2014).
Boerkoel et al., "Leaky Splicing Mutation in the Acid Maltase Gene is Associated with Delayed Onset of Glycogenosis Type II," American Journal of Human Genetics, vol. 56(4), pp. 887-897, (1995).
BR; Search Report and Written Opinion dated Oct. 23, 2019 in the Application No. BR112016005062-2.
Bruno et al., "Correction of Aberrant FGFR1 Alternative RNA Splicing through Targeting of Intronic Regulatory Elements," Human Molecular Genetics, vol. 13, pp. 2409-2420, (2004).
Byrne, B.J. et al., "Pompe disease gene therapy." Human Molecular Genetics, vol. 20, No. RI 1, pp. R61-R68. (Apr. 25, 2011).
Chiu et al., "siRNA Function in RNAi: A Chemical Modification Analysis," RNA, vol. 9, pp. 1034-1048, (2003).
Clayton et al. (Molecular Therapy—Nucleic Acids, 2014, 3, e206, pp. 1-11).
Clayton et al., "Antisense Oligonucleotide-Mediated Suppression of Muscle Glycogen Sunthease 1 Synthesis as an Approach for Substrate Reduction Therapy of Pompe Disease," Molecular Therapy—Nucleic Acids, vol. 3(10), p. e206, (Oct. 2014).
CN; First Office Action dated Feb. 24, 2018 in CN Application No. 201480060730.9.

(56) References Cited

OTHER PUBLICATIONS

CN; Second Office Action dated Nov. 2, 2018 in CN Application No. 201480060730.9.
CN; Third Office Action dated Apr. 11, 2019 in CN Application No. 201480060730.9.
Dardis et al., "Functional Characterization of the Common C.−32−13T>G Mutation of GAA Gene: Identification of Potential Therapeutic Agents," Nucleic Acids Research, vol. 42(2) pp. 1291¬1302, (Jan. 2014).
Database Accession No. ABD32089, "Human PDE4C-derived oligonucleotide Seq ID 14300 from W0200285309," XP002733117, (Jul. 29, 2004).
Database Accession No. AEC47053, "Antisense oligonucleotide targeting human TGF-beta-1 #615 from W02005084712," XP002733116, (Nov. 17, 2005).
Database Accession No. AEL86146, "Human TGF-beta2 mRNA hybridizable oligonucleotide, Seq ID No. 8 from W02006117400," XP002733115, (Jan. 11, 2007).
Database Accession No. AZQ33391, "Human TGFB1/TGFB2/TGFB3 gene targeted antisense oligonucleotide Seq: 1640 from W02011154542," XP 002733118, (Feb. 2, 2012).
Database Accession No. AZX50184, "Human GM-CSF AUG (−118−99) Anti Sense Oligonucleotide, Seq ID No. 10 from W02012092645," XP002733113, (Aug. 16, 2012).
Database Accession No. BAJ91176, "RPM-2 gene targeting antisense oligonucleotide, OL (14) TRPM2, Seq 106 from W02013009979," XP002733114, (Feb. 28, 2013).
DeRuisseau et al., "Neural Deficits Contribute to Respiratory Insufficiency in Pompe Disease," PNAS USA, vol. 106(23), pp. 9419-9424, (2004).
Devereux et al., "A Comprehensive Set of Sequence Analysis Programs for the VAX," Nucleic Acids Research, vol. 12(1), pp. 387-395, (Jan. 1984).
Dokka et al., "Novel Non-Endocytic Delivery of Antisense Oligonucleotides," Advanced Drug Delivery Reviews, vol. 44, pp. 35-49, (2000).
Egholm et al., "PNAs Containing Natural Pyrimidine and Purine Bases Hybridize to Complementary Oligomers Obeying Watson-Crick Base-Pairing Rules, and Mimic DNA in Terms of Base Pair Recognition," Nature, vol. 365(6446), pp. 566-568, (1993).
EP: Examination report dated Nov. 8, 2017 in EP Application No. 14766370.2.
EPO; Examination Report dated Nov. 12, 2018 in EP Application No. 14766370.2.
EPO; Extended Search Report and Opinion dated Sep. 7, 2018 in EP Application No. 16756555.5.
Forte et al., "Small Interfering RNAs and Antisense Oligonucleotides for Treatment of Neurological Diseases," Current Drug Targets, vol. 6, pp. 21-29, (2005).
Hammond et al., "Genetic Therapies for RNA Mis-Splicing Diseases," Trends in Genetics, vol. 27, pp. 196-205, (2011).
Henry et al., "Beyond A, C, G and T: Augmenting Nature's Alphabet," Current Opinion in Chemical Biology, vol. 7(6), pp. 727-733, (Dec. 2003).
Hirao, "Unnatural Base Pair Systems for DNA/RNA-Based Biotechnology," Current Opinion in Chemical Biology, vol. 10(6), pp. 622-627, (2006).
*Homo sapiens* BRCA1/BRCA2-containing complex subunit 3 (BRCC3), transcript variant 1, mRNA, NCBI Reference Sequence: NM_024332.3, retrieved from www.ncbi.nlm.nih.gov on (Oct. 26, 2017).
*Homo sapiens* PC4 and SFRS 1 interacting protein 1 (PSIP1), transcript variant 1, mRNA, NCBI Reference Sequence: NM_021144.3, retrieved from www.ncbi.nlm.nih.gov on (Oct. 26, 2017).
Huie, M.L. et al., "Aberrant splicing in adult onset glycogen storage disease type II (GSDII): molecular identification of an IVS1 (−13 −G) mutation in a majority of patients and a novel IVS10 (+1GT− CT) mutation.", Human Molecular Genetics, vol. 3, No. 12, pp. 2231-2236, (Dec. 4, 1994).
IL; Office Action dated Jan. 8, 2019 in IL Application No. 244334.
Iyer et al., "The Automated Synthesis of Sulfur-Containing Oligodeoxyriboneucleotides Using 3H-1, 2-Benzodithiol-3-One, 1-Dioxide as a Sulfur-Transfer Regent," Journal of Organic Chemistry, vol. 55(15), pp. 4693-4699, (1990).
Jaeger et al., "Transport of Antisense Across the Blood-Brain Barrier," Antisense Therapeutics, Methods in Molecular Medicine™, vol. 106, pp. 237-251, 2005.
JP; Final Rejection dated Apr. 22, 2019 in JP Application No. 2016-540437.
JP; Office Action dated Mar. 26, 2020, in the Application No. 2017545273.
JPO; Office Action dated Sep. 4, 2018 in JP Application No. 2016-540437.
Kool, "Replacing the Nucleobases in DNA with Designer Molecules," Accounts of Chemical Research, vol. 35(11), pp. 936-943, (2002).
Krueger et al., "Synthesis and Properties of Size-Expanded DNAs: Toward Designed, Functional Genetic Systems," Accounts of Chemical Research, vol. 40(2), pp. 141-150, (2007).
Lappalainen et al., "Cationic Liposomes Mediated Delivery of Antisense Oligonucleotides Targeted to HPV 16 E7 mRNA in CaSki Cells," Antiviral Research, vol. 23(2), p. 119-130, (Feb. 1994).
Levin et al., Position-dependent effects of locked nucleic acid (LNA) on DNA sequencing and PCR primers, Nucleic Acids Research, vol. 34, e 142, pp. 1-11. (Oct. 28, 2006).
Limbach et al., "Summary. The Modified Nucleosides of RNA," Nucleic Acid Research, vol. 22(12), pp. 2183-2196, (Jun. 1994).
Martin et al., "A New Access to 21-0-Alkylated Ribonucleosides and Properties of 21-0-Alkylated Oligoribonucleotides," Helvetica Chimica Acta, vol. 78(2), pp. 486-504, (Mar. 1995). (Abstract Only).
Martiniuk et al., "Isolation and Partial Characterization of the Structural Gene for Human Acid Alpha Glucosidase," DNA and Cell Biology, vol. 10, pp. 283-292, (1991).
Mengmeng et al., "The Application of Phosphorodiamidate Morpholino Oligomers in the Research of Gene Function," Journal of Biology, vol. 29(6), pp. 77-80, (Dec. 31, 2013).
Mitrpant Chalermchai et al., "Improved Antisense Oligonucleotide Design to Suppress Aberrant SMN2 Gene Transcript Processing: Towards a Treatment for Spinal Muscular Atrophy." PLOS One, vol. 8, No. 4, E62114, pp. 1-10. (Apr. 2013).
Miyada et al., "Oligonucleotide Hybridization Techniques," Oligomer Hybridization Techniques, Methods Enzymology, vol. 154, pp. 94-107, (1987).
MX; First Office Action dated Jun. 18, 2019, in the Application No. MX/a/2016/002934.
Nielsen et al., "Sequence-Selective Recognition of DNA by Strand Displacement with a Thymine-Substituted Polyamide," Science, vol. 254(5037), pp. 1497-1500, (Dec. 1991).
Obika et al., "Stability and Structural Features of the Duplexes Containing Nucleoside Analogues with a Fixed N-Type Conformation, T-0,4'-C-Methyleneribonucleosides," Tetrahedron Letters, vol. 39(30), p. 5401-5404, (Jul. 1998).
Obika et al., "Synthesis and Properties of 3'-Amino-2',4'-BNA, a Bridged Nucleic Acid with a N3'->P5' Phosphoramidate Linkage," Bioorganic Medicinal Chemistry, vol. 16(20), p. 9230-9237, (Oct. 2008).
Obika et al., "Synthesis of T-0,4'-C-Methyleneuridine and -Cytidine. Novel Bicyclic Nucleosides having a Fixed C3,-Endo Sugar Puckering," Tetrahedron Letters, vol. 38(50), p. 8735-8738, (1997).
Pastores, "Therapeutic Approaches for Lysosomal Storage Diseases," Therapeutics Advances in Endocrinology and Metabolism, vol. 1(4), pp. 177-188, (2010).
PCT; International Preliminary Report on Patentability dated Oct. 23, 2018 in Application No. PCT/US2017/028002.
PCT; International Search Report and Written Opinion dated Sep. 12, 2014 in Application No. PCT/US2014/054384.
PCT; International Search Report dated Nov. 17, 2016 in PCT/US2016/020127.
PCT; International Search Report dated Sep. 21, 2017 in Application No. PCT/US2017/028002.

(56) References Cited

OTHER PUBLICATIONS

PCT; Invitation to Pay Additional Fees and Where Applicable, Protest Fee in Application No. PCT/2018/056572 dated Feb. 19, 2019.
PCT; Written Opinion dated Nov. 17, 2016 in PCT/US2016/020127.
PCT; Written Opinion dated Sep. 21, 2017 in Application No. PCT/US2017/028002.
Predicted: Fukomys damarensis uncharacterized (LOC104866798), transcript variant X3, ncRNA, NCBI Reference Sequence: XR_781573. 1, retrieved from www.ncbi.nlm.nih.gov on (Oct. 26, 2017).
Predicted: Pyrus x Bretschneideri FACT complex subunit SPT16-like (LOC103955324), transcript variant X2, mRNA, NCBI Reference Sequence: X1\4_009367198.2, retrieved from www.ncbi.nlm nih.gov on (Oct. 26, 2017).
Revankar et al., "DNA with Altered Bases," DNA and Aspects of Molecular Biology, Comprehensive Natural Products Chemistry, 7(9): 313-339 (1999).
SG; Search Report dated Jan. 24, 2020 in the Application No. 11201808964P.
SG; Written Opinion dated Jan. 24, 2020 in the Application No. 11201808964P.
Summerton et al., "Morpholino Antisense Oligomers: Design, Preparation, and Properties," Antisense and Nucleic Acid Drug Development, vol. 7(3), pp. 187-195, (1997).
Taniguchi-Ikeda et al., "Pathogenic Exon-Trapping by SVA Retrotransposon and Rescue in Fukuyama Muscular Dystrophy," Nature, vol. 478, pp. 127-131, (2011).
TW; Office Action dated Oct. 15, 2018 in TW Application No. 103130887.
TW; Search Report dated Oct. 11, 2018 in TW Application No. 103130887.
Uhlmann et al., "Antisense Oligomers: A New Therapeutic Principle," Chemical Reviews, vol. 90(4), pp. 543-584, (Jun. 1990).
USPTO; Final Office Action dated Feb. 20, 2019 in U.S. Appl. No. 14/917,173.
USPTO; Non-Final Office Action dated Apr. 18, 2016 in U.S. Appl. No. 14/479,029.
USPTO; Non-Final Office Action dated Jul. 27, 2018 in U.S. Appl. No. 14/917,173.
USPTO; Non-Final Office Action dated Mar. 15, 2019 in U.S. Appl. No. 15/553,911.
USPTO; Non-Final Office Action dated Oct. 31, 2017 in U.S. Appl. No. 14/917,173.
USPTO; Requirement for Restriction dated Sep. 7, 2018 in U.S. Appl. No. 15/553,911.
USPTO; Restriction Requirement dated Mar. 13, 2017 in U.S. Appl. No. 14/917,173.
USPTO; Restriction Requirement dated Sep. 18, 2015 in U.S. Appl. No. 14/479,029.
Van Der Wal, "Antisense Oligonucleotides Promote Exon Inclusion and Correct the Common C.—in Pompe Disease," Molecular Therapy: Nucleic Acids, vol. 7, 32–13T>GGAA Splicing Variant pp. 90-100, (2017).
Vinogradov et al., "Nanogels for Oligonucleotide Delivery to the Brain," Bioconjugate Chemistry, vol. 15(1), pp. 50-60, (2004).
Wengel et al., "LNA (Locked Nucleic Acids): Synthesis and High-Affinity Nucleic Acid Recognition," Chemical Communications, 455-456, (1998).
Wengel et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54(14), p. 3607-3630, (Apr. 1998). (Abstract Only).
Wengel et al., "Synthesis of 3'-C- and 4'-C-Branched Oligodeoxynucleotides and the Development of Locked Nucleic Acid (LNA)," Accounts of Chemical Research, vol. 32(4), p. 301-310, (1999).
Williams, "Cationic Lipids Reduce Time and Dose of C-Myc Antisense Oligodeoxynucleotides Required to Specifically Inhibit Burkitt's Lymphoma Cell Growth," Leukemia, vol. 10(2), pp. 1980-1989, (1996).
Wu et al., "Receptor-Mediated in Vitro Gene Transformation by a Soluble DNA Carrier System," Journal of Biological Chemistry, vol. 262(10), pp. 4429-4432, (Apr. 1987).
Yamada et al., "Synthesis of 21-042-(N-MethylcarbamoyDethyl]Ribonucleosides Using Oxa-Michael Reaction and Chemical and Biological Properties of Oligonucleotide Derivatives Incorporating These Modified Ribonucleosides," Journal of Organic Chemistry, vol. 76(9), pp. 3042-3053, (Mar. 2011).
Yan et al., "Identification and Characterization of a Tissue-Specific Silencer Element in the First Intron of the Human Acid Maltase Gene," Human genetics, vol. 109, pp. 186-190, (2001).
Yan et al., "Transcriptional Regulation of the Human Acid Alpha-Glucosidase Gene," The Journal of Biological Chemistry, vol. 276, pp. 1789-1793, (2001).
Yang et al., "The Molecular Mechanism of the Interaction Between Nucleic Acid and Small Molecules with Anti-Tumor or Anti-Viral Activities," Peking University Medical Press, (Apr. 30, 2009). (Book Abstract Only).
Yoo et al., "21-0-Methyl-Modified Phosphorothioate Antisense Oligonucleotides have Reduced Non-Specific Effects In Vitro," Nucleic Acid Research, vol. 32(6), pp. 2008-2016, (Jan. 2004).
Zampieri et al., "Splicing Mutations in Glycogen-Storage Disease Type II: Evaluation of the Full Spectrum of Mutations and Their Relation to Patients' Phenotypes," European Journal of Human Genetics, vol. 19(4), pp. 422-431, (2011).

| Compound | EC50 [µM] | |
|---|---|---|
| | GM00443 | GM11661 |
| Naked Control (-189,-165) | 0.120 | 0.193 |
| GAA-IVS1(-74-55)-R6 | 0.836 | 0.269 |
| GAA-IVS1(-67-43)-2G/R6 | 0.283 | 0.217 |
| GAA-IVS1(-66-42)-2G/R6 | 0.106 | 0.209 |
| GAA-IVS1(-65-41)-2G/R6 | 0.042 | 0.173 |
| GAA-IVS1.SA.(-189,-167)-G/R6 | 0.116 | 0.277 |
| GAA-IVS1.SA.(-189,-168)-G/R6 | 0.132 | 0.414 |
| GAA-IVS1.SA.(-188,-165)-G/R6 | 0.231 | 0.226 |
| GAA-IVS1.SA.(-189,-165)/R6 | 0.123 | 0.086 |
| GAA-IVS1.SA.(-189,-165)-G/R6 | 0.163 | 0.114 |

FIG. 19

| Compound | GM06485 cells | | | | GM04912 cells | | | |
|---|---|---|---|---|---|---|---|---|
| | Assay #1 | Assay #2 | Assay #3 | Average | Assay #1 | Assay #2 | Assay #3 | Average |
| Naked Control (-189,-165) | 0.166 | 0.131 | 0.056 | 0.117 ± 0.056 | 0.293 | 0.435 | 0.018 | 0.249 ± 0.212 |
| GAA-IVS1(-74-55)-R6 | 0.325 | 0.322 | 0.379 | 0.342 ± 0.032 | 0.630 | 0.130 | 0.181 | 0.314 ± 0.275 |
| GAA-IVS1(-67-43)-2G | | 0.100 | 0.158 | 0.129 ± 0.041 | 0.160 | 0.492 | 0.120 | 0.258 ± 0.204 |
| GAA-IVS1(-66-42)-2G | 0.209 | 0.258 | 0.236 | 0.234 ± 0.025 | 0.366 | 0.128 | 0.218 | 0.237 ± 0.120 |
| GAA-IVS1(-65-41)-2G | 0.149 | 0.217 | 0.208 | 0.191 ± 0.037 | 0.307 | 0.129 | 0.096 | 0.177 ± 0.114 |
| GAA-IVS1.SA.(-189,-167)-G | 0.896 | 0.492 | 0.213 | 0.534 ± 0.343 | 0.396 | 0.326 | 0.171 | 0.297 ± 0.115 |
| GAA-IVS1.SA.(-189,-168)-G | 0.641 | 0.550 | 0.675 | 0.622 ± 0.065 | 0.558 | 0.353 | 0.330 | 0.414 ± 0.126 |
| GAA-IVS1.SA.(-188,-165)-G | 0.348 | 0.441 | 0.030 | 0.273 ± 0.215 | 0.589 | 0.763 | | 0.676 ± 0.123 |
| GAA-IVS1.SA.(-189,-165) | 0.308 | 0.274 | 0.328 | 0.303 ± 0.028 | 0.144 | | 0.158 | 0.151 ± 0.010 |
| GAA-IVS1.SA.(-189,-165)-G | 0.288 | 0.256 | 0.025 | 0.190 ± 0.143 | 0.412 | | 0.002 | 0.207 ± 0.290 |

FIG. 23

SEQUENCE LISTING

```
<160> NUMBER OF SEQ ID NOS: 149

<210> SEQ ID NO 1
<211> LENGTH: 2664
<212> TYPE: DNA
<213> ORGANISM: Homo sapiens
<220> FEATURE:
<221> NAME/KEY: misc_feature
<222> LOCATION: (2652)..(2652)
<223> OTHER INFORMATION: n is t or g

<400> SEQUENCE: 1
gtgagacacc tgacgtctgc cccgcgctgc cggcggtaac atcccagaag cgggtttgaa      60
cgtgcctagc cgtgccccca gcctcttccc ctgagcggag cttgagcccc agacctctag     120
tcctcccggt ctttatctga gttcagctta gagatgaacg gggagccgcc ctcctgtgct     180
gggcttgggg ctggaggctg catcttcccg tttctagggt ttcctttccc cttttgatcg     240
acgcagtgct cagtcctggc cgggacccga gccacctctc ctgctcctgc aggacgcaca     300
tggctgggtc tgaatccctg gggtgaggag caccgtggcc tgagagggg cccctgggcc      360 agctctgaaa tctgaatgtc tcaatcacaa agacccctt aggccaggcc aggggtgact      420
gtctctggtc tttgtccctg gttgctgca catagcaccc gaaaccttg gaaaccgagt       480 gatgagagag ccttttgctc atgaggtgac tgatgaccgg ggacaccagg tggcttcagg     540
atggaagcag atggccagaa agaccaaggc ctgatgacgg gttgggatgg aaaaggggtg     600
aggggctgga gattgagtga atcaccagtg gcttagtcaa ccatgcctgc acaatggaac     660
cccgtaagaa accacaggga tcagagggct tcccgccggg ttgtggaaca caccaaggca     720
ctggagggtg gtgcgagcag agagcacagc atcactgccc ccacctcaca ccaggcccta     780
cgcatctctt ccatacggct gtctgagttt tatcctttgt aataaaccag caactgtaag     840
aaacgcactt tcctgagttc tgtgaccctg aagagggagt cctgggaacc tctgaattta     900
taactagttg atcgaaagta caagtgacaa cctgggattt gccattggcc tctgaagtga     960
aggcagtgtt gtgggactga gcccttaacc tgtggagtct gtgctgactc caggtagtgt    1020
caagattgaa ttgaattgta ggacacccag ccgtgtccag aaagttgcag aattgatggg    1080
tgtgagaaaa accctacaca tttaatgtca gaagtgtggg taaaatgttt caccctccag    1140
cccagagagc cctaatttac cagtggccca cggtggaaca ccacgtccgg ccggggggcag   1200 agcgttccca gccaagcctt ctgtaacatg acatgacagg tcagactccc tcgggccctg    1260
agttcacttc ttcctggtat gtgaccagct cccagtacca gagaaggttg cacagtcctc    1320
tgctccaagg agcttcactg gccaggggct gctttctgaa atccttgcct gcctctgctc    1380
caaggcccgt tcctcagaga cgcagacccc tctgatggct gactttggtt tgaggacctc    1440
```

```
tctgcatccc tcccccatgg ccttgctcct aggacacctt cttcctcctt tccctggggt    1500
cagacttgcc taggtgcggt ggctctccca gccttcccca cgcctcccc atggtgtatt     1560 acacacacca aagggactcc cctattgaaa tccatgcata ttgaatcgca tgtgggttcc    1620
ggctgctcct gggaggagcc aggctaatag aatgtttgcc ataaaatatt aatgtacaga    1680
gaagcgaaac aaaggtcgtt ggtacttgtt aaccttacca gcagaataat gaaagcgaac    1740
ccccatatct catctgcacg cgacatcctt gttgtgtctg tacccgaggc tccaggtgca    1800
gccactgtta cagagactgt gtttcttccc catgtacctc gggggccggg aggggttctg    1860
atctgcaaag tcgccagagg ttaagtcctt tctctcttgt ggctttgcca cccctggagt    1920
gtcaccctca gctgcggtgc ccaggattcc ccactgtggt atgtccgtgc accagtcaat    1980
aggaaaggga gcaaggaaag gtactgggtc cccctaagga catacgagtt gccagaatca    2040
cttccgctga cacccagtgg accaagccgc acctttatgc agaagtgggg ctcccagcca    2100
ggcgtggtca ctcctgaaat cccagcactt cggaaggcca agggggtgg atcacttgag     2160 ctcaggagtt cgagaccagc ctgggtaaca tggcaaaatc ccgtctctac aaaaatacag    2220
aaaattagct gggtgcggtg gtgtgtgcct acagtcccag ctactcagga ggctgaagtg    2280
ggaggattgc ttgagtctgg gaggtggagg ttgcagtgag ccaggatctc accacagcac    2340
tctggcccag cgacagctg tttggcctgt ttcaagtgtc tacctgcctt gctggtcttc     2400
ctggggacat tctaagcgtg tttgatttgt aacattttag cagactgtgc aagtgctctg    2460
cactcccctg ctggagcttt tctcgcccctt ccttctggcc ctctcccag tctagacagc    2520 agggcaacac ccaccctggc caccttaccc cacctgcctg ggtgctgcag tgccagccgc    2580
ggttgatgtc tcagagctgc tttgagagcc ccgtgagtgc cgcccctccc gcctccctgc    2640
tgagcccgct tncttctccc gcag                                           2664

<210> SEQ ID NO 2
<211> LENGTH: 38
<212> TYPE: DNA
<213> ORGANISM: Artificial Sequence
<220> FEATURE:
<223> OTHER INFORMATION: Target Sequence

<400> SEQUENCE: 2
tctcagagct gctttgagag ccccgtgagt gccgcccc                             38

<210> SEQ ID NO 3
<211> LENGTH: 33
<212> TYPE: DNA
<213> ORGANISM: Artificial Sequence
<220> FEATURE:
<223> OTHER INFORMATION: Target Sequence

<400> SEQUENCE: 3
ggagcttttc tcgcccttcc ttctggccct ctc                                  33

<210> SEQ ID NO 4
<211> LENGTH: 578
<212> TYPE: DNA
<213> ORGANISM: Homo sapiens

<400> SEQUENCE: 4
gcctgtagga gctgtccagg ccatctccaa ccatgggagt gaggcacccg ccctgctccc     60
accggctcct ggccgtctgc gccctcgtgt ccttggcaac cgctgcactc ctggggcaca    120
```

```
tcctactcca tgatttcctg ctggttcccc gagagctgag tggctcctcc ccagtcctgg      180
aggagactca cccagctcac cagcagggag ccagcagacc agggcccegg gatgcccagg      240 cacaccccgg ccgtcccaga gcagtgccca cacagtgcga cgtccccccc aacagccgct      300
tcgattgcgc ccctgacaag gccatcaccc aggaacagtg cgaggcccgc ggctgttgct      360
acatccctgc aaagcagggg ctgcagggag cccagatggg gcagccctgg tgcttcttcc      420
cacccagcta ccccagctac aagctggaga acctgagctc ctctgaaatg ggctacacgg      480
ccaccctgac ccgtaccacc cccaccttct tccccaagga catcctgacc ctgcggctgg      540
acgtgatgat ggagactgag aaccgcctcc acttcacg                             578

<210> SEQ ID NO 5
<211> LENGTH: 616
<212> TYPE: DNA
<213> ORGANISM: Homo sapiens

<400> SEQUENCE: 5
gtgggcaggg cagggcgggg ggcggcggcc agggcagagg gtgcgcgtgg acatcgacac       60
ccacgcacct cacaagggtg gggtgcatgt tgcaccactg tgtgctgggc ccttgctggg      120
agcggaggtg tgagcagaca atggcagcgc ccctcgggga gcagtgggga caccacggtg      180
acaggtactc cagaaggcag ggctcggggc tcattcatct ttatgaaaag gtgggtcagg      240
tagagtaggg ctgccagagg ttgcgaatga aacaggatg cccagtaaac ccgaattgca      300 gatacccag gcatgacttt gttttttgt gtaaggatgc aaaatttggg atgtatttat       360
actagaaaag ctgcttgttg tttatctgaa attcagagtt atcaggtgtt ctgtattta       420 cctccatcct gggggaggcg tcctcctcct ggctctgcag atgagggagc cgaggctcag      480
agaggctgaa tgtgctgccc atggtccac atccatgtgt ggctgcacca ggacctgacc      540
tgtccttggc gtgcgggttg ttctctggag agtaaggtgg ctgtggggaa catcaataaa      600
cccccatctc ttctag                                                     616

<210> SEQ ID NO 6
<211> LENGTH: 12
<212> TYPE: PRT
<213> ORGANISM: Artificial Sequence
<220> FEATURE:
<223> OTHER INFORMATION: Cell Penetrating Peptide
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is 6-aminohexanoic acid
<220> FEATURE:
<221> NAME/KEY: misc_feature
<222> LOCATION: (8)..(8)
<223> OTHER INFORMATION: Xaa is 6-aminohexanoic acid
<220> FEATURE:
<221> NAME/KEY: misc_feature
<222> LOCATION: (11)..(11)
<223> OTHER INFORMATION: Xaa is 6-aminohexanoic acid

<400> SEQUENCE: 6

Arg Xaa Arg Arg Xaa Arg Arg Xaa Arg Arg Xaa Arg
1               5                   10

<210> SEQ ID NO 7
<211> LENGTH: 10
<212> TYPE: PRT
```

```
<213> ORGANISM: Artificial Sequence
<220> FEATURE:
<223> OTHER INFORMATION: Cell Penetrating Peptide

<400> SEQUENCE: 7

Arg Phe Phe Arg Phe Phe Arg Phe Phe Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Cell Penetrating Peptide
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is 6-aminohexanoic acid
<220> FEATURE:
<221> NAME/KEY: misc_feature
<222> LOCATION: (8)..(8)
<223> OTHER INFORMATION: Xaa is 6-aminohexanoic acid
<220> FEATURE:
<221> NAME/KEY: misc_feature
<222> LOCATION: (11)..(11)
<223> OTHER INFORMATION: Xaa is 6-aminohexanoic acid
<220> FEATURE:
<221> NAME/KEY: misc_feature
<222> LOCATION: (13)..(13)
<223> OTHER INFORMATION: Xaa is 6-aminohexanoic acid
<220> FEATURE:
<221> NAME/KEY: misc_feature
<222> LOCATION: (14)..(14)
<223> OTHER INFORMATION: Xaa is beta-alanine

<400> SEQUENCE: 8

Arg Xaa Arg Arg Xaa Arg Arg Xaa Arg Arg Xaa Arg Xaa Xaa
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Cell Penetrating Peptide
<220> FEATURE:
<221> NAME/KEY: misc_feature
<222> LOCATION: (11)..(11)
<223> OTHER INFORMATION: Xaa is 6-aminohexanoic acid
<220> FEATURE:
<221> NAME/KEY: misc_feature
<222> LOCATION: (12)..(12)
<223> OTHER INFORMATION: Xaa is beta-alanine

<400> SEQUENCE: 9

Arg Phe Phe Arg Phe Phe Arg Phe Phe Arg Xaa Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Cell Penetrating Peptide

<400> SEQUENCE: 10

Arg Phe Phe Arg Phe Phe Arg Phe Phe Arg Gly
1               5                   10
```

```
<210> SEQ ID NO 11
<211> LENGTH: 7
<212> TYPE: PRT
<213> ORGANISM: Artificial Sequence
<220> FEATURE:
<223> OTHER INFORMATION: Cell Penetrating Peptide

<400> SEQUENCE: 11

Arg Arg Arg Arg Arg Arg Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Cell Penetrating Peptide

<400> SEQUENCE: 12

Arg Arg Arg Arg Arg Arg
1               5

<210> SEQ ID NO 13
<211> LENGTH: 24
<212> TYPE: DNA
<213> ORGANISM: Artificial Sequence
<220> FEATURE:
<223> OTHER INFORMATION: Target Sequence

<400> SEQUENCE: 13
ggccagaagg aaggcgagaa aagc                                        24

<210> SEQ ID NO 14
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (24)..(24)
<223> OTHER INFORMATION: n is t or u

<400> SEQUENCE: 14
gccagaagga aggcgagaaa agcn                                        24

<210> SEQ ID NO 15
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (23)..(23)
<223> OTHER INFORMATION: n is t or u

<400> SEQUENCE: 15
ccagaaggaa ggcgagaaaa gcnc                                        24

<210> SEQ ID NO 16
<211> LENGTH: 24
<212> TYPE: DNA
<213> ORGANISM: Artificial Sequence
<220> FEATURE:
<223> OTHER INFORMATION: Target Sequence
<220> FEATURE:
```

```
<221> NAME/KEY: misc_feature
<222> LOCATION: (22)..(22)
<223> OTHER INFORMATION: n is t or u

<400> SEQUENCE: 16
cagaaggaag gcgagaaaag cncc                                              24

<210> SEQ ID NO 17
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (21)..(21)
<223> OTHER INFORMATION: n is t or u

<400> SEQUENCE: 17
agaaggaagg cgagaaaagc ncca                                              24

<210> SEQ ID NO 18
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (20)..(20)
<223> OTHER INFORMATION: n is t or u

<400> SEQUENCE: 18
gaaggaaggc gagaaaagcn ccag                                              24

<210> SEQ ID NO 19
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (19)..(19)
<223> OTHER INFORMATION: n is t or u

<400> SEQUENCE: 19
aaggaaggcg agaaaagcnc cagc                                              24

<210> SEQ ID NO 20
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (18)..(18)
<223> OTHER INFORMATION: n is t or u

<400> SEQUENCE: 20
aggaaggcga gaaaagcncc agca                                              24

<210> SEQ ID NO 21
<211> LENGTH: 23
<212> TYPE: DNA
<213> ORGANISM: Artificial Sequence
<220> FEATURE:
<223> OTHER INFORMATION: Target Sequence
```

```
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (17)..(17)
<223> OTHER INFORMATION: n is t or u
<220> FEATURE:
<221> NAME/KEY: misc_feature
<222> LOCATION: (19)..(19)
<223> OTHER INFORMATION: n is t or u

<400> SEQUENCE: 21
cggcncncaa agcagcncng aga                                               23

<210> SEQ ID NO 22
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (18)..(18)
<223> OTHER INFORMATION: n is t or u
<220> FEATURE:
<221> NAME/KEY: misc_feature
<222> LOCATION: (20)..(20)
<223> OTHER INFORMATION: n is t or u

<400> SEQUENCE: 22
acggcncnca aagcagcncn gag                                               23

<210> SEQ ID NO 23
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (19)..(19)
<223> OTHER INFORMATION: n is t or u
<220> FEATURE:
<221> NAME/KEY: misc_feature
<222> LOCATION: (21)..(21)
<223> OTHER INFORMATION: n is t or u

<400> SEQUENCE: 23
cacggcncnc aaagcagcnc nga                                               23

<210> SEQ ID NO 24
```

```
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (10)..(10)
<223> OTHER INFORMATION: n is t or u
<220> FEATURE:
<221> NAME/KEY: misc_feature
<222> LOCATION: (20)..(20)
<223> OTHER INFORMATION: n is t or u
<220> FEATURE:
<221> NAME/KEY: misc_feature
<222> LOCATION: (22)..(22)
<223> OTHER INFORMATION: n is t or u

<400> SEQUENCE: 24
ncacggcncn caaagcagcn cng                                              23

<210> SEQ ID NO 25
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (21)..(21)
<223> OTHER INFORMATION: n is t or u
<220> FEATURE:
<221> NAME/KEY: misc_feature
<222> LOCATION: (23)..(23)
<223> OTHER INFORMATION: n is t or u

<400> SEQUENCE: 25
cncacggcnc ncaaagcagc ncn                                              23

<210> SEQ ID NO 26
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (10)..(10)
<223> OTHER INFORMATION: n is t or u
<220> FEATURE:
<221> NAME/KEY: misc_feature
```

```
<222> LOCATION: (12)..(12)
<223> OTHER INFORMATION: n is t or u
<220> FEATURE:
<221> NAME/KEY: misc_feature
<222> LOCATION: (22)..(22)
<223> OTHER INFORMATION: n is t or u

<400> SEQUENCE: 26
acncacggcn cncaaagcag cnc                                              23

<210> SEQ ID NO 27
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (15)..(15)
<223> OTHER INFORMATION: n is t or u
<220> FEATURE:
<221> NAME/KEY: misc_feature
<222> LOCATION: (17)..(17)
<223> OTHER INFORMATION: n is t or u

<400> SEQUENCE: 27
gcggcacnca cggcncncaa agc                                              23

<210> SEQ ID NO 28
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
<221> NAME/KEY: misc_feature
<222> LOCATION: (18)..(18)
<223> OTHER INFORMATION: n is t or u

<400> SEQUENCE: 28
ggcggcacnc acggcncnca aag                                              23

<210> SEQ ID NO 29
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (16)..(16)
<223> OTHER INFORMATION: n is t or u
```

```
<400> SEQUENCE: 29
cggcacncac ggcncncaaa gca                                          23

<210> SEQ ID NO 30
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (12)..(12)
<223> OTHER INFORMATION: n is t or u
<220> FEATURE:
<221> NAME/KEY: misc_feature
<222> LOCATION: (14)..(14)
<223> OTHER INFORMATION: n is t or u

<400> SEQUENCE: 30
gcacncacgg cncncaaagc agc                                          23

<210> SEQ ID NO 31
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (13)..(13)
<223> OTHER INFORMATION: n is t or u
<220> FEATURE:
<221> NAME/KEY: misc_feature
<222> LOCATION: (15)..(15)
<223> OTHER INFORMATION: n is t or u

<400> SEQUENCE: 31
ggcacncacg gcncncaaag cag                                          23

<210> SEQ ID NO 32
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (13)..(13)
<223> OTHER INFORMATION: n is t or u
<220> FEATURE:
<221> NAME/KEY: misc_feature
<222> LOCATION: (23)..(23)
<223> OTHER INFORMATION: n is t or u

<400> SEQUENCE: 32
cacncacggc ncncaaagca gcn                                          23
```

```
<210> SEQ ID NO 33
<211> LENGTH: 23
<212> TYPE: DNA
<213> ORGANISM: Artificial Sequence
<220> FEATURE:
<223> OTHER INFORMATION: Target Sequence

<400> SEQUENCE: 33
gccagaagga aggcgagaaa agc                                               23

<210> SEQ ID NO 34
<211> LENGTH: 22
<212> TYPE: DNA
<213> ORGANISM: Artificial Sequence
<220> FEATURE:
<223> OTHER INFORMATION: Target Sequence

<400> SEQUENCE: 34
ccagaaggaa ggcgagaaaa gc                                                22

<210> SEQ ID NO 35
<211> LENGTH: 21
<212> TYPE: DNA
<213> ORGANISM: Artificial Sequence
<220> FEATURE:
<223> OTHER INFORMATION: Target Sequence

<400> SEQUENCE: 35
cagaaggaag gcgagaaaag c                                                 21

<210> SEQ ID NO 36
<211> LENGTH: 23
<212> TYPE: DNA
<213> ORGANISM: Artificial Sequence
<220> FEATURE:
<223> OTHER INFORMATION: Target Sequence

<400> SEQUENCE: 36
ggccagaagg aaggcgagaa aag                                               23

<210> SEQ ID NO 37
<211> LENGTH: 22
<212> TYPE: DNA
<213> ORGANISM: Artificial Sequence
<220> FEATURE:
<223> OTHER INFORMATION: Target Sequence

<400> SEQUENCE: 37
ggccagaagg aaggcgagaa aa                                                22

<210> SEQ ID NO 38
<211> LENGTH: 21
<212> TYPE: DNA
<213> ORGANISM: Artificial Sequence
<220> FEATURE:
<223> OTHER INFORMATION: Target Sequence

<400> SEQUENCE: 38
ggccagaagg aaggcgagaa a                                                 21

<210> SEQ ID NO 39
<211> LENGTH: 23
<212> TYPE: DNA
<213> ORGANISM: Artificial Sequence
<220> FEATURE:
```

```
<223> OTHER INFORMATION: Target Sequence
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (16)..(16)
<223> OTHER INFORMATION: n is t or u

<400> SEQUENCE: 39
cggcacncac ggcncncaaa gca                                            23

<210> SEQ ID NO 40
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (15)..(15)
<223> OTHER INFORMATION: n is t or u
<220> FEATURE:
<221> NAME/KEY: misc_feature
<222> LOCATION: (17)..(17)
<223> OTHER INFORMATION: n is t or u

<400> SEQUENCE: 40
gcggcacnca cggcncncaa agc                                            23

<210> SEQ ID NO 41
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
<221> NAME/KEY: misc_feature
<222> LOCATION: (18)..(18)
<223> OTHER INFORMATION: n is t or u

<400> SEQUENCE: 41
ggcggcacnc acggcncnca aag                                            23

<210> SEQ ID NO 42
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(1)
<223> OTHER INFORMATION: n is t or u

<400> SEQUENCE: 42
```

```
ngggggagagg gccagaaggaa aggc                                              24

<210> SEQ ID NO 43
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(1)
<223> OTHER INFORMATION: n is t or u

<400> SEQUENCE: 43 ngggggagagg gccagaaggaa agc                                               23

<210> SEQ ID NO 44
<211> LENGTH: 22
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(1)
<223> OTHER INFORMATION: n is t or u

<400> SEQUENCE: 44 ngggggagagg gccagaaggaa ac                                                22

<210> SEQ ID NO 45
<211> LENGTH: 23
<212> TYPE: DNA
<213> ORGANISM: Artificial Sequence
<220> FEATURE:
<223> OTHER INFORMATION: Target Sequence

<400> SEQUENCE: 45
ggccagaagg aagcgagaaa agc                                                 23

<210> SEQ ID NO 46
<211> LENGTH: 22
<212> TYPE: DNA
<213> ORGANISM: Artificial Sequence
<220> FEATURE:
<223> OTHER INFORMATION: Target Sequence

<400> SEQUENCE: 46
ggccagaagg aacgagaaaa gc                                                  22

<210> SEQ ID NO 47
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (17)..(17)
<223> OTHER INFORMATION: n is t or u

<400> SEQUENCE: 47
aggaagcgag aaaagcncca gca                                                 23

<210> SEQ ID NO 48
<211> LENGTH: 22
<212> TYPE: DNA
```

```
<213> ORGANISM: Artificial Sequence
<220> FEATURE:
<223> OTHER INFORMATION: Target Sequence
<220> FEATURE:
<221> NAME/KEY: misc_feature
<222> LOCATION: (16)..(16)
<223> OTHER INFORMATION: n is t or u

<400> SEQUENCE: 48
aggaacgaga aaagcnccag ca                                              22

<210> SEQ ID NO 49
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (18)..(18)
<223> OTHER INFORMATION: n is t or u
<220> FEATURE:
<221> NAME/KEY: misc_feature
<222> LOCATION: (20)..(20)
<223> OTHER INFORMATION: n is t or u

<400> SEQUENCE: 49
cgggcncnca aagcagcncn gaga                                            24

<210> SEQ ID NO 50
<211> LENGTH: 22
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
<221> NAME/KEY: misc_feature
<222> LOCATION: (18)..(18)
<223> OTHER INFORMATION: n is t or u

<400> SEQUENCE: 50
cgcncncaaa gcagcncnga ga                                              22

<210> SEQ ID NO 51
<211> LENGTH: 21
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (3)..(3)
<223> OTHER INFORMATION: n is t or u
```

```
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (15)..(15)
<223> OTHER INFORMATION: n is t or u
<220> FEATURE:
<221> NAME/KEY: misc_feature
<222> LOCATION: (17)..(17)
<223> OTHER INFORMATION: n is t or u

<400> SEQUENCE: 51
ccncncaaag cagcncngag a                                             21

<210> SEQ ID NO 52
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (17)..(17)
<223> OTHER INFORMATION: n is t or u
<220> FEATURE:
<221> NAME/KEY: misc_feature
<222> LOCATION: (19)..(19)
<223> OTHER INFORMATION: n is t or u

<400> SEQUENCE: 52
ggcggcacnc acgggcncnc aaag                                          24

<210> SEQ ID NO 53
<211> LENGTH: 22
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (15)..(15)
<223> OTHER INFORMATION: n is t or u
<220> FEATURE:
<221> NAME/KEY: misc_feature
<222> LOCATION: (17)..(17)
<223> OTHER INFORMATION: n is t or u

<400> SEQUENCE: 53
ggcggcacnc acgcncncaa ag                                            22

<210> SEQ ID NO 54
<211> LENGTH: 21
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (14)..(14)
```

```
<223> OTHER INFORMATION: n is t or u
<220> FEATURE:
<221> NAME/KEY: misc_feature
<222> LOCATION: (16)..(16)
<223> OTHER INFORMATION: n is t or u

<400> SEQUENCE: 54
ggcggcacnc accncncaaa g                                              21

<210> SEQ ID NO 55
<211> LENGTH: 24
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (17)..(17)
<223> OTHER INFORMATION: n is t or u

<400> SEQUENCE: 55
gcgggagggg cggcacncac gggc                                           24

<210> SEQ ID NO 56
<211> LENGTH: 23
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (17)..(17)
<223> OTHER INFORMATION: n is t or u

<400> SEQUENCE: 56
gcgggagggg cggcacncac ggc                                            23

<210> SEQ ID NO 57
<211> LENGTH: 22
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (17)..(17)
<223> OTHER INFORMATION: n is t or u

<400> SEQUENCE: 57
gcgggagggg cggcacncac gc                                             22

<210> SEQ ID NO 58
<211> LENGTH: 21
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (17)..(17)
<223> OTHER INFORMATION: n is t or u

<400> SEQUENCE: 58
gcgggagggg cggcacncac c                                              21

<210> SEQ ID NO 59
<211> LENGTH: 25
<212> TYPE: DNA
<213> ORGANISM: Artificial Sequence
```

```
<220> FEATURE:
<223> OTHER INFORMATION: Target Sequence

<400> SEQUENCE: 59
ggccagaagg aagggcgaga aaagc                                              25

<210> SEQ ID NO 60
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (24)..(24)
<223> OTHER INFORMATION: n is t or u

<400> SEQUENCE: 60
ccagaaggaa gggcgagaaa agcnc                                              25

<210> SEQ ID NO 61
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (20)..(20)
<223> OTHER INFORMATION: n is t or u

<400> SEQUENCE: 61
aaggaagggc gagaaaagcn ccagc                                              25

<210> SEQ ID NO 62
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (17)..(17)
<223> OTHER INFORMATION: n is t or u

<400> SEQUENCE: 62
gcgggagggg cggcacncac ggggc                                              25

<210> SEQ ID NO 63
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(1)
<223> OTHER INFORMATION: n is t or u

<400> SEQUENCE: 63 ngggagagg gccagaagga agggc                                               25

<210> SEQ ID NO 64
<211> LENGTH: 25
<212> TYPE: DNA
<213> ORGANISM: Artificial Sequence
<220> FEATURE:
<223> OTHER INFORMATION: Target Sequence
<220> FEATURE:
```

```
<221> NAME/KEY: misc_feature
<222> LOCATION: (22)..(22)
<223> OTHER INFORMATION: n is t or u

<400> SEQUENCE: 64
agaaggaagg gcgagaaaag cncca                                              25

<210> SEQ ID NO 65
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (15)..(15)
<223> OTHER INFORMATION: n is t or u
<220> FEATURE:
<221> NAME/KEY: misc_feature
<222> LOCATION: (17)..(17)
<223> OTHER INFORMATION: n is t or u
<220> FEATURE:
<221> NAME/KEY: misc_feature
<222> LOCATION: (24)..(24)
<223> OTHER INFORMATION: n is t or u

<400> SEQUENCE: 65
gcncncaaag cagcncngag acanc                                              25

<210> SEQ ID NO 66
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
<221> NAME/KEY: misc_feature
<222> LOCATION: (23)..(23)
<223> OTHER INFORMATION: n is t or u

<400> SEQUENCE: 66
cncncaaagc agcncngaga canca                                              25

<210> SEQ ID NO 67
<211> LENGTH: 25
<212> TYPE: DNA
<213> ORGANISM: Artificial Sequence
<220> FEATURE:
<223> OTHER INFORMATION: Target Sequence
```

```
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (13)..(13)
<223> OTHER INFORMATION: n is t or u
<220> FEATURE:
<221> NAME/KEY: misc_feature
<222> LOCATION: (15)..(15)
<223> OTHER INFORMATION: n is t or u
<220> FEATURE:
<221> NAME/KEY: misc_feature
<222> LOCATION: (22)..(22)
<223> OTHER INFORMATION: n is t or u

<400> SEQUENCE: 67
ncncaaagca gcncngagac ancaa                                              25

<210> SEQ ID NO 68
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (2)..(2)
<223> OTHER INFORMATION: n is t or u
<220> FEATURE:
<221> NAME/KEY: misc_feature
<222> LOCATION: (12)..(12)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (21)..(21)
<223> OTHER INFORMATION: n is t or u

<400> SEQUENCE: 68
cncaaagcag cncngagaca ncaac                                              25

<210> SEQ ID NO 69
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(1)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (13)..(13)
<223> OTHER INFORMATION: n is t or u
<220> FEATURE:
<221> NAME/KEY: misc_feature
<222> LOCATION: (20)..(20)
<223> OTHER INFORMATION: n is t or u

<400> SEQUENCE: 69
```
ncaaagcagc ncngagacan caacc                               25

<210> SEQ ID NO 70
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (10)..(10)
<223> OTHER INFORMATION: n is t or u
<220> FEATURE:
<221> NAME/KEY: misc_feature
<222> LOCATION: (12)..(12)
<223> OTHER INFORMATION: n is t or u
<220> FEATURE:
<221> NAME/KEY: misc_feature
<222> LOCATION: (19)..(19)
<223> OTHER INFORMATION: n is t or u

<400> SEQUENCE: 70
caaagcagcn cngagacanc aaccg                               25

<210> SEQ ID NO 71
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (18)..(18)
<223> OTHER INFORMATION: n is t or u

<400> SEQUENCE: 71
aaagcagcnc ngagacanca accgc                               25

<210> SEQ ID NO 72
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (10)..(10)
<223> OTHER INFORMATION: n is t or u
<220> FEATURE:
<221> NAME/KEY: misc_feature
<222> LOCATION: (17)..(17)
<223> OTHER INFORMATION: n is t or u

<400> SEQUENCE: 72
aagcagcncn gagacancaa ccgcg                               25

<210> SEQ ID NO 73
<211> LENGTH: 25
<212> TYPE: DNA
<213> ORGANISM: Artificial Sequence

```
<220> FEATURE:
<223> OTHER INFORMATION: Target Sequence
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (16)..(16)
<223> OTHER INFORMATION: n is t or u

<400> SEQUENCE: 73
agcagcncng agacancaac cgcgg                                                25

<210> SEQ ID NO 74
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (15)..(15)
<223> OTHER INFORMATION: n is t or u

<400> SEQUENCE: 74
gcagcncnga gacancaacc gcggc                                                25

<210> SEQ ID NO 75
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (5)..(5)
<223> OTHER INFORMATION: n is t or u
<220> FEATURE:
<221> NAME/KEY: misc_feature
<222> LOCATION: (7)..(7)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (25)..(25)
<223> OTHER INFORMATION: n is t or u

<400> SEQUENCE: 75
cagcncngag acancaaccg cggcn                                                25

<210> SEQ ID NO 76
<211> LENGTH: 25
<212> TYPE: DNA
<213> ORGANISM: Artificial Sequence
<220> FEATURE:
<223> OTHER INFORMATION: Target Sequence
<220> FEATURE:
```

<220> FEATURE:
<221> NAME/KEY: misc_feature
<222> LOCATION: (25)..(25)
<223> OTHER INFORMATION: n is t or u

<400> SEQUENCE: 76
gccagaagga agggcgagaa aagcn                                               25

<210> SEQ ID NO 77
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (23)..(23)
<223> OTHER INFORMATION: n is t or u

<400> SEQUENCE: 77
cagaaggaag ggcgagaaaa gcncc                                               25

<210> SEQ ID NO 78
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (21)..(21)
<223> OTHER INFORMATION: n is t or u

<400> SEQUENCE: 78
gaaggaaggg cgagaaaagc nccag                                               25

<210> SEQ ID NO 79
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (19)..(19)
<223> OTHER INFORMATION: n is t or u

<400> SEQUENCE: 79
aggaagggcg agaaaagcnc cagca                                               25

<210> SEQ ID NO 80
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (3)..(3)
<223> OTHER INFORMATION: n is t or u
<220> FEATURE:
<221> NAME/KEY: misc_feature
<222> LOCATION: (12)..(12)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (24)..(24)
<223> OTHER INFORMATION: n is t or u

<400> SEQUENCE: 80
acncacgggg cncncaaagc agcnc                                          25

<210> SEQ ID NO 81
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
<221> NAME/KEY: misc_feature
<222> LOCATION: (18)..(18)
<223> OTHER INFORMATION: n is t or u
<220> FEATURE:
<221> NAME/KEY: misc_feature
<222> LOCATION: (25)..(25)
<223> OTHER INFORMATION: n is t or u

<400> SEQUENCE: 81
ggcncncaaa gcagcncnga gacan                                          25

<210> SEQ ID NO 82
<211> LENGTH: 20
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (4)..(4)
<223> OTHER INFORMATION: n is t or u
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (16)..(16)
<223> OTHER INFORMATION: n is t or u
<220> FEATURE:
<221> NAME/KEY: misc_feature
<222> LOCATION: (18)..(18)
<223> OTHER INFORMATION: n is t or u

<400> SEQUENCE: 82
ggcncncaaa gcagcncnga                                                20

<210> SEQ ID NO 83
<211> LENGTH: 20
<212> TYPE: DNA
<213> ORGANISM: Artificial Sequence
<220> FEATURE:
<223> OTHER INFORMATION: Target Sequence

<400> SEQUENCE: 83
gagagggcca gaaggaaggg                                                20

<210> SEQ ID NO 84

```
<211> LENGTH: 20
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(3)
<223> OTHER INFORMATION: n is t or u
<220> FEATURE:
<221> NAME/KEY: misc_feature
<222> LOCATION: (8)..(8)
<223> OTHER INFORMATION: n is t or u
<220> FEATURE:
<221> NAME/KEY: misc_feature
<222> LOCATION: (10)..(11)
<223> OTHER INFORMATION: n is t or u
<220> FEATURE:
<221> NAME/KEY: misc_feature
<222> LOCATION: (20)..(20)
<223> OTHER INFORMATION: n is t or u

<400> SEQUENCE: 84
nnngccangn nacccaggcn                                          20

<210> SEQ ID NO 85
<211> LENGTH: 20
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (16)..(16)
<223> OTHER INFORMATION: n is t or u

<400> SEQUENCE: 85
gcgcacccnc ngcccnggcc                                          20

<210> SEQ ID NO 86
<211> LENGTH: 25
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (6)..(6)
<223> OTHER INFORMATION: n is t or u
<220> FEATURE:
<221> NAME/KEY: misc_feature
<222> LOCATION: (9)..(9)
<223> OTHER INFORMATION: n is t or u
<220> FEATURE:
<221> NAME/KEY: misc_feature
<222> LOCATION: (11)..(11)
<223> OTHER INFORMATION: n is t or u
<220> FEATURE:
<221> NAME/KEY: misc_feature
<222> LOCATION: (14)..(14)
<223> OTHER INFORMATION: n is t or u
<220> FEATURE:
<221> NAME/KEY: misc_feature
<222> LOCATION: (18)..(18)
<223> OTHER INFORMATION: n is t or u
<220> FEATURE:
<221> NAME/KEY: misc_feature
```

```
<222> LOCATION: (22)..(22)
<223> OTHER INFORMATION: n is t or u
<220> FEATURE:
<221> NAME/KEY: misc_feature
<222> LOCATION: (25)..(25)
<223> OTHER INFORMATION: n is t or u

<400> SEQUENCE: 86
ggcccnggnc ngcnggcncc cngcn                                              25

<210> SEQ ID NO 87
<211> LENGTH: 24
<212> TYPE: DNA
<213> ORGANISM: Artificial Sequence
<220> FEATURE:
<223> OTHER INFORMATION: Target Sequence

<400> SEQUENCE: 87
gccagaagga aggcgagaaa agct                                               24

<210> SEQ ID NO 88
<211> LENGTH: 24
<212> TYPE: DNA
<213> ORGANISM: Artificial Sequence
<220> FEATURE:
<223> OTHER INFORMATION: Target Sequence

<400> SEQUENCE: 88
ccagaaggaa ggcgagaaaa gctc                                               24

<210> SEQ ID NO 89
<211> LENGTH: 24
<212> TYPE: DNA
<213> ORGANISM: Artificial Sequence
<220> FEATURE:
<223> OTHER INFORMATION: Target Sequence

<400> SEQUENCE: 89
cagaaggaag gcgagaaaag ctcc                                               24

<210> SEQ ID NO 90
<211> LENGTH: 24
<212> TYPE: DNA
<213> ORGANISM: Artificial Sequence
<220> FEATURE:
<223> OTHER INFORMATION: Target Sequence

<400> SEQUENCE: 90
agaaggaagg cgagaaaagc tcca                                               24

<210> SEQ ID NO 91
<211> LENGTH: 24
<212> TYPE: DNA
<213> ORGANISM: Artificial Sequence
<220> FEATURE:
<223> OTHER INFORMATION: Target Sequence

<400> SEQUENCE: 91
gaaggaaggc gagaaaagct ccag                                               24

<210> SEQ ID NO 92
<211> LENGTH: 24
<212> TYPE: DNA
<213> ORGANISM: Artificial Sequence
<220> FEATURE:
<223> OTHER INFORMATION: Target Sequence
```

<400> SEQUENCE: 92
aaggaaggcg agaaaagctc cagc                                          24

<210> SEQ ID NO 93
<211> LENGTH: 24
<212> TYPE: DNA
<213> ORGANISM: Artificial Sequence
<220> FEATURE:
<223> OTHER INFORMATION: Target Sequence

<400> SEQUENCE: 93
aggaaggcga gaaagctcc agca                                           24

<210> SEQ ID NO 94
<211> LENGTH: 23
<212> TYPE: DNA
<213> ORGANISM: Artificial Sequence
<220> FEATURE:
<223> OTHER INFORMATION: Target Sequence

<400> SEQUENCE: 94
cggctctcaa agcagctctg aga                                           23

<210> SEQ ID NO 95
<211> LENGTH: 23
<212> TYPE: DNA
<213> ORGANISM: Artificial Sequence
<220> FEATURE:
<223> OTHER INFORMATION: Target Sequence

<400> SEQUENCE: 95
acggctctca agcagctct gag                                            23

<210> SEQ ID NO 96
<211> LENGTH: 23
<212> TYPE: DNA
<213> ORGANISM: Artificial Sequence
<220> FEATURE:
<223> OTHER INFORMATION: Target Sequence

<400> SEQUENCE: 96
cacggctctc aaagcagctc tga                                           23

<210> SEQ ID NO 97
<211> LENGTH: 23
<212> TYPE: DNA
<213> ORGANISM: Artificial Sequence
<220> FEATURE:
<223> OTHER INFORMATION: Target Sequence

<400> SEQUENCE: 97
tcacggctct caaagcagct ctg                                           23

<210> SEQ ID NO 98
<211> LENGTH: 23
<212> TYPE: DNA
<213> ORGANISM: Artificial Sequence
<220> FEATURE:
<223> OTHER INFORMATION: Target Sequence

<400> SEQUENCE: 98
ctcacggctc tcaaagcagc tct                                           23

<210> SEQ ID NO 99
<211> LENGTH: 23

```
<212> TYPE: DNA
<213> ORGANISM: Artificial Sequence
<220> FEATURE:
<223> OTHER INFORMATION: Target Sequence

<400> SEQUENCE: 99
actcacggct ctcaaagcag ctc                                             23

<210> SEQ ID NO 100
<211> LENGTH: 23
<212> TYPE: DNA
<213> ORGANISM: Artificial Sequence
<220> FEATURE:
<223> OTHER INFORMATION: Target Sequence

<400> SEQUENCE: 100
gcggcactca cggctctcaa agc                                             23

<210> SEQ ID NO 101
<211> LENGTH: 23
<212> TYPE: DNA
<213> ORGANISM: Artificial Sequence
<220> FEATURE:
<223> OTHER INFORMATION: Target Sequence

<400> SEQUENCE: 101
ggcggcactc acggctctca aag                                             23

<210> SEQ ID NO 102
<211> LENGTH: 23
<212> TYPE: DNA
<213> ORGANISM: Artificial Sequence
<220> FEATURE:
<223> OTHER INFORMATION: Target Sequence

<400> SEQUENCE: 102
cggcactcac ggctctcaaa gca                                             23

<210> SEQ ID NO 103
<211> LENGTH: 23
<212> TYPE: DNA
<213> ORGANISM: Artificial Sequence
<220> FEATURE:
<223> OTHER INFORMATION: Target Sequence

<400> SEQUENCE: 103
gcactcacgg ctctcaaagc agc                                             23

<210> SEQ ID NO 104
<211> LENGTH: 23
<212> TYPE: DNA
<213> ORGANISM: Artificial Sequence
<220> FEATURE:
<223> OTHER INFORMATION: Target Sequence

<400> SEQUENCE: 104
ggcactcacg gctctcaaag cag                                             23

<210> SEQ ID NO 105
<211> LENGTH: 23
<212> TYPE: DNA
<213> ORGANISM: Artificial Sequence
<220> FEATURE:
<223> OTHER INFORMATION: Target Sequence

<400> SEQUENCE: 105
```
cactcacggc tctcaaagca gct                                             23

<210> SEQ ID NO 106
<211> LENGTH: 23
<212> TYPE: DNA
<213> ORGANISM: Artificial Sequence
<220> FEATURE:
<223> OTHER INFORMATION: Target Sequence

<400> SEQUENCE: 106
cggcactcac ggctctcaaa gca                                             23

<210> SEQ ID NO 107
<211> LENGTH: 23
<212> TYPE: DNA
<213> ORGANISM: Artificial Sequence
<220> FEATURE:
<223> OTHER INFORMATION: Target Sequence

<400> SEQUENCE: 107
gcggcactca cggctctcaa agc                                             23

<210> SEQ ID NO 108
<211> LENGTH: 23
<212> TYPE: DNA
<213> ORGANISM: Artificial Sequence
<220> FEATURE:
<223> OTHER INFORMATION: Target Sequence

<400> SEQUENCE: 108
ggcggcactc acggctctca aag                                             23

<210> SEQ ID NO 109
<211> LENGTH: 24
<212> TYPE: DNA
<213> ORGANISM: Artificial Sequence
<220> FEATURE:
<223> OTHER INFORMATION: Target Sequence

<400> SEQUENCE: 109
tggggagagg gccagaagga aggc                                            24

<210> SEQ ID NO 110
<211> LENGTH: 23
<212> TYPE: DNA
<213> ORGANISM: Artificial Sequence
<220> FEATURE:
<223> OTHER INFORMATION: Target Sequence

<400> SEQUENCE: 110
tggggagagg gccagaagga agc                                             23

<210> SEQ ID NO 111
<211> LENGTH: 22
<212> TYPE: DNA
<213> ORGANISM: Artificial Sequence
<220> FEATURE:
<223> OTHER INFORMATION: Target Sequence

<400> SEQUENCE: 111
tggggagagg gccagaagga ac                                              22

<210> SEQ ID NO 112
<211> LENGTH: 23
<212> TYPE: DNA
<213> ORGANISM: Artificial Sequence

```
<220> FEATURE:
<223> OTHER INFORMATION: Target Sequence

<400> SEQUENCE: 112
aggaagcgag aaaagctcca gca                                               23

<210> SEQ ID NO 113
<211> LENGTH: 22
<212> TYPE: DNA
<213> ORGANISM: Artificial Sequence
<220> FEATURE:
<223> OTHER INFORMATION: Target Sequence

<400> SEQUENCE: 113
aggaacgaga aaagctccag ca                                                22

<210> SEQ ID NO 114
<211> LENGTH: 24
<212> TYPE: DNA
<213> ORGANISM: Artificial Sequence
<220> FEATURE:
<223> OTHER INFORMATION: Target Sequence

<400> SEQUENCE: 114
cgggctctca aagcagctct gaga                                              24

<210> SEQ ID NO 115
<211> LENGTH: 22
<212> TYPE: DNA
<213> ORGANISM: Artificial Sequence
<220> FEATURE:
<223> OTHER INFORMATION: Target Sequence

<400> SEQUENCE: 115
cgctctcaaa gcagctctga ga                                                22

<210> SEQ ID NO 116
<211> LENGTH: 21
<212> TYPE: DNA
<213> ORGANISM: Artificial Sequence
<220> FEATURE:
<223> OTHER INFORMATION: Target Sequence

<400> SEQUENCE: 116
cctctcaaag cagctctgag a                                                 21

<210> SEQ ID NO 117
<211> LENGTH: 24
<212> TYPE: DNA
<213> ORGANISM: Artificial Sequence
<220> FEATURE:
<223> OTHER INFORMATION: Target Sequence

<400> SEQUENCE: 117
ggcggcactc acgggctctc aaag                                              24

<210> SEQ ID NO 118
<211> LENGTH: 22
<212> TYPE: DNA
<213> ORGANISM: Artificial Sequence
<220> FEATURE:
<223> OTHER INFORMATION: Target Sequence

<400> SEQUENCE: 118
ggcggcactc acgctctcaa ag                                                22
```

```
<210> SEQ ID NO 119
<211> LENGTH: 21
<212> TYPE: DNA
<213> ORGANISM: Artificial Sequence
<220> FEATURE:
<223> OTHER INFORMATION: Target Sequence

<400> SEQUENCE: 119
ggcggcactc acctctcaaa g                                             21

<210> SEQ ID NO 120
<211> LENGTH: 24
<212> TYPE: DNA
<213> ORGANISM: Artificial Sequence
<220> FEATURE:
<223> OTHER INFORMATION: Target Sequence

<400> SEQUENCE: 120
gcgggagggg cggcactcac gggc                                          24

<210> SEQ ID NO 121
<211> LENGTH: 23
<212> TYPE: DNA
<213> ORGANISM: Artificial Sequence
<220> FEATURE:
<223> OTHER INFORMATION: Target Sequence

<400> SEQUENCE: 121
gcgggagggg cggcactcac ggc                                           23

<210> SEQ ID NO 122
<211> LENGTH: 22
<212> TYPE: DNA
<213> ORGANISM: Artificial Sequence
<220> FEATURE:
<223> OTHER INFORMATION: Target Sequence

<400> SEQUENCE: 122
gcgggagggg cggcactcac gc                                            22

<210> SEQ ID NO 123
<211> LENGTH: 21
<212> TYPE: DNA
<213> ORGANISM: Artificial Sequence
<220> FEATURE:
<223> OTHER INFORMATION: Target Sequence

<400> SEQUENCE: 123
gcgggagggg cggcactcac c                                             21

<210> SEQ ID NO 124
<211> LENGTH: 25
<212> TYPE: DNA
<213> ORGANISM: Artificial Sequence
<220> FEATURE:
<223> OTHER INFORMATION: Target Sequence

<400> SEQUENCE: 124
ccagaaggaa gggcgagaaa agctc                                         25

<210> SEQ ID NO 125
<211> LENGTH: 25
<212> TYPE: DNA
<213> ORGANISM: Artificial Sequence
<220> FEATURE:
<223> OTHER INFORMATION: Target Sequence
```

```
<400> SEQUENCE: 125
aaggaagggc gagaaaagct ccagc                                              25

<210> SEQ ID NO 126
<211> LENGTH: 25
<212> TYPE: DNA
<213> ORGANISM: Artificial Sequence
<220> FEATURE:
<223> OTHER INFORMATION: Target Sequence

<400> SEQUENCE: 126
gcgggagggg cggcactcac ggggc                                              25

<210> SEQ ID NO 127
<211> LENGTH: 25
<212> TYPE: DNA
<213> ORGANISM: Artificial Sequence
<220> FEATURE:
<223> OTHER INFORMATION: Target Sequence

<400> SEQUENCE: 127
tggggagagg gccagaagga agggc                                              25

<210> SEQ ID NO 128
<211> LENGTH: 20
<212> TYPE: DNA
<213> ORGANISM: Artificial Sequence
<220> FEATURE:
<223> OTHER INFORMATION: Target Sequence

<400> SEQUENCE: 128
ggctctcaaa gcagctctga                                                    20

<210> SEQ ID NO 129
<211> LENGTH: 25
<212> TYPE: DNA
<213> ORGANISM: Artificial Sequence
<220> FEATURE:
<223> OTHER INFORMATION: Target Sequence

<400> SEQUENCE: 129
agaaggaagg gcgagaaaag ctcca                                              25

<210> SEQ ID NO 130
<211> LENGTH: 25
<212> TYPE: DNA
<213> ORGANISM: Artificial Sequence
<220> FEATURE:
<223> OTHER INFORMATION: Target Sequence

<400> SEQUENCE: 130
gctctcaaag cagctctgag acatc                                              25

<210> SEQ ID NO 131
<211> LENGTH: 25
<212> TYPE: DNA
<213> ORGANISM: Artificial Sequence
<220> FEATURE:
<223> OTHER INFORMATION: Target Sequence

<400> SEQUENCE: 131
ctctcaaagc agctctgaga catca                                              25

<210> SEQ ID NO 132
```

```
<211> LENGTH: 25
<212> TYPE: DNA
<213> ORGANISM: Artificial Sequence
<220> FEATURE:
<223> OTHER INFORMATION: Target Sequence

<400> SEQUENCE: 132
tctcaaagca gctctgagac atcaa                                          25

<210> SEQ ID NO 133
<211> LENGTH: 25
<212> TYPE: DNA
<213> ORGANISM: Artificial Sequence
<220> FEATURE:
<223> OTHER INFORMATION: Target Sequence

<400> SEQUENCE: 133
ctcaaagcag ctctgagaca tcaac                                          25

<210> SEQ ID NO 134
<211> LENGTH: 25
<212> TYPE: DNA
<213> ORGANISM: Artificial Sequence
<220> FEATURE:
<223> OTHER INFORMATION: Target Sequence

<400> SEQUENCE: 134
tcaaagcagc tctgagacat caacc                                          25

<210> SEQ ID NO 135
<211> LENGTH: 25
<212> TYPE: DNA
<213> ORGANISM: Artificial Sequence
<220> FEATURE:
<223> OTHER INFORMATION: Target Sequence

<400> SEQUENCE: 135
caaagcagct ctgagacatc aaccg                                          25

<210> SEQ ID NO 136
<211> LENGTH: 25
<212> TYPE: DNA
<213> ORGANISM: Artificial Sequence
<220> FEATURE:
<223> OTHER INFORMATION: Target Sequence

<400> SEQUENCE: 136
aaagcagctc tgagacatca accgc                                          25

<210> SEQ ID NO 137
<211> LENGTH: 25
<212> TYPE: DNA
<213> ORGANISM: Artificial Sequence
<220> FEATURE:
<223> OTHER INFORMATION: Target Sequence

<400> SEQUENCE: 137
aagcagctct gagacatcaa ccgcg                                          25

<210> SEQ ID NO 138
<211> LENGTH: 25
<212> TYPE: DNA
<213> ORGANISM: Artificial Sequence
<220> FEATURE:
<223> OTHER INFORMATION: Target Sequence

<400> SEQUENCE: 138
```
agcagctctg agacatcaac cgcgg 25

<210> SEQ ID NO 139
<211> LENGTH: 25
<212> TYPE: DNA
<213> ORGANISM: Artificial Sequence
<220> FEATURE:
<223> OTHER INFORMATION: Target Sequence

<400> SEQUENCE: 139
gcagctctga gacatcaacc gcggc 25

<210> SEQ ID NO 140
<211> LENGTH: 25
<212> TYPE: DNA
<213> ORGANISM: Artificial Sequence
<220> FEATURE:
<223> OTHER INFORMATION: Target Sequence

<400> SEQUENCE: 140
cagctctgag acatcaaccg cggct 25

<210> SEQ ID NO 141
<211> LENGTH: 25
<212> TYPE: DNA
<213> ORGANISM: Artificial Sequence
<220> FEATURE:
<223> OTHER INFORMATION: Target Sequence

<400> SEQUENCE: 141
gccagaagga agggcgagaa aagct 25

<210> SEQ ID NO 142
<211> LENGTH: 25
<212> TYPE: DNA
<213> ORGANISM: Artificial Sequence
<220> FEATURE:
<223> OTHER INFORMATION: Target Sequence

<400> SEQUENCE: 142
cagaaggaag ggcgagaaaa gctcc 25

<210> SEQ ID NO 143
<211> LENGTH: 25
<212> TYPE: DNA
<213> ORGANISM: Artificial Sequence
<220> FEATURE:
<223> OTHER INFORMATION: Target Sequence

<400> SEQUENCE: 143
gaaggaaggg cgagaaaagc tccag 25

<210> SEQ ID NO 144
<211> LENGTH: 25
<212> TYPE: DNA
<213> ORGANISM: Artificial Sequence
<220> FEATURE:
<223> OTHER INFORMATION: Target Sequence

<400> SEQUENCE: 144
aggaagggcg agaaaagctc cagca 25

<210> SEQ ID NO 145
<211> LENGTH: 25
<212> TYPE: DNA

```
<213> ORGANISM: Artificial Sequence
<220> FEATURE:
<223> OTHER INFORMATION: Target Sequence

<400> SEQUENCE: 145
actcacgggg ctctcaaagc agctc                                              25

<210> SEQ ID NO 146
<211> LENGTH: 25
<212> TYPE: DNA
<213> ORGANISM: Artificial Sequence
<220> FEATURE:
<223> OTHER INFORMATION: Target Sequence

<400> SEQUENCE: 146
ggctctcaaa gcagctctga gacat                                              25

<210> SEQ ID NO 147
<211> LENGTH: 20
<212> TYPE: DNA
<213> ORGANISM: Artificial Sequence
<220> FEATURE:
<223> OTHER INFORMATION: Target Sequence

<400> SEQUENCE: 147
gcgcaccctc tgccctggcc                                                    20

<210> SEQ ID NO 148
<211> LENGTH: 25
<212> TYPE: DNA
<213> ORGANISM: Artificial Sequence
<220> FEATURE:
<223> OTHER INFORMATION: Target Sequence

<400> SEQUENCE: 148
ggccctggtc tgctggctcc ctgct                                              25

<210> SEQ ID NO 149
<211> LENGTH: 20
<212> TYPE: DNA
<213> ORGANISM: Artificial Sequence
<220> FEATURE:
<223> OTHER INFORMATION: Target Sequence

<400> SEQUENCE: 149
tttgccatgt tacccaggct                                                    20
```

ANTISENSE OLIGOMERS AND METHODS OF USING THE SAME FOR TREATING DISEASES ASSOCIATED WITH THE ACID ALPHA-GLUCOSIDASE GENE

RELATED APPLICATIONS

This application is a continuation application of U.S. patent application Ser. No. 16/094,858, filed Oct. 18, 2018, which application is a U.S.C. § 371 filing of International Application No. PCT/US2017/028002, filed Apr. 17, 2017, which application claims priority to U.S. Provisional Application No. 62/324,185 filed on Apr. 18, 2016, the contents of which are incorporated in their entirety.

SEQUENCE LISTING

This application contains a Sequence Listing in computer readable format. The Sequence Listing is provided as a file entitled 719241-SPT-8136USCON-SEQ-TEXT-6-9-2021.txt created Jun. 9, 2021 which is 45,635 bytes in size. The information in the computer readable format of the Sequence Listing is incorporated herein by reference in its entirety.

FIELD OF THE DISCLOSURE

The present disclosure relates to antisense oligomers and related compositions and methods for inducing exon inclusion as a treatment for glycogen storage disease type II (GSD-II) (also known as Pompe disease, glycogenosis II, acid maltase deficiency (AMD), acid alpha-glucosidase deficiency, and lysosomal alpha-glucosidase deficiency), and more specifically relates to inducing inclusion of exon 2 and thereby restoring levels of enzymatically active acid alpha-glucosidase (GAA) protein encoded by the GAA gene.

DESCRIPTION OF THE RELATED ART

Alternative splicing increases the coding potential of the human genome by producing multiple proteins from a single gene. Inappropriate alternative splicing is also associated with a growing number of human diseases.

GSD-II is an inherited autosomal recessive lysosomal storage disorder caused by deficiency of an enzyme called acid alpha-glucosidase (GAA). The role of GAA within the body is to break down glycogen. Reduced or absent levels of GAA activity leads to the accumulation of glycogen in the affected tissues, including the heart, skeletal muscles (including those involved with breathing), liver, and nervous system. This accumulation of glycogen is believed to cause progressive muscle weakness and respiratory insufficiency in individuals with GSD-II. GSD-II can occur in infants, toddlers, or adults, and the prognosis varies according to the time of onset and severity of symptoms. Clinically, GSD-II may manifest with a broad and continuous spectrum of severity ranging from severe (infantile) to milder late onset adult form. The patients eventually die due to respiratory insufficiency. There is a good correlation between the severity of the disease and the residual acid alpha-glucosidase activity, the activity being 10-20% of normal in late onset and less than 2% in early onset forms of the disease. It is estimated that GSD-II affects approximately 5,000 to 10,000 people worldwide.

The most common mutation associated with the adult onset form of disease is IVS1-13T>G. Found in over two thirds of adult onset GSD-II patients, this mutation may confer a selective advantage in heterozygous individuals or is a very old mutation. The wide ethnic variation of adult onset GSD-II individuals with this mutation argues against a common founder.

The GAA gene consists of 20 exons spanning some 20 kb. The 3.4 kb mRNA encodes a protein with a molecular weight of approximately 105 kD. The IVS1-13T>G mutation leads to the loss of exon 2 (577 bases) which contains the initiation AUG codon.

Treatment for GSD-II has involved drug treatment strategies, dietary manipulations, and bone marrow transplantation without significant success. In recent years, enzyme replacement therapy (ERT) has provided new hope for GSD-II patients. For example, Myozyme®, a recombinant GAA protein drug, received approval for use in patients with GSD-II disease in 2006 in both the U.S. and Europe. Myozyme® depends on mannose-6-phosphates (M6P) on the surface of the GAA protein for delivery to lysosomes.

Antisense technology, used mostly for RNA down regulation, recently has been adapted to alter the splicing process. Processing the primary gene transcripts (pre-mRNA) of many genes involves the removal of introns and the precise splicing of exons where a donor splice site is joined to an acceptor splice site. Splicing is a precise process, involving the coordinated recognition of donor and acceptor splice sites, and the branch point (upstream of the acceptor splice site) with a balance of positive exon splice enhancers (predominantly located within the exon) and negative splice motifs (splice silencers are located predominantly in the introns).

Effective agents that can alter splicing of GAA pre-mRNAs are likely to be useful therapeutically for improved treatment of GSD-II.

SUMMARY

In one aspect, the disclosure features a modified antisense oligonucleotide of 10 to 40 nucleobases. The modified antisense oligonucleotide includes a targeting sequence complementary to a target region within the pre-mRNA of the human alpha glucosidase (GAA) gene (e.g., within intron 1 of GAA, such as a target region within SEQ ID NO:1), wherein the target region comprises at least one additional nucleobase compared to the targeting sequence, wherein the at least one additional nucleobase has no complementary nucleobase in the targeting sequence, and wherein the at least one additional nucleobase is internal to the target region. The interaction between the targeting region and the targeting sequence may otherwise be 100% complementarity but may also include lower thresholds of complementarity (e.g., 80%, 81%, 82%, 83%, 84%, 85%, 86%, 87%, 88%, 89%, 90%, 91%, 92%, 93%, 94%, 95%, 96%, 97%, 98%, 99%). The target region may include at least one of SEQ ID NO: 2 or SEQ ID NO: 3. Optionally, the target region may include SEQ ID NO: 4. Optionally, the target region may include SEQ ID NO: 5. The modified antisense oligonucleotide may promote retention of exon 2 in the GAA mRNA upon binding of the targeting sequence to the target region. The target region may include from one to three additional nucleobases compared to the targeting sequence. However, more than three additional nucleobases can also be present in the target region. Further, the additional nucleobases can be separated from each other along the target region. The modified antisense oligonucleotide may induce GAA enzyme activity at least two fold according to an enzyme activity test as compared to a second antisense oligonucleotide that is fully complementary to the target region within SEQ ID NO: 1. The modified antisense oligonucleotide may induce GAA enzyme activity at least three fold or at least four fold according to an enzyme activity test as compared to a second antisense oligonucleotide that is fully complementary to the target region within SEQ ID NO: 1.

In another aspect, the disclosure features an antisense oligomer compound of formula (I):

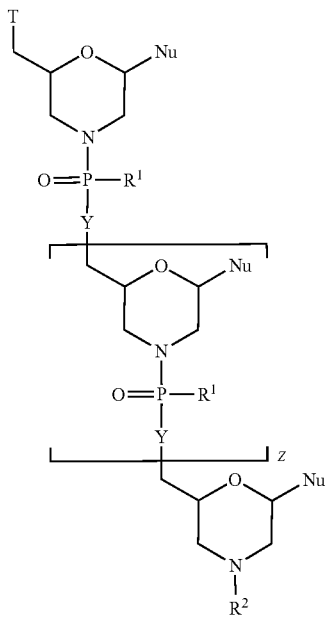

(I)

or a pharmaceutically acceptable salt thereof, wherein:
each Nu is a nucleobase which taken together form a targeting sequence;
Z is an integer from 8 to 38;
each Y is independently selected from O and $-NR^4$, wherein each $R^4$ is independently selected from H, $C_1$-$C_6$ alkyl, aralkyl, $-C(=NH)NH_2$, $-C(O)(CH_2)_n NR^5C(=NH)NH_2$, $-C(O)(CH_2)_2 NHC(O)(CH_2)_5 NR^5C(=NH)NH_2$, and G, wherein $R^5$ is selected from H and $C_1$-$C_6$ alkyl and n is an integer from 1 to 5;
T is selected from OH and a moiety of the formula:

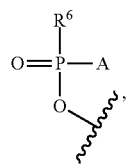

wherein:
A is selected from $-OH$, $-N(R^7)_2$, and $R^1$ wherein each $R^7$ is independently selected from H and $C_1$-$C_6$ alkyl, and $R^6$ is selected from OH, $-N(R^9)CH_2C(O)NH_2$, and a moiety of the formula:

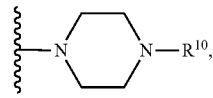

wherein:
$R^9$ is selected from H and $C_1$-$C_6$ alkyl; and
$R^{10}$ is selected from G, $-C(O)-R^{11}OH$, acyl, trityl, 4-methoxytrityl,
$-C(=NH)NH_2$, $-C(O)(CH_2)_m NR^{12}C(=NH)NH_2$, and
$-C(O)(CH_2)_2 NHC(O)(CH_2)_5 NR^{12}C(=NH)NH_2$,
wherein:
m is an integer from 1 to 5,
$R^{11}$ is of the formula $-(O-alkyl)_y-$ wherein y is an integer from 3 to 10 and
each of the y alkyl groups is independently selected from $C_2$-$C_6$ alkyl; and
$R^{12}$ is selected from H and $C_1$-$C_6$ alkyl;
each instance of $R^1$ is independently selected from:
$-N(R^{13})_2$, wherein each $R^{13}$ is independently selected from H and $C_1$-$C_6$ alkyl;
a moiety of formula (II):

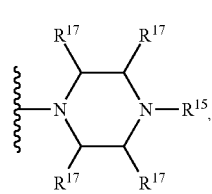

(II)

wherein:
$R^{15}$ is selected from H, G, $C_1$-$C_6$ alkyl, $-C(=NH)NH_2$,
$-C(O)(CH_2)_q NR^{18}C(=NH)NH_2$, and
$-C(O)(CH_2)_2 NHC(O)(CH_2)_5 NR^{18}C(=NH)NH_2$, wherein:
$R^{18}$ is selected from H and $C_1$-$C_6$ alkyl; and
q is an integer from 1 to 5, and
each $R^{17}$ is independently selected from H and methyl; and
a moiety of formula(III):

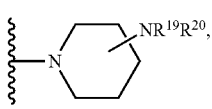

(III)

wherein:
$R^{19}$ is selected from H, $C_1$-$C_6$ alkyl, $-C(=NH)NH_2$, $-C(O)(CH_2)_r NR^{22}C(=NH)NH_2$,
$-C(O)CH(NH_2)(CH_2)_3 NHC(=NH)NH_2$,
$-C(O)(CH_2)_2 NHC(O)(CH_2)_5 NR^{22}C(=NH)NH_2$,
$-C(O)CH(NH_2)(CH_2)_4 NH_2$ and G, wherein:
$R^{22}$ is selected from H and $C_1$-$C_6$ alkyl; and
r is an integer from 1 to 5, and
$R^{20}$ is selected from H and $C_1$-$C_6$ alkyl; or
$R^{19}$ and $R^{20}$ together with the nitrogen atom to which they are attached form a heterocyclic or heteroaryl ring having from 5 to 7 ring atoms and optionally containing an additional heteroatom selected from oxygen, nitrogen, and sulfur; and R² is selected from H, G, acyl, trityl, 4-methoxytrityl, benzoyl, stearoyl, C₁-C₆ alkyl, —C(=NH)NH₂, —C(O)—R²³, —C(O)(CH₂)ₛNR²⁴C(=NH)NH₂, —C(O)(CH₂)₂NHC(O)(CH₂)₅NR²⁴C(=NH)NH₂, —C(O)CH(NH₂)(CH₂)₃NHC(=NH)NH₂, and a moiety of the formula:

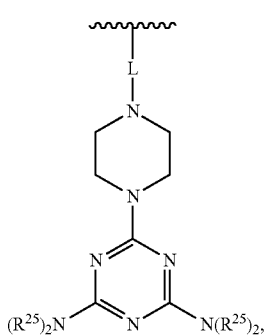

wherein,
R²³ is of the formula —(O-alkyl)ᵥ-OH wherein v is an integer from 3 to 10 and each of the v alkyl groups is independently selected from C₂-C₆ alkyl; and
R²⁴ is selected from H and C₁-C₆ alkyl;
s is an integer from 1 to 5;
L is selected from —C(O)(CH₂)₆C(O)— and —C(O)(CH₂)₂S₂(CH₂)₂C(O)—; and
each R²⁵ is of the formula —(CH₂)₂OC(O)N(R²⁶)₂ wherein each R²⁶ is of the formula —(CH₂)₆NHC(=NH)NH₂, wherein G is a cell penetrating peptide ("CPP") and linker moiety selected from —C(O)(CH₂)₅NH-CPP, —C(O)(CH₂)₂NH-CPP, —C(O)(CH₂)₂NHC(O)(CH₂)₅NH-CPP, —C(O)CH₂NH-CPP, and:

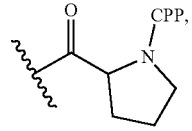

wherein the CPP is attached to the linker moiety by an amide bond at the CPP carboxy terminus, and
wherein G may be present in one occurrence or is absent.

In certain embodiments, each R¹ is —N(CH₃)₂. In some embodiments, about 50-90% of the R₁ groups are dimethylamino (i.e. —N(CH₃)₂). In certain embodiments, about 66% of the R₁ groups are dimethylamino.

In some non-limiting embodiments, the targeting sequence is selected from the sequences of Tables 2A-2C, wherein X is selected from uracil (U) or thymine (T). In some non-limiting embodiments, each R¹ is —N(CH₃)₂ and the targeting sequence is selected from the sequences of Table 2A-2C, wherein X is selected from uracil (U) or thymine (T).

In some embodiments of the disclosure, R₁ may be selected from:

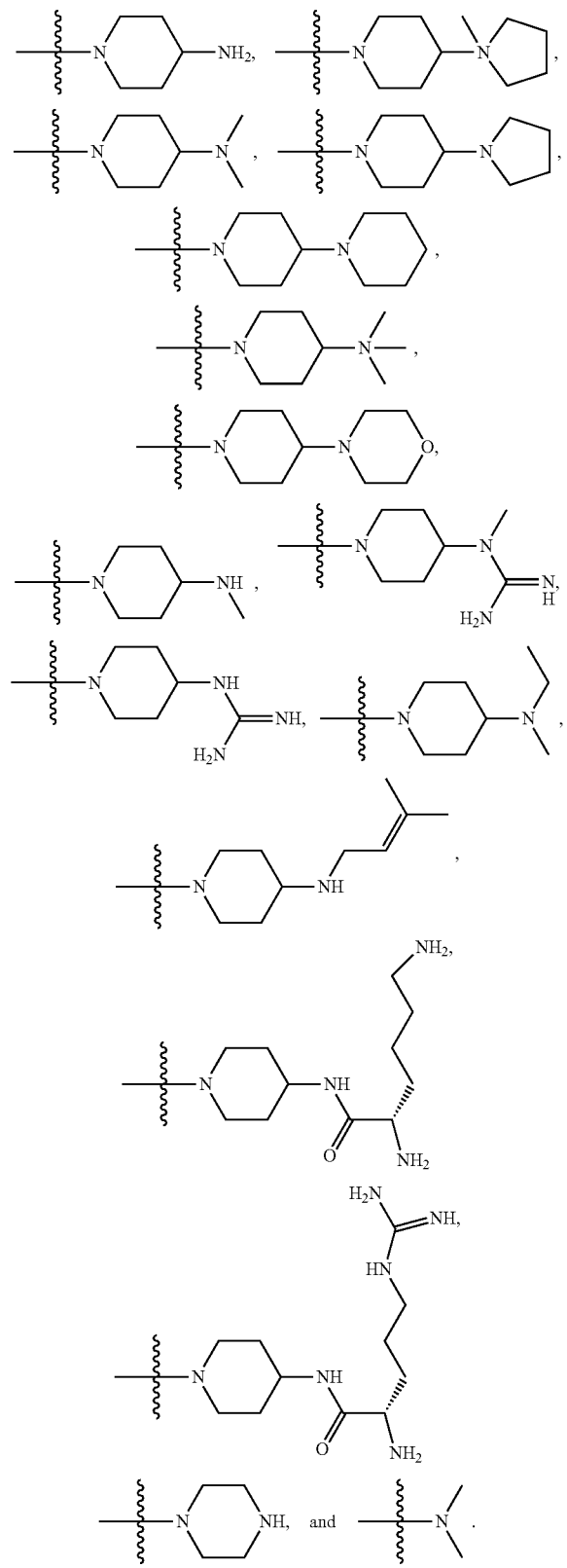

In certain embodiments, T is selected from:

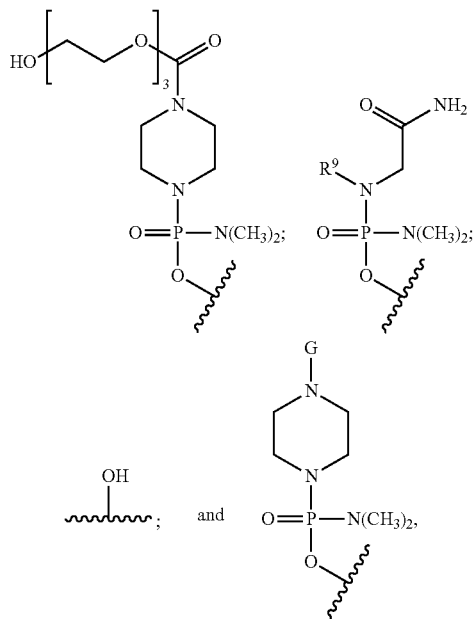

and

Y is O at each occurrence. In some embodiments, $R^2$ is selected from H, G, acyl, trityl, 4-methoxytrityl, benzoyl, and stearoyl.

In certain embodiments, T is of the formula:

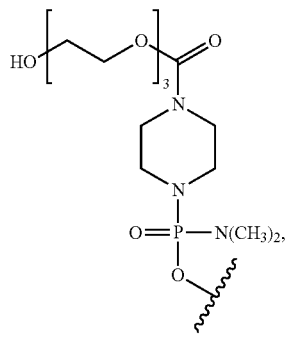

Y is O at each occurrence and $R^2$ is G.

In certain embodiments, T is of the formula:

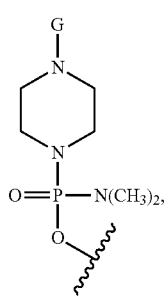

and Y is O at each occurrence.

In certain embodiments, T is of the formula:

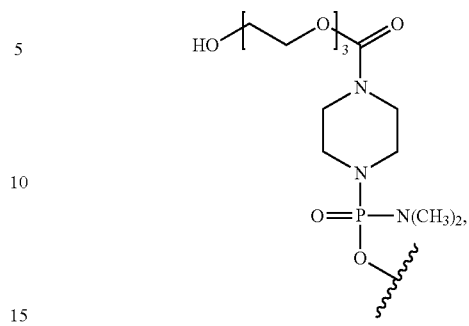

Y is O at each occurrence, each $R^1$ is —$N(CH_3)_2$, and $R^2$ is H.

In another aspect, the disclosure features an antisense oligomer compound of formula (VII):

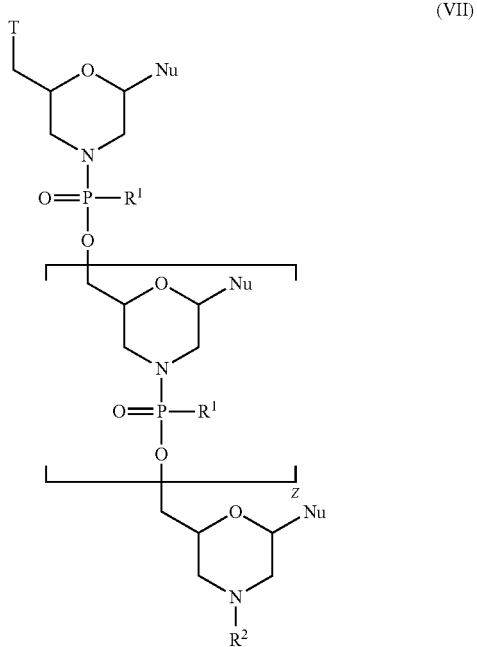

(VII)

or a pharmaceutically acceptable salt thereof,
where each Nu is a nucleobase which taken together forms a targeting sequence;
Z is an integer from 8 to 38;
T is selected from:

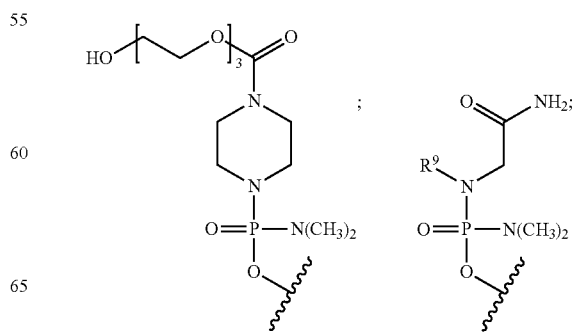

-continued

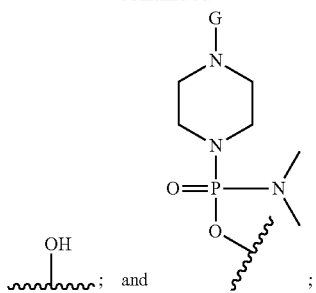
; and
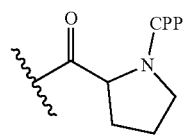
;

each $R^1$ is —N($R^4$)$_2$ wherein each $R^4$ is independently $C_1$-$C_6$ alkyl; and $R^2$ is selected from H, G, acyl, trityl, 4-methoxytrityl, benzoyl, and stearoyl, wherein G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

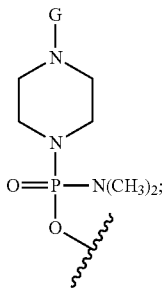

wherein the CPP is attached to the linker moiety by an amide bond at the CPP carboxy terminus, and wherein T is

```
        G
        |
        N
       / \
      /   \
      \   /
       \ /
        N
        |
  O=P—N(CH₃)₂;
        |
        O
        ⁓
``` or $R^2$ is G.

In some embodiments, the targeting sequence of an antisense oligomer of the disclosure including, for example, some embodiments of the antisense oligomers of formula (I) and (IV), is selected from the sequences outlined in Tables 2A-2C, as described herein, and as follows:

I.
a)
    SEQ ID NO: 13
(GGC CAG AAG GAA GGC GAG AAA AGC)
wherein Z is 22;

b)
    SEQ ID NO: 14
(GCC AGA AGG AAG GC GAG AAA AGC X)
wherein Z is 22;

c)
    SEQ ID NO: 15
(CCA GAA GGA AGG CGA GAA AAG CXC)
wherein Z is 22;

d)
    SEQ ID NO: 16
(CAG AAG GAA GGC GAG AAA AGC XCC)
wherein Z is 22;

e)
    SEQ ID NO: 17
(AGA AGG AAG GCG AGA AAA GCX CCA)
wherein Z is 22;

f)
    SEQ ID NO: 18
(GAA GGA AGG CGA GAA AAG CXC CAG)
wherein Z is 22;

g)
    SEQ ID NO: 19
(AAG GAA GGC GAG AAA AGC XCC AGC)
wherein Z is 22;

h)
    SEQ ID NO: 20
(AGG AAG GCG AGA AAA GCX CCA GCA)
wherein Z is 22;

i)
    SEQ ID NO: 21
(CGG CXC XCA AAG CAG CXC XGA GA)
wherein Z is 21;

j)
    SEQ ID NO: 22
(ACG GCX CXC AAA GCA GCX CXG AG)
wherein Z is 21;

k)
    SEQ ID NO: 23
(CAC GGC XCX CAA AGC AGC XCX GA)
wherein Z is 21;

l)
    SEQ ID NO: 24
(XCA CGG CXC XCA AAG CAG CXC XG)
wherein Z is 21;

m)
    SEQ ID NO: 25
(CXC ACG GCX CXC AAA GCA GCX CX)
wherein Z is 21;

n)
    SEQ ID NO: 26
(ACX CAC GGC XCX CAA AGC AGC XC)
wherein Z is 21;

o)
    SEQ ID NO: 27
(GCG GCA CXC ACG GCX CXC AAA GC)
wherein Z is 21;

p)
    SEQ ID NO: 28
(GGC GGC ACX CAC GGC XCX CAA AG)
wherein Z is 21;

q)
    SEQ ID NO: 29
(CGG CAC XCA CGG CXC XCA AAG CA)
wherein Z is 21;

r)
    SEQ ID NO: 30
(GCA CXC ACG GCX CXC AAA GCA GC)
wherein Z is 21;

-continued s)

(GGC ACX CAC GGC XCX CAA AGC AG)
wherein Z is 21;

t)

(CAC XCA CGG CXC XCA AAG CAG CX)
wherein Z is 21;

u)

(GCC AGA AGG AAG GCG AGA AAA GC)
wherein Z is 21;

v)

(CCA GAA GGA AGG CGA GAA AAG C)
wherein Z is 19;

w)

(CAG AAG GAA GGC GAG AAA AGC)
wherein Z is 19;

x)

(GGC CAG AAG GAA GGC GAG AAA AG)
wherein Z is 21;

y)

(GGC CAG AAG GAA GGC GAG AAA A)
wherein Z is 19;

z)

(GGC CAG AAG GAA GGC GAG AAA)
wherein Z is 19;

aa)

(CGG CAC XCA CGGC XCX CAA AGC A)
wherein Z is 21;

bb)

(GCG GCA CXC ACGG CXC XCA AAG C)
wherein Z is 21;

cc)

(GGC GGC ACX CAC G GCX CXC AAA G)
wherein Z is 21;

dd)

(XGG GGA GAG GGC CAG AAG GAA GGC)
wherein Z is 22;

ee)

(XGG GGA GAG GGC CAG AAG GAA GC)
wherein Z is 21;

ff)

(XGG GGA GAG GGC CAG AAG GAA C)
wherein Z is 20;

gg)

(GGC CAG AAG GAA GCG AGA AAA GC)
wherein Z is 21;

hh)

(GGC CAG AAG GAA CGA GAA AAG C)
wherein Z is 20;

SEQ ID NO: 31

SEQ ID NO: 32

SEQ ID NO: 33

SEQ ID NO: 34

SEQ ID NO: 35

SEQ ID NO: 36

SEQ ID NO: 37

SEQ ID NO: 38

SEQ ID NO: 39

SEQ ID NO: 40

SEQ ID NO: 41

SEQ ID NO: 42

SEQ ID NO: 43

SEQ ID NO: 44

SEQ ID NO: 45

SEQ ID NO: 46 ii)

(AGG AAG CGA GAA AAG CXC CAG CA)
wherein Z is 21;

jj)

(AGG AAC GAG AAA AGC XCC AGC A)
wherein Z is 20;

kk)

(CGG GCX CXC AAA GCA GCX CXG AGA)
wherein Z is 22;

ll)

(CGC XCX CAA AGC AGC XCX GAG A)
wherein Z is 20;

mm)

(CCX CXC AAA GCA GCX CXG AGA)
wherein Z is 19;

nn)

(GGC GGC ACX CAC GGG CXC XCA AAG)
wherein Z is 22;

oo)

(GGC GGC ACX CAC GCX CXC AAA G)
wherein Z is 20;

pp)

(GGC GGC ACX CAC CXC XCA AAG)
wherein Z is 19;

qq)

(GCG GGA GGG GCG GCA CXC ACG GGC)
wherein Z is 22;

rr)

(GCG GGA GGG GCG GCA CXC ACG GC)
wherein Z is 21;

ss)

(GCG GGA GGG GCG GCA CXC ACG C)
wherein Z is 20;

and tt)

(GCG GGA GGG GCG GCA CXC ACC) wherein Z is 19,
wherein X is selected from uracil (U) or
thymine (T);

II.
a)

(GGC CAG AAG GAA GGG CGA GAA AAG C)
wherein Z is 23;

b)

(CCA GAA GGA AGG GCG AGA AAA GCX C)
wherein Z is 23;

c)

(AAG GAA GGG CGA GAA AAG CXC CAG C)
wherein Z is 23;

SEQ ID NO: 47

SEQ ID NO: 48

SEQ ID NO: 49

SEQ ID NO: 50

SEQ ID NO: 51

SEQ ID NO: 52

SEQ ID NO: 53

SEQ ID NO: 54

SEQ ID NO: 55

SEQ ID NO: 56

SEQ ID NO: 57

SEQ ID NO: 58

SEQ ID NO: 59

SEQ ID NO: 60

SEQ ID NO: 61

-continued d)
(GCG GGA GGG GCG GCA CXC ACG GGG C)
wherein Z is 23;
SEQ ID NO: 62 e)
(XGG GGA GAG GGC CAG AAG GAA GGG C)
wherein Z is 23;
SEQ ID NO: 63 f)
(AGA AGG AAG GGC GAG AAA AGC XCC A)
wherein Z is 23;
SEQ ID NO: 64 g)
(GCX CXC AAA GCA GCX CXG AGA CAX C)
wherein Z is 23;
SEQ ID NO: 65 h)
(CXC XCA AAG CAG CXC XGA GAC AXC A)
wherein Z is 23;
SEQ ID NO: 66 i)
(XCX CAA AGC AGC XCX GAG ACA XCA A)
wherein Z is 23;
SEQ ID NO: 67 j)
(CXC AAA GCA GCX CXG AGA CAX CAA C)
wherein Z is 23;
SEQ ID NO: 68 k)
(XCA AAG CAG CXC XGA GAC AXC AAC C)
wherein Z is 23;
SEQ ID NO: 69 l)
(CAA AGC AGC XCX GAG ACA XCA ACC G)
wherein Z is 23;
SEQ ID NO: 70 m)
(AAA GCA GCX CXG AGA CAX CAA CCG C)
wherein Z is 23;
SEQ ID NO: 71 n)
(AAG CAG CXC XGA GAC AXC AAC CGC G)
wherein Z is 23;
SEQ ID NO: 72 o)
(AGC AGC XCX GAG ACA XCA ACC GCG G)
wherein Z is 23;
SEQ ID NO: 73 p)
(GCA GCX CXG AGA CAX CAA CCG CGG C)
wherein Z is 23;
and q)
(CAG CXC XGA GAC AXC AAC CGC GGC X)
wherein Z is 23,
wherein X is selected from uracil (U) or thymine (T);
and III.
a)
(GCC AGA AGG AAG GGC GAG AAA AGC X)
wherein Z is 23;
SEQ ID NO: 76 b)
(CAG AAG GAA GGG CGA GAA AAG CXC C)
wherein Z is 23;
SEQ ID NO: 77 c)
(GAA GGA AGG GCG AGA AAA GCX CCA G)
wherein Z is 23;
SEQ ID NO: 78 d)
(AGG AAG GGC GAG AAA AGC XCC AGC A)
wherein Z is 23;
SEQ ID NO: 79 e)
(ACX CAC GGG GCX CXC AAA GCA GCX C)
wherein Z is 23;
SEQ ID NO: 80 f)
(GGCXCXCAAAGCAGCXCXGAGACAX)
wherein Z is 23;
SEQ ID NO: 81 g)
(GGC XCX CAA AGC AGC XCX GA)
wherein Z is 18;
SEQ ID NO: 82 h)
(GAG AGG GCC AGA AGG AAG GG)
wherein Z is 18;
SEQ ID NO: 83 i)
(XXX GCC AXG XXA CCC AGG CX)
wherein Z is 18;
SEQ ID NO: 84 j)
(GCG CAC CCX CXG CCC XGG CC)
wherein Z is 18;
and
SEQ ID NO: 85 k)
(GGC CCX GGX CXG CXG GCX CCC XGC X)
wherein Z is 23,
wherein X is selected from uracil (U) or thymine (T).
SEQ ID NO: 86

In certain embodiments, the targeting sequence is selected from the group consisting of SEQ ID NOs: 13, 27-29, 34-36, 59, and 82. In certain embodiments, the targeting sequence is selected from the group consisting of SEQ ID NOs: 13, 27-29, 34-36, and 59. In certain embodiments, the targeting sequence is selected from the group consisting of SEQ ID NOs: 13, 27-29, and 34-36. In certain embodiments, each instance of X in any one of SEQ ID NOs: 13, 27-29, 34-36, 59, and 82 is T.

In some embodiments including, for example, some embodiments of the antisense oligomers of formula (I) and (IV), the targeting sequence is complementary to a target region within intron 1 (SEQ ID NO: 1) of a pre-mRNA of the human alpha glucosidase (GAA) gene. In some embodiments, the targeting sequence is complementary to a target region in exon 2 or intron 2 of the human GAA gene. In various embodiments including, for example, embodiments of the antisense oligomers of formula (I) and (IV), the targeting sequence is complementary to a target region within intron 1 (SEQ ID NO: 1) of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. In certain embodiments, the targeting sequence comprises a sequence selected from SEQ ID NOs:13-86, as shown in Tables 2A-2C herein. In certain embodiments, the targeting sequence comprises a sequence selected from Tables 2A and 2B. In certain embodiments, the targeting sequence is selected from the group consisting of SEQ ID NOs: 13, 27-29, 34-36, 59, and 82. Further, and with respect to the sequences outlined in Tables 2A-2C (or Tables 2B and 2C) herein, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present.

In some embodiments, at least one X of SEQ ID NOS: 13-86 is T. In some embodiments, at least one X of SEQ ID NOS: 13-86 is U. In some embodiments, each X of SEQ ID NOS: 13-86 is T. In some embodiments, each X of SEQ ID NOS: 13-86 is U. In various embodiments, at least one X of the targeting sequence is T. In various embodiments, each X of the targeting sequence is T. In various embodiments, at least one X of the targeting sequence is U. In various embodiments, each X of the targeting sequence is U.

These and other aspects of the present disclosure will become apparent upon reference to the following detailed description and attached drawings. All references disclosed herein are hereby incorporated by reference in their entirety as if each was incorporated individually.

BRIEF DESCRIPTION OF THE DRAWINGS

FIG. 19 is a data summary table depicting the $EC_{50}$ (in µM) for various PPMO compounds.

FIG. 23 is a data summary table depicting the $EC_{50}$ (in µM) for various PPMO compounds.

DETAILED DESCRIPTION

I. Definitions

Figure 1:
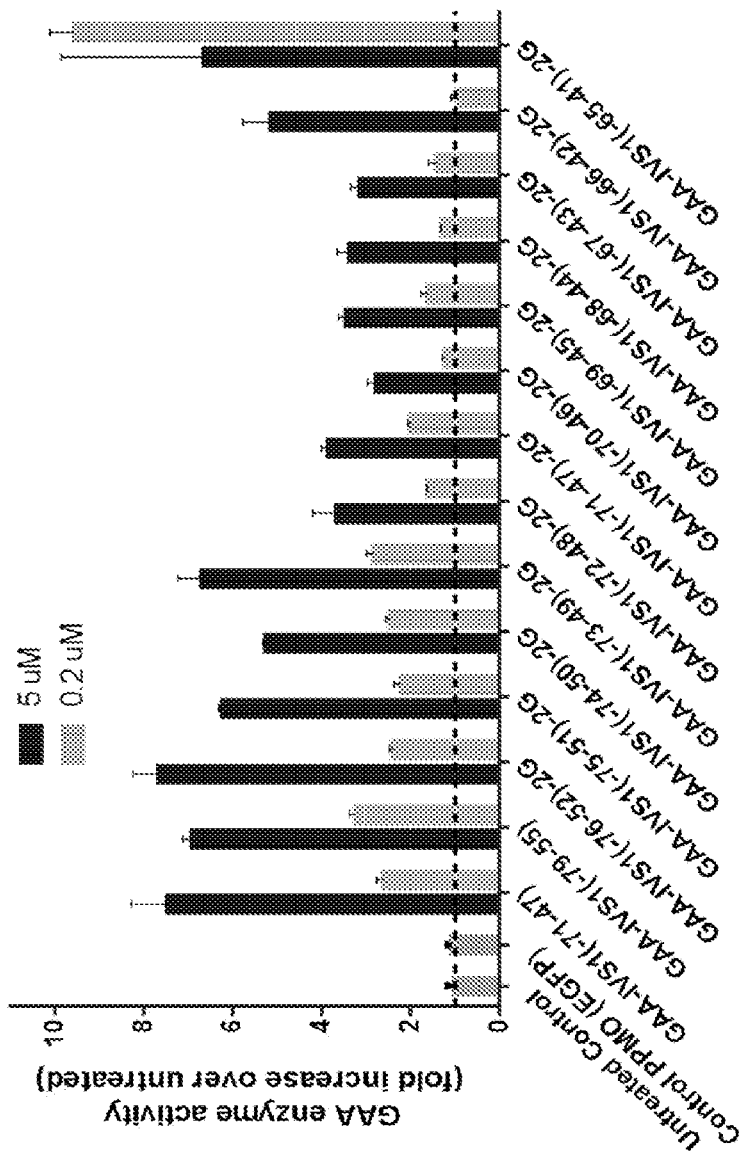
FIGS. 1 and 2 are bar graphs depicting GAA enzyme activity (Enzyme Assay) found for various PMO compounds during screening. The Y axis represents fold increase in GAA enzyme activity relative to untreated control. "N" refers to the number of replicates evaluated in each study. The horizontal hashed line signifies the level of GAA activity in untreated cells. Individual compounds were dosed at 5 µM and 0.2 µM. The horizontal hashed line signifies the level of GAA activity in untreated cells.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligomers of the disclosure into a cell by methods routine in the art, e.g., transfection (e.g., liposome, calcium-phosphate, polyethyleneimine), electroporation (e.g., nucleofection), microinjection).

As used herein, the term "alkyl" is intended to include linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_1$-$C_6$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

As used herein, the term "Alkoxy" means a subset of alkyl in which an alkyl group as defined above with the indicated number of carbons attached through an oxygen bridge. For example, "alkoxy" refers to groups —O-alkyl, wherein the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

As used herein, the term "aryl" used alone or as part of a larger moiety as in "aralkyl", "aralkoxy", or "aryloxyalkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "acyl" means a C(O)R group (in which R signifies H, alkyl or aryl as defined above). Examples of acyl groups include formyl, acetyl, benzoyl, phenylacetyl and similar groups.

The term "homolog" as used herein means compounds differing regularly by the successive addition of the same chemical group. For example, a homolog of a compound may differ by the addition of one or more —$CH_2$— groups, amino acid residues, nucleotides, or nucleotide analogs.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. In some embodiments, the CPPs are of the formula —$[(C(O)CHR'NH)_m]R''$ wherein R' is a side chain of a naturally occurring amino acid or a one- or two-carbon homolog thereof, R'' is selected from Hydrogen or acyl, and m is an integer up to 50. CPP's may also have the formula —$[(C(O)CHR'NH)_m]R^a$ wherein R' is a side chain of a naturally occurring amino acid or a one- or two-carbon homolog thereof, and where Ra is selected from Hydrogen, acyl, benzoyl, or stearoyl. CPPs of any structure may be linked to the 3' or 5' end of an antisense oligomer via a "linker" such as, for example, —C(O)(CH$_2$)$_5$NH—, —C(O)(CH$_2$)$_2$NH—, —C(O)(CH$_2$)$_2$NH—C(O)(CH$_2$)$_5$NH—, or —C(O)CH$_2$NH—. Additional CPPs are well-known in the art and are disclosed, for example, in U.S. Application No. 2010/0016215, which is incorporated by reference in its entirety. In other embodiments, m is an integer selected from 1 to 50 where, when m is 1, the moiety is a single amino acid or derivative thereof.

As used herein, "amino acid" refers to a compound consisting of a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine and Arginine. Additionally, as used herein, "amino acid" also includes derivatives of amino acids such as esters, and amides, and salts, as well as other derivatives, including derivatives having pharmacoproperties upon metabolism to an active form. Accordingly, the term "amino acid" is understood to include naturally occurring and non-naturally occurring amino acids.

As used herein, "an electron pair" refers to a valence pair of electrons that are not bonded or shared with other atoms.

As used herein, "homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide," "isolated oligonucleotide," or "isolated oligomer" as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The terms "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art, and may include increases in the inclusion of exon 2 in a GAA-coding pre-mRNA, or increases in the expression of functional GAA enzyme in a cell, tissue, or subject in need thereof. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7. 1.8), the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a glycogen storage disease such as Pompe disease, for example, a decrease in the accumulation of glycogen in one or more tissues. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 1, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, an "antisense oligonucleotide," "antisense oligomer" or "oligonucleotide" refers to a linear sequence of nucleotides, or nucleotide analogs, which allows the nucleobase to hybridize to a target sequence in an RNA by Watson-Crick base pairing, to form an oligomer:RNA heteroduplex within the target sequence. The terms "antisense oligonucleotide", "modified antisense oligonucleotide", "antisense oligomer", "oligomer" and "compound" may be used interchangeably to refer to an oligomer. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), tricyclo-DNA oligomers, tricyclo-phosphorothioate oligomers, and 2'-O-Methyl oligomers, among other antisense agents known in the art.

Included are non-naturally-occurring oligomers, or "oligonucleotide analogs," including oligomers having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligomer analogs support bases capable of hydrogen bonding by Watson-Crick base pairing to standard polynucleotide bases, where the analog backbone presents the bases in a manner to permit such hydrogen bonding in a sequence-specific fashion between the oligomer analog molecule and bases in a standard polynucleotide (e.g., single-stranded RNA or single-stranded DNA). Preferred analogs are those having a substantially uncharged, phosphorus containing backbone.

A "nuclease-resistant" oligomer refers to one whose backbone is substantially resistant to nuclease cleavage, in non-hybridized or hybridized form; by common extracellular and intracellular nucleases in the body (for example, by exonucleases such as 3'-exonucleases, endonucleases, RNase H); that is, the oligomer shows little or no nuclease cleavage under normal nuclease conditions in the body to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2, 6-diaminopurine; 5-methyl cytosine; $C_5$-propynyl-modified pyrimidines; 9-(aminoethoxy)phenoxazine (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated.

Further examples of base pairing moieties include, but are not limited to, expanded-size nucleobases in which one or more benzene rings has been added. Nucleic base replacements described in the Glen Research catalog (www.glen-research.com); Krueger A T et al, Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligomers described herein. Examples of expanded-size nucleobases are shown below:

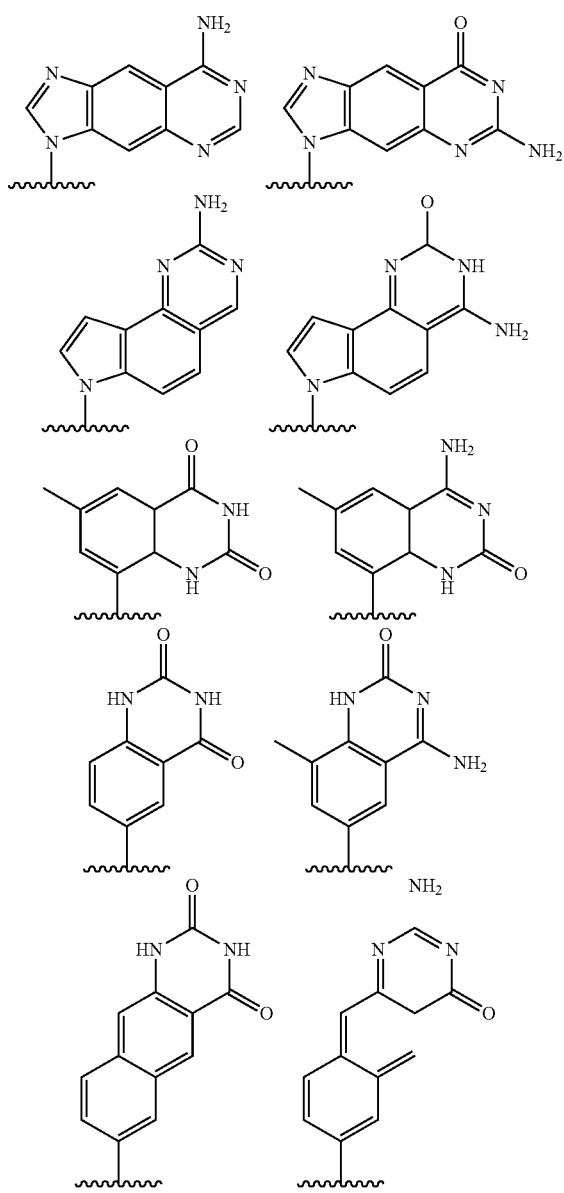

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

An oligomer "specifically hybridizes" to a target polynucleotide if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

As used herein, "sufficient length" refers to an antisense oligomer or a targeting sequence thereof that is complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 or more, such as 8-40, and such as 15-40 contiguous nucleobases in a region of GAA intron 1, exon 2, or intron 2, or a region spanning any of the foregoing. An antisense oligomer of sufficient length has at least a minimal number of nucleotides to be capable of specifically hybridizing to a region of the GAA pre-mRNA repeat in the mutant RNA. Preferably an oligomer of sufficient length is from 8 to 30 nucleotides in length. More preferably, an oligomer of sufficient length is from 9 to 27 nucleotides in length. Even more preferably, an oligomer of sufficient length is from 15 to 40 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected.

Reference also may be made to the BLAST family of programs as for example disclosed by Altschul et al., Nucl. Acids Res. 25:3389, 1997.

A "subject" or a "subject in need thereof" includes a mammalian subject such as a human subject. Exemplary mammalian subjects have or are at risk for having GSD-II (or Pompe disease). As used herein, the term "GSD-II" refers to glycogen storage disease type II (GSD-II or Pompe disease), a human autosomal recessive disease that is often characterized by under expression of GAA protein in affected individuals. In certain embodiments, a subject has reduced expression and/or activity of GAA protein in one or more tissues, for example, heart, skeletal muscle, liver, and nervous system tissues. In some embodiments, the subject has increased accumulation of glycogen in one or more tissues, for example, heart, skeletal muscle, liver, and nervous system tissues. In specific embodiments, the subject has a IVS1-13T>G mutation or other mutation that leads to reduced expression of functional GAA protein (see, e.g., Zampieri et al., European J. Human Genetics. 19:422-431, 2011).

As used herein, the term "target" refers to a RNA region, and specifically, to a region identified by the GAA gene. In a particular embodiment the target is a region within intron 1 of the GAA-coding pre-mRNA (e.g., SEQ ID NO:1), which is responsible for suppression of a signal that promotes exon 2 inclusion. In another embodiment the target region is a region of the mRNA of GAA exon 2. In a further embodiment, the target comprises one or more discrete subregions of intron 1 of the GAA-coding pre-mRNA. These subregions include, but are not limited to, the sequences defined by SEQ ID NO: 2 and SEQ ID NO: 3.

The term "target sequence" refers to a portion of the target RNA against which the oligomer analog is directed, that is, the sequence to which the oligomer analog will hybridize by Watson-Crick base pairing of a complementary sequence.

The term "targeting sequence" is the sequence in the oligomer or oligomer analog that is complementary (meaning, in addition, substantially complementary) to the "target sequence" in the RNA genome. The entire sequence, or only a portion, of the antisense oligomer may be complementary to the target sequence. For example, in an oligomer having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases in the oligomer, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

As used herein, the terms "TEG" or "triethylene glycol tail" refer to triethylene glycol moieties conjugated to the oligonucleotide, e.g., at its 3'- or 5'-end. For example, in some embodiments, "TEG" includes wherein, for example, T of the compound of formula (I), (VI), or (VII) is of the formula:

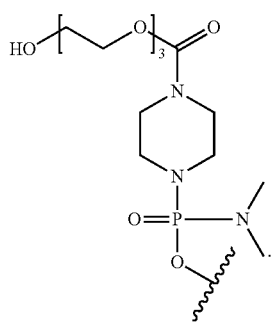

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Sequences for Splice Modulation of GAA

Certain embodiments relate to methods for enhancing the level of exon 2-containing GAA-coding mRNA relative to exon-2 deleted GAA mRNA in a cell, comprising contacting the cell with an antisense oligomer of sufficient length and complementarity to specifically hybridize to a region within the GAA gene, such that the level of exon 2-containing GAA mRNA relative to exon-2 deleted GAA mRNA in the cell is enhanced. In some embodiments, the cell is in a subject, and the method comprises administering to the antisense oligomer to the subject.

An antisense oligomer can be designed to block or inhibit or modulate translation of mRNA or to inhibit or modulate pre-mRNA splice processing, or induce degradation of targeted mRNAs, and may be said to be "directed to" or "targeted against" a target sequence with which it hybridizes. In certain embodiments, the target sequence includes a region including a 3' or 5' splice site of a pre-processed mRNA, a branch point, or other sequence involved in the regulation of splicing. The target sequence may be within an exon or within an intron or spanning an intron/exon junction.

In certain embodiments, the antisense oligomer has sufficient sequence complementarity to a target RNA (i.e., the RNA for which splice site selection is modulated) to block a region of a target RNA (e.g., pre-mRNA) in an effective manner. In exemplary embodiments, such blocking of GAA pre-mRNA serves to modulate splicing, either by masking a binding site for a native protein that would otherwise modulate splicing and/or by altering the structure of the targeted RNA. In some embodiments, the target RNA is target pre-mRNA (e.g., GAA gene pre-mRNA).

An antisense oligomer having a sufficient sequence complementarity to a target RNA sequence to modulate splicing of the target RNA means that the antisense agent has a sequence sufficient to trigger the masking of a binding site for a native protein that would otherwise modulate splicing and/or alters the three-dimensional structure of the targeted RNA. Likewise, an oligomer reagent having a sufficient sequence complementary to a target RNA sequence to modulate splicing of the target RNA means that the oligomer reagent has a sequence sufficient to trigger the masking of a binding site for a native protein that would otherwise modulate splicing and/or alters the three-dimensional structure of the targeted RNA.

In certain embodiments, the antisense oligomer has sufficient length and complementarity to a sequence in intron 1 of the human GAA pre-mRNA, exon 2 of the human GAA pre-mRNA, or intron 2 of the human GAA pre-mRNA. Also included are antisense oligomers which are complementary to a region that spans intron 1/exon 2 of the human GAA pre-mRNA, or a region that spans exon 2/intron 2 of the human GAA pre-mRNA. The intron 1 (SEQ ID NO: 1), exon 2 (SEQ ID NO: 4), and intron 2 (SEQ ID NO: 5) sequences for human the GAA gene are shown in Table 1 below (The highlighted T/G near the 3' end of SEQ ID NO:1 is the IVS1-13T>G mutation described above; the nucleotide at this position is either T or G).

TABLE 1

Target sequences for GAA-targeted oligomers (from NG_009822)

| Name | Sequence (5'-3') | SEQ ID NO |
|---|---|---|
| GAA-IVS1 | GTGAGACACCTGACGTCTGCCCCGCGCTGCCGGCGGTAACATC<br>CCAGAAGCGGGTTTGAACGTGCCTAGCCGTGCCCCCAGCCTCT<br>TCCCCTGAGCGGAGCTTGAGCCCCAGACCTCTAGTCCTCCCGG<br>TCTTTATCTGAGTTCAGCTTAGAGATGAACGGGGAGCCGCCCT<br>CCTGTGCTGGGCTTGGGGCTGGAGGCTGCATCTTCCCGTTTCTA<br>GGGTTTCCTTTCCCCTTTTGATCGACGCAGTGCTCAGTCCTGGC<br>CGGGACCCGAGCCACCTCTCCTGCTCCTGCAGGACGCACATGG<br>CTGGGTCTGAATCCCTGGGGTGAGGAGCACCGTGGCCTGAGA<br>GGGGGCCCCTGGGCCAGCTCTGAAATCTGAATGTCTCAATCAC<br>AAAGACCCCCTTAGGCCAGGCCAGGGGTGACTGTCTCTGGTCT<br>TTGTCCCTGGTTGCTGGCACATAGCACCCGAAACCCTTGGAAA<br>CCGAGTGATGAGAGAGCCTTTTGCTCATGAGGTGACTGATGAC<br>CGGGGACACCAGGTGGCTTCAGGATGGAAGCAGATGGCCAGA<br>AAGACCAAGGCCTGATGACGGGTTGGGATGGAAAAGGGGTGA<br>GGGGCTGGAGATTGAGTGAATCACCAGTGGCTTAGTCAACCAT<br>GCCTGCACAATGGAACCCCGTAAGAAACCACAGGGATCAGAG<br>GGCTTCCCGCCGGGTTGTGGAACACACCAAGGCACTGGAGGG<br>TGGTGCGAGCAGAGAGCACAGCATCACTGCCCCCACCTCACAC<br>CAGGCCCTACGCATCTCTTCCATACGGCTGTCTGAGTTTTATCC<br>TTTGTAATAAACCAGCAACTGTAAGAAACGCACTTTCCTGAGT<br>TCTGTGACCCTGAAGAGGGAGTCCTGGGAACCTCTGAATTTAT<br>AACTAGTTGATCGAAAGTACAAGTGACAACCTGGGATTTGCCA<br>TTGGCCTCTGAAGTGAAGGCAGTGTTGTGGGACTGAGCCCTTA<br>ACCTGTGGAGTCTGTGCTGACTCCAGGTAGTGTCAAGATTGAA<br>TTGAATTGTAGGACACCCAGCCGTGTCCAGAAAGTTGCAGAAT<br>TGATGGGTGTGAGAAAAACCCTACACATTTAATGTCAGAAGTG<br>TGGGTAAAATGTTTCACCCTCCAGCCCAGAGAGCCCTAATTTA<br>CCAGTGGCCCACGGTGGAACACCACGTCCGGCCGGGGCAGA<br>GCGTTCCCAGCCAAGCCTTCTGTAACATGACATGACAGGTCAG<br>ACTCCCTCGGGCCCTGAGTTCACTTCTTCCTGGTATGTGACCAG<br>CTCCCAGTACCAGAGAAGGTTGCACAGTCCTCTGCTCCAAGGA<br>GCTTCACTGGCCAGGGGCTGCTTTCTGAAATCCTTGCCTGCCTC<br>TGCTCCAAGGCCCGTTCCTCAGAGACGCAGACCCCTCTGATGG<br>CTGACTTTGGTTTGAGGACCTCTCTGCATCCCTCCCCCATGGCC<br>TTGCTCCTAGGACACCTTCTTCCTCCTTTCCTGGGGTCAGACT<br>TGCCTAGGTGCGGTGGCTCTCCCAGCCTTCCCCACGCCCTCCCC<br>ATGGTGTATTACACACACCAAAGGGACTCCCCTATTGAAATCC<br>ATGCATATTGAATCGCATGTGGGTTCCGGCTGCTCCTGGGAGG<br>AGCCAGGCTAATAGAATGTTTGCCATAAAATATTAATGTACAG<br>AGAAGCGAAACAAAGGTCGTTGGTACTTGTTAACCTTACCAGC<br>AGAATAATGAAAGCGAACCCCCATATCTCATCTGCACGCGACA<br>TCCTTGTTGTGTCTGTACCCGAGGCTCCAGGTGCAGCCACTGTT<br>ACAGAGACTGTGTTTCTTCCCCATGTACCTCGGGGGCCGGGAG<br>GGGGTTCTGATCTGCAAAGTCGCCAGAGGTTAAGTCCTTTCTCT<br>CTTGTGGCTTTGCCACCCCTGGAGTGTCACCCTCAGCTGCGGT<br>GCCCAGGATTCCCCACTGTGGTATGTCCGTGCACCAGTCAATA<br>GGAAAGGGAGCAAGGAAAGGTACTGGGTCCCCCTAAGGACAT<br>ACGAGTTGCCAGAATCACTTCCGCTGACACCCAGTGGACCAAG<br>CCGCACCTTTATGCAGAAGTGGGGCTCCCAGCCAGGCGTGGTC<br>ACTCCTGAAATCCCAGCACTTCGGAAGGCCAAGGGGGGTGGA<br>TCACTTGAGCTCAGGAGTTCGAGACCAGCCTGGGTAACATGGC<br>AAAATCCCGTCTCTACAAAAATACAGAAAATTAGCTGGGTGCG<br>GTGGTGTGTGCCTACAGTCCCAGCTACTCAGGAGGCTGAAGTG<br>GGAGGATTGCTTGAGTCTGGGAGGTGGAGGTTGCAGTGAGCC<br>AGGATCTCACCACAGCACTCTGGCCCAGGCGACAGCTGTTTGG<br>CCTGTTTCAAGTGTCTACCTGCCTTGCTGGTCTTCCTGGGGACA<br>TTCTAAGCGTGTTTGATTTGTAACATTTTAGCAGACTGTGCAAG<br>TGCTCTGCACTCCCCTGCTGGAGCTTTTCTCGCCCTTCCTTCTG<br>GCCCTCTCCCCAGTCTAGACAGCAGGGCAACACCCACCCTGGC<br>CACCTTACCCCACCTGCCTGGGTGCTGCAGTGCCAGCCGCGGT<br>TGATGTCTCAGAGCTGCTTTGAGAGCCCCGTGAGTGCCGCCCC<br>TCCCGCCTCCCTGCTGAGCCCGCTTT/GCTTCTCCCGCAG | 1 |
| GAA-IVS1 (-76-38) | TCTCAGAGCTGCTTTGAGAGCCCCGTGAGTGCCGCCCC | 2 |
| GAA-IVS1 (-192-160) | GGAGCTTTTCTCGCCCTTCCTTCTGGCCCTCTC | 3 |
| GAA-exon2 | GCCTGTAGGAGCTGTCCAGGCCATCTCCAACCATGGGAGTGAG<br>GCACCCGCCCTGCTCCCACCGGCTCCTGGCCGTCTGCGCCCTC<br>GTGTCCTTGGCAACCGCTGCACTCCTGGGGCACATCCTACTCC | 4 |

TABLE 1-continued

Target sequences for GAA-targeted oligomers (from NG_009822)

| Name | Sequence (5'-3') | SEQ ID NO |
|---|---|---|
| | ATGATTTCCTGCTGGTTCCCCGAGAGCTGAGTGGCTCCTCCCC AGTCCTGGAGGAGACTCACCCAGCTCACCAGCAGGGAGCCAG CAGACCAGGGCCCCGGGATGCCCAGGCACACCCCGGCCGTCC CAGAGCAGTGCCCACACAGTGCGACGTCCCCCCCAACAGCCG CTTCGATTGCGCCCCTGACAAGGCCATCACCCAGGAACAGTGC GAGGCCCGCGGCTGTTGCTACATCCCTGCAAAGCAGGGGCTGC AGGGAGCCCAGATGGGGCAGCCCTGGTGCTTCTTCCCACCCAG CTACCCCAGCTACAAGCTGGAGAACCTGAGCTCCTCTGAAATG GGCTACACGGCCACCCTGACCCGTACCACCCCCACCTTCTTCC CCAAGGACATCCTGACCCTGCGGCTGGACGTGATGATGGAGA CTGAGAACCGCCTCCACTTCACG | |
| GAA-IVS2 | GTGGGCAGGGCAGGGGCGGGGCGGCGGCCAGGGCAGAGGG TGCGCGTGGACATCGACACCCACGCACCTCACAAGGGTGGGG TGCATGTTGCACCACTGTGTGCTGGGCCCTTGCTGGGAGCGGA GGTGTGAGCAGACAATGGCAGCGCCCCTCGGGGAGCAGTGGG GACACCACGGTGACAGGTACTCCAGAAGGCAGGGCTCGGGGC TCATTCATCTTTATGAAAAGGTGGGTCAGGTAGAGTAGGGCTG CCAGAGGTTGCGAATGAAAACAGGATGCCCAGTAAACCCGAA TTGCAGATACCCCAGGCATGACTTTGTTTTTTTGTGTAAGGATG CAAAATTTGGGATGTATTTATACTAGAAAAGCTGCTTGTTGTTT ATCTGAAATTCAGAGTTATCAGGTGTTCTGTATTTTACCTCCAT CCTGGGGGAGGCGTCCTCCTCCTGGCTCTGCAGATGAGGGAGC CGAGGCTCAGAGAGGCTGAATGTGCTGCCCATGGTCCCACATC CATGTGTGGCTGCACCAGGACCTGACCTGTCCTTGGCGTGCGG GTTGTTCTCTGGAGAGTAAGGTGGCTGTGGGGAACATCAATAA ACCCCCATCTCTTCTAG | 5 |

In certain embodiments, antisense targeting sequences are designed to hybridize to a region of one or more of the target sequences listed in Table 1. Selected antisense targeting sequences can be made shorter, e.g., about 12 bases, or longer, e.g., about 40 bases, and include a small number of mismatches, as long as the sequence is sufficiently complementary to effect splice modulation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligomers with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 14-15 bases is generally long enough to have a unique complementary sequence. In certain embodiments, a minimum length of complementary bases may be required to achieve the requisite binding Tm, as discussed herein.

In certain embodiments, oligomers as long as 40 bases may be suitable, where at least a minimum number of bases, e.g., 10-12 bases, are complementary to the target sequence. In some embodiments, facilitated or active uptake in cells is optimized at oligomer lengths of less than about 30 bases. For PMO oligomers, described further herein, an optimum balance of binding stability and uptake generally occurs at lengths of 18-25 bases. Included in the disclosure are antisense oligomers (e.g., PMOs, PMO-X, PNAs, LNAs, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to the target sequences of Table 1 (e.g., SEQ ID NOS:1-5, a sequence that spans SEQ ID NOS:1/4 or SEQ ID NOS:4/5).

The antisense oligomers typically comprises a base sequence which is sufficiently complementary to a sequence or region within or adjacent to intron 1, exon 2, or intron 2 of the pre-mRNA sequence of the human GAA gene. In certain embodiments, the oligomers are complementary to SEQ ID NO: 2 and SEQ ID NO: 3. Ideally, an antisense oligomer is able to effectively modulate aberrant splicing of the GAA pre-mRNA, and thereby increase expression of active GAA protein. This requirement is optionally met when the oligomer compound has the ability to be actively taken up by mammalian cells, and once taken up, form a stable duplex (or heteroduplex) with the target mRNA, optionally with a Tm greater than about 40° C. or 45° C.

In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo. Hence, certain oligomers may have substantial complementarity, meaning, about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the v target sequence, it is effective to stably and specifically bind to the target sequence, such that splicing of the target pre-RNA is modulated.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Hamres et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80C or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (45-50° C. or greater) at a length of 25 bases or less are generally preferred over those requiring greater than 25 bases for high Tm values.

Tables 2A, 2B, and 2C show exemplary targeting sequences (in a 5'-to-3' orientation) complementary to pre-mRNA sequences of the human GAA gene.

TABLE 2A

Table 2A - Exemplary Targeting Sequences (Deletion Sequences)

| Coordinates | Targeting Sequence (TS)* (5'-3') | TS SEQ ID NO |
|---|---|---|
| GAA-IVS1.SA.(-189, -165)-G | GGC CAG AAG GAA GGC GAG AAA AGC | 13 |
| GAA-IVS1.SA.(-190, -166)-G | GCC AGA AGG AAG GC GAG AAA AGC X | 14 |
| GAA-IVS1.SA.(-191, -167)-G | CCA GAA GGA AGG CGA GAA AAG CXC | 15 |
| GAA-IVS1.SA.(-192, -168)-G | CAG AAG GAA GGC GAG AAA AGC XCC | 16 |
| GAA-IVS1.SA.(-193, -169)-G | AGA AGG AAG GCG AGA AAA GCX CCA | 17 |
| GAA-IVS1.SA.(-194, -170)-G | GAA GGA AGG CGA GAA AAG CXC CAG | 18 |
| GAA-IVS1.SA.(-195, -171)-G | AAG GAA GGC GAG AAA AGC XCC AGC | 19 |
| GAA-IVS1.SA.(-196, -172)-G | AGG AAG GCG AGA AAA GCX CCA GCA | 20 |
| GAA-IVS1(-76-52)-2G | CGG CXC XCA AAG CAG CXC XGA GA | 21 |
| GAA-IVS1(-75-51)-2G | ACG GCX CXC AAA GCA GCX CXG AG | 22 |
| GAA-IVS1(-74-50)-2G | CAC GGC XCX CAA AGC AGC XCX GA | 23 |
| GAA-IVS1(-73-49)-2G | XCA CGG CXC XCA AAG CAG CXC XG | 24 |
| GAA-IVS1(-72-48)-2G | CXC ACG GCX CXC AAA GCA GCX CX | 25 |
| GAA-IVS1(-71-47)-2G | ACX CAC GGC XCX CAA AGC AGC XC | 26 |
| GAA-IVS1(-66-42)-2G | GCG GCA CXC ACG GCX CXC AAA GC | 27 |
| GAA-IVS1(-65-41)-2G | GGC GGC ACX CAC GGC XCX CAA AG | 28 |
| GAA-IVS1(-67-43)-2G | CGG CAC XCA CGG CXC XCA AAG CA | 29 |
| GAA-IVS1(-69-45)-2G | GCA CXC ACG GCX CXC AAA GCA GC | 30 |
| GAA-IVS1(-68-44)-2G | GGC ACX CAC GGC XCX CAA AGC AG | 31 |
| GAA-IVS1(-70-46)-2G | CAC XCA CGG CXC XCA AAG CAG CX | 32 |
| GAA-IVS1.SA.(-189, -166)-G | GCC AGA AGG AAG GCG AGA AAA GC | 33 |
| GAA-IVS1.SA.(-189, -167)-G | CCA GAA GGA AGG CGA GAA AAG C | 34 |
| GAA-IVS1.SA.(-189, -168)-G | CAG AAG GAA GGC GAG AAA AGC | 35 |
| GAA-IVS1.SA.(-188, -165)-G | GGC CAG AAG GAA GGC GAG AAA AG | 36 |
| GAA-IVS1.SA.(-187, -165)-G | GGC CAG AAG GAA GGC GAG AAA A | 37 |
| GAA-IVS1.SA.(-186, -165)-G | GGC CAG AAG GAA GGC GAG AAA | 38 |
| GAA-IVS1(-67-43)-2G | CGG CAC XCA CGGC XCX CAA AGC A | 39 |

TABLE 2A-continued

Table 2A - Exemplary Targeting Sequences (Deletion Sequences)

| Coordinates | Targeting Sequence (TS)* (5'-3') | TS SEQ ID NO |
|---|---|---|
| GAA-IVS1(-66-42)-2G | GCG GCA CXC ACGG CXC XCA AAG C | 40 |
| GAA-IVS1(-65-41)-2G | GGC GGC ACX CAC G GCX CXC AAA G | 41 |
| GAA-IVS1.SA.(-180, -156)-G | XGG GGA GAG GGC CAG AAG GAA GGC | 42 |
| GAA-IVS1.SA.(-180, -156)-2G | XGG GGA GAG GGC CAG AAG GAA GC | 43 |
| GAA-IVS1.SA.(-180, -156)-3G | XGG GGA GAG GGC CAG AAG GAA C | 44 |
| GAA-IVS1.SA.(-189, -165)-2G | GGC CAG AAG GAA GCG AGA AAA GC | 45 |
| GAA-IVS1.SA.(-189, -165)-3G | GGC CAG AAG GAA CGA GAA AAG C | 46 |
| GAA-IVS1.SA.(-196, -172)-2G | AGG AAG CGA GAA AAG CXC CAG CA | 47 |
| GAA-IVS1.SA.(-196, -172)-3G | AGG AAC GAG AAA AGC XCC AGC A | 48 |
| GAA-IVS1(-76-52)-G | CGG GCX CXC AAA GCA GCX CXG AGA | 49 |
| GAA-IVS1(-76-52)-3G | CGC XCX CAA AGC AGC XCX GAG A | 50 |
| GAA-IVS1(-76-52)-4G | CCX CXC AAA GCA GCX CXG AGA | 51 |
| GAA-IVS1(-65-41)-G | GGC GGC ACX CAC GGG CXC XCA AAG | 52 |
| GAA-IVS1(-65-41)-3G | GGC GGC ACX CAC GCX CXC AAA G | 53 |
| GAA-IVS1(-65-41)-4G | GGC GGC ACX CAC CXC XCA AAG | 54 |
| GAA-IVS1(-57-33)-G | GCG GGA GGG GCG GCA CXC ACG GGC | 55 |
| GAA-IVS1(-57-33)-2G | GCG GGA GGG GCG GCA CXC ACG GC | 56 |
| GAA-IVS1(-57-33)-3G | GCG GGA GGG GCG GCA CXC ACG C | 57 |
| GAA-IVS1(-57-33)-4G | GCG GGA GGG GCG GCA CXC ACC | 58 |

For any of the sequences in Table 2A, each X is independently selected from thymine (T) or uracil (U).
"-G", "-2G", "-3G", or "-4G" designate targeting sequences which are complementary to a target region within intron 1(SEQ ID NO: 137) of a pre-mRNA of the human alpha glucosidase (GAA) gene, wherein the target region comprises one, two, three, or four additional nucleobases compared to the targeting sequence, wherein those additional nucleobases are cytosines, and wherein the one, two, three, or four additional nucleobases have no corresponding complementary nucleobases in the targeting sequence (hence, -G (guanine), -2G, -3G, or -4G). The additional nucleobases are internal to the target region.

TABLE 2B

Table 2B - Exemplary Targeting Sequences

| Coordinates | Targeting Sequence (TS)* (5'-3') | TS SEQ ID NO |
|---|---|---|
| GAA-IVS1.SA.(-189, -165) | GGC CAG AAG GAA GGG CGA GAA AAG C | 59 |
| GAA-IVS1.SA.(-191, -167) | CCA GAA GGA AGG GCG AGA AAA GCX C | 60 |
| GAA-IVS1.SA.(-195, -171) | AAG GAA GGG CGA GAA AAG CXC CAG C | 61 |
| GAA-IVS1(-57-33) | GCG GGA GGG GCG GCA CXC ACG GGG C | 62 |
| GAA-IVS1.SA.(-180, -156) | XGG GGA GAG GGC CAG AAG GAA GGG C | 63 |
| GAA-IVS1.SA.(-193, -169) | AGA AGG AAG GGC GAG AAA AGC XCC A | 64 |
| GAA-IVS1(-80-56) | GCX CXC AAA GCA GCX CXG AGA CAX C | 65 |
| GAA-IVS1(-81-57) | CXC XCA AAG CAG CXC XGA GAC AXC A | 66 |

TABLE 2B-continued

Table 2B - Exemplary Targeting Sequences

| Coordinates | Targeting Sequence (TS)* (5'-3') | TS SEQ ID NO |
|---|---|---|
| GAA-IVS1(-82-58) | XCX CAA AGC AGC XCX GAG ACA XCA A | 67 |
| GAA-IVS1(-83-59) | CXC AAA GCA GCX CXG AGA CAX CAA C | 68 |
| GAA-IVS1(-84-60) | XCA AAG CAG CXC XGA GAC AXC AAC C | 69 |
| GAA-IVS1(-85-61) | CAA AGC AGC XCX GAG ACA XCA ACC G | 70 |
| GAA-IVS1(-86-62) | AAA GCA GCX CXG AGA CAX CAA CCG C | 71 |
| GAA-IVS1(-87-63) | AAG CAG CXC XGA GAC AXC AAC CGC G | 72 |
| GAA-IVS1(-88-64) | AGC AGC XCX GAG ACA XCA ACC GCG G | 73 |
| GAA-IVS1(-89-65) | GCA GCX CXG AGA CAX CAA CCG CGG C | 74 |
| GAA-IVS1(-90-66) | CAG CXC XGA GAC AXC AAC CGC GGC X | 75 |

For any of the sequences in Table 2B, each X is independently selected from thymine (T) or uracil (U).

TABLE 2C

Table 2C - Exemplary Targeting Sequences

| Coordinates | Targeting Sequence (TS)* (5'-3') | TS SEQ ID NO |
|---|---|---|
| GAA-IVS1.SA.(-190, -166) | GCC AGA AGG AAG GGC GAG AAA AGC X | 76 |
| GAA-IVS1.SA.(-192, -168) | CAG AAG GAA GGG CGA GAA AAG CXC C | 77 |
| GAA-IVS1.SA.(-194, -170) | GAA GGA AGG GCG AGA AAA GCX CCA G | 78 |
| GAA-IVS1.SA.(-196, -172) | AGG AAG GGC GAG AAA AGC XCC AGC A | 79 |
| GAA-IVS1(-71-47) | ACX CAC GGG GCX CXC AAA GCA GCX C | 80 |
| GAA-IVS1(-79-55) | GGCXCXCAAAGCAGCXCXGAGACAX | 81 |
| GAA-IVS1(-74-55) | GGC XCX CAA AGC AGC XCX GA | 82 |
| GAA-IVS1(-179-160) | GAG AGG GCC AGA AGG AAG GG | 83 |
| GAA-IVS1.2178.20 | XXX GCC AXG XXA CCC AGG CX | 84 |
| GAA-IVS2.27.20 | GCG CAC CCX CXG CCC XGG CC | 85 |
| GAAEx2A(+202+226) | GGC CCX GGX CXG CXG GCX CCC XGC X | 86 |

For any of the sequences in Table 2C, each X is independently selected from thymine (T) or uracil (U).

Certain antisense oligomers thus comprise, consist, or consist essentially of a sequence in Tables 2A-2C or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of the SEQ ID NOS outlined in Tables 2A-2C. In certain embodiments, the targeting sequence is selected from the group consisting of SEQ ID NOs: 13, 27-29, 34-36, 59, and 82. For non-contiguous portions, intervening nucleotides can be deleted. Additional examples of variants include oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of the SEQ ID NOS outlined in Tables 2A-C. In some embodiments, any of the antisense oligomers or compounds comprising, consisting of, or consisting essentially of such variant sequences suppress an ISS and/or ESS element in the GAA pre-mRNA. In some embodiments, the antisense oligomer or compound with a targeting sequence that comprises, consists of, or consists essentially of such a variant sequence suppresses an ISS and/or ESS element in the GAA pre-mRNA. In some embodiments, the antisense oligomer or compound with a targeting sequence that comprises, consists of, or consists essentially of such a variant sequence increases, enhances, or promotes exon 2 retention in the mature GAA mRNA, optionally, by at least about 10%, 15%, 20%, 25%, 30%, 35%, 40%, 45%, 50%, 55%, 60%, or 65% or more relative to a control, according to at least one of the examples or methods described herein. In some embodiments, the antisense oligomer or compound with a targeting sequence that comprises, consists of, or consists essentially of such a variant sequence increases, enhances, or promotes GAA protein expression in a cell, optionally, by at least about 10%, 15%, 20%, 25%, 30%, 35%, 40%, 45%, 50%, 55%, 60%, or 65% or more relative to a control, according to at least one of the examples or methods described herein. In some embodiments, the antisense oligomer or compound comprising, consisting of, or consisting essentially of such a variant sequence increases, enhances, or promotes GAA enzymatic activity in a cell, optionally, by at least about 10%, 15%, 20%, 25%, 30%, 35%, 40%, 45%, 50%, 55%, 60%, or 65% or more relative to a control, according to at least one of the examples or methods described herein. As exemplified herein, a cell (e.g., a fibroblast cell) can be obtained from a patient having a IVS1-13T>G mutation.

In some embodiments, certain antisense oligomers comprise, consist, or consist essentially of a sequence as detailed in Table 2B (or Table 2C) or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of SEQ ID NOS outlined in Table 2B or 2C. For non-contiguous portions, intervening nucleotides can be deleted. Additional examples of variants include oligomers having about or at least about 70% sequence identity or homology, e.g., 70%, 71%, 72%, 73%, 74%, 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOS outlined in Table 2B or 2C. In some embodiments, the antisense oligomer or compound with a targeting sequence that comprises, consists of, or consists essentially of such a variant sequence suppresses an ISS and/or ESS element in the GAA pre-mRNA. In some embodiments, the antisense oligomer or compound with a targeting sequence that comprises, consists of, or consists essentially of such a variant sequence increases, enhances, or promotes exon 2 retention in the mature GAA mRNA, optionally, by at least about 10%, 15%, 20%, 25%, 30%, 35%, 40%, 45%, 50%, 55%, 60%, or 65% or more relative to a control, according to at least one of the examples or methods described herein. In some embodiments, the antisense oligomer or compound with a targeting sequence that comprises, consists of, or consists essentially of such a variant sequence increases, enhances, or promotes GAA protein expression in a cell, optionally, by at least about 10%, 15%, 20%, 25%, 30%, 35%, 40%, 45%, 50%, 55%, 60%, or 65% or more relative to a control, according to at least one of the examples or methods described herein. In some embodiments, the antisense oligomer or compound comprising, consisting of, or consisting essentially of such a variant sequence increases, enhances, or promotes GAA enzymatic activity in a cell, optionally, by at least about 10%, 15%, 20%, 25%, 30%, 35%, 40%, 45%, 50%, 55%, 60%, or 65% or more relative to a control, according to at least one of the examples or methods described herein. As exemplified herein, a cell (e.g., a fibroblast cell) can be obtained from a patient having a IVS1-13T>G mutation.

In various aspects an antisense oligomer or compound is provided, comprising a targeting sequence that is complementary (e.g., at least 80, 81, 82, 83, 84, 85, 86, 87, 88, 89, 90, 91, 92, 93, 94, 95, 96, 97, 98, 99, or 100% complementary) to a target region of the human GAA pre-mRNA, optionally where the targeting sequences is as set forth in any one of Tables 2A-2C. In another aspect, an antisense oligomer or compound is provided, comprising a variant targeting sequence, such as any of those described herein, wherein the variant targeting sequence binds to a target region of the human pre-mRNA that is complementary (e.g., 80%-100% complementary) to one or more of the targeting sequences set forth in any one of Tables 2A-2C. In some embodiments, the antisense oligomer or compound binds to a target sequence comprising at least 10 (e.g., at least 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40) consecutive bases of the human GAA pre-mRNA (e.g., any of SEQ ID NOs:1, 2, or 3 or a sequence that spans a GAA pre-mRNA splice junction defined by SEQ ID NO:1/4 or SEQ ID NO:4/5). In some embodiments, the target sequence is complementary (e.g., at least 80, 81, 82, 83, 84, 85, 86, 87, 88, 89, 90, 91, 92, 93, 94, 95, 96, 97, 98, 99, or 100% complementary) to one or more of the targeting sequences set forth in any one of Tables 2A-2C. In some embodiments, the target sequence is complementary (e.g., at least 80, 81, 82, 83, 84, 85, 86, 87, 88, 89, 90, 91, 92, 93, 94, 95, 96, 97, 98, 99, or 100% complementary) to at least 10 (e.g., at least 11, 12, 13, 14, 15, 16, 17, 18, 19, 20, 21, 22, 23, 24, 25, 26, 27, or 28) consecutive bases of one or more of the targeting sequences set forth in any one of Tables 2A-2C. In some embodiments, the target sequence is defined by an annealing site (e.g., GAA-IVS1.SA.(−189,−165)) as set forth in one or more of the Tables herein.

The activity of antisense oligomers and variants thereof can be assayed according to routine techniques in the art. For example, splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed polynucleotide) from a cell, tissue or organism, and by hybridizing the mRNA/cDNA with a reference polynucleotide that is a complement of the assayed nucleic acid, or a fragment thereof cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

III. Antisense Oligomer Chemistries

A. General Characteristics

Certain antisense oligomers of the instant disclosure specifically hybridize to an intronic splice silencer element or an exonic splice silencer element. Some antisense oligomers comprise a targeting sequence set forth in Tables 2A-2C, a fragment of at least 10 contiguous nucleotides of a targeting sequence in Tables 2A-2C, or variant having at least 80% sequence identity to a targeting sequence in Tables 2A-2C. Specific antisense oligomers consist or consist essentially of a targeting sequence set forth in Tables 2A-2C. In some embodiments, the oligomer is nuclease-resistant.

In certain embodiments, the antisense oligomer comprises a non-natural chemical backbone selected from a phosphoramidate or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing, and a targeting sequence complementary to a region within intron 1 (SEQ ID. NO: 1) [including portions identified by SEQ ID NO: 2 and SEQ ID NO: 3], intron 2 (SEQ ID. NO: 5), or exon 2 (SEQ ID. NO: 4) of a pre-mRNA of the human acid alpha-glucosidase (GAA) gene. For example, in some embodiments, the targeting sequence is selected from the sequences outlined in Tables 2A-2C, wherein X is selected from uracil (U) or thymine (T). Further, and for example, the targeting sequence is selected from the sequences outlined in Tables 2A-2C. In some embodiments, an oligonucleotide described herein has a targeting sequence set forth in Tables 4A-4C.

Antisense oligomers of the disclosure generally comprise a plurality of nucleotide subunits each bearing a nucleobase which taken together form or comprise a targeting sequence, for example, as discussed above. Accordingly, in some embodiments, the antisense oligomers range in length from about 10 to about 40 subunits, more preferably about 10 to 30 subunits, and typically 15-25 subunits. For example, antisense compounds of the disclosure may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subunits in length, or range from 10 subunits to 40 subunits, 10 subunits to 30 subunits, 14 subunits to 25 subunits, 15 subunits to 30 subunits, 17 subunits to 30 subunits, 17 subunits to 27 subunits, 10 subunits to 27 subunits, 10 subunits to 25 subunits, and 10 subunits to 20 subunits. In certain embodiments, the antisense oligomer is about 10 to about 40 or about 5 to about 30 nucleotides in length. In some embodiments, the antisense oligomer is about 14 to about 25 or about 17 to about 27 nucleotides in length.

In various embodiments, an antisense oligomer may comprise a completely modified backbone, for example, 100% of the backbone is modified (for example, a 25 mer antisense oligomer comprises its entire backbone modified with any combination of the backbone modifications as described herein). In various embodiments, an antisense oligomer may comprise about 100% to 2.5% of its backbone modified. In various embodiments, an antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its backbone modified, and iterations in between. In other embodiments, an antisense oligomer may comprise any combination of backbone modifications as described herein.

In various embodiments, an antisense oligomer may comprise, consist of, or consist essentially of phosphoramidate morpholino oligomers and phosphorodiamidate morpholino oligomers (PMO), phosphorothioate modified oligomers, 2' O-methyl modified oligomers, peptide nucleic acid (PNA), locked nucleic acid (LNA), phosphorothioate oligomers, 2' O-MOE modified oligomers, 2'-fluoro-modified oligomer, 2'O,4'C-ethylene-bridged nucleic acids (ENAs), tricyclo-DNAs, tricyclo-DNA phosphorothioate nucleotides, 2'-O-[2-(N-methylcarbamoyl)ethyl] modified oligomers, morpholino oligomers, peptide-conjugated phosphoramidate morpholino oligomers (PPMO), phosphorodiamidate morpholino oligomers having a phosphorous atom with (i) a covalent bonds to the nitrogen atom of a morpholino ring, and (ii) a second covalent bond to a (1,4-piperazin)-1-yl substituent or to a substituted (1,4-piperazin)-1-yl (PMOplus), and phosphorodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl (PMO-X) chemistries, including combinations of any of the foregoing.

In some embodiments, the backbone of the antisense oligomer is substantially uncharged, and is optionally recognized as a substrate for active or facilitated transport across the cell membrane. In some embodiments, all the internucloeside linkages are uncharged. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm. Exemplary antisense oligomer targeting sequences are listed in Tables 2A, 2B, and 2C.

In certain embodiments, the antisense oligomer has at least one internucleoside linkage that is positively charged or cationic at physiological pH. In some embodiments, the antisense oligomer has at least one internucleoside linkage that exhibits a pKa between about 5.5 and about 12. In further embodiments, the antisense oligomer contains about, at least about, or no more than about 1, 2, 3, 4, 5, 6, 7, 8, 9, or 10 internucleoside linkages that exhibits a pKa between about 4.5 and about 12. In some embodiments, the antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. Optionally, the antisense oligomer has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. While not being bound by any one theory, it is believed that the presence of a cationic linkage or linkages (e.g., APN group or APN derivative) in the oligomer facilitates binding to the negatively charged phosphates in the target nucleotide. Thus, the formation of a heteroduplex between mutant RNA and the cationic linkage-containing oligomer may be held together by both an ionic attractive force and Watson-Crick base pairing.

In some embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In specific embodiments, an oligomer of about 19-20 subunits may have 2-10, e.g., 4-8, cationic linkages, and the remainder uncharged linkages. In other specific embodiments, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 15 to 20 to 30 or more (including all integers in between), and can be interspersed throughout the oligomer.

In some embodiments, an antisense oligomer may have about or up to about 1 cationic linkage per every 2-5 or 2, 3, 4, or 5 uncharged linkages, such as about 4-5 or 4 or 5 per every 10 uncharged linkages.

Certain embodiments include antisense oligomers that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the backbone linkages are cationic. In certain embodiments, enhancement may be seen with a small number e.g., 10-20% cationic linkages, or where the number of cationic linkages are in the range 50-80%, such as about 60%.

In some embodiments, the cationic linkages are interspersed along the backbone. Such oligomers optionally contain at least two consecutive uncharged linkages; that is, the oligomer optionally does not have a strictly alternating pattern along its entire length. In specific instances, each one or two cationic linkage(s) is/are separated along the backbone by at least 1, 2, 3, 4, or 5 uncharged linkages.

Also included are oligomers having blocks of cationic linkages and blocks of uncharged linkages. For example, a central block of uncharged linkages may be flanked by blocks of cationic linkages, or vice versa. In some embodiments, the oligomer has approximately equal-length 5', 3' and center regions, and the percentage of cationic linkages in the center region is greater than about 50%, 60%, 70%, or 80% of the total number of cationic linkages.

In certain antisense oligomers, the bulk of the cationic linkages (e.g., 70, 75%, 80%, 90% of the cationic linkages) are distributed close to the "center-region" backbone linkages, e.g., the 6, 7, 8, 9, 10, 11, 12, 13, 14, or 15 centermost linkages. For example, a 16, 17, 18, 19, 20, 21, 22, 23, or 24-mer oligomer with may have at least 50%, 60%, 70%, or 80% of the total cationic linkages localized to the 8, 9, 10, 11, or 12 centermost linkages.

B. Backbone Chemistry Features

The antisense oligomers can employ a variety of antisense chemistries. Examples of oligomer chemistries include, without limitation, phosphoramidate morpholino oligomers and phosphorodiamidate morpholino oligomers (PMO), phosphorothioate modified oligomers, 2' O-methyl modified oligomers, peptide nucleic acid (PNA), locked nucleic acid (LNA), phosphorothioate oligomers, 2' O-MOE modified oligomers, 2'-fluoro-modified oligomer, 2'O,4'C-ethylene-bridged nucleic acids (ENAs), tricyclo-DNAs, tricyclo-DNA phosphorothioate nucleotides, 2'-O-[2-(N-methylcarbamoyl)ethyl] modified oligomers, morpholino oligomers, peptide-conjugated phosphoramidate morpholino oligomers (PPMO), phosphorodiamidate morpholino oligomers having a phosphorous atom with (i) a covalent bonds to the nitrogen atom of a morpholino ring, and (ii) a second covalent bond to a (1,4-piperazin)-1-yl substituent or to a substituted (1,4-piperazin)-1-yl (PMOplus), and phosphorodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl (PMO-X) chemistries, including combinations of any of the foregoing. In general, PNA and LNA chemistries can utilize shorter targeting sequences because of their relatively high target binding strength relative to PMO and 2'O-Me modified oligomers. Phosphorothioate and 2'O-Me-modified chemistries can be combined to generate a 2'O-Me-phosphorothioate backbone. See, e.g., PCT Publication Nos. WO/2013/112053 and WO/2009/008725, which are hereby incorporated by reference in their entireties.

In some instances, antisense oligomers such as PMOs can be conjugated to cell penetrating peptides (CPPs) to facilitate intracellular delivery. Peptide-conjugated PMOs are called PPMOs and certain embodiments include those described in PCT Publication No. WO/2012/150960, incorporated herein by reference in its entirety. In some embodiments, an arginine-rich peptide sequence conjugated or linked to, for example, the 3' terminal end of an antisense oligomer as described herein may be used. In certain embodiments, an arginine-rich peptide sequence conjugated or linked to, for example, the 5' terminal end of an antisense oligomer as described herein may be used.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA is depicted below:

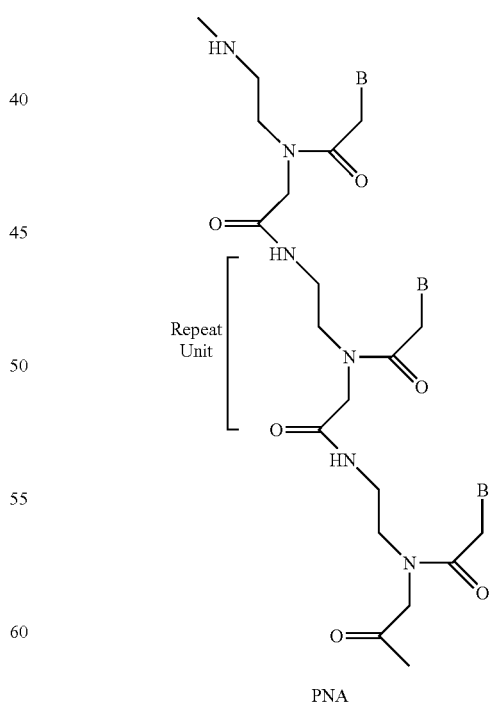

PNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

2. Locked Nucleic Acids (LNAs)

Antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a $C_{3'}$-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230, which are hereby incorporated by reference in their entirety. A non-limiting example of an LNA is depicted below:

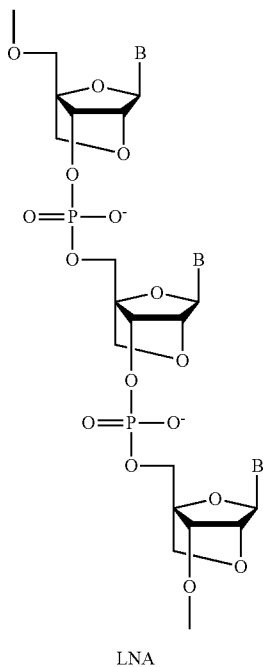

LNA

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. Further embodiments include an LNA containing compound where each LNA subunit is separated by a DNA subunit. Certain compounds are composed of alternating LNA and DNA subunits where the intersubunit linker is phosphorothioate.

2'O,4'C-ethylene-bridged nucleic acids (ENAs) are another member of the class of BNAs. A non-limiting example is depicted below:

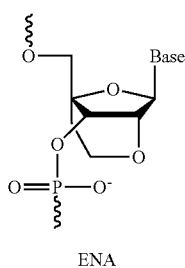

ENA

ENA oligomers and their preparation are described in Obika et al., *Tetrahedron Ltt* 38 (50): 8735, which is hereby incorporated by reference in its entirety. Compounds of the disclosure may incorporate one or more ENA subunits.

3. Phosphorothioates

"Phosphorothioates" (or S-oligos) are a variant of normal DNA in which one of the nonbridging oxygens is replaced by a sulfur. A non-limiting example of a phosphorothioate is depicted below:

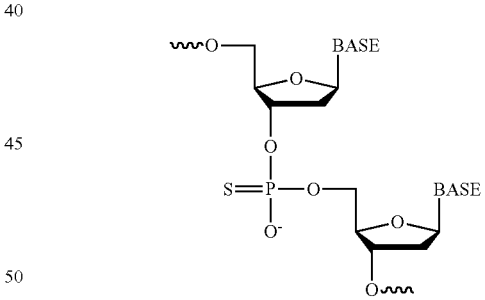

The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which are hereby incorporated by reference in their entirety). The latter methods avoid the problem of elemental sulfur's insolubility in most organic solvents and the toxicity of carbon disulfide. The TETD and BDTD methods also yield higher purity phosphorothioates.

4. Triclyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in International Patent Application Publication No. WO 2010/115993, which are hereby incorporated by reference in their entirety. Compounds of the disclosure may incorporate one or more tricycle-DNA nucleotides; in some cases, the compounds may be entirely composed of tricycle-DNA nucleotides.

Tricyclo-phosphorothioate nucleotides are tricyclo-DNA nucleotides with phosphorothioate intersubunit linkages. Tricyclo-phosphorothioate nucleotides and their synthesis are described in International Patent Application Publication No. WO 2013/053928, which are hereby incorporated by reference in their entirety. Compounds of the disclosure may incorporate one or more tricycle-DNA nucleotides; in some cases, the compounds may be entirely composed of tricycle-DNA nucleotides. A non-limiting example of a tricycle-DNA/tricycle-phophothioate nucleotide is depicted below:

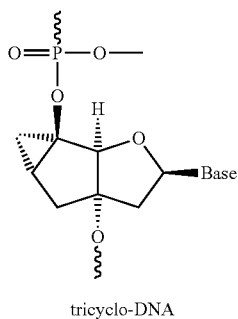

tricyclo-DNA

5. 2' O-Methyl, 2' O-MOE, and 2'-F Oligomers

"2'O-Me oligomer" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligomers (PTOs) for further stabilization. 2'O-Me oligomers (phosphodiester or phosphothioate) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer is depicted below:

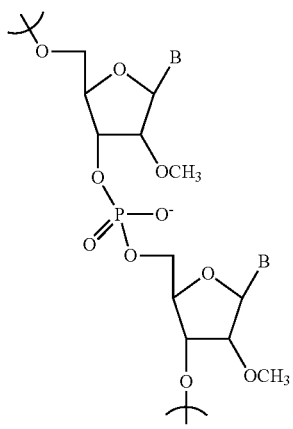

2' O-Me oligomers may also comprise a phosphorothioate linkage (2' O-Me phosphorothioate oligomers). 2' O-Methoxyethyl Oligomers (2'-O MOE), like 2' O-Me oligomers, carry a methoxyethyl group at the 2'-OH residue of the ribose molecule and are discussed in Martin et al., *Helv Chim. Acta*, 78, 486-504, 1995, which are hereby incorporated by reference in their entirety. A non-limiting example of a 2' O-MOE nucleotide is depicted below:

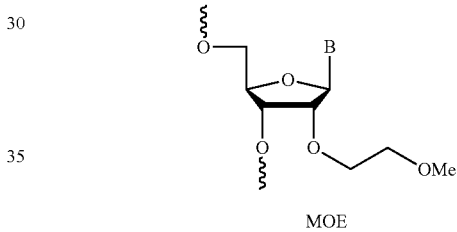

MOE

In contrast to the preceding alkylated 2'OH ribose derivatives, 2'-fluoro oligomers have a fluoro radical in at the 2' position in place of the 2'OH. A non-limiting example of a 2'-F oligomer is depicted below:

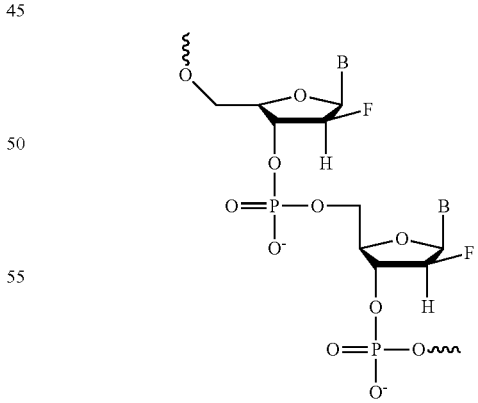

2'-fluoro oligomers are further described in WO 2004/043977, which is hereby incorporated by reference in its entirety. Compounds of the disclosure may incorporate one or more 2'O-Methyl, 2' O-MOE, and 2'-F subunits and may utilize any of the intersubunit linkages described here. In some instances, a compound of the disclosure could be composed of entirely 2'O-Methyl, 2' O-MOE, or 2'-F subunits. One embodiment of a compound of the disclosure is composed entirely of 2'O-methyl subunits.

6. 2'-O-[2-(N-methylcarbamoyl)ethyl] Oligonucleotides (MCEs)

MCEs are another example of 2'O modified ribonucleosides useful in the compounds of the disclosure. Here, the 2'OH is derivatized to a 2-(N-methylcarbamoyl)ethyl moiety to increase nuclease resistance. A non-limiting example of an MCE oligomer is depicted below:

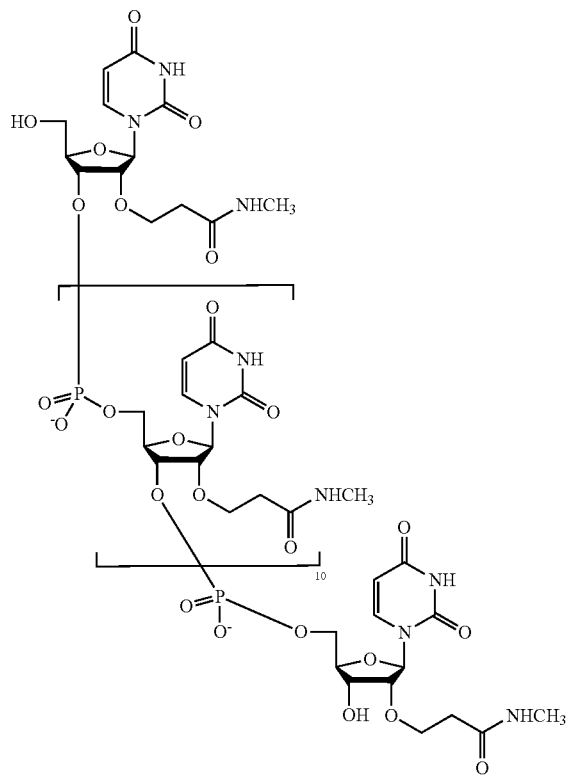

MCEs and their synthesis are described in Yamada et al., *J. Org. Chem.*, 76(9):3042-53, which is hereby incorporated by reference in its entirety. Compounds of the disclosure may incorporate one or more MCE subunits.

7. Stereo Specific Oligomers

Stereo specific oligomers are those which the stereo chemistry of each phosphorous-containing linkage is fix by the method of synthesis such that a substantially pure single oligomer is produced. A non-limiting example of a stereo specific oligomer is depicted below:

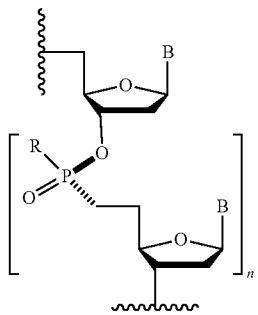

In the above example, each phosphorous of the oligomer has the same stereo chemistry. Additional examples include the oligomers described above. For example, LNAs, ENAs, Tricyclo-DNAs, MCEs, 2' O-Methyl, 2' O-MOE, 2'-F, and morpholino-based oligomers can be prepared with stereo-specific phosphorous-containing internucleoside linkages such as, for example, phosphorothioate, phosphodiester, phosphoramidate, phosphorodiamidate, or other phorous-containing internucleoside linkages. Stereo specific oligomers, methods of preparation, chirol controlled synthesis, chiral design, and chiral auxiliaries for use in preparation of such oligomers are detailed, for example, in WO2015107425, WO2015108048, WO2015108046, WO2015108047, WO2012039448, WO2010064146, WO2011034072, WO2014010250, WO2014012081, WO20130127858, and WO2011005761, each of which is hereby incorporated by reference in its entirety.

8. Morpholino-Based Oligomers

Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety. Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of morpholino-based oligomers described herein, one nitrogen is always pendant to the backbone chain. The second nitrogen, in a phosphorodiamidate linkage, is typically the ring nitrogen in a morpholine ring structure.

"PMO-X" refers to phosphorodiamidate morpholino-based oligomers having a phosphorus atom with (i) a covalent bond to the nitrogen atom of a morpholine ring and (ii) a second covalent bond to the ring nitrogen of a 4-aminopiperdin-1-yl (i.e., APN) or a derivative of 4-aminopiperdin-1-yl. Exemplary PMO-X oligomers are disclosed in PCT Application No. PCT/US2011/38459 and PCT Publication No. WO 2013/074834, which are hereby incorporated by reference in their entirety. PMO-X includes "PMO-apn" or "APN," which refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, an antisense oligomer comprising a targeting sequence as set forth in Tables 2A, 2B, or 2C comprises at least one APN-containing linkage or APN derivative-containing linkage. Various embodiments include morpholino-based oligomers that have about 10%, 15%, 20%, 25%, 30%, 35%, 40%, 45%, 50%, 55%, 60%, 6%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In some embodiments, the antisense oligomer is a compound of formula (I):

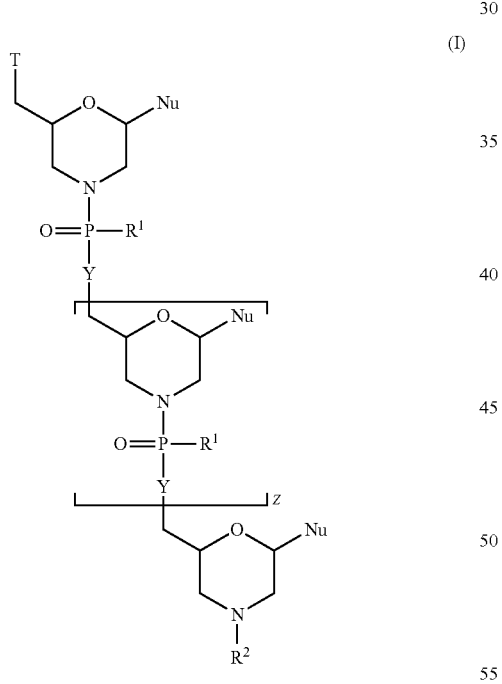

(I)

or a pharmaceutically acceptable salt thereof, wherein:

each Nu is a nucleobase which taken together form a targeting sequence;

Z is an integer from 8 to 38;

each Y is independently selected from O and —NR$^4$, wherein each R$^4$ is independently selected from H, $C_1$-$C_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and $C_1$-$C_6$ alkyl and n is an integer from 1 to 5;

T is selected from OH and a moiety of the formula:

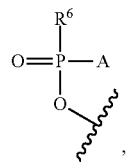

wherein:

A is selected from —OH, —N(R$^7$)$_2$, and R$^1$ wherein each R$^7$ is independently selected from H and $C_1$-$C_6$ alkyl, and R$^6$ is selected from OH, —N(R$^9$)CH$_2$C(O)NH$_2$, and a moiety of the formula:

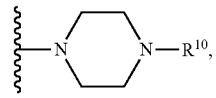

wherein:

R$^9$ is selected from H and $C_1$-$C_6$ alkyl; and

R$^{10}$ is selected from G, —C(O)—R$^{11}$OH, acyl, trityl, 4-methoxytrityl,

—C(=NH)NH$_2$, —C(O)(CH$_2$)$_m$NR$^{12}$C(=NH)NH$_2$, and

—C(O)(CH$_2$)$_2$NHC(O)(CH$_2$)$_5$NR$^{12}$C(=NH)NH$_2$, wherein:

m is an integer from 1 to 5,

R$^{11}$ is of the formula —(O-alkyl)$_y$- wherein y is an integer from 3 to 10 and each of the y alkyl groups is independently selected from $C_2$-$C_6$ alkyl; and R$^{12}$ is selected from H and $C_1$-$C_6$ alkyl;

each instance of R$^1$ is independently selected from:

—N(R$^{13}$)$_2$, wherein each R$^{13}$ is independently selected from H and $C_1$-$C_6$ alkyl;

a moiety of formula (II):

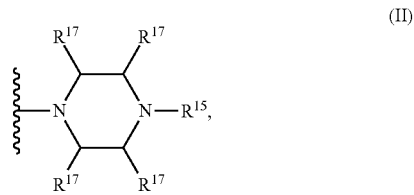

(II)

wherein:

R$^{15}$ is selected from H, G, $C_1$-$C_6$ alkyl, —C(=NH)NH$_2$,

—C(O)(CH$_2$)$_q$NR$^{18}$C(=NH)NH$_2$, and

—C(O)(CH$_2$)$_2$NHC(O)(CH$_2$)$_5$NR$^{18}$C(=NH)NH$_2$, wherein:

R$^{18}$ is selected from H and $C_1$-$C_6$ alkyl; and q is an integer from 1 to 5, and each R$^{17}$ is independently selected from H and methyl; and a moiety of formula(III):

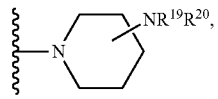

wherein:
R$^{19}$ is selected from H, C$_1$-C$_6$ alkyl, —C(=NH)NH$_2$, —C(O)(CH$_2$)$_r$NR$^{22}$C(=NH)NH$_2$,
—C(O)CH(NH$_2$)(CH$_2$)$_3$NHC(=NH)NH$_2$,
—C(O)(CH$_2$)$_2$NHC(O)(CH$_2$)$_5$NR$^{22}$C(=NH)NH$_2$,
—C(O)CH(NH$_2$)(CH$_2$)$_4$NH$_2$ and G, wherein:
R$^{22}$ is selected from H and C$_1$-C$_6$ alkyl; and
r is an integer from 1 to 5, and
R$^{20}$ is selected from H and C$_1$-C$_6$ alkyl; or
R$^{19}$ and R$^{20}$ together with the nitrogen atom to which they are attached form a heterocyclic or heteroaryl ring having from 5 to 7 ring atoms and optionally containing an additional heteroatom selected from oxygen, nitrogen, and sulfur; and R$^2$ is selected from H, G, acyl, trityl, 4-methoxytrityl, benzoyl, stearoyl, C$_1$-C$_6$ alkyl, —C(=NH)NH$_2$, —C(O)—R$^{23}$, —C(O)(CH$_2$)$_s$NR$^{24}$C(=NH)NH$_2$,
—C(O)(CH$_2$)$_2$NHC(O)(CH$_2$)$_5$NR$^{24}$C(=NH)NH$_2$,
—C(O)CH(NH$_2$)(CH$_2$)$_3$NHC(=NH)NH$_2$,
and a moiety of the formula:

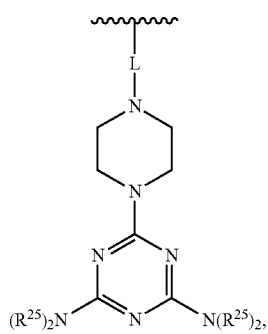

wherein,
R$^{23}$ is of the formula —(O-alkyl)$_v$-OH wherein v is an integer from 3 to 10 and each of the v alkyl groups is independently selected from C$_2$-C$_6$ alkyl; and
R$^{24}$ is selected from H and C$_1$-C$_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each R$^{25}$ is of the formula —(CH$_2$)$_2$OC(O)N(R$^{26}$)$_2$ wherein each R$^{26}$ is of the formula —(CH$_2$)$_6$NHC(=NH)NH$_2$,
wherein G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

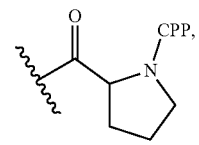

wherein the CPP is attached to the linker moiety by an amide bond at the CPP carboxy terminus, and
wherein G may be present in one occurrence or is absent.
In some embodiments, R$^2$ is a moiety of the formula:

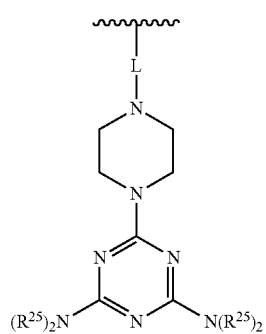

where L is selected from —C(O)(CH$_2$)$_6$C(O)— or —C(O)(CH$_2$)$_2$S$_2$(CH$_2$)$_2$C(O)—, and and each R$^{25}$ is of the formula —(CH$_2$)$_2$OC(O)N(R$^{26}$)$_2$ wherein each R$^{26}$ is of the formula —(CH$_2$)$_6$NHC(=NH)NH$_2$. Such moieties are further described in U.S. Pat. No. 7,935,816 incorporated herein by reference in its entirety.

In certain embodiments, R$^2$ may comprise either moiety depicted below:

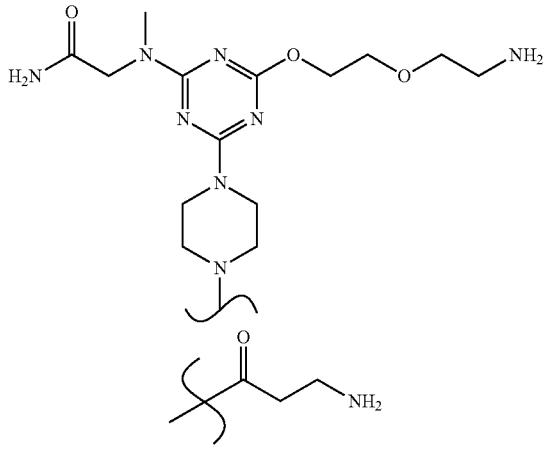

In certain embodiments, each R$^1$ is —N(CH$_3$)$_2$. In some embodiments, about 50-90% of the R$_1$ groups are dimethylamino (i.e. —N(CH$_3$)$_2$). In certain embodiments, about 66% of the R$_1$ groups are dimethylamino.

In some non-limiting embodiments, the targeting sequence is selected from the sequences of Tables 2A-2C, wherein X is selected from uracil (U) or thymine (T). In some non-limiting embodiments, each R$^1$ is —N(CH$_3$)$_2$ and the targeting sequence is selected from the sequences of Table 2A-2C, wherein X is selected from uracil (U) or thymine (T).

In some embodiments of the disclosure, $R_1$ may be selected from:
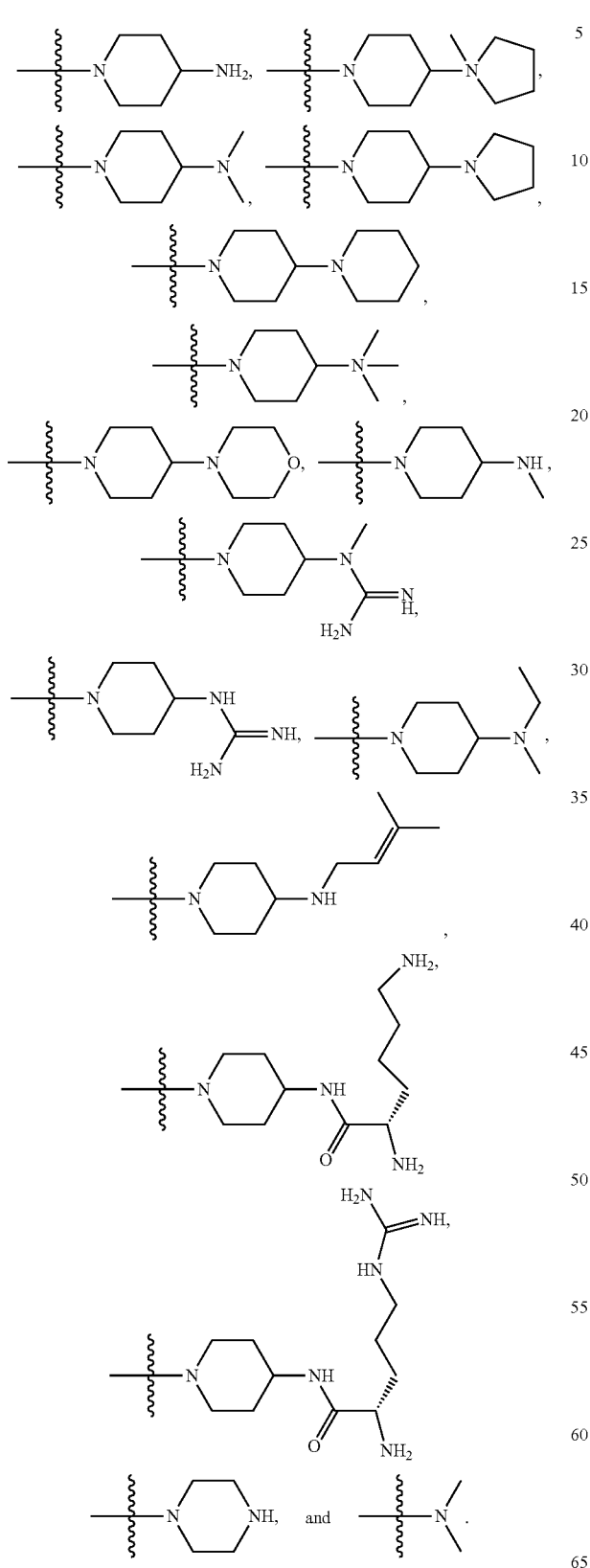
In some embodiments, at least one $R^1$ is:
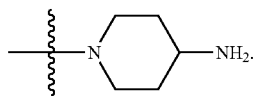
In certain embodiments, T is selected from:
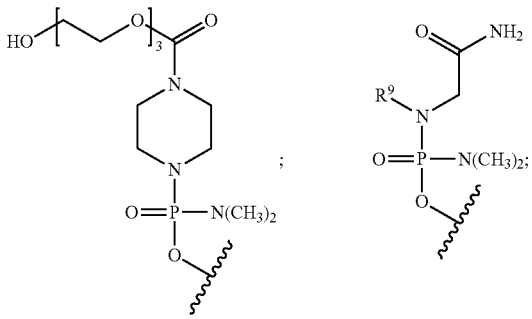
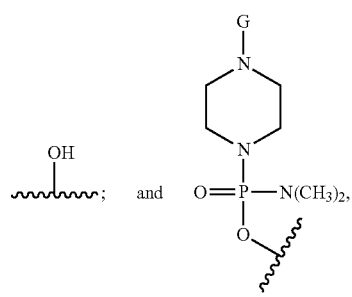
Y is O at each occurrence. In some embodiments, $R^2$ is selected from H, G, acyl, trityl, 4-methoxytrityl, benzoyl, and stearoyl.
In various embodiments, T is selected from:
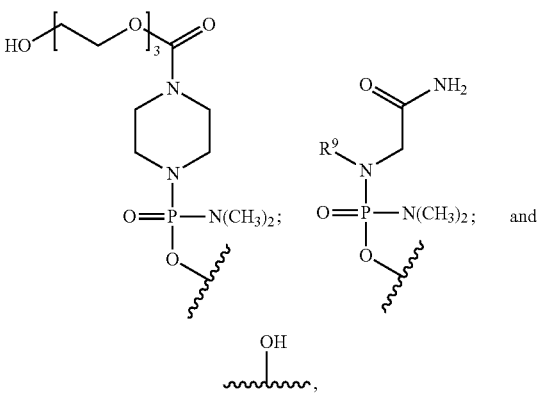
Y is O at each occurrence and $R^2$ is G.

In some embodiments, T is of the formula:

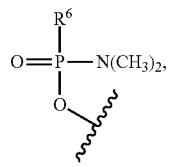

R⁶ is of the formula:

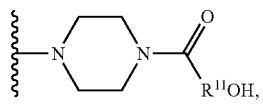

Y is O at each occurrence and $R^2$ is G.
In certain embodiments, T is of the formula:

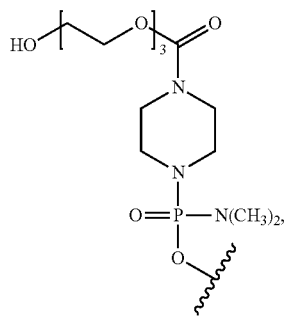

Y is O at each occurrence and $R^2$ is G. In some embodiments, T is of the formula:

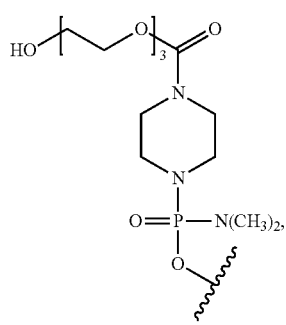

Y is O at each occurrence, each $R^1$ is —N(CH$_3$)$_2$, and $R^2$ is G.

In certain embodiments, T is of the formula:

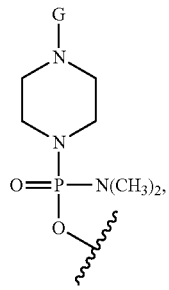

and Y is O at each occurrence. In some embodiments, T is of the formula:

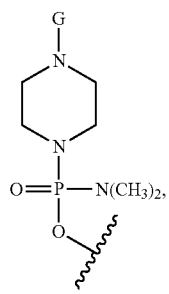

Y is O at each occurrence, each $R^1$ is —N(CH$_3$)$_2$, and $R^2$ is acetyl.

In certain embodiments, T is of the formula:

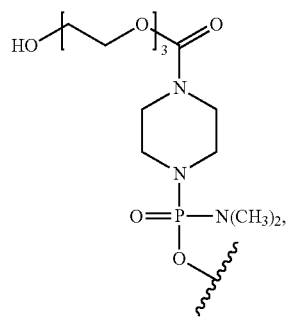

Y is O at each occurrence, each $R^1$ is —N(CH$_3$)$_2$, and $R^2$ is H.

In some embodiments, $R^2$ is selected from H, acyl, trityl, 4-methoxytrityl, benzoyl, and stearoyl.

In various embodiments, $R^2$ is selected from H or G. In a particular embodiment, $R^2$ is G. In some embodiments, $R^2$ is H or acyl. In some embodiments, each $R^1$ is —N(CH$_3$)$_2$. In some embodiments, at least one instance of $R^1$ is —N(CH$_3$)$_2$. In certain embodiments, each instance of $R^1$ is —N(CH$_3$)$_2$.

In some embodiments, G is of the formula:

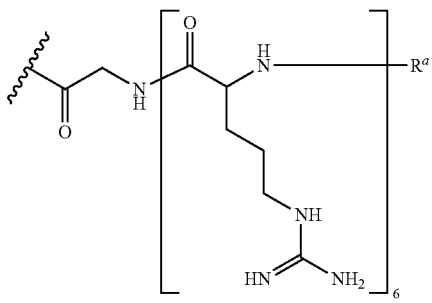

wherein $R^a$ is selected from H, acyl, benzoyl, and stearoyl. In some embodiments, $R^a$ is acetyl.

In certain embodiments, the CPP is of the formula:

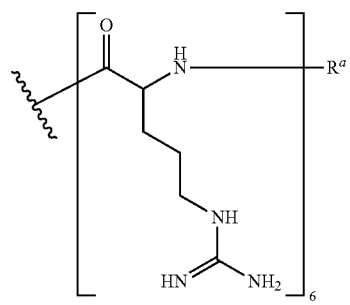

wherein $R^a$ is selected from H, acyl, benzoyl, and stearoyl. In some embodiments, $R^a$ is acetyl.

In another aspect, the antisense oligomer is a compound of formula (Ia):

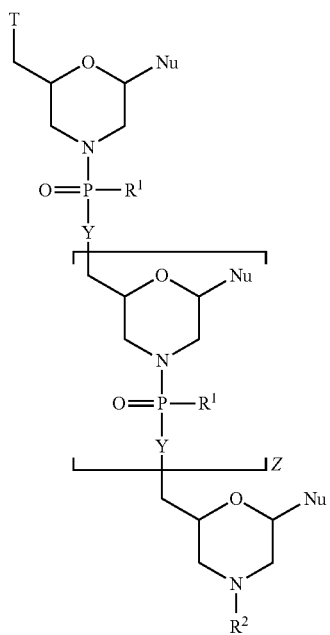

(Ia)

or a pharmaceutically acceptable salt thereof, wherein:
each Nu is a nucleobase which taken together form a targeting sequence;
Z is an integer from about 13 to about 38;
each Y is independently selected from O and $-NR^4$, wherein each $R^4$ is independently selected from H, $C_1$-$C_6$ alkyl, aralkyl, $-C(=NH)NH_2$, $-C(O)(CH_2)_n$ $NR^5C(=NH)NH_2$, $-C(O)(CH_2)_2NHC(O)(CH_2)_5$ $NR^5C(=NH)NH_2$, and G, wherein $R^5$ is selected from H and $C_1$-$C_6$ alkyl and n is an integer from 1 to 5;
T is selected from OH and a moiety of the formula:

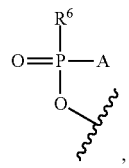

wherein:
A is selected from $-OH$, $-N(R^7)_2$, and $R^1$ wherein:
each $R^7$ is independently selected from H and $C_1$-$C_6$ alkyl, and
$R^6$ is selected from OH, $-N(R^9)CH_2C(O)NH_2$, and a moiety of the formula:

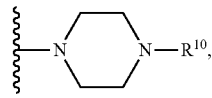

wherein:
$R^9$ is selected from H and $C_1$-$C_6$ alkyl; and
$R^{10}$ is selected from G, $-C(O)-R^{11}OH$, acyl, trityl, 4-methoxytrityl,
$-C(=NH)NH_2$, $-C(O)(CH_2)_mNR^{12}C(=NH)$ $NH_2$, and
$-C(O)(CH_2)_2NHC(O)(CH_2)_5NR^{12}C(=NH)NH_2$,
wherein:
m is an integer from 1 to 5,
$R^{11}$ is of the formula $-(O-alkyl)_y-$ wherein y is an integer from 3 to 10 and
each of the y alkyl groups is independently selected from $C_2$-$C_6$ alkyl; and
$R^{12}$ is selected from H and $C_1$-$C_6$ alkyl;
each instance of $R^1$ is independently selected from:
$-N(R^{13})_2$, wherein each $R^{13}$ is independently selected from H and $C_1$-$C_6$ alkyl; a moiety of formula (II):

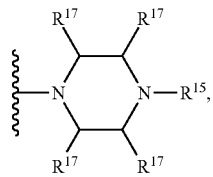

(II)

wherein:
$R^{15}$ is selected from H, G, $C_1$-$C_6$ alkyl, $-C(=NH)NH_2$,
$-C(O)(CH_2)_qNR^{18}C(=NH)NH_2$, and
$-C(O)(CH_2)_2NHC(O)(CH_2)_5NR^{18}C(=NH)$ $NH_2$, wherein:

$R^{18}$ is selected from H and $C_1$-$C_6$ alkyl; and
q is an integer from 1 to 5; and
each $R^{17}$ is independently selected from H and methyl; and
a moiety of formula(III):

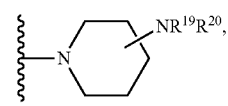

wherein:
$R^{19}$ is selected from H, $C_1$-$C_6$ alkyl, —C(=NH)NH$_2$, —C(O)(CH$_2$)$_r$NR$^{22}$C(=NH)NH$_2$,
—C(O)CH(NH$_2$)(CH$_2$)$_3$NHC(=NH)NH$_2$,
—C(O)(CH$_2$)$_2$NHC(O)(CH$_2$)$_5$NR$^{22}$C(=NH)NH$_2$,
—C(O)CH(NH$_2$)(CH$_2$)$_4$NH$_2$ and G, wherein:
  $R^{22}$ is selected from H and $C_1$-$C_6$ alkyl; and
  r is an integer from 1 to 5, and
$R^{20}$ is selected from H and $C_1$-$C_6$ alkyl; or
$R^{19}$ and $R^{20}$ together with the nitrogen atom to which they are attached form a heterocyclic or heteroaryl ring having from 5 to 7 ring atoms and optionally containing an additional heteroatom selected from oxygen, nitrogen, and sulfur; and
$R^2$ is selected from H, G, acyl, trityl, 4-methoxytrityl, benzoyl, stearoyl, $C_1$-$C_6$ alkyl, —C(=NH)NH$_2$, —C(O)—R$^{23}$, —C(O)(CH$_2$)$_s$NR$^{24}$C(=NH)NH$_2$, —C(O)(CH$_2$)$_2$NHC(O)(CH$_2$)$_5$NR$^{24}$C(=NH)NH$_2$, —C(O)CH(NH$_2$)(CH$_2$)$_3$NHC(=NH)NH$_2$,
and a moiety of the formula:

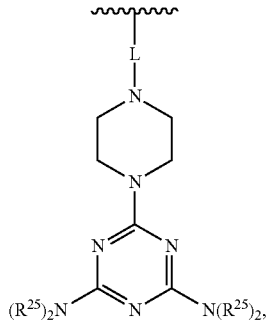

wherein,
$R^{23}$ is of the formula —(O-alkyl)$_v$-OH wherein v is an integer from 3 to 10 and each of the v alkyl groups is independently selected from $C_2$-$C_6$ alkyl; and
$R^{24}$ is selected from H and $C_1$-$C_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each $R^{25}$ is of the formula —(CH$_2$)$_2$OC(O)N(R$^{26}$)$_2$ wherein each R$^{26}$ is of the formula —(CH$_2$)$_6$NHC(=NH)NH$_2$,
wherein G is a cell penetrating peptide ("CPP") and linker moiety comprising the formula —C(O)CH$_2$NH-CPP, where CPP is of the formula:

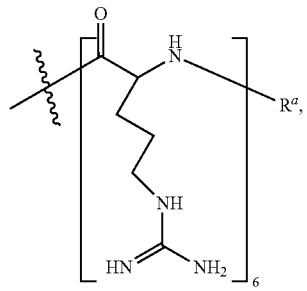

wherein $R^a$ is H or acyl, and
wherein G may be present in one occurance or is absent.
In certain embodiments, T is selected from:

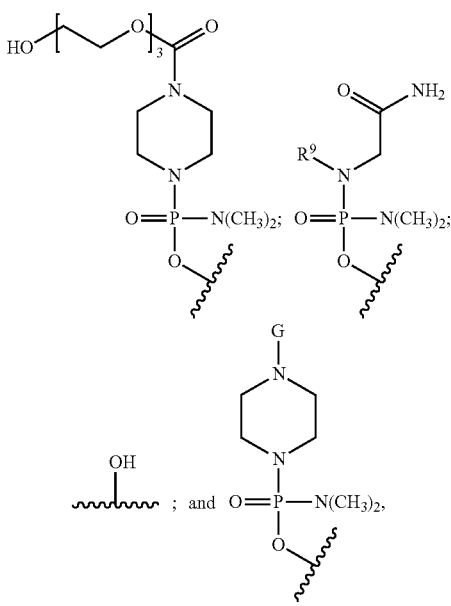

Y is O at each occurrence. In some embodiments, $R^2$ is selected from H, G, acyl, trityl, 4-methoxytrityl, benzoyl, and stearoyl.

In various embodiments, T is selected from:

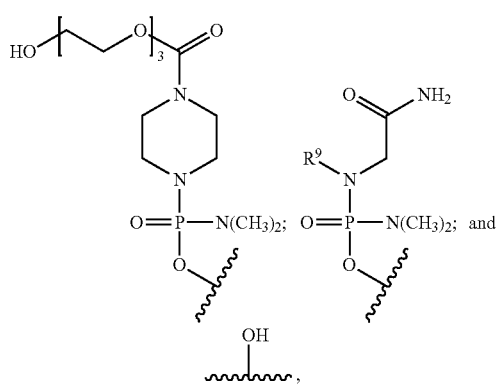

Y is O at each occurrence and $R^2$ is G.

In some embodiments, T is of the formula:

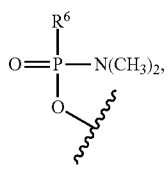

$R^6$ is of the formula:

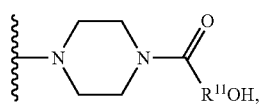

Y is O at each occurrence and $R^2$ is G.
In certain embodiments, T is of the formula:

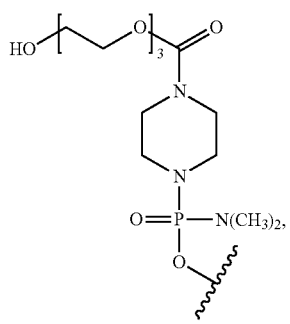

Y is O at each occurrence and $R^2$ is G. In some embodiments, T is of the formula:

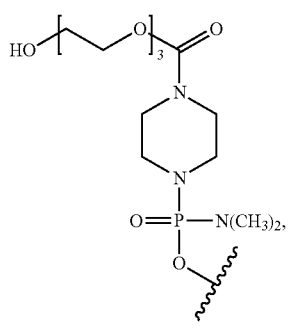

Y is O at each occurrence, each $R^1$ is —$N(CH_3)_2$, and $R^2$ is G.

In certain embodiments, T is of the formula:

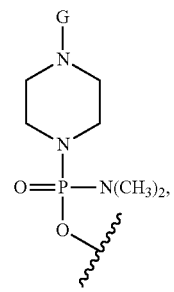

and Y is O at each occurrence. In some embodiments, T is of the formula:

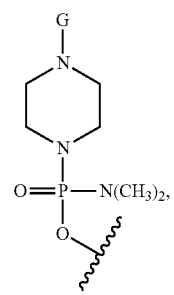

Y is O at each occurrence, each $R^1$ is —$N(CH_3)_2$, and $R^2$ is acetyl.

In certain embodiments, T is of the formula:

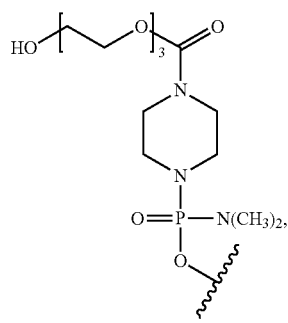

Y is O at each occurrence, each $R^1$ is —$N(CH_3)_2$, and $R^2$ is H.

In some embodiments, $R^2$ is selected from H, acyl, trityl, 4-methoxytrityl, benzoyl, and stearoyl.

In various embodiments, $R^2$ is selected from H or G. In a particular embodiment, $R^2$ is G. In some embodiments, $R^2$ is H or acyl. In some embodiments, each $R^1$ is —$N(CH_3)_2$. In some embodiments, at least one instance of $R^1$ is —$N(CH_3)_2$. In certain embodiments, each instance of $R^1$ is —$N(CH_3)_2$.

In some embodiments, $R^a$ is acetyl.

In some embodiments including, for example, embodiments of the antisense oligomers of formula (I) and (Ia), the targeting sequence is complementary to a target region within intron 1 (SEQ ID NO: 1) of a pre-mRNA of the human alpha glucosidase (GAA) gene. In various embodiments including, for example, embodiments of the antisense oligomers of formula (I) and (Ia), the targeting sequence is complementary to a target region within intron 1 (SEQ ID NO: 1) of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. In certain embodiments, the targeting sequence comprises a sequence selected from SEQ ID NOs:13-86, as shown in Tables 2A-2C herein. In certain embodiments, the targeting sequence comprises a sequence selected from Tables 2A and 2B. In certain embodiments, the targeting sequence is selected from the group consisting of SEQ ID NOs: 13, 27-29, 34-36, 59, and 82. Further, and with respect to the sequences outlined in Tables 2A-2C (or Tables 2B and 2C) herein, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present.

In certain embodiments, the antisense oligomer of the disclosure is a compound of formula (IVa):

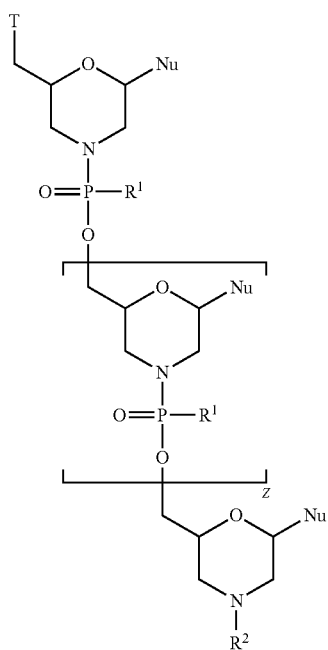

(IVa)

or a pharmaceutically acceptable salt thereof, wherein:
  each Nu is a nucleobase which taken together forms a targeting sequence;
  Z is an integer from 8 to 38;
  T is selected from OH and a moiety of the formula:

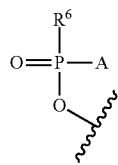

wherein:
  A is selected from —OH, —N($R^7$)$_2$$R^g$, and $R^1$ wherein:
    each $R^7$ is independently selected from H and $C_1$-$C_6$ alkyl, and
    $R^8$ is selected from an electron pair and H, and
  $R^6$ is selected from OH, —N($R^9$)$CH_2$C(O)$NH_2$, and a moiety of the formula:

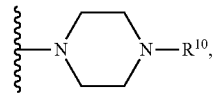

wherein:
  $R^9$ is selected from H and $C_1$-$C_6$ alkyl; and
  $R^{10}$ is selected from —C(O)—$R^{11}$OH, acyl, trityl, 4-methoxytrityl,
    —C(=NH)$NH_2$, —C(O)($CH_2$)$_m$$NR^{12}$C(=NH)$NH_2$, and
    —C(O)($CH_2$)$_2$NHC(O)($CH_2$)$_5$$NR^{12}$C(=NH)$NH_2$,
    wherein:
      m is an integer from 1 to 5,
      R" is of the formula —(O-alkyl)$_y$- wherein y is an integer from 3 to 10 and
        each of the y alkyl groups is independently selected from $C_2$-$C_6$ alkyl; and
      $R^{12}$ is selected from H and $C_1$-$C_6$ alkyl;
  each instance of $R^1$ is independently —N($R^{13}$)$_2$$R^{14}$, wherein each $R^{13}$ is independently selected from H and $C_1$-$C_6$ alkyl, and $R^{14}$ is selected from an electron pair and H; and
  $R^2$ is selected from H, acyl, trityl, 4-methoxytrityl, benzoyl, stearoyl, and $C_1$-$C_6$ alkyl.

In certain embodiments, T is selected from:

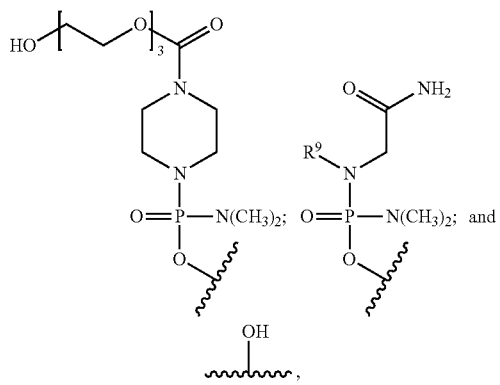

Y is O at each occurrence. In some embodiments, R² is selected from H, acyl, trityl, 4-methoxytrityl, benzoyl, and stearoyl.

In various embodiments, T is selected from:

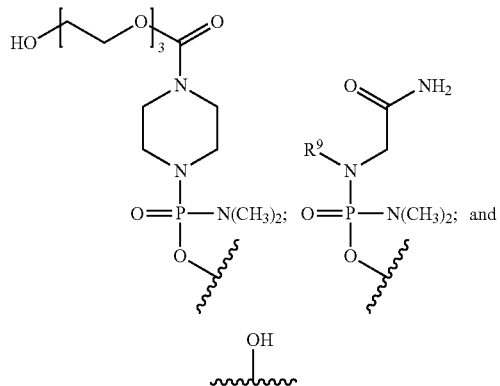

In some embodiments, T is of the formula:

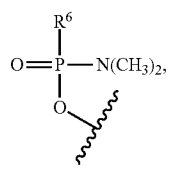

and

R⁶ is of the formula:

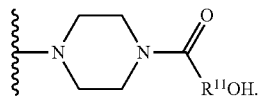

In certain embodiments, T is of the formula:

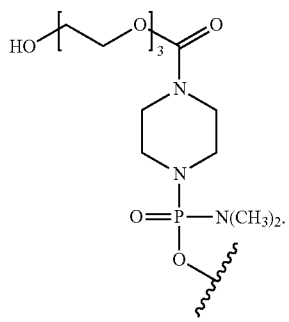

In some embodiments, R² is H, trityl, or acyl. In some embodiments, at least one instance of R¹ is —N(CH₃)₂. In some embodiments, each R¹ is —N(CH₃)₂.

In certain embodiments, the antisense oligomer of the disclosure is a compound of formula (IVb):

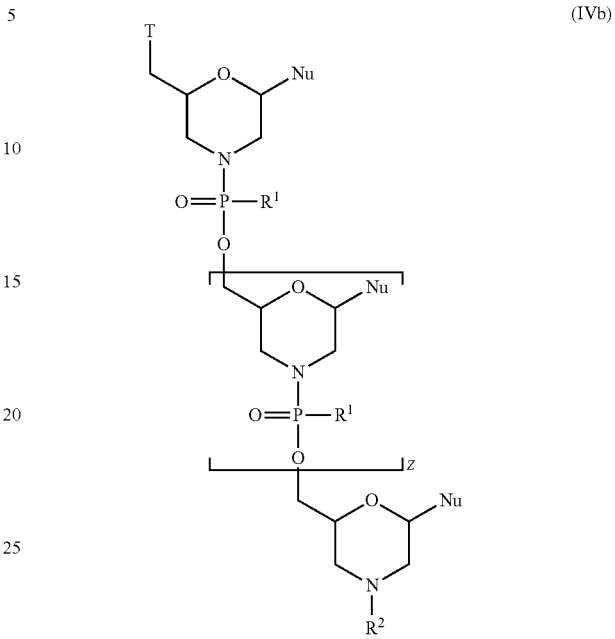

or a pharmaceutically acceptable salt thereof, where:
each Nu is a nucleobase which taken together forms a targeting sequence;
Z is an integer from 8 to 38;
T is selected from a moiety of the formula:

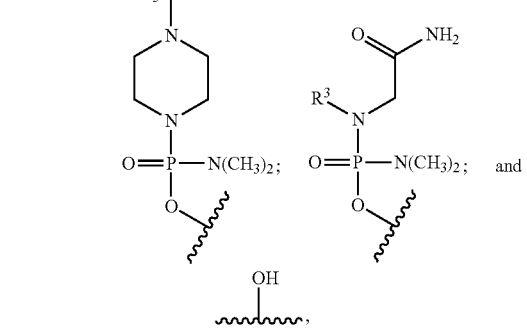

wherein R³ is selected from H and $C_1$-$C_6$ alkyl;
each instance of R¹ is independently —N(R⁴)₂, wherein each R⁴ is independently selected from H and $C_1$-$C_6$ alkyl; and
R² is selected from H, acyl, trityl, 4-methoxytrityl, benzoyl, stearoyl, and $C_1$-$C_6$ alkyl.

In various embodiments, R² is selected from H or acyl. In some embodiments, R² is H.

In certain embodiments, T is of the formula:

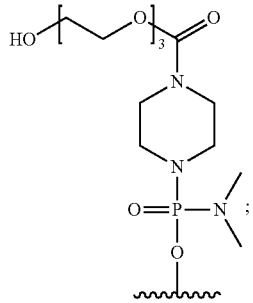

R² is hydrogen.

In certain embodiments, the antisense oligomer of the disclosure is a compound of formula (IVc):

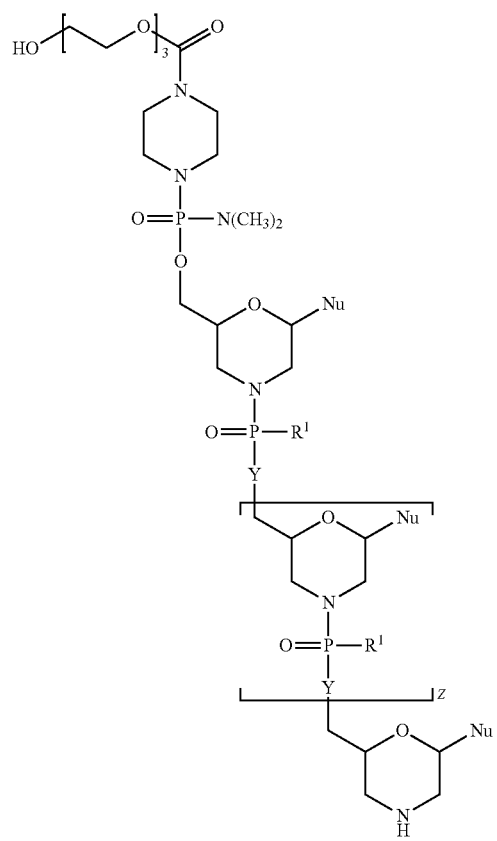

(IVc)

or a pharmaceutically acceptable salt thereof, wherein:
  each Nu is a nucleobase which taken together form a targeting sequence;
  Z is an integer from 8 to 38;
  each Y is O;
  each R¹ is independently selected from the group consisting of:

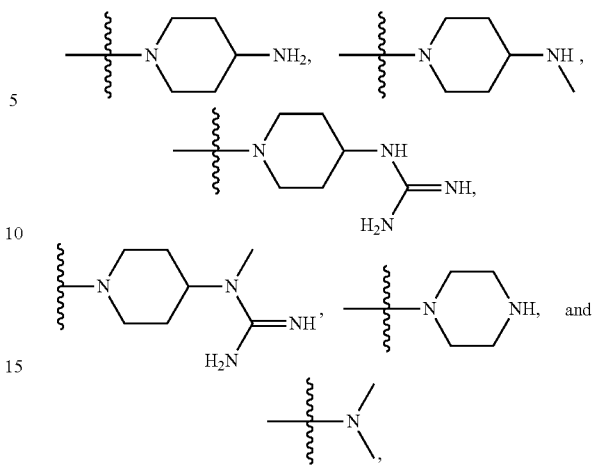

wherein at least one R¹ is —N(CH₃)₂.

In some embodiments, the targeting sequence is selected from SEQ ID NOS: 4 to 30, 133 to 255, or 296 to 342, wherein X is selected from uracil (U) or thymine (T). In some embodiments, each R¹ is —N(CH₃)₂.

In certain embodiments, the antisense oligomer is a compound of formula (V):

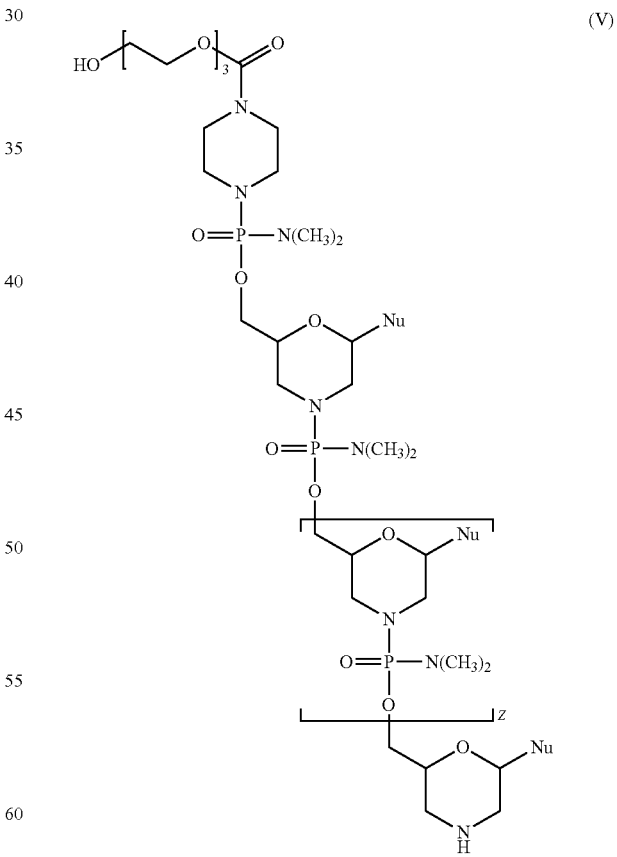

(V)

or a pharmaceutically acceptable salt thereof, wherein:
  each Nu is a nucleobase which taken together form a targeting sequence; and
  Z is an integer from 8 to 38.

In some embodiments including, for example, embodiments of the antisense oligomers of formula (IVa), (IVb), (IVc) and (V), the targeting sequence is complementary to a target region within intron 1 (SEQ ID NO: 1) of a pre-mRNA of the human alpha glucosidase (GAA) gene. In various embodiments including, for example, embodiments of the antisense oligomers of formula (IVa), (IVb), (IVc) and (V), the targeting sequence is complementary to a target region within intron 1 (SEQ ID NO: 1) of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. In certain embodiments, the targeting sequence comprises a sequence selected from SEQ ID NO: 13-SEQ ID NO: 86, as shown in Tables 2A-2C herein. In certain embodiments, the targeting sequence is selected from the group consisting of SEQ ID NOs: 13, 27-29, 34-36, 59, and 82. In certain embodiments, the targeting sequence comprises a sequence selected from Tables 2A-2C. Further, and with respect to the sequences outlined in Tables 2A-2C (or Tables 2B and 2C) herein, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present.

In certain embodiments, the antisense oligomer is a compound of formula (VI):

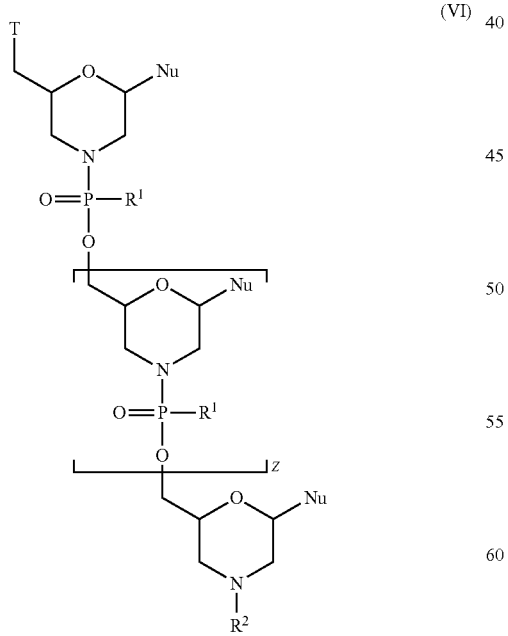

(VI)

or a pharmaceutically acceptable salt thereof,
where each Nu is a nucleobase which taken together forms a targeting sequence;

Z is an integer from 8 to 38;
T is selected from:

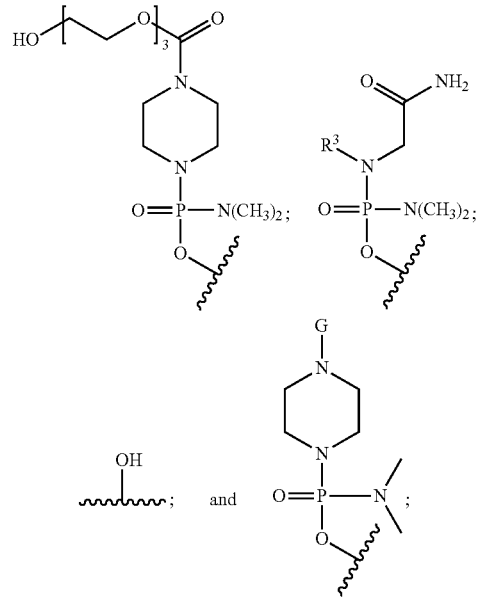

each $R^1$ is independently selected from the group consisting of:

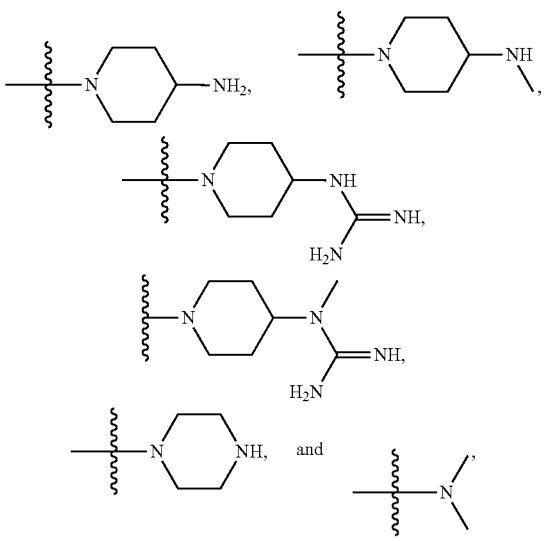

$R^2$ is selected from H, G, acyl, trityl, 4-methoxytrityl, benzoyl, and stearoyl, wherein G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

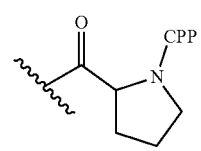

wherein the CPP is attached to the linker moiety by an amide bond at the CPP carboxy terminus, and
wherein T is

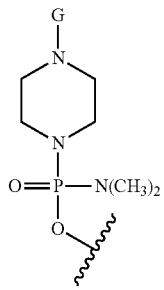

or R² is G.

In certain embodiments, T is of the formula:

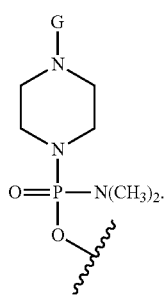

and R² is G. In certain embodiments, at least one occurrence of R¹ is —N(CH₃)₂. In some embodiments, each occurrence of R¹ is —N(CH₃)₂. In some embodiments, T is of the formula:

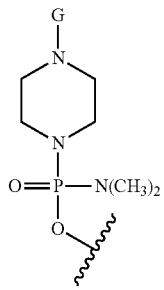

In certain embodiments, at least one occurrence of R¹ is —N(CH₃)₂. In some embodiments, each occurrence of R¹ is —N(CH₃)₂.

In some embodiments, T is of the formula:

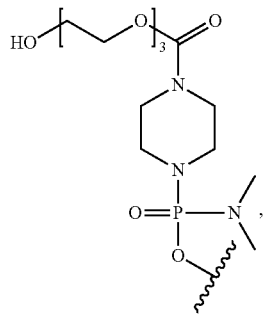

R² is G, and each occurrence of R¹ is —N(CH₃)₂.

In certain embodiments, R² is selected from H, acetyl, trityl, 4-methoxytrityl, benzoyl, and stearoyl and T is of the formula:

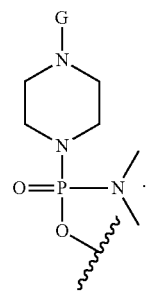

In various embodiments, R² is acetyl. In certain embodiments, at least one occurrence of R¹ is —N(CH₃)₂. In some embodiments, each occurrence of R¹ is —N(CH₃)₂.

In various embodiments, R² is selected from H, acyl, trityl, 4-methoxytrityl, benzoyl, and stearoyl.

In certain embodiments, R² is acetyl, T is of the formula:

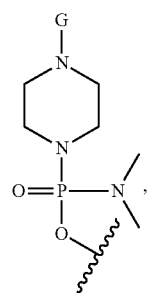

and each occurrence of R¹ is —N(CH₃)₂.

In some embodiments, wherein G is of the formula:

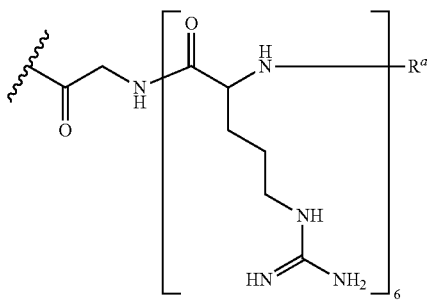

wherein $R^a$ is selected from H, acyl, benzoyl, and stearoyl. In some embodiments, $R^a$ is acetyl.

In some embodiments, the CPP is of the formula:

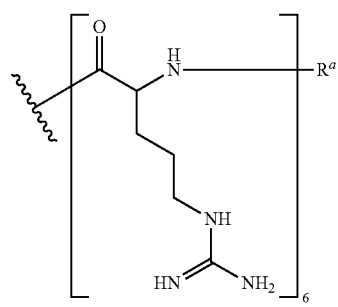

wherein $R^a$ is selected from H, acyl, benzoyl, and stearoyl. In some embodiments, $R^a$ is acetyl.

In certain embodiments, the antisense oligomer is a compound of formula (VII):

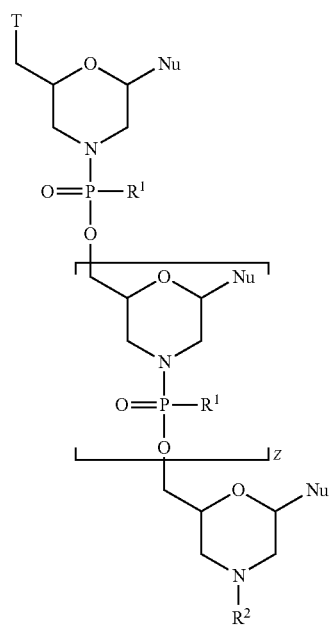

(VII)

or a pharmaceutically acceptable salt thereof,
where each Nu is a nucleobase which taken together forms a targeting sequence;

Z is an integer from 8 to 38;
T is selected from:

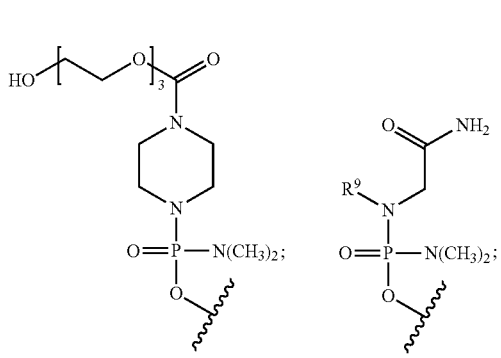

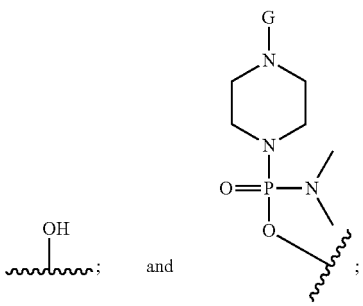

each $R^1$ is $-N(R^4)_2$ wherein each $R^4$ is independently $C_1$-$C_6$ alkyl; and $R^2$ is selected from H, G, acyl, trityl, 4-methoxytrityl, benzoyl, and stearoyl, wherein G is a cell penetrating peptide ("CPP") and linker moiety selected from $-C(O)(CH_2)_5$NH-CPP, $-C(O)(CH_2)_2$NH-CPP, $-C(O)(CH_2)_2$NHC(O)(CH$_2$)$_5$NH-CPP, $-C(O)CH_2$NH-CPP, and:

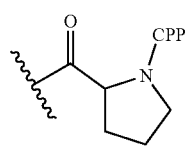

wherein the CPP is attached to the linker moiety by an amide bond at the CPP carboxy terminus, and wherein T is

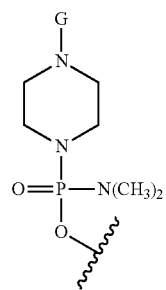

or $R^2$ is G.

In some embodiments, at least one instance of $R^1$ is —$N(CH_3)_2$. In certain embodiments, each instance of $R^1$ is —$N(CH_3)_2$.

In certain embodiments, T is of the formula:

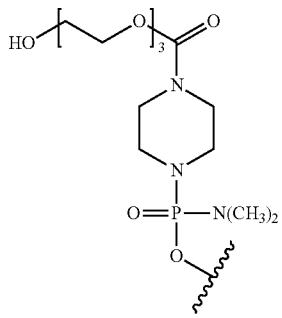

and $R^2$ is G. In some embodiments, at least one instance of $R^1$ is —$N(CH_3)_2$. In certain embodiments, each instance of $R^1$ is —$N(CH_3)_2$.

In various embodiments, G is of the formula:

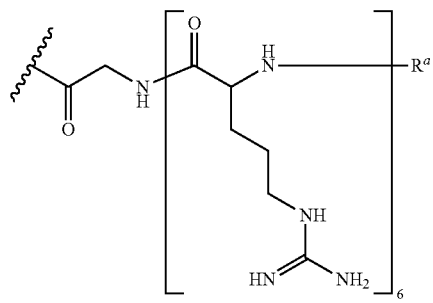

wherein $R^a$ is selected from H, acyl, benzoyl, and stearoyl. In some embodiments, $R^a$ is acetyl.

In certain embodiments, the CPP is of the formula:

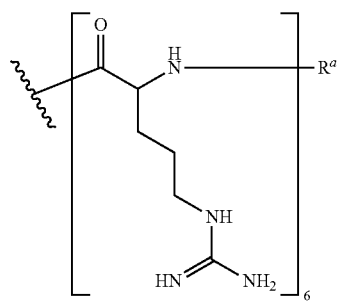

wherein $R^a$ is selected from H, acetyl, benzoyl, and stearoyl. In some embodiments, $R^a$ is acetyl.

In certain embodiments, the antisense oligomer is a compound of formula (VIIa):

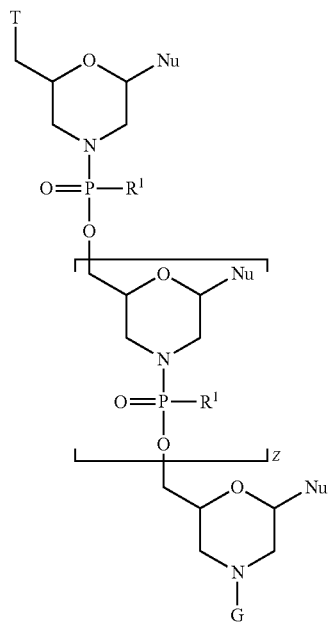

(VIIa)

or a pharmaceutically acceptable salt thereof,
where each Nu is a nucleobase which taken together forms a targeting sequence;
Z is an integer from 8 to 38;
T is selected from:

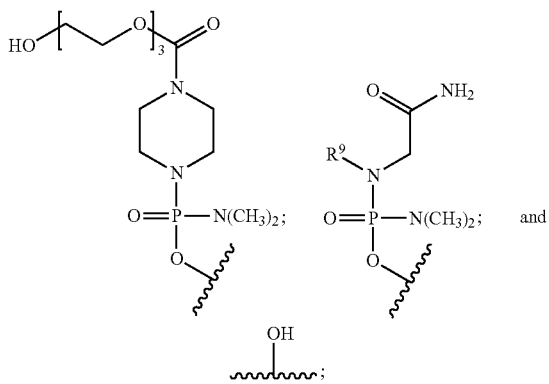

each instance of $R^1$ is —$N(R^4)_2$ wherein each $R^4$ is independently $C_1$-$C_6$ alkyl; and
G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

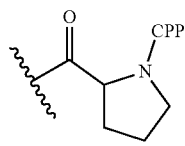

wherein the CPP is attached to the linker moiety by an amide bond at the CPP carboxy terminus.

In some embodiments, at least one instance of $R^1$ is —$N(CH_3)_2$. In certain embodiments, each instance of $R^1$ is —$N(CH_3)_2$.

In some embodiments, G is of the formula:

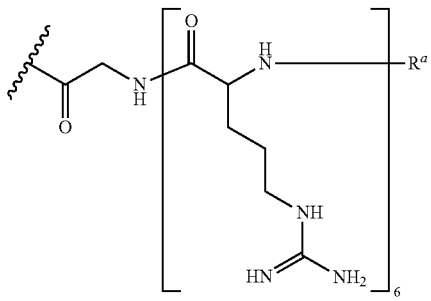

wherein $R^a$ is selected from H, acyl, benzoyl, and stearoyl. In some embodiments, $R^a$ is acetyl.

In various embodiments, each instance of $R^1$ is —$N(CH_3)_2$, G is of the formula:

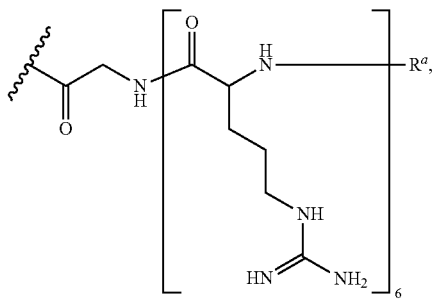

and $R^a$ is acetyl.

In certain embodiments, the CPP is of the formula:

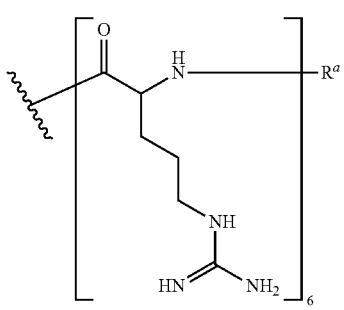

wherein $R^a$ is selected from H, acyl, benzoyl, and stearoyl. In some embodiments, $R^a$ is acetyl. In various embodiments, each instance of $R^1$ is —$N(CH_3)_2$, the CPP is of the formula:

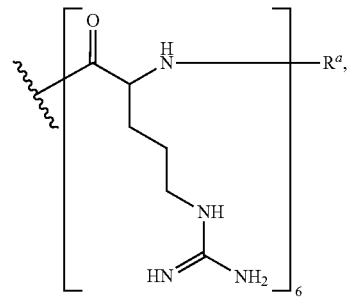

and
$R^a$ is acetyl.

In various aspects, an antisense oligonucleotide of the disclosure includes a compound of formula (VIIb):

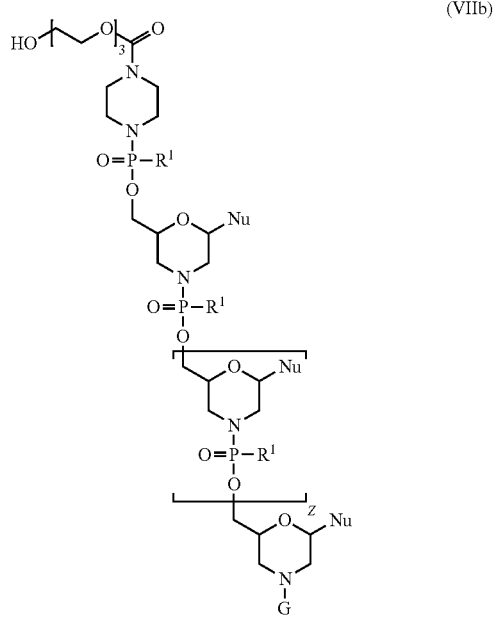

(VIIb)

or a pharmaceutically acceptable salt thereof, wherein:
where each Nu is a nucleobase which taken together forms a targeting sequence;
Z is an integer from 8 to 38;
each instance of $R^1$ is —$N(R^4)_2$ wherein each $R^4$ is independently $C_1$-$C_6$ alkyl; and
G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

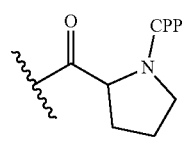

wherein the CPP is attached to the linker moiety by an amide bond at the CPP carboxy terminus.

In some embodiments, at least one instance of $R^1$ is —$N(CH_3)_2$. In certain embodiments, each instance of $R^1$ is —$N(CH_3)_2$.

In some embodiments, G is of the formula:

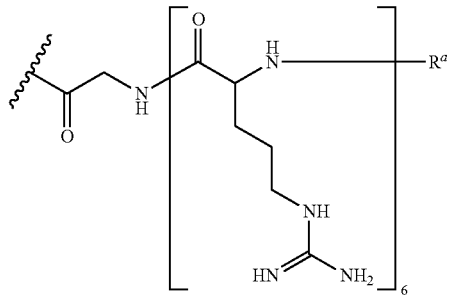

wherein $R^a$ is selected from H, acyl, benzoyl, and stearoyl. In some embodiments, R is acetyl.

In various embodiments, each instance of $R^1$ is —N(CH$_3$)$_2$, G is of the formula:

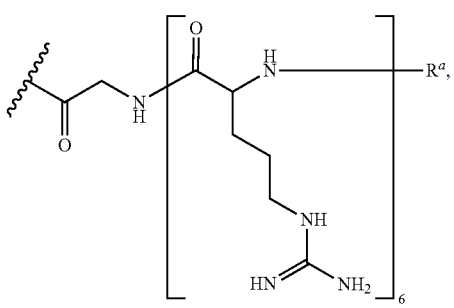

and $R^a$ is acetyl.

In certain embodiments, the CPP is of the formula:

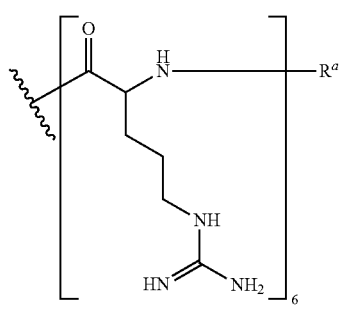

wherein $R^a$ is selected from H, acyl, benzoyl, and stearoyl. In some embodiments, $R^a$ is acetyl. In various embodiments, each instance of $R^1$ is —N(CH$_3$)$_2$, the CPP is of the formula:

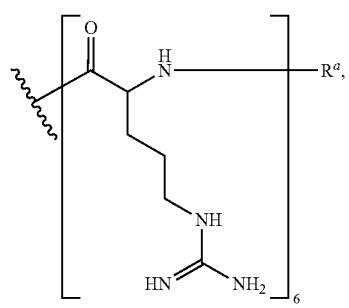

$R^a$ is acetyl.

In various aspects, an antisense oligonucleotide of the disclosure includes a compound of formula (VIIc):

(VIIc)

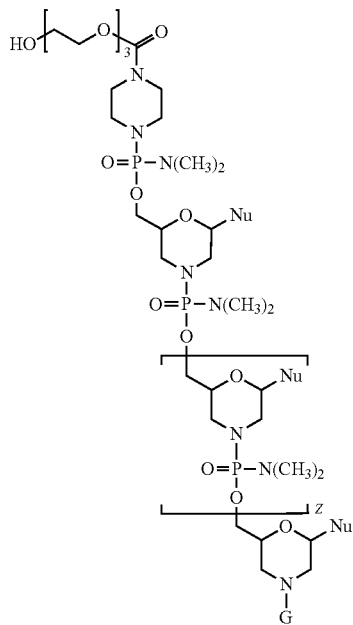

or a pharmaceutically acceptable salt thereof, wherein:

where each Nu is a nucleobase which taken together forms a targeting sequence;

Z is an integer from 8 to 38; and

G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

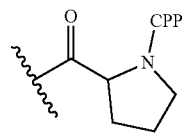

wherein the CPP is attached to the linker moiety by an amide bond at the CPP carboxy terminus.

In some embodiments, G is of the formula:

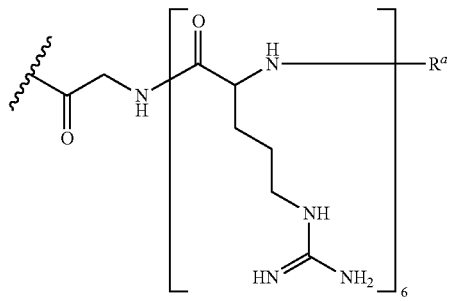

wherein $R^a$ is selected from H, acyl, benzoyl, and stearoyl. In some embodiments, R is acetyl.

In various embodiments, G is of the formula:

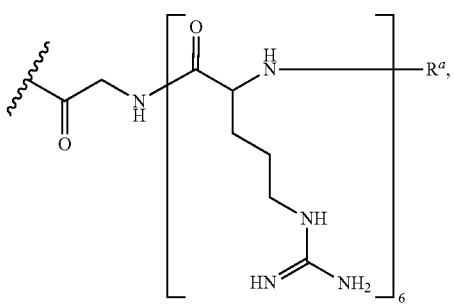

and
$R^a$ is acetyl.

In certain embodiments, the CPP is of the formula:

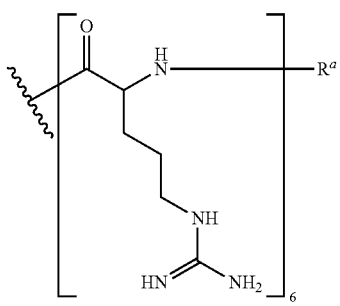

wherein $R^a$ is selected from H, acyl, benzoyl, and stearoyl. In some embodiments, $R^a$ is acetyl. In various embodiments, the CPP is of the formula:

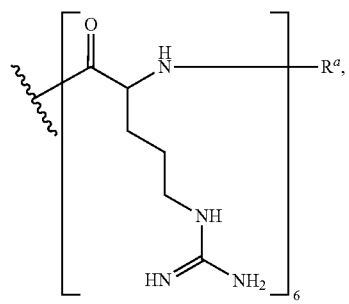

and
$R^a$ is acetyl.

In various aspects, an antisense oligomer of the disclosure is a compound of formula (VIId):

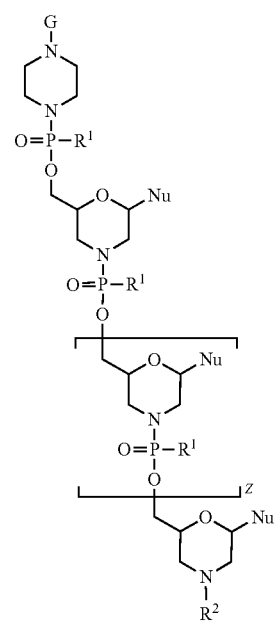

(VIId)

wherein:
each Nu is a nucleobase which taken together forms a targeting sequence;
Z is an integer from 8 to 38;
each instance of $R^1$ is $-N(R^4)_2$ wherein each $R^4$ is independently $C_1$-$C_6$ alkyl; and $R^2$ is selected from H, trityl, 4-methoxytrityl, acetyl, benzoyl, and stearoyl; and
G is a cell penetrating peptide ("CPP") and linker moiety selected from $-C(O)(CH_2)_5NH$-CPP, $-C(O)(CH_2)_2NH$-CPP, $-C(O)(CH_2)_2NHC(O)(CH_2)_5NH$-CPP, $-C(O)CH_2NH$-CPP, and:

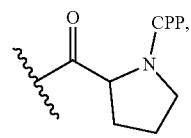

wherein the CPP is attached to the linker moiety by an amide bond at the CPP carboxy terminus.

In some embodiments, at least one instance of $R^1$ is —N(CH$_3$)$_2$. In certain embodiments, each instance of $R^1$ is —N(CH$_3$)$_2$.

In some embodiments, G is of the formula:

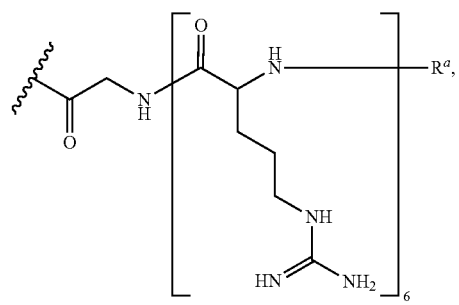

wherein $R^a$ is selected from H, acyl, benzoyl, and stearoyl. In some embodiments, $R^a$ is acetyl.

In various embodiments, each instance of $R^1$ is —N(CH$_3$)$_2$, G is of the formula:

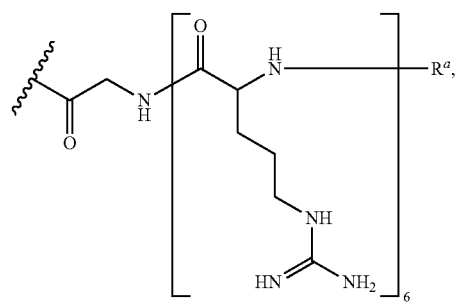

and
$R^a$ is acetyl.

In certain embodiments, the CPP is of the formula:

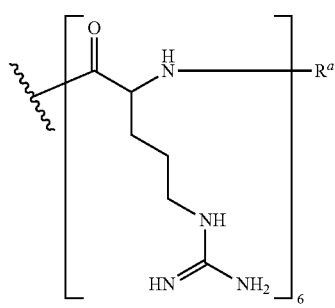

wherein $R^a$ is selected from H, acyl, benzoyl, and stearoyl. In some embodiments, $R^a$ is acetyl. In various embodiments, each instance of $R^1$ is —N(CH$_3$)$_2$, the CPP is of the formula:

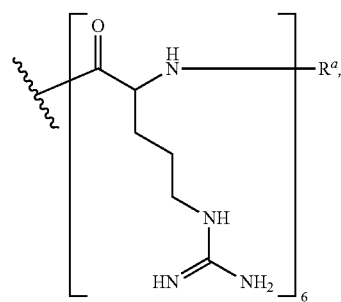

and
$R^a$ is acetyl.

In various aspects, an antisense oligonucleotide of the disclosure includes a compound of formula (VIIe):

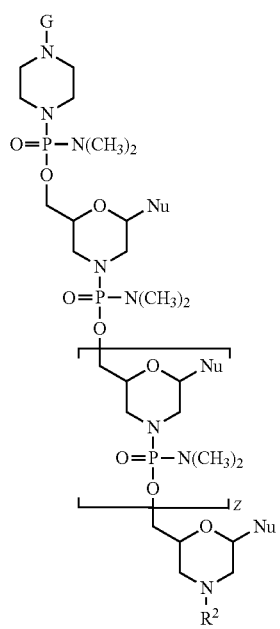

(VIIe)

or a pharmaceutically acceptable salt thereof, wherein:
each Nu is a nucleobase which taken together forms a targeting sequence;
Z is an integer from 8 to 38;
$R^2$ is selected from H, trityl, 4-methoxytrityl, acetyl, benzoyl, and stearoyl; and
G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, —C(O)CH$_2$NH-CPP, and:

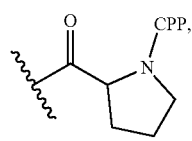

wherein the CPP is attached to the linker moiety by an amide bond at the CPP carboxy terminus.

In some embodiments, G is of the formula:

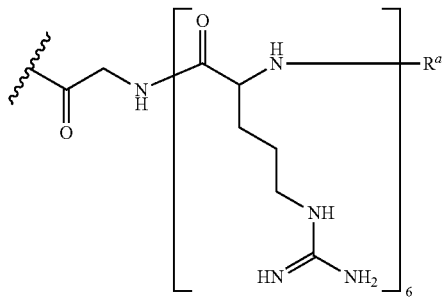

wherein $R^a$ is selected from H, acyl, benzoyl, and stearoyl. In some embodiments, $R^a$ is acetyl.

In various embodiments, G is of the formula:

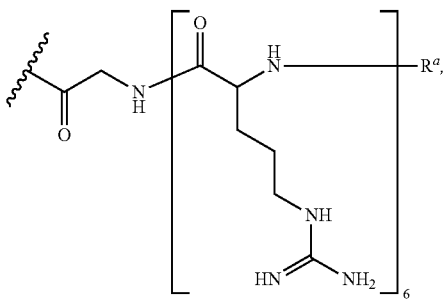

and
$R^a$ is acetyl.

In certain embodiments, the CPP is of the formula:

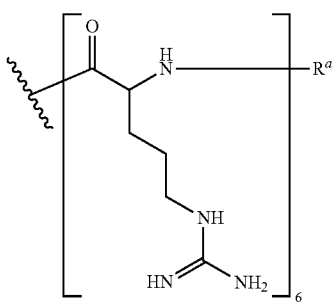

wherein $R^a$ is selected from H, acyl, benzoyl, and stearoyl. In some embodiments, $R^a$ is acetyl. In various embodiments, the CPP is of the formula:

$R^a$ is acetyl.

In some embodiments including, for example, embodiments of the antisense oligomers of formula (VI), (VII), (VIIa), (VIIb), (VIIc), (VIId), (VIIe), and (VIII), the targeting sequence is complementary to a target region within intron 1 (SEQ ID NO: 1) of a pre-mRNA of the human alpha glucosidase (GAA) gene. In various embodiments including, for example, embodiments of the antisense oligomers of formula (VI), (VII), (VIIa), (VIIb), (VIIc), (VIId), (VIIe), and (VIII), the targeting sequence is complementary to a target region within intron 1 (SEQ ID NO: 1) of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. In certain embodiments, the targeting sequence comprises a sequence selected from SEQ ID NO: 13-SEQ ID NO: 86 (e.g., SEQ ID NOS: 13-58 or 59-75). In certain embodiments, the targeting sequence is selected from the group consisting of SEQ ID NOs: 13, 27-29, 34-36, 59, and 82. In certain embodiments, the targeting sequence comprises a sequence selected from Tables 2A-2C. Further, and with respect to the sequences outlined in Tables 2A-2C herein, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present.

In some embodiments of any of the antisense oligomers, methods, or compositions described herein, Z is an integer from 8 to 28, from 15 to 38, 15 to 28, 8 to 25, from 15 to 25, from 10 to 38, from 10 to 25, from 12 to 38, from 12 to 25, from 14 to 38, or from 14 to 25. In some embodiments of any of the antisense oligomers, methods, or compositions described herein, Z is 12, 13, 14, 15, 16, 17, 18, 19, 20, 21, 22, 23, 24, 25, 26, 27, 28, 29, 30, 31, 32, 33, 34, 35, 36, 37, or 38. In some embodiments of any of the antisense oligomers, methods, or compositions described herein, Z is 12, 13, 14, 15, 16, 17, 18, 19, 20, 21, 22, 23, 24, 25, 26, 27, or 28. In some embodiments of any of the antisense oligomers, methods, or compositions described herein, Z is 15, 16, 17, 18, 19, 20, 21, 22, 23, 24, or 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 8 to 28.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 15 to 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 15 to 28.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 8 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 15 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 10 to 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 10 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 12 to 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 12 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 14 to 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 14 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is 12, 13, 14, 15, 16, 17, 18, 19, 20, 21, 22, 23, 24, 25, 26, 27, 28, 29, 30, 31, 32, 33, 34, 35, 36, 37, or 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is 12, 13, 14, 15, 16, 17, 18, 19, 20, 21, 22, 23, 24, 25, 26, 27, or 28.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is 15, 16, 17, 18, 19, 20, 21, 22, 23, 24, or 25.

In some embodiments, each Nu of the antisense oligomers of the disclosure, including compounds of formula (I), (Ia), (IVa), (IVb), (IVc), (V), (VI), (VII), (VIIa), (VIIb), (VIIc), (VIId), (VIIe), and (VIII), is independently selected from the group consisting of adenine, guanine, thymine, uracil, cytosine, hypoxanthine, 2,6-diaminopurine, 5-methyl cytosine, $C_5$-propynyl-modified pyrimidines, and 9-(aminoethoxy) phenoxazine.

In some embodiments, the targeting sequence of the antisense oligomers of the disclosure, including compounds of formula (I), (Ia), (IVa), (IVb), (IVc), (V), (VI), (VII), (VIIa), (VIIb), (VIIc), (VIId), (VIIe), and (VIII), is complementary 10 or more contiguous nucleotides in a target region within intron 1 (SEQ ID. NO. 1), intron 2 (SEQ ID. NO. 60), or exon 2 (SEQ ID. NO. 61) of a pre-mRNA of the human acid alpha-glucosidase (GAA) gene. In certain embodiments, the targeting sequence of the antisense oligomers of the disclosure, including compounds of formula (I), (Ia), (IVa), (IVb), (IVc), (V), (VI), (VII), (VIIa), (VIIb), (VIIc), (VIId), (VIIe), and (VIII), comprises a sequence selected from the sequences of Tables 2A-2C, as described herein, is a fragment of at least 12 contiguous nucleotides of a sequence selected from Tables 2A-2C, as described herein, or is variant having at least 90% sequence identity to a sequence selected from Tables 2A-2C, as described herein (where X is selected from uracil (U) or thymine (T) as applicable depending on the referenced Table). In certain embodiments, the targeting sequence is selected from the group consisting of SEQ ID NOs: 13, 27-29, 34-36, 59, and 82.

Additional antisense oligomers/chemistries that can be used in accordance with the present disclosure include those described in the following patents and patent publications, the contents of which are incorporated herein by reference: PCT Publication Nos. WO/2007/002390; WO/2010/120820; and WO/2010/148249; U.S. Pat. No. 7,838,657; and U.S. Application No. 2011/0269820.

The antisense oligonucleotides can be prepared by stepwise solid-phase synthesis, employing methods known in the art and described in the references cited herein.

C. CPPs and Arginine-Rich Peptide Conjugates of PMOs (PPMOs)

In certain embodiments, the antisense oligonucleotide is conjugated to a cell-penetrating peptide (referred to herein as "CPP"). In some embodiments, the CPP is an arginine-rich peptide. The term "arginine-rich" refers to a CPP having at least 2, and preferably 2, 3, 4, 5, 6, 7, or 8 arginine residues, each optionally separated by one or more uncharged, hydrophobic residues, and optionally containing about 6-14 amino acid residues. As explained below, a CPP is preferably linked at its carboxy terminus to the 3' and/or 5' end of an antisense oligonucleotide through a linker, which may also be one or more amino acids, and is preferably also capped at its amino terminus by a substituent $R^a$ with $R^a$ selected from H, acyl, benzoyl, or stearoyl. In some embodiments, $R^a$ is acetyl.

As seen in the table below, Non-limiting examples of CPP's for use herein include —(RXR)$_4$-R$^a$, R-(FFR)$_3$—R$^a$, —B—X—(RXR)$_4$—R$^a$, —B—X—R-(FFR)$_3$-R$^a$, -GLY-R-(FFR)$_3$-R$^a$, -GLY-R$^6$—R$^a$ and —R$_6$—R$^a$, wherein R$^a$ is selected from H, acyl, benzoyl, and stearoyl, and wherein R is arginine, X is 6-aminohexanoic acid, B is β-alanine, F is phenylalanine and GLY (or G) is glycine. The CPP "$R^6$" is meant to indicate a peptide of six (6) arginine residues linked together via amide bonds (and not a single substituent e.g. $R^6$). In some embodiments, $R^a$ is acetyl.

Exemplary CPPs are provided in Table 2D (SEQ ID NOS:6-12).

TABLE 2D

Exemplary Cell-Penetrating Peptides

| Name | Sequence | SEQ ID NO: |
|---|---|---|
| $(RXR)_4$ | RXRRXRRXRRXR | 6 |
| $(RFF)_3R$ | RFFRFFRFFR | 7 |
| $(RXR)_4XB$ | RXRRXRRXRRXRXB | 8 |
| $(RFF)_3RXB$ | RFFRFFRFFRXB | 9 |
| $(RFF)_3RG$ | RFFRFFRFFR | 10 |
| $R_6G$ | RRRRRRG | 11 |
| $R_6$ | RRRRRR | 12 |

X is 6-aminohexanoic acid; B is β-alanine; F is phenylalanine; G is glycine

CPPs, their synthesis, and methods of conjugating to an oligomer are further described in U.S. Application Publication No. 2012/0289457 and International Patent Application Publication Nos. WO 2004/097017, WO 2009/005793, and WO 2012/150960, the disclosures of which are incorporated herein by reference in their entirety.

In some embodiments, an antisense oligonucleotide comprises a substituent "G," defined as the combination of a CPP and a linker. The linker bridges the CPP at its carboxy terminus to the 3'-end and/or the 5'-end of the oligonucleotide. In various embodiments, an antisense oligonucleotide may comprise only one CPP linked to the 3' end of the oligomer. In other embodiments, an antisense oligonucleotide may comprise only one CPP linked to the 5' end of the oligomer.

The linker within G may comprise, for example, 1, 2, 3, 4, or 5 amino acids.

In particular embodiments, G is selected from:
—C(O)(CH$_2$)$_5$NH-CPP;
—C(O)(CH$_2$)$_2$NH-CPP;
—C(O)(CH$_2$)$_2$NHC(O)(CH$_2$)$_5$NH-CPP;
—C(O)CH$_2$NH-CPP, and the formula:

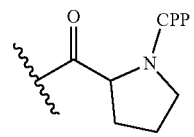

wherein the CPP is attached to the linker moiety by an amide bond at the CPP carboxy terminus.

In various embodiments, the CPP is an arginine-rich peptide as defined above and seen in Table 2D. In certain embodiments, the arginine-rich CPP is —$R^6$-$R^a$, (i.e., six arginine residues; SEQ ID NO: 12), wherein $R^a$ is selected from H, acyl, benzoyl, and stearoyl. $R^a$ is acetyl. In various embodiments, the CPP is selected from SEQ ID NOS: 6, 7, or 12, and the linker is selected from the group described above. In some embodiments, the CPP is SEQ ID NO: 12 and the linker is Gly.

In certain embodiments, G is —C(O)CH$_2$NH-$R^6$-$R^a$ covalently bonded to an antisense oligomer of the disclosure at the 5' and/or 3' end of the oligomer, wherein $R^a$ is H, acyl, benzoyl, or stearoyl to cap the amino terminus of the $R^6$. $R^a$ is acetyl. In these non-limiting example, the CPP is —$R^6$-$R^a$ and the linker is —C(O)CH$_2$NH—, (i.e. GLY). This particular example of G=—C(O)CH$_2$NH-$R^6$-$R^a$ is also exemplified by the following structure:

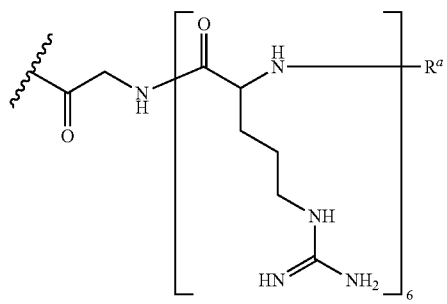

wherein $R^a$ is selected from H, acyl, benzoyl, and stearoyl. In some embodiments, G is selected from SEQ ID NOS: 3-6. In certain embodiments, G is SEQ ID NO: 6. In some embodiments, $R^a$ is acetyl.

In various embodiments, the CPP is —$R_6$—$R^a$, also exemplified as the following formula:

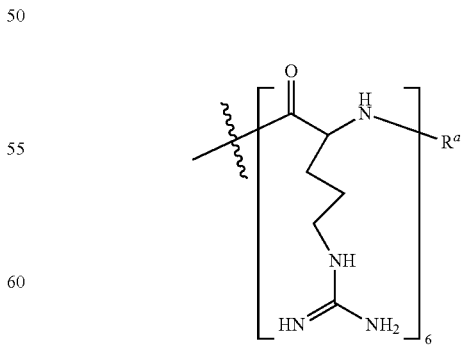

wherein $R^a$ is selected from H, acyl, benzoyl, and stearoyl. In certain embodiments, the CPP is SEQ ID NO: XX. In some embodiments, $R^a$ is acetyl.

In some embodiments, the CPP is —(RXR)$_4$-R$^a$, also exemplified as the following

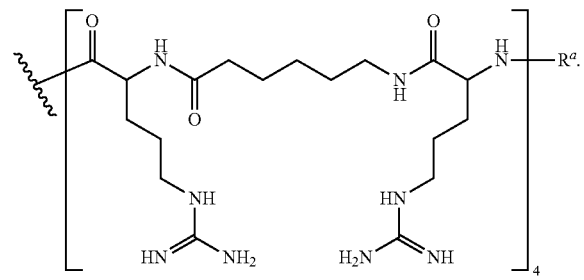

In various embodiments, the CPP is —R-(FFR)$_3$-R$^a$, also exemplified as the following formula:

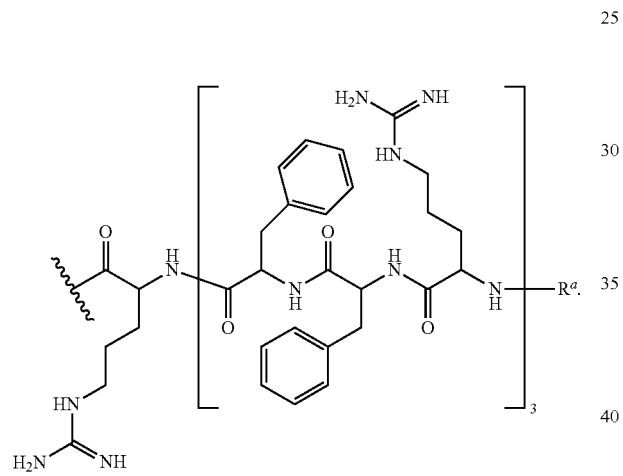

In various embodiments, G is selected from:
—C(O)(CH$_2$)$_5$NH-CPP;
—C(O)(CH$_2$)$_2$NH-CPP;
—C(O)(CH$_2$)$_2$NHC(O)(CH$_2$)$_5$NH-CPP;
—C(O)CH$_2$NH-CPP, and the formula:

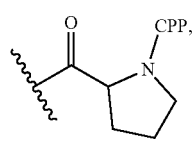

wherein the CPP is attached to the linker moiety by an amide bond at the CPP carboxy terminus, and wherein the CPP is selected from:

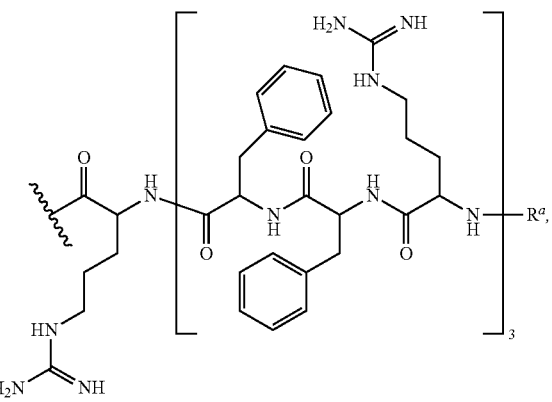

(—R—(FFR)$_3$—R$^a$),

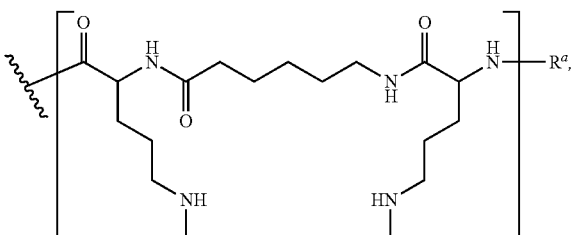

(—(RXR)$_4$—R$^a$), or

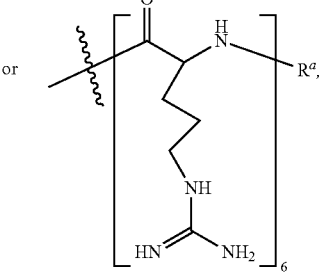

(—R$_6$—R$^a$). In some embodiments, R$^a$ is acetyl

In some embodiments, an antisense oligomer of the disclosure is a compound of formula (VIII) selected from:

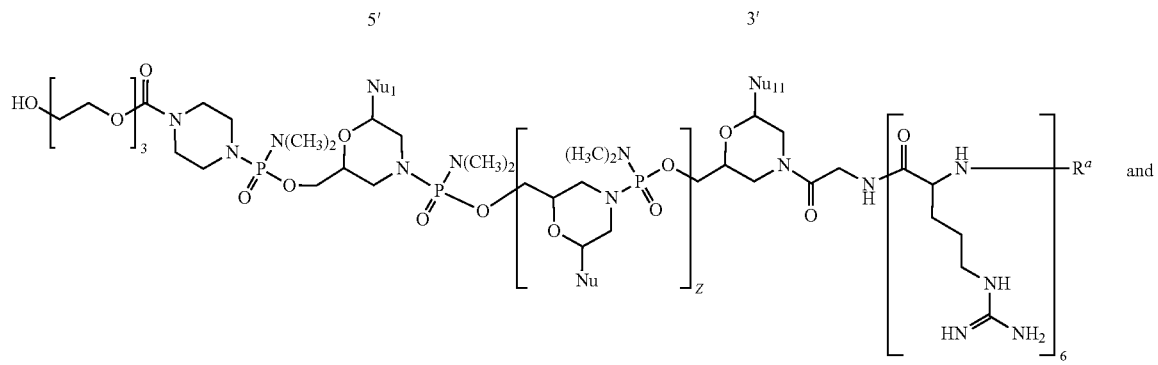

(VIIIa)

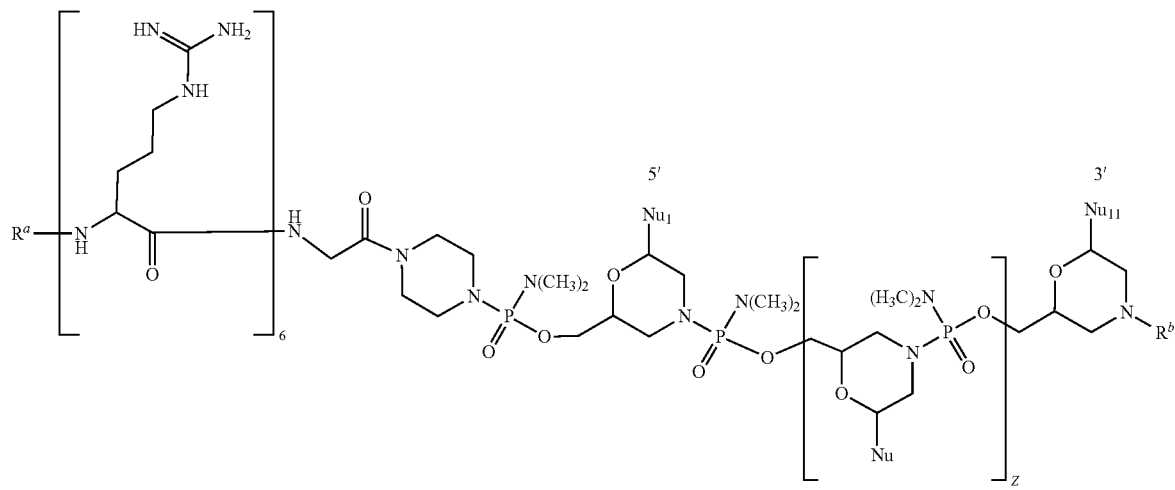

(VIIIb)

or a pharmaceutically acceptable salt of either of the foregoing, wherein:

each Nu is a purine or pyrimidine base-pairing moiety which taken together form a targeting sequence;

Z is an integer from 8 to 38;

$R^a$ is selected from H, acetyl, benzoyl, and stearoyl; and $R^b$ is selected from H, acetyl, benzoyl, stearoyl, trityl, and 4-methoxytrityl.

In some embodiments, including, for example, embodiments of the antisense oligomers of formula (VIII), the targeting sequence is complementary to a target region within intron 1 (SEQ ID NO: 1) of a pre-mRNA of the human alpha glucosidase (GAA) gene.

In various embodiments, including, for example, embodiments of the antisense oligomers of formula (VIII), the targeting sequence is complementary to a target region within intron 1 (SEQ ID NO: 1) of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. In certain embodiments, the targeting sequence comprises a sequence selected from SEQ ID NO: 13-SEQ ID NO: 86 (e.g., any one of SEQ ID NOs: 13-58 or 59-75). In certain embodiments, the targeting sequence comprises a sequence selected from Tables 2A-2C. In certain embodiments, the targeting sequence comprises a sequence selected from Tables 2A and 2B. Further, and with respect to the sequences outlined in Tables 2A-2C herein, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present.

In some embodiments, the targeting sequence of an antisense oligomers of the disclosure, including, for example, some embodiments of the antisense oligomers of formula (I), (Ia), (IVa), (IVb), (IVc), (V), (VI), (VII), (VIIa), (VIIb), (VIIc), (VIId), (VIIe), and (VIII), is selected from the sequences outlined in Tables 2A-2C, as described herein, and as follows:

I.

uu)
(GGC CAG AAG GAA GGC GAG AAA AGC)
wherein Z is 22;
SEQ ID NO: 13 vv)
(GCC AGA AGG AAG GC GAG AAA AGC X)
wherein Z is 22;
SEQ ID NO: 14 ww)
(CCA GAA GGA AGG CGA GAA AAG CXC)
wherein Z is 22;
SEQ ID NO: 15 xx)
(CAG AAG GAA GGC GAG AAA AGC XCC)
wherein Z is 22;
SEQ ID NO: 16 yy)
(AGA AGG AAG GCG AGA AAA GCX CCA)
wherein Z is 22;
SEQ ID NO: 17 zz)
(GAA GGA AGG CGA GAA AAG CXC CAG)
wherein Z is 22;
SEQ ID NO: 18 aaa)
(AAG GAA GGC GAG AAA AGC XCC AGC)
wherein Z is 22;
SEQ ID NO: 19 bbb)
(AGG AAG GCG AGA AAA GCX CCA GCA)
wherein Z is 22;
SEQ ID NO: 20 ccc)
(CGG CXC XCA AAG CAG CXC XGA GA)
wherein Z is 21;
SEQ ID NO: 21 ddd)
(ACG GCX CXC AAA GCA GCX CXG AG)
wherein Z is 21;
SEQ ID NO: 22 eee)
(CAC GGC XCX CAA AGC AGC XCX GA)
wherein Z is 21;
SEQ ID NO: 23 fff)
(XCA CGG CXC XCA AAG CAG CXC XG)
wherein Z is 21;
SEQ ID NO: 24 ggg)
(CXC ACG GCX CXC AAA GCA GCX CX)
wherein Z is 21;
SEQ ID NO: 25 hhh)
(ACX CAC GGC XCX CAA AGC AGC XC)
wherein Z is 21;
SEQ ID NO: 26 iii)
(GCG GCA CXC ACG GCX CXC AAA GC)
wherein Z is 21;
SEQ ID NO: 27 jjj)
(GGC GGC ACX CAC GGC XCX CAA AG)
wherein Z is 21;
SEQ ID NO: 28 kkk)
(CGG CAC XCA CGG CXC XCA AAG CA)
wherein Z is 21;
SEQ ID NO: 29 lll)
(GCA CXC ACG GCX CXC AAA GCA GC)
wherein Z is 21;
SEQ ID NO: 30 mmm)
(GGC ACX CAC GGC XCX CAA AGC AG)
wherein Z is 21;
SEQ ID NO: 31 nnn)
(CAC XCA CGG CXC XCA AAG CAG CX)
wherein Z is 21;
SEQ ID NO: 32 ooo)
(GCC AGA AGG AAG GCG AGA AAA GC)
wherein Z is 21;
SEQ ID NO: 33 ppp)
(CCA GAA GGA AGG CGA GAA AAG C)
wherein Z is 19;
SEQ ID NO: 34 qqq)
(CAG AAG GAA GGC GAG AAA AGC)
wherein Z is 19;
SEQ ID NO: 35 rrr)
(GGC CAG AAG GAA GGC GAG AAA AG)
wherein Z is 21;
SEQ ID NO: 36 sss)
(GGC CAG AAG GAA GGC GAG AAA A)
wherein Z is 19;
SEQ ID NO: 37 ttt)
(GGC CAG AAG GAA GGC GAG AAA)
wherein Z is 19;
SEQ ID NO: 38 uuu)
(CGG CAC XCA CGGC XCX CAA AGC A)
wherein Z is 21;
SEQ ID NO: 39 vvv)
(GCG GCA CXC ACGG CXC XCA AAG C)
wherein Z is 21;
SEQ ID NO: 40 www)
(GGC GGC ACX CAC G GCX CXC AAA G)
wherein Z is 21;
SEQ ID NO: 41 xxx)
(XGG GGA GAG GGC CAG AAG GAA GGC)
wherein Z is 22;
SEQ ID NO: 42 yyy)
(XGG GGA GAG GGC CAG AAG GAA GC)
wherein Z is 21;
SEQ ID NO: 43 zzz)
(XGG GGA GAG GGC CAG AAG GAA C)
wherein Z is 20;
SEQ ID NO: 44 aaaa)
(GGC CAG AAG GAA GCG AGA AAA GC) SEQ ID NO: 45
wherein Z is 21;

bbbb)
(GGC CAG AAG GAA CGA GAA AAG C) SEQ ID NO: 46
wherein Z is 20;

cccc)
(AGG AAG CGA GAA AAG CXC CAG CA) SEQ ID NO: 47
wherein Z is 21;

dddd)
(AGG AAC GAG AAA AGC XCC AGC A) SEQ ID NO: 48
wherein Z is 20;

eeee)
(CGG GCX CXC AAA GCA GCX CXG AGA) SEQ ID NO: 49
wherein Z is 22;

ffff)
(CGC XCX CAA AGC AGC XCX GAG A) SEQ ID NO: 50
wherein Z is 20;

gggg)
(CCX CXC AAA GCA GCX CXG AGA) SEQ ID NO: 51
wherein Z is 19;

hhhh)
(GGC GGC ACX CAC GGG CXC XCA AAG) SEQ ID NO: 52
wherein Z is 22;

iiii)
(GGC GGC ACX CAC GCX CXC AAA G) SEQ ID NO: 53
wherein Z is 20;

jjjj)
(GGC GGC ACX CAC CXC XCA AAG) SEQ ID NO: 54
wherein Z is 19;

kkkk)
(GCG GGA GGG GCG GCA CXC ACG GGC) SEQ ID NO: 55
wherein Z is 22;

llll)
(GCG GGA GGG GCG GCA CXC ACG GC) SEQ ID NO: 56
wherein Z is 21;

mmmm)
(GCG GGA GGG GCG GCA CXC ACG C) SEQ ID NO: 57
wherein Z is 20;
and nnnn)
(GCG GGA GGG GCG GCA CXC ACC) wherein Z is 19, SEQ ID NO: 58
wherein X is selected from uracil (U) or thymine (T);

II.
r)
(GGC CAG AAG GAA GGG CGA GAA AAG C) SEQ ID NO: 59
wherein Z is 23;

s)
(CCA GAA GGA AGG GCG AGA AAA GCX C) SEQ ID NO: 60
wherein Z is 23;

t)
(AAG GAA GGG CGA GAA AAG CXC CAG C) SEQ ID NO: 61
wherein Z is 23;

u)
(GCG GGA GGG GCG GCA CXC ACG GGG C) SEQ ID NO: 62
wherein Z is 23;

v)
(XGG GGA GAG GGC CAG AAG GAA GGG C) SEQ ID NO: 63
wherein Z is 23;

w)
(AGA AGG AAG GGC GAG AAA AGC XCC A) SEQ ID NO: 64
wherein Z is 23;

x)
(GCX CXC AAA GCA GCX CXG AGA CAX C) SEQ ID NO: 65
wherein Z is 23;

y)
(CXC XCA AAG CAG CXC XGA GAC AXC A) SEQ ID NO: 66
wherein Z is 23;

z)
(XCX CAA AGC AGC XCX GAG ACA XCA A) SEQ ID NO: 67
wherein Z is 23;

aa)
(CXC AAA GCA GCX CXG AGA CAX CAA C) SEQ ID NO: 68
wherein Z is 23;

bb)
(XCA AAG CAG CXC XGA GAC AXC AAC C) SEQ ID NO: 69
wherein Z is 23;

cc)
(CAA AGC AGC XCX GAG ACA XCA ACC G) SEQ ID NO: 70
wherein Z is 23;

dd)
(AAA GCA GCX CXG AGA CAX CAA CCG C) SEQ ID NO: 71
wherein Z is 23;

ee)
(AAG CAG CXC XGA GAC AXC AAC CGC G) SEQ ID NO: 72
wherein Z is 23;

ff)
(AGC AGC XCX GAG ACA XCA ACC GCG G) SEQ ID NO: 73
wherein Z is 23;

gg)
(GCA GCX CXG AGA CAX CAA CCG CGG C) SEQ ID NO: 74
wherein Z is 23;
and

-continued hh)
SEQ ID NO: 75
(CAG CXC XGA GAC AXC AAC CGC GGC X)
wherein Z is 23,
wherein X is selected from uracil (U) or thymine
(T);
and III.
1)
SEQ ID NO: 76
(GCC AGA AGG AAG GGC GAG AAA AGC X)
wherein Z is 23;

m)
SEQ ID NO: 77
(CAG AAG GAA GGG CGA GAA AAG CXC C)
wherein Z is 23;

n)
SEQ ID NO: 78
(GAA GGA AGG GCG AGA AAA GCX CCA G)
wherein Z is 23;

o)
SEQ ID NO: 79
(AGG AAG GGC GAG AAA AGC XCC AGC A)
wherein Z is 23;

p)
SEQ ID NO: 80
(ACX CAC GGG GCX CXC AAA GCA GCX C)
wherein Z is 23;

q)
SEQ ID NO: 81
(GGCXCXCAAAGCAGCXCXGAGACAX)
wherein Z is 23;

r)
SEQ ID NO: 82
(GGC XCX CAA AGC AGC XCX GA)
wherein Z is 18;

s)
SEQ ID NO: 83
(GAG AGG GCC AGA AGG AAG GG)
wherein Z is 18;

t)
SEQ ID NO: 84
(XXX GCC AXG XXA CCC AGG CX)
wherein Z is 18;

u)
SEQ ID NO: 85
(GCG CAC CCX CXG CCC XGG CC)
wherein Z is 18;
and v)
SEQ ID NO: 86
(GGC CCX GGX CXG CXG GCX CCC XGC X)
wherein Z is 23,
wherein X is selected from uracil (U) or thymine
(T).

In certain embodiments, the targeting sequence is selected from the group consisting of SEQ ID NOs: 13, 27-29, 34-36, 59, and 82. In certain embodiments, the targeting sequence is selected from the group consisting of SEQ ID NOs: 13, 27-29, 34-36, and 59. In certain embodiments, the targeting sequence is selected from the group consisting of SEQ ID NOs: 13, 27-29, and 34-36. In certain embodiments, each instance of X in any one of SEQ ID NOs: 13, 27-29, 34-36, 59, and 82 is T.

In some embodiments, the targeting sequence of the antisense oligomer compound of formula (I) is selected from the sequences outlined in Tables 2A-2C. In some embodiments, the targeting sequence of the antisense oligomer compound of formula (Ia) is selected from the sequences outlined in Tables 2A-2C. In some embodiments, the targeting sequence of the antisense oligomer compound of formula (IVa) is selected from the sequences outlined in Tables 2A-2C. In some embodiments, the targeting sequence of the antisense oligomer compound of formula (IVb) is selected from the sequences outlined in Tables 2A-2C. In some embodiments, the targeting sequence of the antisense oligomer compound of formula (IVc) is selected from the sequences outlined in Tables 2A-2C. In some embodiments, the targeting sequence of the antisense oligomer compound of formula (V) is selected from the sequences outlined in Tables 2A-2C. In some embodiments, the targeting sequence of the antisense oligomer compound of formula (VI) is selected from the sequences outlined in Tables 2A-2C. In some embodiments, the targeting sequence of the antisense oligomer compound of formula (VII) is selected from the sequences outlined in Tables 2A-2C. In some embodiments, the targeting sequence of the antisense oligomer compound of formula (VIIa) is selected from the sequences outlined in Tables 2A-2C. In some embodiments, the targeting sequence of the antisense oligomer compound of formula (VIIb) is selected from the sequences outlined in Tables 2A-2C. In some embodiments, the targeting sequence of the antisense oligomer compound of formula (VIIc) is selected from the sequences outlined in Tables 2A-2C. In some embodiments, the targeting sequence of the antisense oligomer compound of formula (VIId) is selected from the sequences outlined in Tables 2A-2C. In some embodiments, the targeting sequence of the antisense oligomer compound of formula (VIIe) is selected from the sequences outlined in Tables 2A-2C. In some embodiments, the targeting sequence of the antisense oligomer compound of formula (VIII) is selected from the sequences outlined in Tables 2A-2C.

In some embodiments, at least one X of sequences outlined in Tables 2A-2C is T. In some embodiments, at least one X of sequences outlined in Tables 2A-2C is U. In some embodiments, each X of sequences outlined in Tables 2A-2C is T. In some embodiments, each X of sequences outlined in Tables 2A-2C is U. In various embodiments, at least one X of the targeting sequence is T. In various embodiments, each X of the targeting sequence is T. In various embodiments, at least one X of the targeting sequence is U. In various embodiments, each X of the targeting sequence is U.

Further, in some embodiments, an antisense oligomer of the disclosure is a compound of formula (XX):

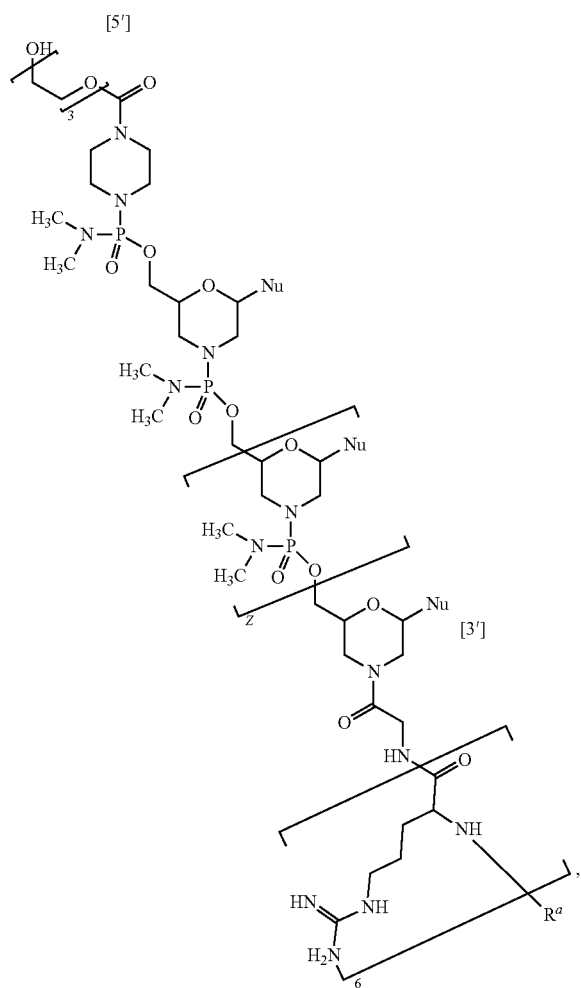

(XX)

or a pharmaceutically acceptable salt thereof, wherein:

I.
a) each Nu is a nucleobase which taken together form the targeting sequence (5' to 3') of: SEQ ID NO: 13 (GGC CAG AAG GAA GGC GAG AAA AGC) wherein Z is 22;
b) each Nu is a nucleobase which taken together form the targeting sequence (5' to 3') of: SEQ ID NO: 14 (GCC AGA AGG AAG GC GAG AAA AGC X) wherein Z is 22;
c) each Nu is a nucleobase which taken together form the targeting sequence (5' to 3') of: SEQ ID NO: 15 (CCA GAA GGA AGG CGA GAA AAG CXC) wherein Z is 22;
d) each Nu is a nucleobase which taken together form the targeting sequence (5' to 3') of: SEQ ID NO: 16 (CAG AAG GAA GGC GAG AAA AGC XCC) wherein Z is 22;
e) each Nu is a nucleobase which taken together form the targeting sequence (5' to 3') of: SEQ ID NO: 17 (AGA AGG AAG GCG AGA AAA GCX CCA) wherein Z is 22;
f) each Nu is a nucleobase which taken together form the targeting sequence (5' to 3') of: SEQ ID NO: 18 (GAA GGA AGG CGA GAA AAG CXC CAG) wherein Z is 22;
g) each Nu is a nucleobase which taken together form the targeting sequence (5' to 3') of: SEQ ID NO: 19 (AAG GAA GGC GAG AAA AGC XCC AGC) wherein Z is 22;
h) each Nu is a nucleobase which taken together form the targeting sequence (5' to 3') of: SEQ ID NO: 20 (AGG AAG GCG AGA AAA GCX CCA GCA) wherein Z is 22;
i) each Nu is a nucleobase which taken together form the targeting sequence (5' to 3') of: SEQ ID NO: 21 (CGG CXC XCA AAG CAG CXC XGA GA) wherein Z is 21;
j) each Nu is a nucleobase which taken together form the targeting sequence (5' to 3') of: SEQ ID NO: 22 (ACG GCX CXC AAA GCA GCX CXG AG) wherein Z is 21;
k) each Nu is a nucleobase which taken together form the targeting sequence (5' to 3') of: SEQ ID NO: 23 (CAC GGC XCX CAA AGC AGC XCX GA) wherein Z is 21;
l) each Nu is a nucleobase which taken together form the targeting sequence (5' to 3') of: SEQ ID NO: 24 (XCA CGG CXC XCA AAG CAG CXC XG) wherein Z is 21;
m) each Nu is a nucleobase which taken together form the targeting sequence (5' to 3') of: SEQ ID NO: 25 (CXC ACG GCX CXC AAA GCA GCX CX) wherein Z is 21;
n) each Nu is a nucleobase which taken together form the targeting sequence (5' to 3') of: SEQ ID NO: 26 (ACX CAC GGC XCX CAA AGC AGC XC) wherein Z is 21;
o) each Nu is a nucleobase which taken together form the targeting sequence (5' to 3') of: SEQ ID NO: 27 (GCG GCA CXC ACG GCX CXC AAA GC) wherein Z is 21;
p) each Nu is a nucleobase which taken together form the targeting sequence (5' to 3') of: SEQ ID NO: 28 (GGC GGC ACX CAC GGC XCX CAA AG) wherein Z is 21;
q) each Nu is a nucleobase which taken together form the targeting sequence (5' to 3') of: SEQ ID NO: 29 (CGG CAC XCA CGG CXC XCA AAG CA) wherein Z is 21;
r) each Nu is a nucleobase which taken together form the targeting sequence (5' to 3') of: SEQ ID NO: 30 (GCA CXC ACG GCX CXC AAA GCA GC) wherein Z is 21;
s) each Nu is a nucleobase which taken together form the targeting sequence (5' to 3') of: SEQ ID NO: 31 (GGC ACX CAC GGC XCX CAA AGC AG) wherein Z is 21;
t) each Nu is a nucleobase which taken together form the targeting sequence (5' to 3') of: SEQ ID NO: 32 (CAC XCA CGG CXC XCA AAG CAG CX) wherein Z is 21;
u) each Nu is a nucleobase which taken together form the targeting sequence (5' to 3') of: SEQ ID NO: 33 (GCC AGA AGG AAG GCG AGA AAA GC) wherein Z is 21;
v) each Nu is a nucleobase which taken together form the targeting sequence (5' to 3') of: SEQ ID NO: 34 (CCA GAA GGA AGG CGA GAA AAG C) wherein Z is 20;
w) each Nu is a nucleobase which taken together form the targeting sequence (5' to 3') of: SEQ ID NO: 35 (CAG AAG GAA GGC GAG AAA AGC) wherein Z is 19;
x) each Nu is a nucleobase which taken together form the targeting sequence (5' to 3') of: SEQ ID NO: 36 (GGC CAG AAG GAA GGC GAG AAA AG) wherein Z is 21;
y) each Nu is a nucleobase which taken together form the targeting sequence (5' to 3') of: SEQ ID NO: 37 (GGC CAG AAG GAA GGC GAG AAA A) wherein Z is 20;
z) each Nu is a nucleobase which taken together form the targeting sequence (5' to 3') of: SEQ ID NO: 38 (GGC CAG AAG GAA GGC GAG AAA) wherein Z is 19;

aa) each Nu is a nucleobase which taken together form the targeting sequence (5' to 3') of: SEQ ID NO: 39 (CGG CAC XCA CGGC XCX CAA AGC A) wherein Z is 21;

bb) each Nu is a nucleobase which taken together form the targeting sequence (5' to 3') of: SEQ ID NO: 40 (GCG GCA CXC ACGG CXC XCA AAG C) wherein Z is 21;

cc) each Nu is a nucleobase which taken together form the targeting sequence (5' to 3') of: SEQ ID NO: 41 (GGC GGC ACX CAC G GCX CXC AAA G) wherein Z is 21;

dd) each Nu is a nucleobase which taken together form the targeting sequence (5' to 3') of: SEQ ID NO: 42 (XGG GGA GAG GGC CAG AAG GAA GGC) wherein Z is 22;

ee) each Nu is a nucleobase which taken together form the targeting sequence (5' to 3') of: SEQ ID NO: 43 (XGG GGA GAG GGC CAG AAG GAA GC) wherein Z is 21;

ff) each Nu is a nucleobase which taken together form the targeting sequence (5' to 3') of: SEQ ID NO: 44 (XGG GGA GAG GGC CAG AAG GAA C) wherein Z is 20;

gg) each Nu is a nucleobase which taken together form the targeting sequence (5' to 3') of: SEQ ID NO: 45 (GGC CAG AAG GAA GCG AGA AAA GC) wherein Z is 21;

hh) each Nu is a nucleobase which taken together form the targeting sequence (5' to 3') of: SEQ ID NO: 46 (GGC CAG AAG GAA CGA GAA AAG C) wherein Z is 20;

ii) each Nu is a nucleobase which taken together form the targeting sequence (5' to 3') of: SEQ ID NO: 47 (AGG AAG CGA GAA AAG CXC CAG CA) wherein Z is 21;

jj) each Nu is a nucleobase which taken together form the targeting sequence (5' to 3') of: SEQ ID NO: 48 (AGG AAC GAG AAA AGC XCC AGC A) wherein Z is 20;

kk) each Nu is a nucleobase which taken together form the targeting sequence (5' to 3') of: SEQ ID NO: 49 (CGG GCX CXC AAA GCA GCX CXG AGA) wherein Z is 22;

ll) each Nu is a nucleobase which taken together form the targeting sequence (5' to 3') of: SEQ ID NO: 50 (CGC XCX CAA AGC AGC XCX GAG A) wherein Z is 20;

mm) each Nu is a nucleobase which taken together form the targeting sequence (5' to 3') of: SEQ ID NO: 51 (CCX CXC AAA GCA GCX CXG AGA) wherein Z is 19;

nn) each Nu is a nucleobase which taken together form the targeting sequence (5' to 3') of: SEQ ID NO: 52 (GGC GGC ACX CAC GGG CXC XCA AAG) wherein Z is 22;

oo) each Nu is a nucleobase which taken together form the targeting sequence (5' to 3') of: SEQ ID NO: 53 (GGC GGC ACX CAC GCX CXC AAA G) wherein Z is 20;

pp) each Nu is a nucleobase which taken together form the targeting sequence (5' to 3') of: SEQ ID NO: 54 (GGC GGC ACX CAC CXC XCA AAG) wherein Z is 19;

qq) each Nu is a nucleobase which taken together form the targeting sequence (5' to 3') of: SEQ ID NO: 55 (GCG GGA GGG GCG GCA CXC ACG GGC) wherein Z is 22;

rr) each Nu is a nucleobase which taken together form the targeting sequence (5' to 3') of: SEQ ID NO: 56 (GCG GGA GGG GCG GCA CXC ACG GC) wherein Z is 21;

ss) each Nu is a nucleobase which taken together form the targeting sequence (5' to 3') of: SEQ ID NO: 57 (GCG GGA GGG GCG GCA CXC ACG C) wherein Z is 20; and tt) each Nu is a nucleobase which taken together form the targeting sequence (5' to 3') of: SEQ ID NO: 58 (GCG GGA GGG GCG GCA CXC ACC) wherein Z is 19, wherein X is selected from uracil (U) or thymine (T);

II.

a) each Nu is a nucleobase which taken together form the targeting sequence (5' to 3') of: SEQ ID NO: 59 (GGC CAG AAG GAA GGG CGA GAA AAG C) wherein Z is 23;

b) each Nu is a nucleobase which taken together form the targeting sequence (5' to 3') of: SEQ ID NO: 60 (CCA GAA GGA AGG GCG AGA AAA GCX C) wherein Z is 23;

c) each Nu is a nucleobase which taken together form the targeting sequence (5' to 3') of: SEQ ID NO: 61 (AAG GAA GGG CGA GAA AAG CXC CAG C) wherein Z is 23;

d) each Nu is a nucleobase which taken together form the targeting sequence (5' to 3') of: SEQ ID NO: 62 (GCG GGA GGG GCG GCA CXC ACG GGG C) wherein Z is 23;

e) each Nu is a nucleobase which taken together form the targeting sequence (5' to 3') of: SEQ ID NO: 63 (XGG GGA GAG GGC CAG AAG GAA GGG C) wherein Z is 23;

f) each Nu is a nucleobase which taken together form the targeting sequence (5' to 3') of: SEQ ID NO: 64 (AGA AGG AAG GGC GAG AAA AGC XCC A) wherein Z is 23;

g) each Nu is a nucleobase which taken together form the targeting sequence (5' to 3') of: SEQ ID NO: 65 (GCX CXC AAA GCA GCX CXG AGA CAX C) wherein Z is 23;

h) each Nu is a nucleobase which taken together form the targeting sequence (5' to 3') of: SEQ ID NO: 66 (CXC XCA AAG CAG CXC XGA GAC AXC A) wherein Z is 23;

i) each Nu is a nucleobase which taken together form the targeting sequence (5' to 3') of: SEQ ID NO: 67 (XCX CAA AGC AGC XCX GAG ACA XCA A) wherein Z is 23;

j) each Nu is a nucleobase which taken together form the targeting sequence (5' to 3') of: SEQ ID NO: 68 (CXC AAA GCA GCX CXG AGA CAX CAA C) wherein Z is 23;

k) each Nu is a nucleobase which taken together form the targeting sequence (5' to 3') of: SEQ ID NO: 69 (XCA AAG CAG CXC XGA GAC AXC AAC C) wherein Z is 23;

l) each Nu is a nucleobase which taken together form the targeting sequence (5' to 3') of: SEQ ID NO: 70 (CAA AGC AGC XCX GAG ACA XCA ACC G) wherein Z is 23;

m) each Nu is a nucleobase which taken together form the targeting sequence (5' to 3') of: SEQ ID NO: 71 (AAA GCA GCX CXG AGA CAX CAA CCG C) wherein Z is 23;

n) each Nu is a nucleobase which taken together form the targeting sequence (5' to 3') of: SEQ ID NO: 72 (AAG CAG CXC XGA GAC AXC AAC CGC G) wherein Z is 23;

o) each Nu is a nucleobase which taken together form the targeting sequence (5' to 3') of: SEQ ID NO: 73 (AGC AGC XCX GAG ACA XCA ACC GCG G) wherein Z is 23;

p) each Nu is a nucleobase which taken together form the targeting sequence (5' to 3') of: SEQ ID NO: 74 (GCA GCX CXG AGA CAX CAA CCG CGG C) wherein Z is 23; and q) each Nu is a nucleobase which taken together form the targeting sequence (5' to 3') of: SEQ ID NO: 75 (CAG CXC XGA GAC AXC AAC CGC GGC X) wherein Z is 23, wherein X is selected from uracil (U) or thymine (T); and

III.

a) each Nu is a nucleobase which taken together form the targeting sequence (5' to 3') of: SEQ ID NO: 76 (GCC AGA AGG AAG GGC GAG AAA AGC X) wherein Z is 23;

b) each Nu is a nucleobase which taken together form the targeting sequence (5' to 3') of: SEQ ID NO: 77 (CAG AAG GAA GGG CGA GAA AAG CXC C) wherein Z is 23;

c) each Nu is a nucleobase which taken together form the targeting sequence (5' to 3') of: SEQ ID NO: 78 (GAA GGA AGG GCG AGA AAA GCX CCA G) wherein Z is 23;

d) each Nu is a nucleobase which taken together form the targeting sequence (5' to 3') of: SEQ ID NO: 79 (AGG AAG GGC GAG AAA AGC XCC AGC A) wherein Z is 23;

e) each Nu is a nucleobase which taken together form the targeting sequence (5' to 3') of: SEQ ID NO: 80 (ACX CAC GGG GCX CXC AAA GCA GCX C) wherein Z is 23;

f) each Nu is a nucleobase which taken together form the targeting sequence (5' to 3') of: SEQ ID NO: 81 (GGCXCXCAAAGCAGCXCXGAGACAX) wherein Z is 23;

g) each Nu is a nucleobase which taken together form the targeting sequence (5' to 3') of: SEQ ID NO: 82 (GGC XCX CAA AGC AGC XCX GA) wherein Z is 18;

h) each Nu is a nucleobase which taken together form the targeting sequence (5' to 3') of: SEQ ID NO: 83 (GAG AGG GCC AGA AGG AAG GG) wherein Z is 18;

i) each Nu is a nucleobase which taken together form the targeting sequence (5' to 3') of: SEQ ID NO: 84 (XXX GCC AXG XXA CCC AGG CX) wherein Z is 18;

j) each Nu is a nucleobase which taken together form the targeting sequence (5' to 3') of: SEQ ID NO: 85 (GCG CAC CCX CXG CCC XGG CC) wherein Z is 18; and k) each Nu is a nucleobase which taken together form the targeting sequence (5' to 3') of: SEQ ID NO: 86 (GGC CCX GGX CXG CXG GCX CCC XGC X) wherein Z is 23, wherein X is selected from uracil (U) or thymine (T); and wherein $R^a$ is H or acetyl.

In some embodiments, at least one X of SEQ ID NOS: 13-86 is T. In some embodiments, at least one X of SEQ ID NOS: 13-86 is U. In some embodiments, each X of SEQ ID NOS: 13-86 is T. In some embodiments, each X of SEQ ID NOS: 13-86 is U. In various embodiments, at least one X of the targeting sequence is T. In various embodiments, each X of the targeting sequence is T. In various embodiments, at least one X of the targeting sequence is U. In various embodiments, each X of the targeting sequence is U.

In certain embodiments, the targeting sequence is selected from the group consisting of SEQ ID NOs: 13, 27-29, 34-36, 59, and 82. In some embodiments, at least one X of SEQ ID NOS: 13, 27-29, 34-36, 59, and 82 is T. In some embodiments, at least one X of SEQ ID NOS: 13, 27-29, 34-36, 59, and 82 is U. In some embodiments, each X of SEQ ID NOS: 13, 27-29, 34-36, 59, and 82 is T. In some embodiments, each X of SEQ ID NOS: 13, 27-29, 34-36, 59, and 82 is U.

In some embodiments of the antisense oligomers of the disclosure including, for example, antisense oligomers of formula (XX), the antisense oligomer can be of formula (XXI):

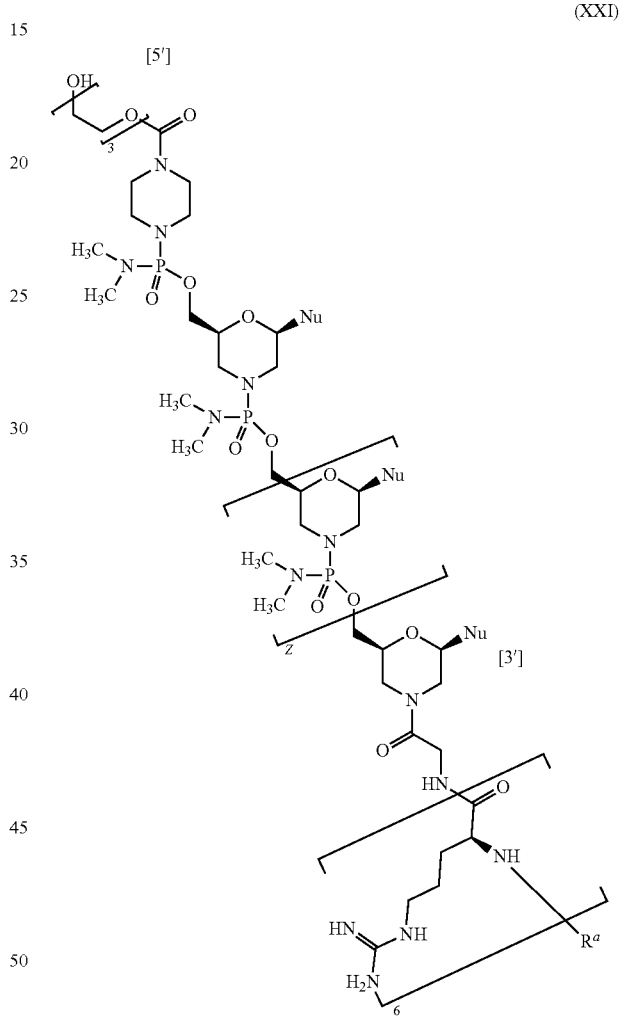

(XXI)

or a pharmaceutically acceptable salt thereof, wherein:

I.

a) each Nu is a nucleobase which taken together form the targeting sequence (5' to 3') of: SEQ ID NO: 13 (GGC CAG AAG GAA GGC GAG AAA AGC) wherein Z is 22;

b) each Nu is a nucleobase which taken together form the targeting sequence (5' to 3') of: SEQ ID NO: 14 (GCC AGA AGG AAG GC GAG AAA AGC X) wherein Z is 22;

c) each Nu is a nucleobase which taken together form the targeting sequence (5' to 3') of: SEQ ID NO: 15 (CCA GAA GGA AGG CGA GAA AAG CXC) wherein Z is 22;

d) each Nu is a nucleobase which taken together form the targeting sequence (5' to 3') of: SEQ ID NO: 16 (CAG AAG GAA GGC GAG AAA AGC XCC) wherein Z is 22;
e) each Nu is a nucleobase which taken together form the targeting sequence (5' to 3') of: SEQ ID NO: 17 (AGA AGG AAG GCG AGA AAA GCX CCA) wherein Z is 22;
f) each Nu is a nucleobase which taken together form the targeting sequence (5' to 3') of: SEQ ID NO: 18 (GAA GGA AGG CGA GAA AAG CXC CAG) wherein Z is 22;
g) each Nu is a nucleobase which taken together form the targeting sequence (5' to 3') of: SEQ ID NO: 19 (AAG GAA GGC GAG AAA AGC XCC AGC) wherein Z is 22;
h) each Nu is a nucleobase which taken together form the targeting sequence (5' to 3') of: SEQ ID NO: 20 (AGG AAG GCG AGA AAA GCX CCA GCA) wherein Z is 22;
i) each Nu is a nucleobase which taken together form the targeting sequence (5' to 3') of: SEQ ID NO: 21 (CGG CXC XCA AAG CAG CXC XGA GA) wherein Z is 21;
j) each Nu is a nucleobase which taken together form the targeting sequence (5' to 3') of: SEQ ID NO: 22 (ACG GCX CXC AAA GCA GCX CXG AG) wherein Z is 21;
k) each Nu is a nucleobase which taken together form the targeting sequence (5' to 3') of: SEQ ID NO: 23 (CAC GGC XCX CAA AGC AGC XCX GA) wherein Z is 21;
l) each Nu is a nucleobase which taken together form the targeting sequence (5' to 3') of: SEQ ID NO: 24 (XCA CGG CXC XCA AAG CAG CXC XG) wherein Z is 21;
m) each Nu is a nucleobase which taken together form the targeting sequence (5' to 3') of: SEQ ID NO: 25 (CXC ACG GCX CXC AAA GCA GCX CX) wherein Z is 21;
n) each Nu is a nucleobase which taken together form the targeting sequence (5' to 3') of: SEQ ID NO: 26 (ACX CAC GGC XCX CAA AGC AGC XC) wherein Z is 21;
o) each Nu is a nucleobase which taken together form the targeting sequence (5' to 3') of: SEQ ID NO: 27 (GCG GCA CXC ACG GCX CXC AAA GC) wherein Z is 21;
p) each Nu is a nucleobase which taken together form the targeting sequence (5' to 3') of: SEQ ID NO: 28 (GGC GGC ACX CAC GGC XCX CAA AG) wherein Z is 21;
q) each Nu is a nucleobase which taken together form the targeting sequence (5' to 3') of: SEQ ID NO: 29 (CGG CAC XCA CGG CXC XCA AAG CA) wherein Z is 21;
r) each Nu is a nucleobase which taken together form the targeting sequence (5' to 3') of: SEQ ID NO: 30 (GCA CXC ACG GCX CXC AAA GCA GC) wherein Z is 21;
s) each Nu is a nucleobase which taken together form the targeting sequence (5' to 3') of: SEQ ID NO: 31 (GGC ACX CAC GGC XCX CAA AGC AG) wherein Z is 21;
t) each Nu is a nucleobase which taken together form the targeting sequence (5' to 3') of: SEQ ID NO: 32 (CAC XCA CGG CXC XCA AAG CAG CX) wherein Z is 21;
u) each Nu is a nucleobase which taken together form the targeting sequence (5' to 3') of: SEQ ID NO: 33 (GCC AGA AGG AAG GCG AGA AAA GC) wherein Z is 21;
v) each Nu is a nucleobase which taken together form the targeting sequence (5' to 3') of: SEQ ID NO: 34 (CCA GAA GGA AGG CGA GAA AAG C) wherein Z is 20;
w) each Nu is a nucleobase which taken together form the targeting sequence (5' to 3') of: SEQ ID NO: 35 (CAG AAG GAA GGC GAG AAA AGC) wherein Z is 19;
x) each Nu is a nucleobase which taken together form the targeting sequence (5' to 3') of: SEQ ID NO: 36 (GGC CAG AAG GAA GGC GAG AAA AG) wherein Z is 21;
y) each Nu is a nucleobase which taken together form the targeting sequence (5' to 3') of: SEQ ID NO: 37 (GGC CAG AAG GAA GGC GAG AAA A) wherein Z is 20;
z) each Nu is a nucleobase which taken together form the targeting sequence (5' to 3') of: SEQ ID NO: 38 (GGC CAG AAG GAA GGC GAG AAA) wherein Z is 19;
aa) each Nu is a nucleobase which taken together form the targeting sequence (5' to 3') of: SEQ ID NO: 39 (CGG CAC XCA CGG CXC X CAA AGC A) wherein Z is 21;
bb) each Nu is a nucleobase which taken together form the targeting sequence (5' to 3') of: SEQ ID NO: 40 (GCG GCA CXC ACG G CXC XCA AAG C) wherein Z is 21;
cc) each Nu is a nucleobase which taken together form the targeting sequence (5' to 3') of: SEQ ID NO: 41 (GGC GGC ACX CAC G GCX CXC AAA G) wherein Z is 21;
dd) each Nu is a nucleobase which taken together form the targeting sequence (5' to 3') of: SEQ ID NO: 42 (XGG GGA GAG GGC CAG AAG GAA GGC) wherein Z is 22;
ee) each Nu is a nucleobase which taken together form the targeting sequence (5' to 3') of: SEQ ID NO: 43 (XGG GGA GAG GGC CAG AAG GAA GC) wherein Z is 21;
ff) each Nu is a nucleobase which taken together form the targeting sequence (5' to 3') of: SEQ ID NO: 44 (XGG GGA GAG GGC CAG AAG GAA C) wherein Z is 20;
gg) each Nu is a nucleobase which taken together form the targeting sequence (5' to 3') of: SEQ ID NO: 45 (GGC CAG AAG GAA GCG AGA AAA GC) wherein Z is 21;
hh) each Nu is a nucleobase which taken together form the targeting sequence (5' to 3') of: SEQ ID NO: 46 (GGC CAG AAG GAA CGA GAA AAG C) wherein Z is 20;
ii) each Nu is a nucleobase which taken together form the targeting sequence (5' to 3') of: SEQ ID NO: 47 (AGG AAG CGA GAA AAG CXC CAG CA) wherein Z is 21;
jj) each Nu is a nucleobase which taken together form the targeting sequence (5' to 3') of: SEQ ID NO: 48 (AGG AAC GAG AAA AGC XCC AGC A) wherein Z is 20;
kk) each Nu is a nucleobase which taken together form the targeting sequence (5' to 3') of: SEQ ID NO: 49 (CGG GCX CXC AAA GCA GCX CXG AGA) wherein Z is 22;
ll) each Nu is a nucleobase which taken together form the targeting sequence (5' to 3') of: SEQ ID NO: 50 (CGC XCX CAA AGC AGC XCX GAG A) wherein Z is 20;
mm) each Nu is a nucleobase which taken together form the targeting sequence (5' to 3') of: SEQ ID NO: 51 (CCX CXC AAA GCA GCX CXG AGA) wherein Z is 19;
nn) each Nu is a nucleobase which taken together form the targeting sequence (5' to 3') of: SEQ ID NO: 52 (GGC ACX CAC GGG CXC XCA AAG) wherein Z is 22;
oo) each Nu is a nucleobase which taken together form the targeting sequence (5' to 3') of: SEQ ID NO: 53 (GGC GGC ACX CAC GCX CXC AAA G) wherein Z is 20;

pp) each Nu is a nucleobase which taken together form the targeting sequence (5' to 3') of: SEQ ID NO: 54 (GGC GGC ACX CAC CXC XCA AAG) wherein Z is 19;
qq) each Nu is a nucleobase which taken together form the targeting sequence (5' to 3') of: SEQ ID NO: 55 (GCG GGA GGG GCG GCA CXC ACG GGC) wherein Z is 22;
rr) each Nu is a nucleobase which taken together form the targeting sequence (5' to 3') of: SEQ ID NO: 56 (GCG GGA GGG GCG GCA CXC ACG GC) wherein Z is 21;
ss) each Nu is a nucleobase which taken together form the targeting sequence (5' to 3') of: SEQ ID NO: 57 (GCG GGA GGG GCG GCA CXC ACG C) wherein Z is 20; and
tt) each Nu is a nucleobase which taken together form the targeting sequence (5' to 3') of: SEQ ID NO: 58 (GCG GGA GGG GCG GCA CXC ACC) wherein Z is 19, wherein X is selected from uracil (U) or thymine (T);

II.
a) each Nu is a nucleobase which taken together form the targeting sequence (5' to 3') of: SEQ ID NO: 59 (GGC CAG AAG GAA GGG CGA GAA AAG C) wherein Z is 23;
b) each Nu is a nucleobase which taken together form the targeting sequence (5' to 3') of: SEQ ID NO: 60 (CCA GAA GGA AGG GCG AGA AAA GCX C) wherein Z is 23;
c) each Nu is a nucleobase which taken together form the targeting sequence (5' to 3') of: SEQ ID NO: 61 (AAG GAA GGG CGA GAA AAG CXC CAG C) wherein Z is 23;
d) each Nu is a nucleobase which taken together form the targeting sequence (5' to 3') of: SEQ ID NO: 62 (GCG GGA GGG GCG GCA CXC ACG GGG C) wherein Z is 23;
e) each Nu is a nucleobase which taken together form the targeting sequence (5' to 3') of: SEQ ID NO: 63 (XGG GGA GAG GGC CAG AAG GAA GGG C) wherein Z is 23;
f) each Nu is a nucleobase which taken together form the targeting sequence (5' to 3') of: SEQ ID NO: 64 (AGA AGG AAG GGC GAG AAA AGC XCC A) wherein Z is 23;
g) each Nu is a nucleobase which taken together form the targeting sequence (5' to 3') of: SEQ ID NO: 65 (GCX CXC AAA GCA GCX CXG AGA CAX C) wherein Z is 23;
h) each Nu is a nucleobase which taken together form the targeting sequence (5' to 3') of: SEQ ID NO: 66 (CXC XCA AAG CAG CXC XGA GAC AXC A) wherein Z is 23;
i) each Nu is a nucleobase which taken together form the targeting sequence (5' to 3') of: SEQ ID NO: 67 (XCX CAA AGC AGC XCX GAG ACA XCA A) wherein Z is 23;
j) each Nu is a nucleobase which taken together form the targeting sequence (5' to 3') of: SEQ ID NO: 68 (CXC AAA GCA GCX CXG AGA CAX CAA C) wherein Z is 23;
k) each Nu is a nucleobase which taken together form the targeting sequence (5' to 3') of: SEQ ID NO: 69 (XCA AAG CAG CXC XGA GAC AXC AAC C) wherein Z is 23;
l) each Nu is a nucleobase which taken together form the targeting sequence (5' to 3') of: SEQ ID NO: 70 (CAA AGC AGC XCX GAG ACA XCA ACC G) wherein Z is 23;
m) each Nu is a nucleobase which taken together form the targeting sequence (5' to 3') of: SEQ ID NO: 71 (AAA GCA GCX CXG AGA CAX CAA CCG C) wherein Z is 23;
n) each Nu is a nucleobase which taken together form the targeting sequence (5' to 3') of: SEQ ID NO: 72 (AAG CAG CXC XGA GAC AXC AAC CGC G) wherein Z is 23;
o) each Nu is a nucleobase which taken together form the targeting sequence (5' to 3') of: SEQ ID NO: 73 (AGC AGC XCX GAG ACA XCA ACC GCG G) wherein Z is 23;
p) each Nu is a nucleobase which taken together form the targeting sequence (5' to 3') of: SEQ ID NO: 74 (GCA GCX CXG AGA CAX CAA CCG CGG C) wherein Z is 23; and
q) each Nu is a nucleobase which taken together form the targeting sequence (5' to 3') of: SEQ ID NO: 75 (CAG CXC XGA GAC AXC AAC CGC GGC X) wherein Z is 23,
wherein X is selected from uracil (U) or thymine (T); and III.
l) each Nu is a nucleobase which taken together form the targeting sequence (5' to 3') of: SEQ ID NO: 76 (GCC AGA AGG AAG GGC GAG AAA AGC X) wherein Z is 23;
m) each Nu is a nucleobase which taken together form the targeting sequence (5' to 3') of: SEQ ID NO: 77 (CAG AAG GAA GGG CGA GAA AAG CXC C) wherein Z is 23;
n) each Nu is a nucleobase which taken together form the targeting sequence (5' to 3') of: SEQ ID NO: 78 (GAA GGA AGG GCG AGA AAA GCX CCA G) wherein Z is 23;
o) each Nu is a nucleobase which taken together form the targeting sequence (5' to 3') of: SEQ ID NO: 79 (AGG AAG GGC GAG AAA AGC XCC AGC A) wherein Z is 23;
p) each Nu is a nucleobase which taken together form the targeting sequence (5' to 3') of: SEQ ID NO: 80 (ACX CAC GGG GCX CXC AAA GCA GCX C) wherein Z is 23;
q) each Nu is a nucleobase which taken together form the targeting sequence (5' to 3') of: SEQ ID NO: 81 (GGCXCXCAAAGCAGCXCXGAGACAX) wherein Z is 23;
r) each Nu is a nucleobase which taken together form the targeting sequence (5' to 3') of: SEQ ID NO: 82 (GGC XCX CAA AGC AGC XCX GA) wherein Z is 18;
s) each Nu is a nucleobase which taken together form the targeting sequence (5' to 3') of: SEQ ID NO: 83 (GAG AGG GCC AGA AGG AAG GG) wherein Z is 18;

t) each Nu is a nucleobase which taken together form the targeting sequence (5' to 3') of: SEQ ID NO: 84 (XXX GCC AXG XXA CCC AGG CX) wherein Z is 18;

u) each Nu is a nucleobase which taken together form the targeting sequence (5' to 3') of: SEQ ID NO: 85 (GCG CAC CCX CXG CCC XGG CC) wherein Z is 18; and v) each Nu is a nucleobase which taken together form the targeting sequence (5' to 3') of: SEQ ID NO: 86 (GGC CCX GGX CXG CXG GCX CCC XGC X) wherein Z is 23, wherein X is selected from uracil (U) or thymine (T); and wherein $R^a$ is H or acetyl.

In some embodiments, at least one X of SEQ ID NOS: 13-86 is T. In some embodiments, at least one X of SEQ ID NOS: 13-86 is U. In some embodiments, each X of SEQ ID NOS: 13-86 is T. In some embodiments, each X of SEQ ID NOS: 13-86 is U. In various embodiments, at least one X of the targeting sequence is T. In various embodiments, each X of the targeting sequence is T. In various embodiments, at least one X of the targeting sequence is U. In various embodiments, each X of the targeting sequence is U.

In certain embodiments, the targeting sequence is selected from the group consisting of SEQ ID NOs: 13, 27-29, 34-36, 59, and 82. In some embodiments, at least one X of SEQ ID NOS: 13, 27-29, 34-36, 59, and 82 is T. In some embodiments, at least one X of SEQ ID NOS: 13, 27-29, 34-36, 59, and 82 is U. In some embodiments, each X of SEQ ID NOS: 13-86 is T. In some embodiments, each X of SEQ ID NOS: 13, 27-29, 34-36, 59, and 82 is U.

In some embodiments, the antisense oligomer is a compound of formula (XXII), or a pharmaceutically acceptable salt thereof, selected from:

(XXII a)

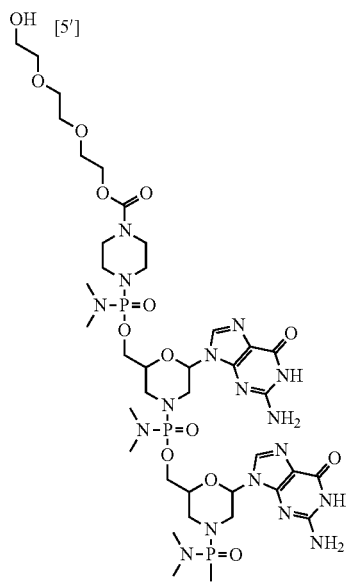

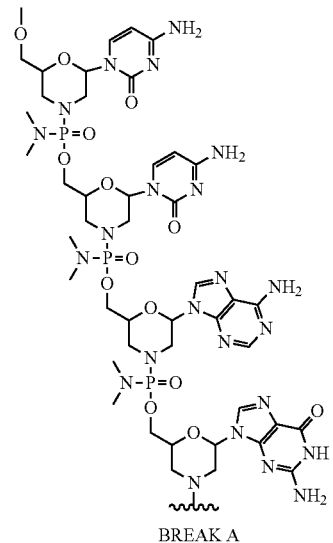

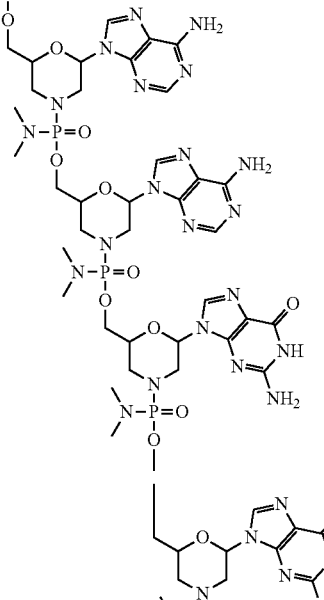

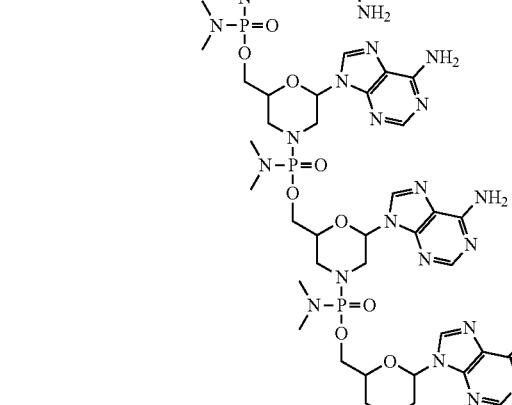

111
-continued
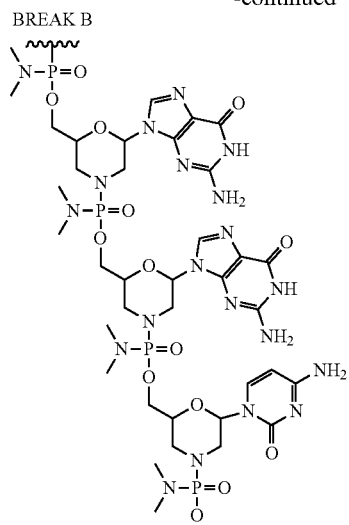
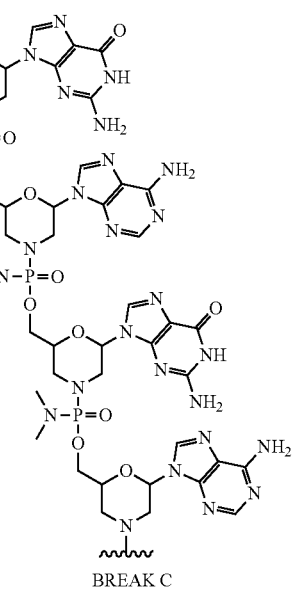
BREAK C
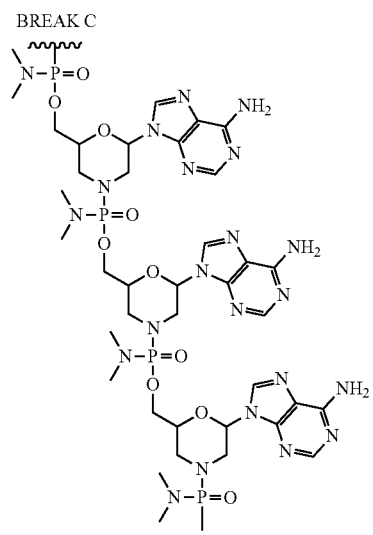
112
-continued
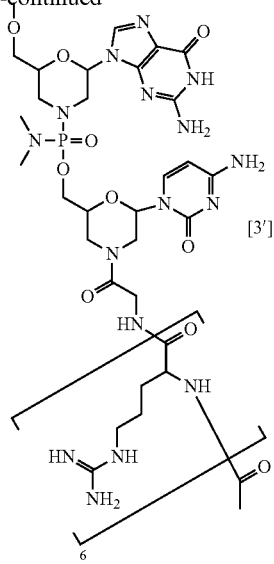
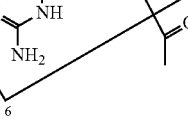
(XXII b)
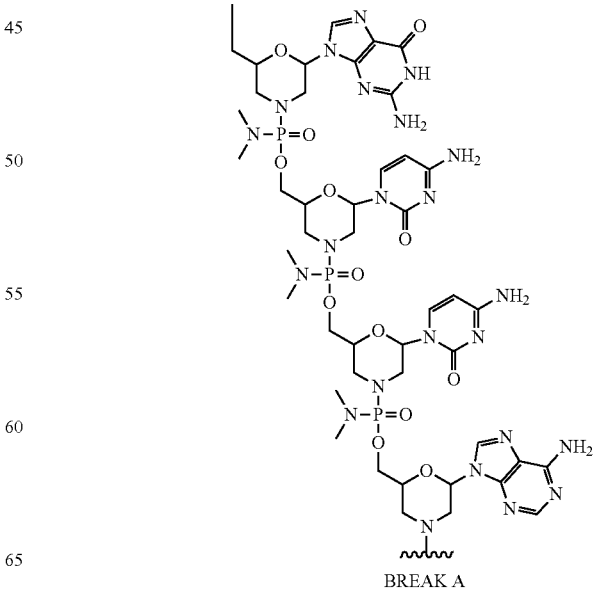
BREAK A 113
-continued
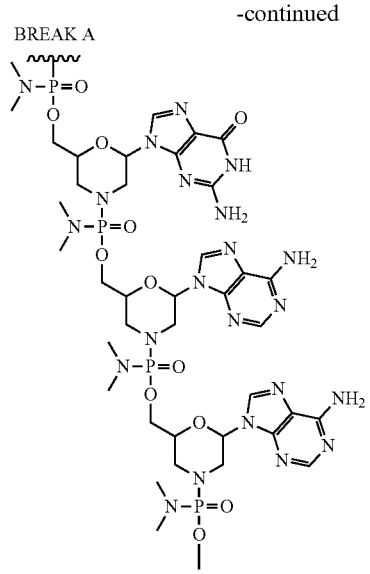
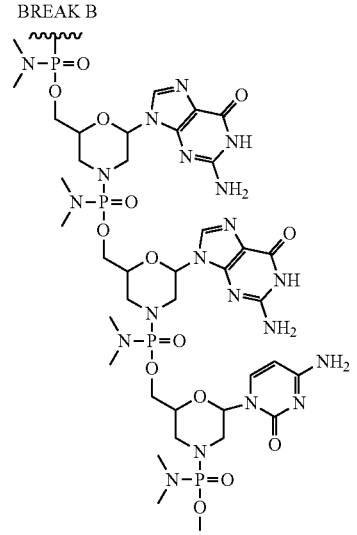
114
-continued
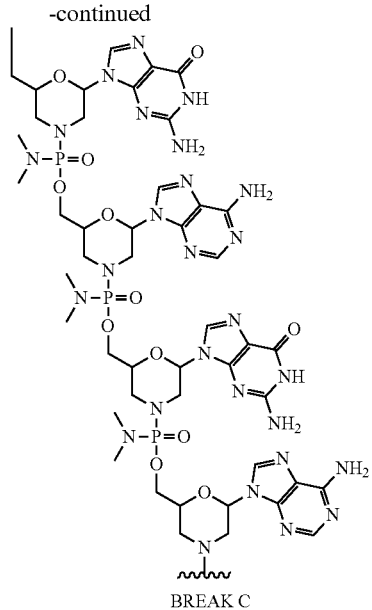
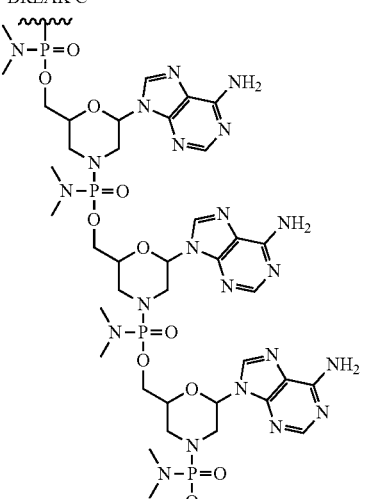
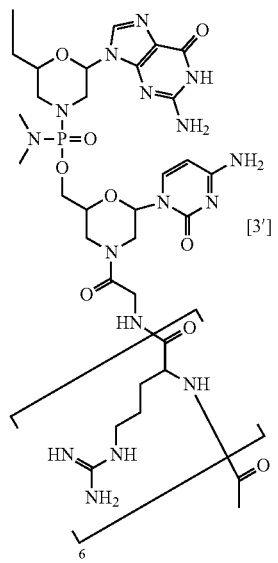

115
-continued
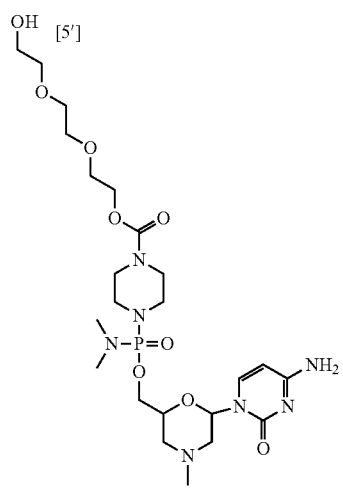
(XXIIc)
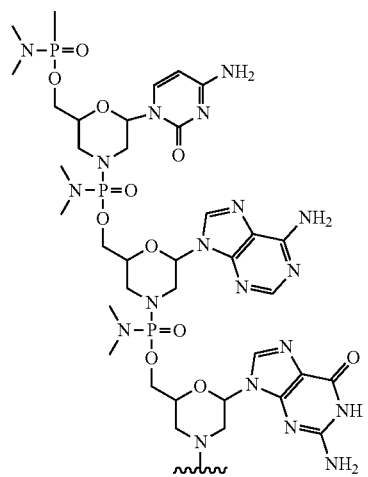
BREAK A
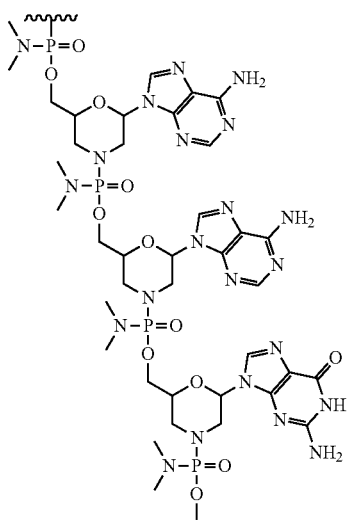
116
-continued
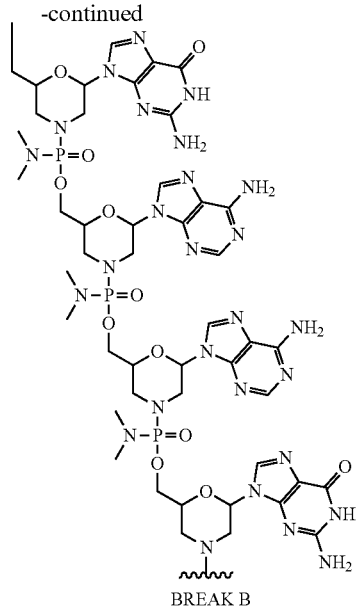
BREAK B
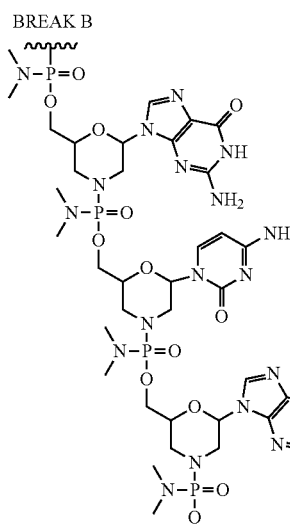
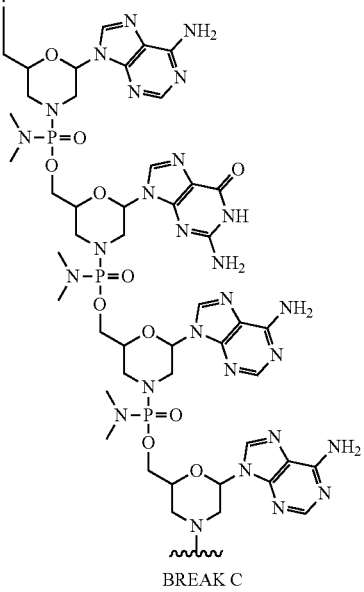
BREAK C

117
-continued
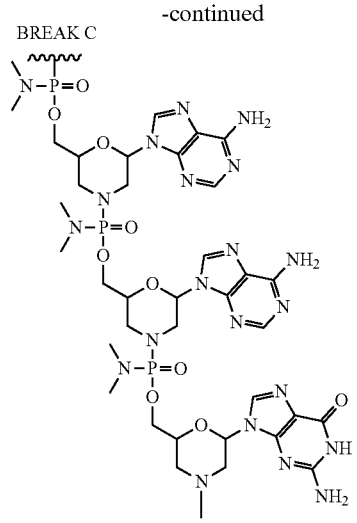
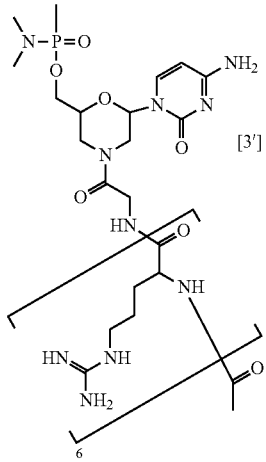
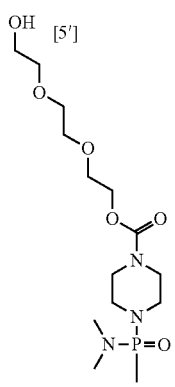
118
-continued
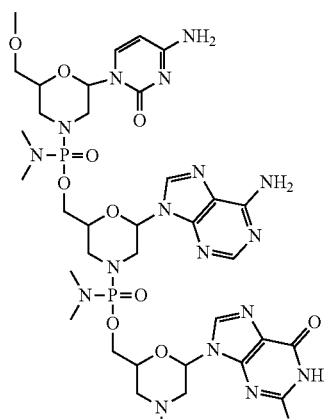
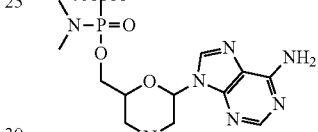
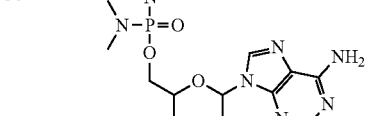
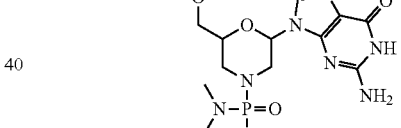
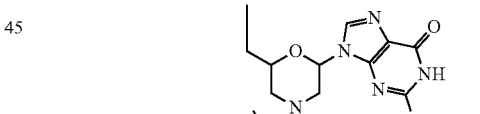
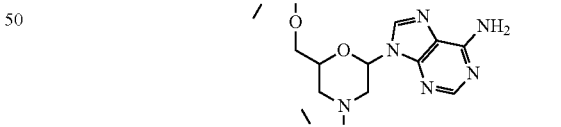
(XXII d)

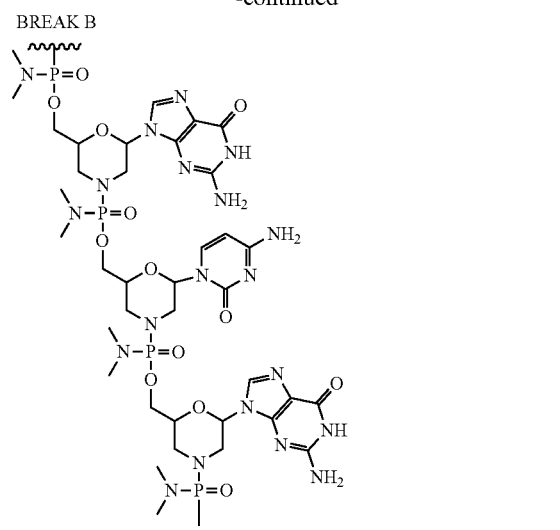
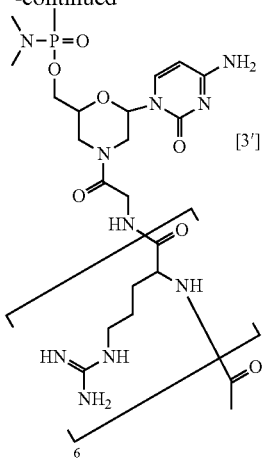
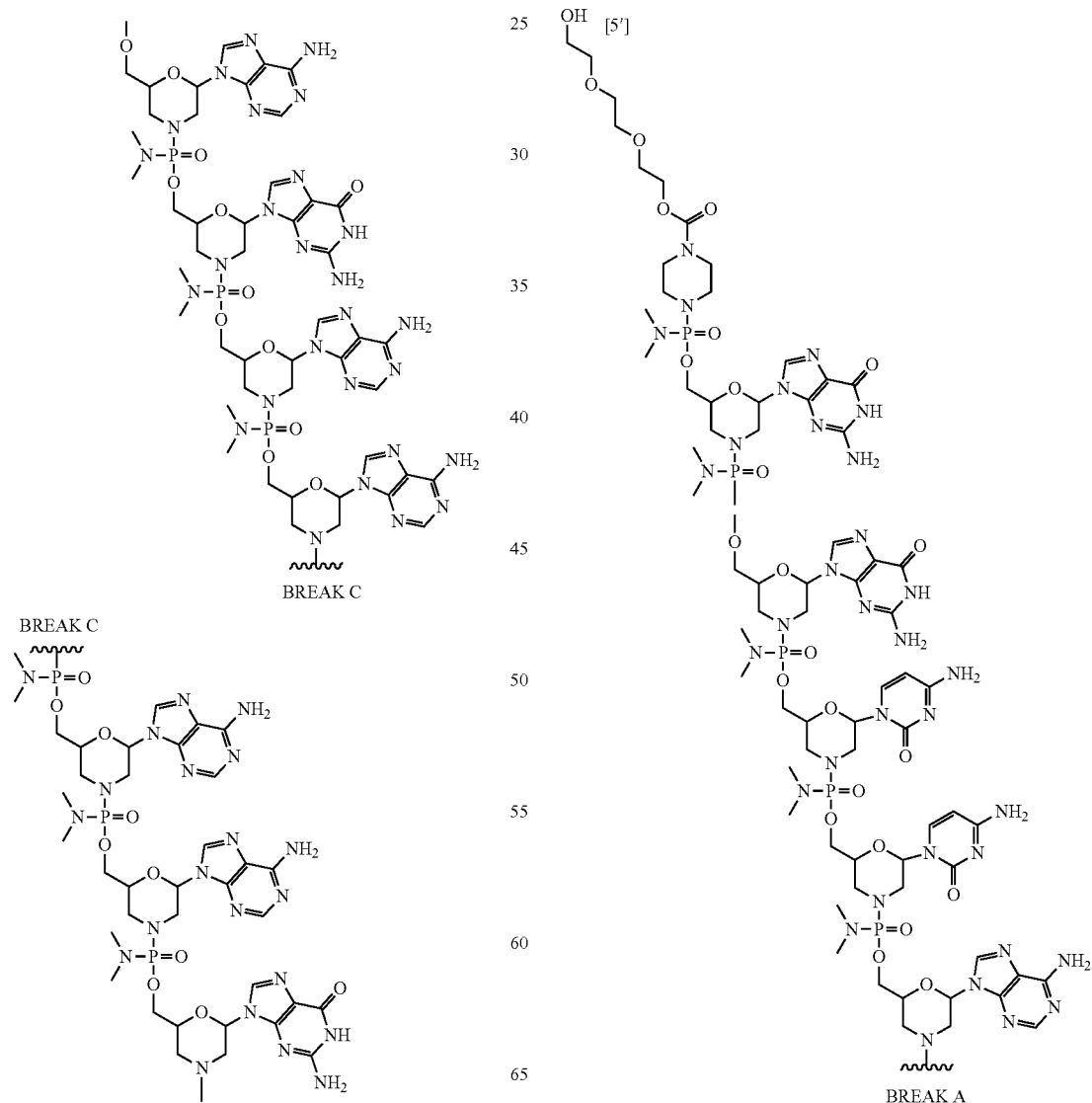

121
-continued
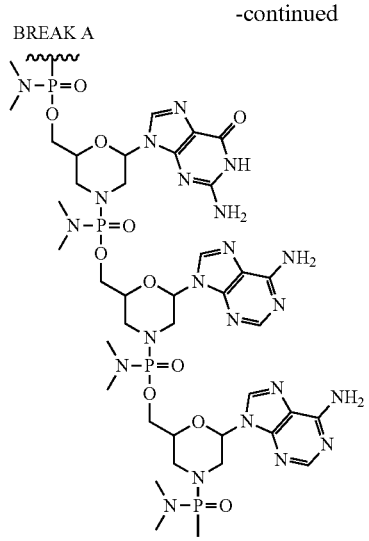
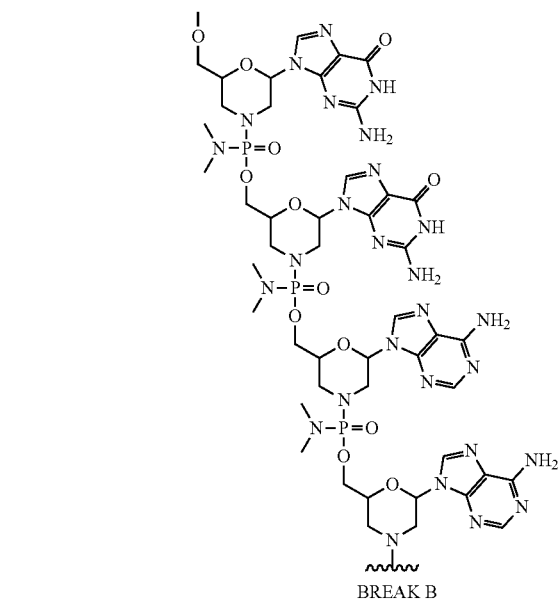
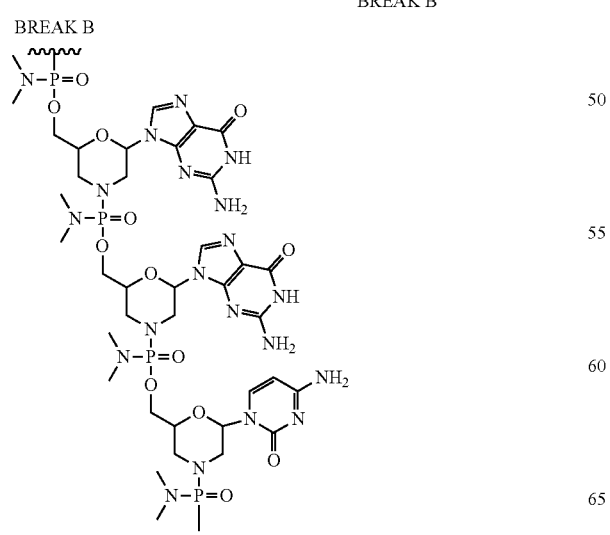
122
-continued
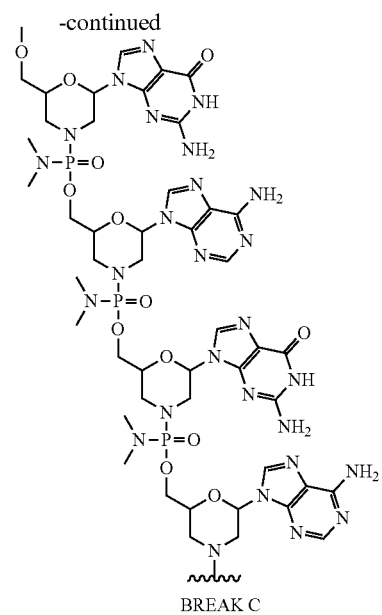
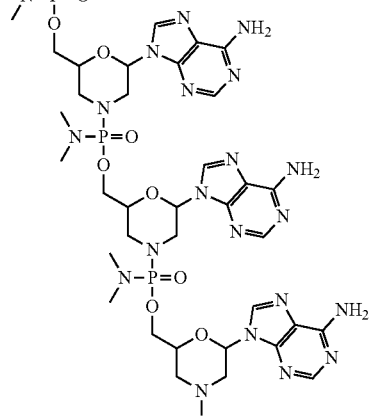
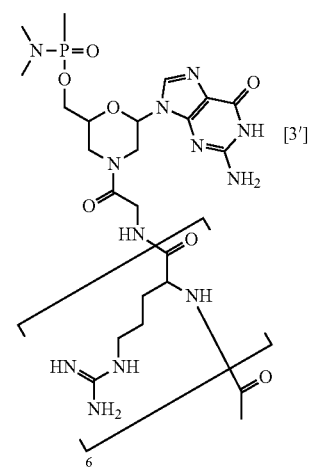

123
-continued
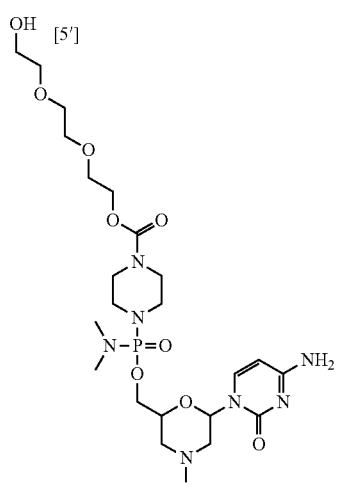
(XXII f)
124
-continued
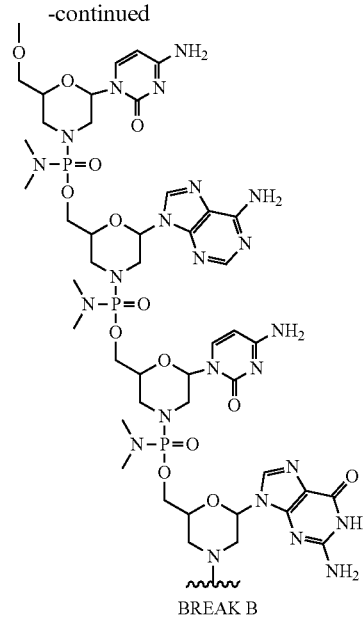
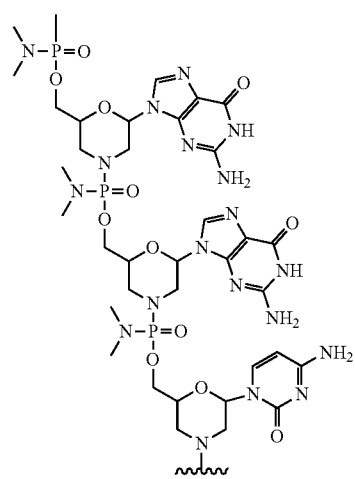
BREAK A
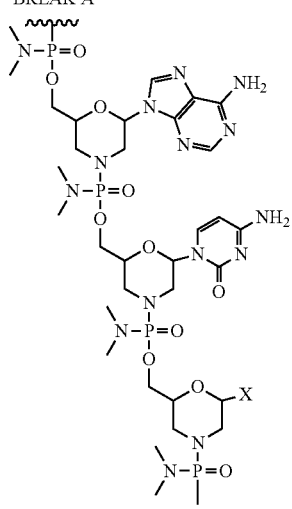
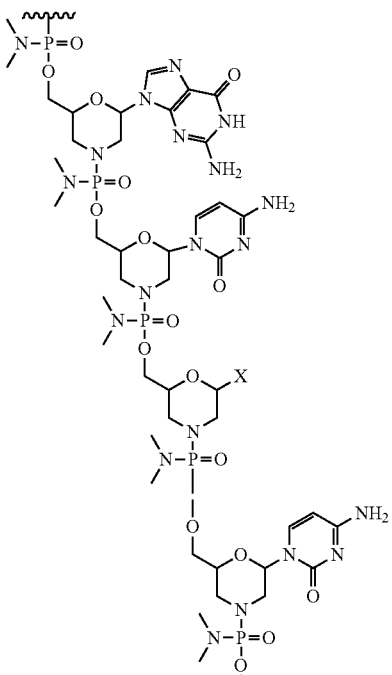
BREAK C 125
-continued
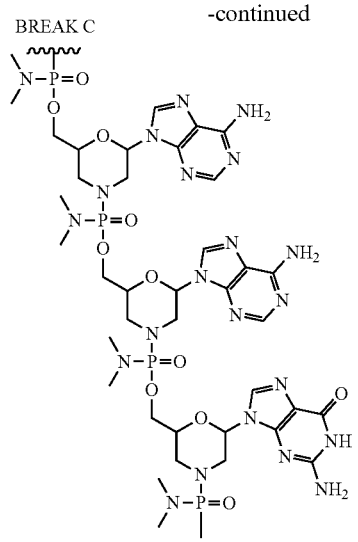
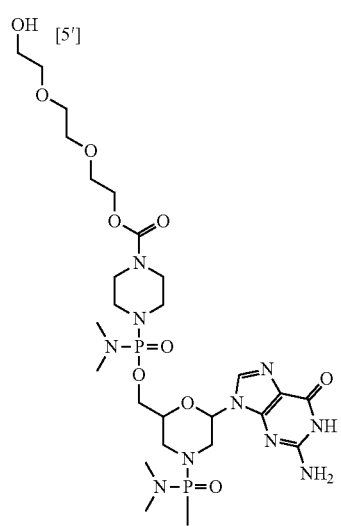
(XXII g)
126
-continued
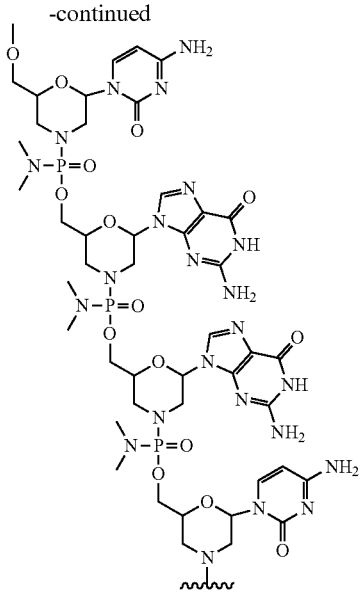
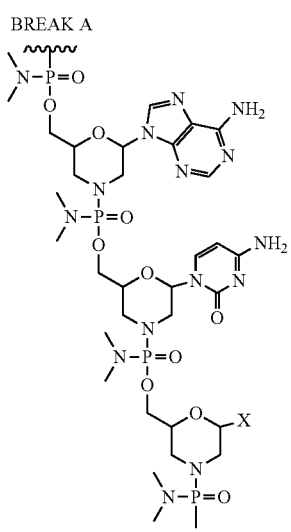
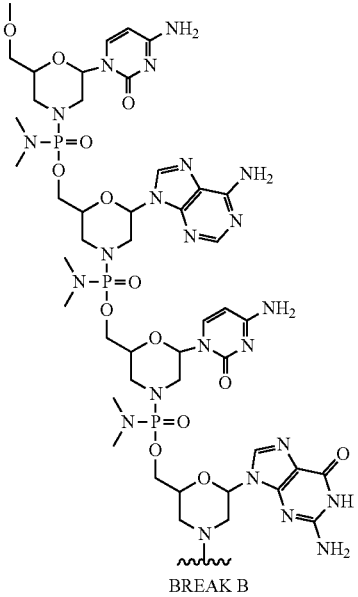

127
-continued
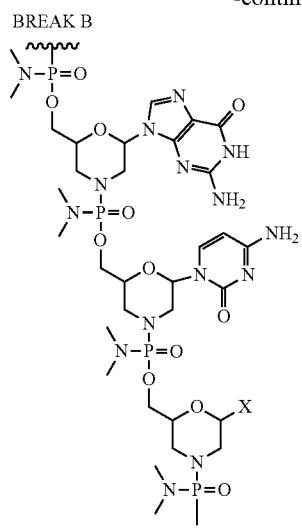
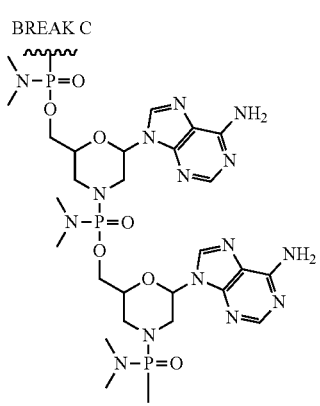
128
-continued
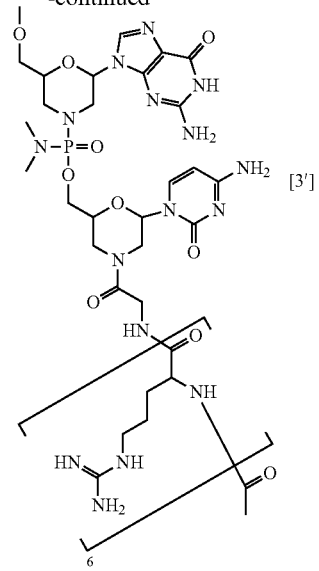
(XXII h)
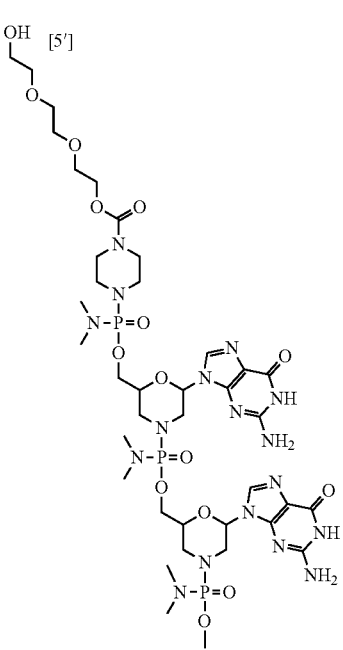

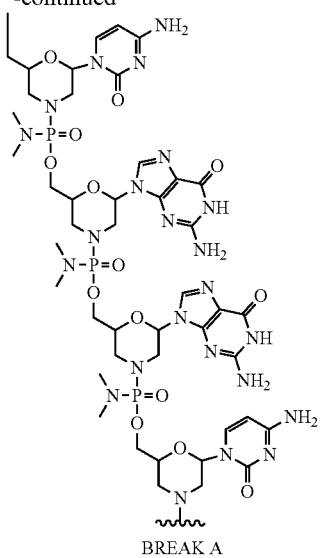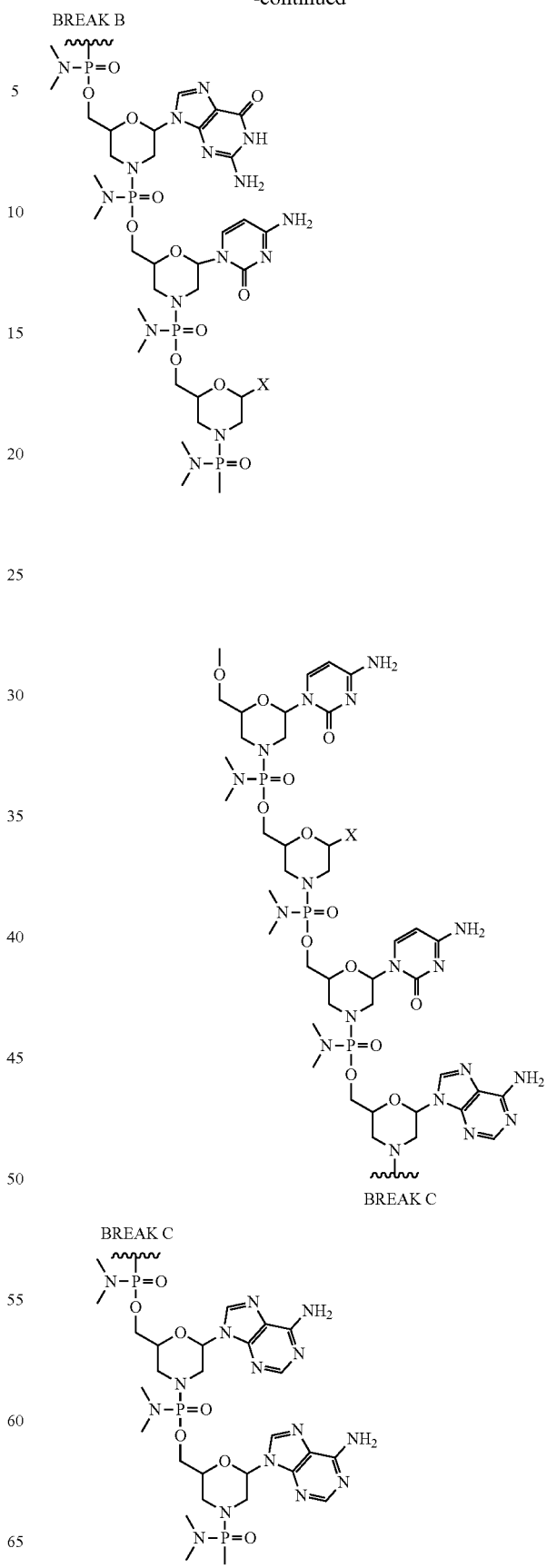

131
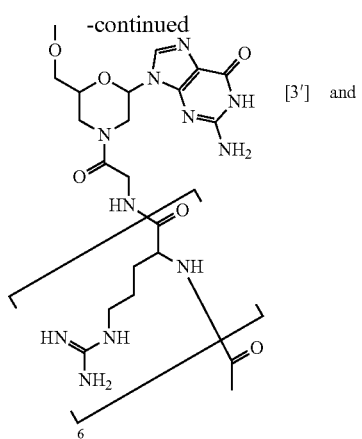
[3'] and
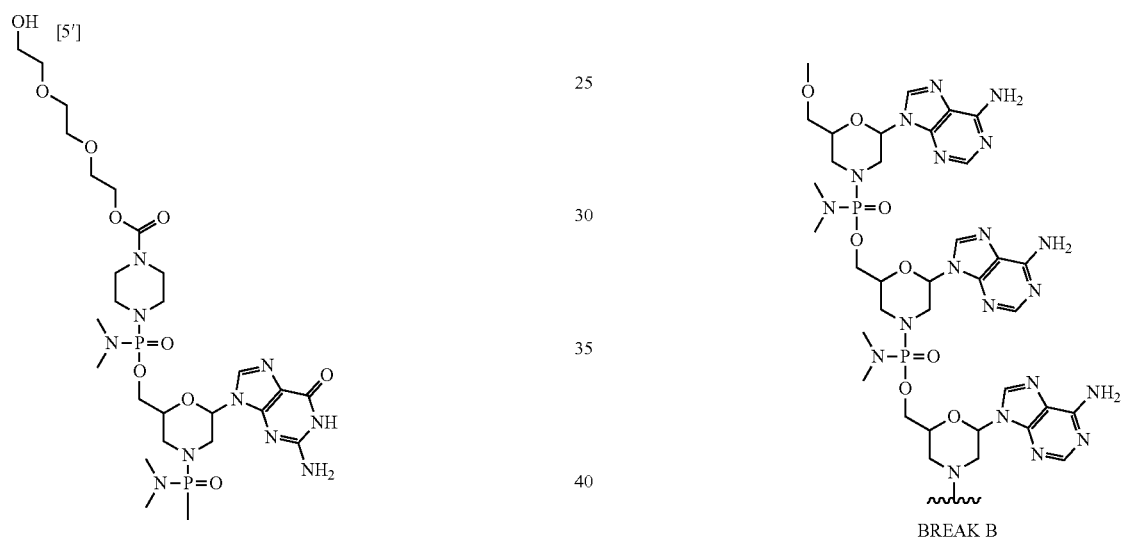
132
(XXIIi)
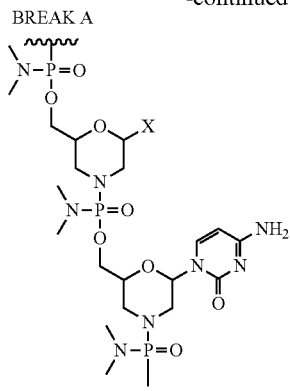

-continued

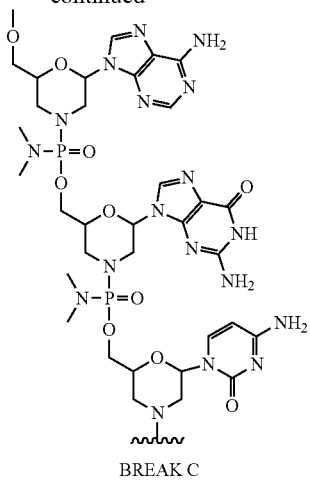

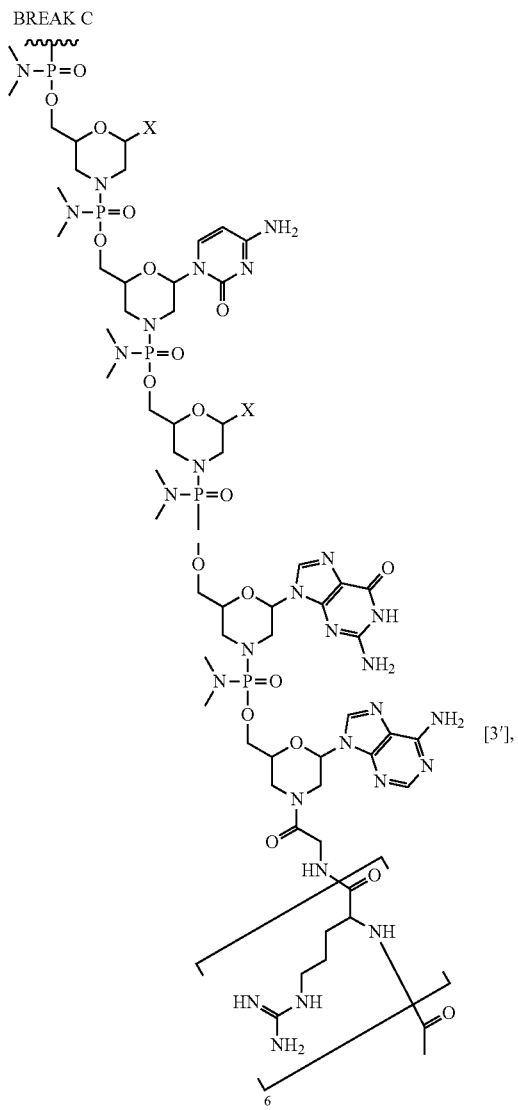

wherein X at each occurrence is independently selected from

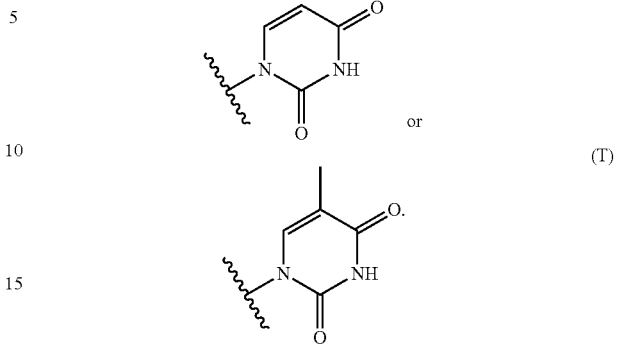

In some embodiments, each X is T. In other embodiments, each X is U. In some embodiments, the antisense oligomer of formula (XXII) is formula (XXII a) wherein at least one X is U. In some embodiments, the compound of formula (XXII) is formula (XXII a) wherein at least one X is T. In some embodiments, the compound of formula (XXII) is formula (XXII a) wherein each X is U. In some embodiments, the compound of formula (XXII) is formula (XXII a) wherein each X is T.

In some embodiments, the antisense oligomer of formula (XXII) is formula (XXII b) wherein at least one X is U. In some embodiments, the compound of formula (XXII) is formula (XXII b) wherein at least one X is T. In some embodiments, the compound of formula (XXII) is formula (XXII b) wherein each X is U. In some embodiments, the compound of formula (XXII) formula (XXII b) wherein each X is T.

In some embodiments, the antisense oligomer of formula (XXII) is formula (XXII c) wherein at least one X is U. In some embodiments, the compound of formula (XXII) is formula (XXII c) wherein at least one X is T. In some embodiments, the compound of formula (XXII) is formula (XXII c) wherein each X is U. In some embodiments, the compound of formula (XXII) is formula (XXII c) wherein each X is T.

In some embodiments, the antisense oligomer of formula (XXII) is formula (XXII d) wherein at least one X is U. In some embodiments, the compound of formula (XXII) is formula (XXII d) wherein at least one X is T. In some embodiments, the compound of formula (XXII) is formula (XXII d) wherein each X is U. In some embodiments, the compound of formula (XXII) is formula (XXII d) wherein each X is T.

In some embodiments, the antisense oligomer of formula (XXII) is formula (XXII e) wherein at least one X is U. In some embodiments, the compound of formula (XXII) is formula (XXII e) wherein at least one X is T. In some embodiments, the compound of formula (XXII) is formula (XXII e) wherein each X is U. In some embodiments, the compound of formula (XXII) is formula (XXII e) wherein each X is T.

In some embodiments, the antisense oligomer of formula (XXII) is formula (XXII f) wherein at least one X is U. In some embodiments, the compound of formula (XXII) is formula (XXII f) wherein at least one X is T. In some embodiments, the compound of formula (XXII) is formula (XXII f) wherein each X is U. In some embodiments, the compound of formula (XXII) is formula (XXII f) wherein each X is T.

In some embodiments, the antisense oligomer of formula (XXII) is formula (XXII g) wherein at least one X is U. In some embodiments, the compound of formula (XXII) is formula (XXII g) wherein at least one X is T. In some embodiments, the compound of formula (XXII) is formula (XXII g) wherein each X is U. In some embodiments, the compound of formula (XXII) is formula (XXII g) wherein each X is T.

In some embodiments, the antisense oligomer of formula (XXII) is formula (XXII h) wherein at least one X is U. In some embodiments, the compound of formula (XXII) is formula (XXII h) wherein at least one X is T. In some embodiments, the compound of formula (XXII) is formula (XXII h) wherein each X is U. In some embodiments, the compound of formula (XXII) is formula (XXII h) wherein each X is T.

In some embodiments, the antisense oligomer of formula (XXII) is formula (XXII i) wherein at least one X is U. In some embodiments, the compound of formula (XXII) is formula (XXII i) wherein at least one X is T. In some embodiments, the compound of formula (XXII) is formula (XXII i) wherein each X is U. In some embodiments, the compound of formula (XXII) is formula (XXII i) wherein each X is T.

In some embodiments of the antisense oligomers of the disclosure including, for example, the antisense oligomers of formula (XXII), the antisense oligomers is a compound of formula (XXIII), or a pharmaceutically acceptable salt thereof, selected from:

(XXIII a)

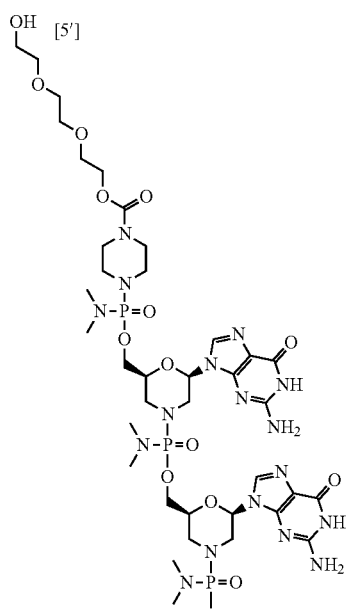

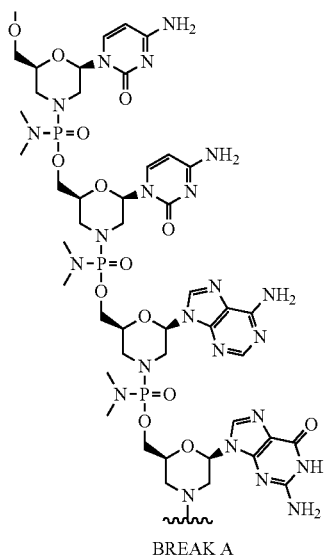

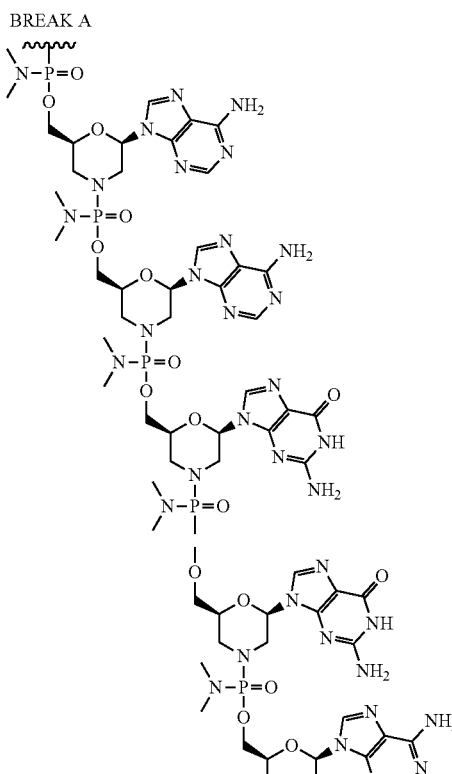

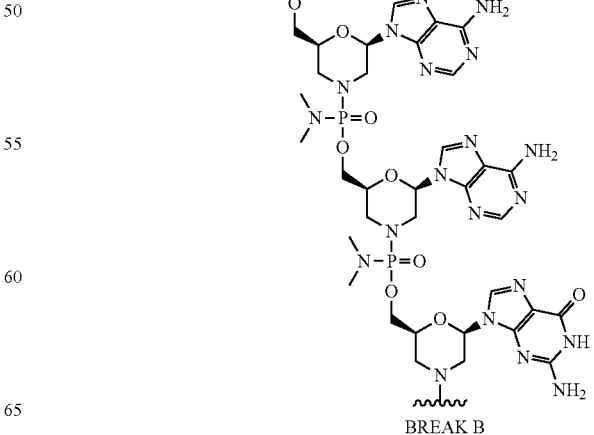

137
-continued
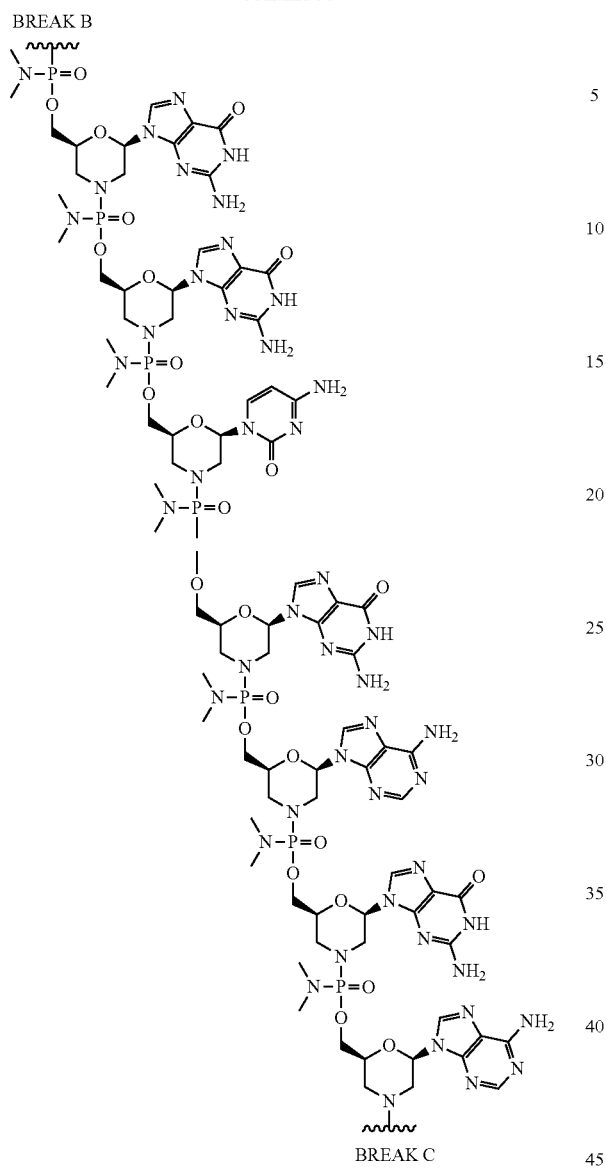
138
-continued
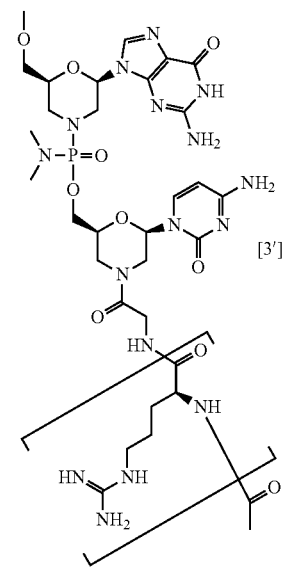
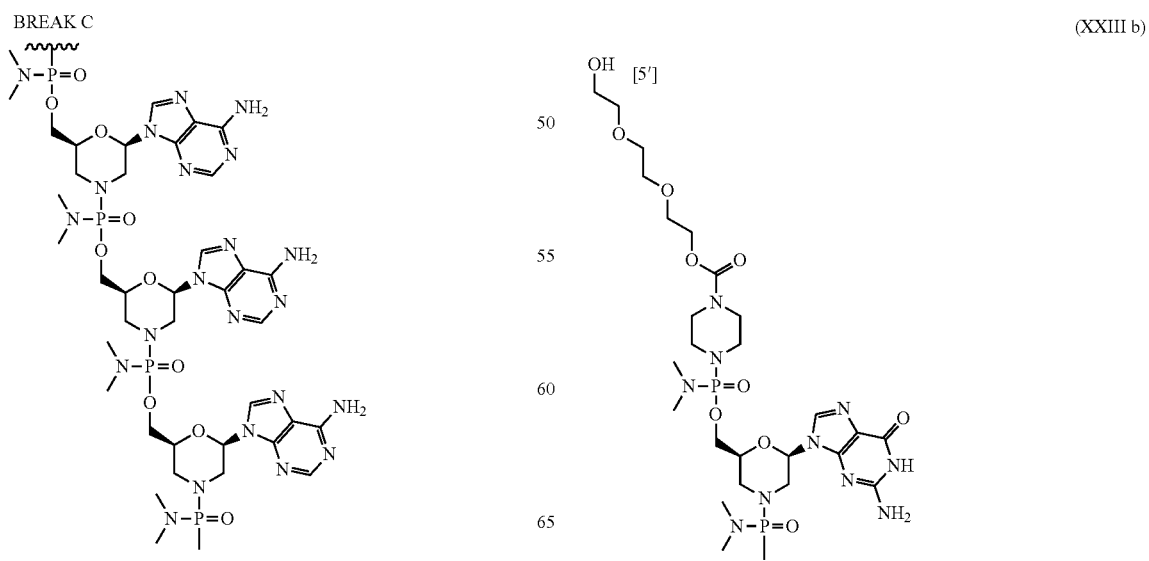

139
-continued
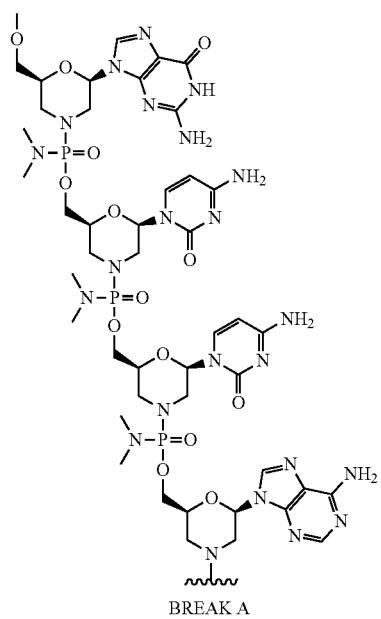
BREAK A
140
-continued
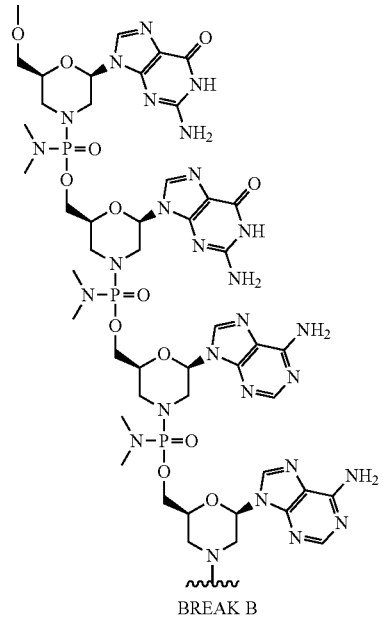
BREAK B
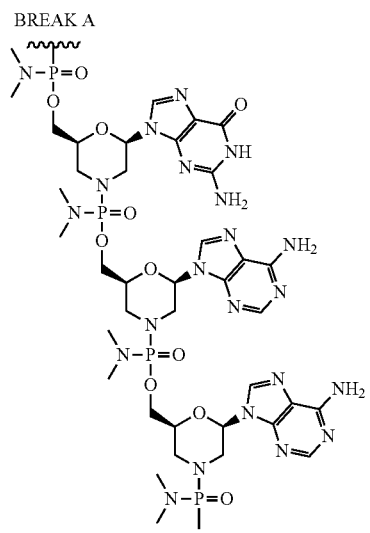
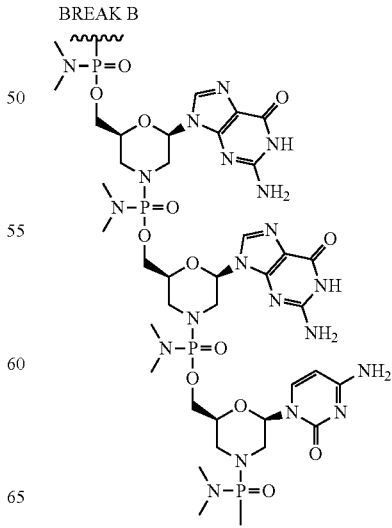

141
-continued
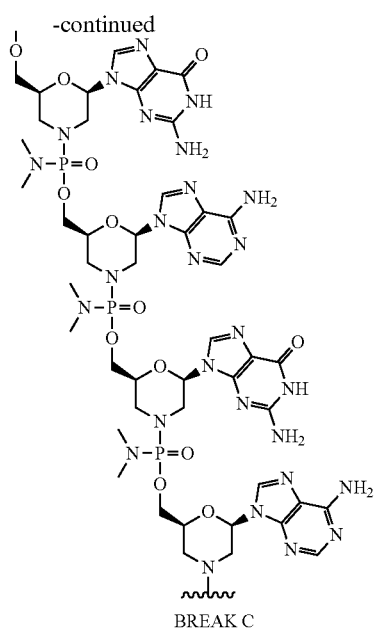
BREAK C
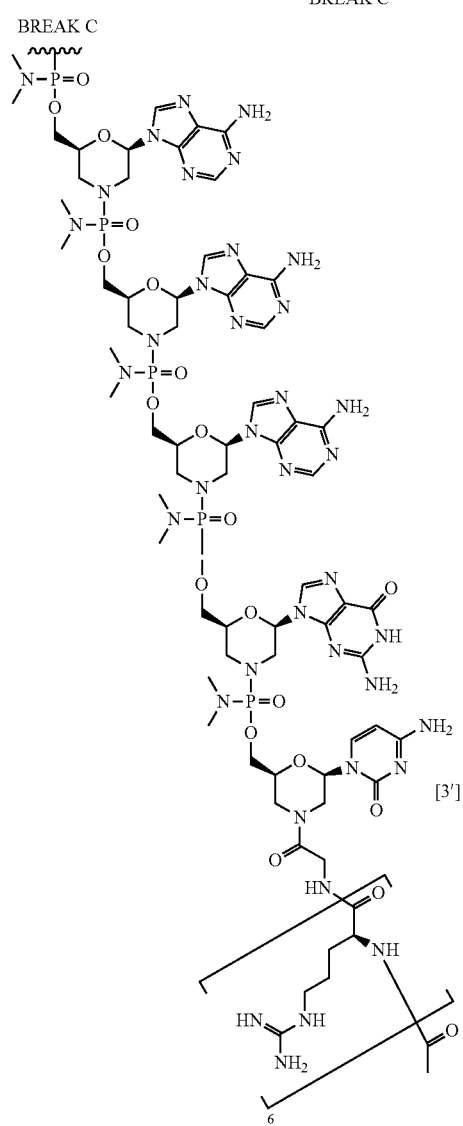
142
-continued
(XXIII c)
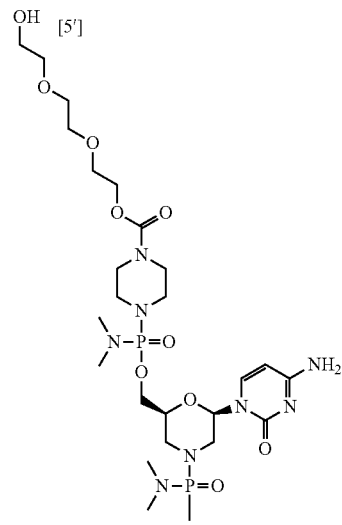
BREAK C
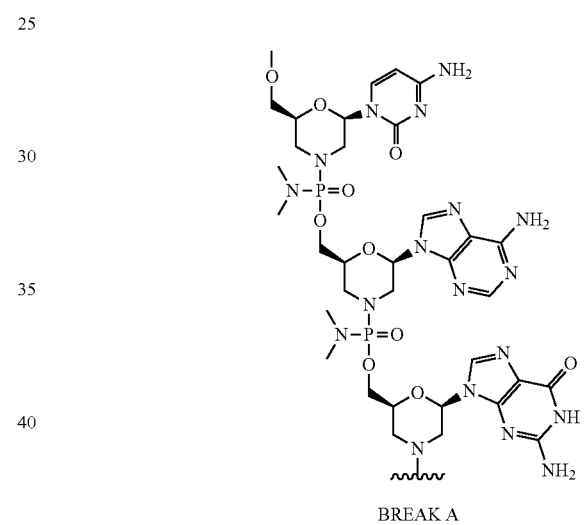
BREAK A
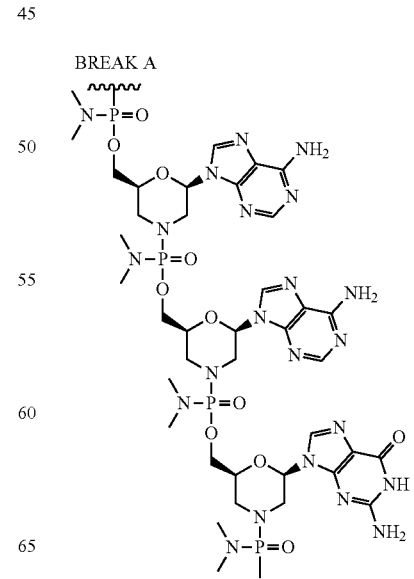

143
-continued
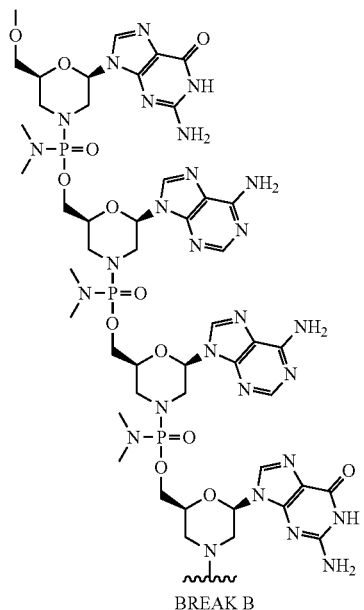
BREAK B
BREAK B
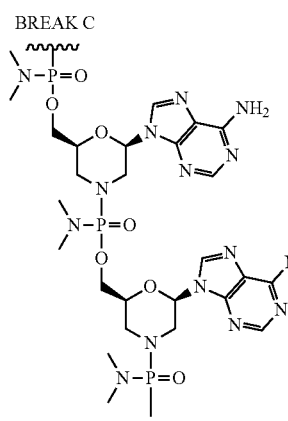
144
-continued
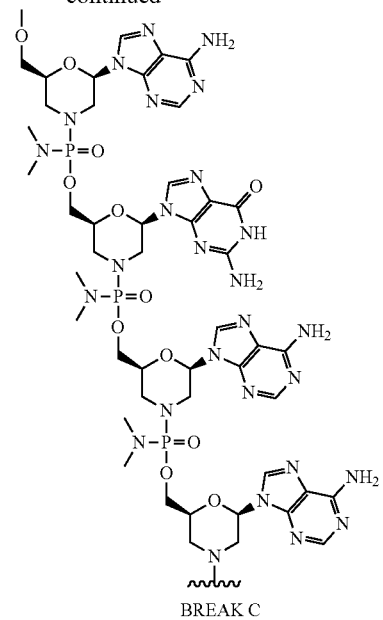
BREAK C
BREAK C
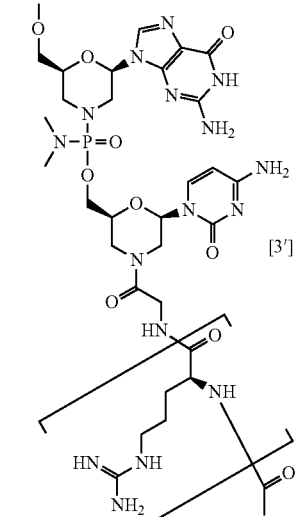

(XXIII d)
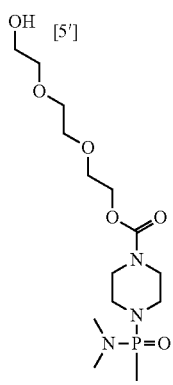
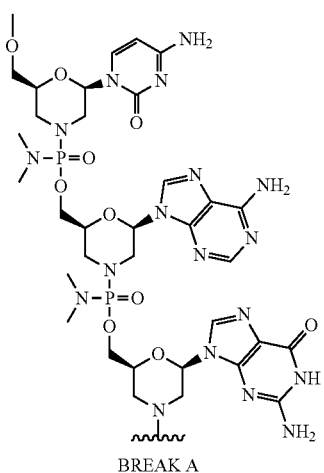
BREAK A
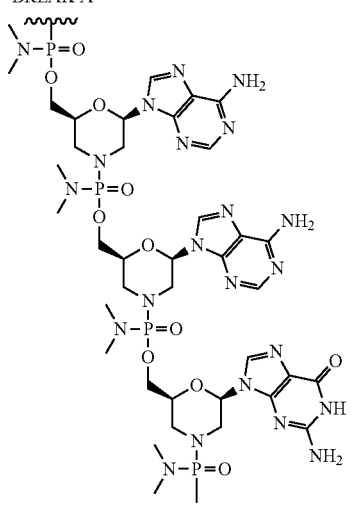
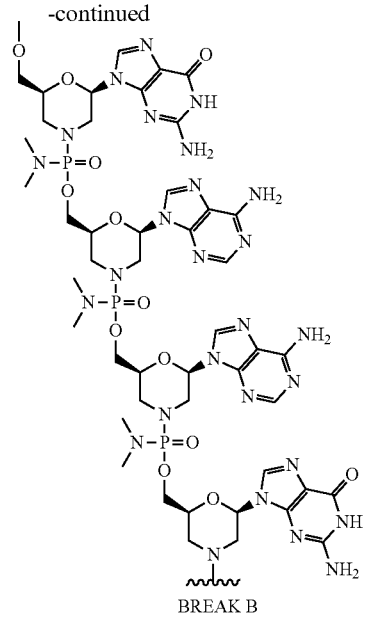
BREAK B
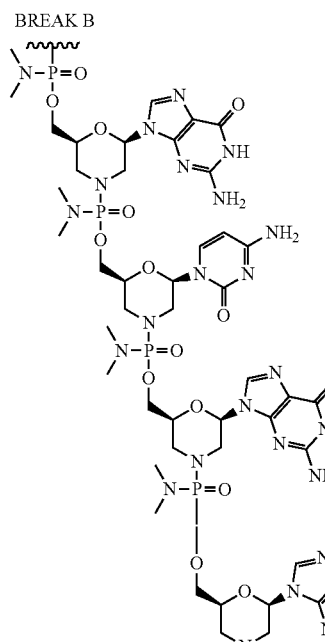
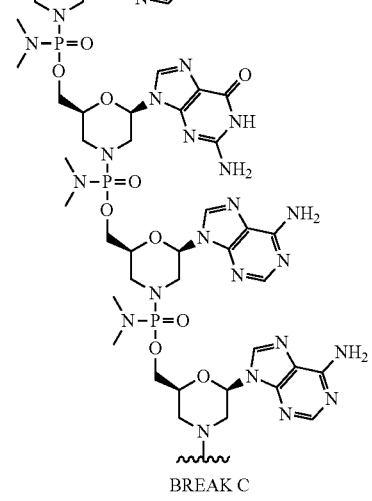
BREAK C

147
-continued
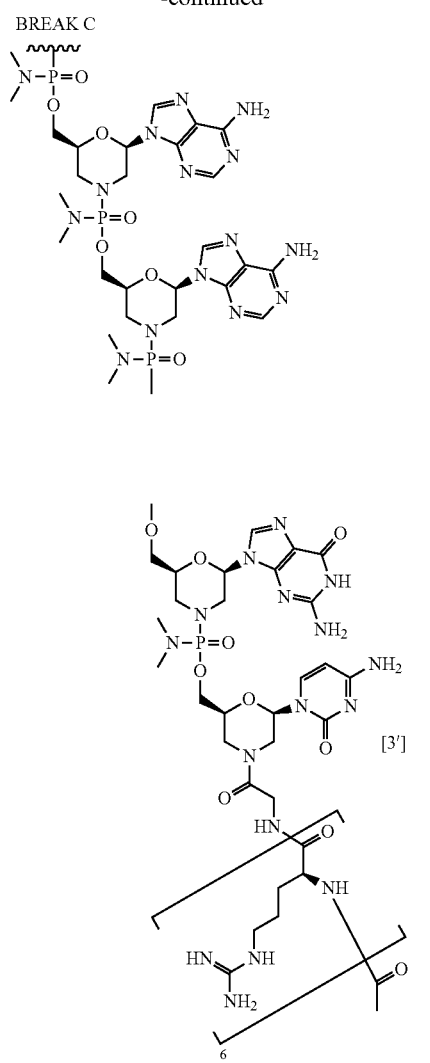
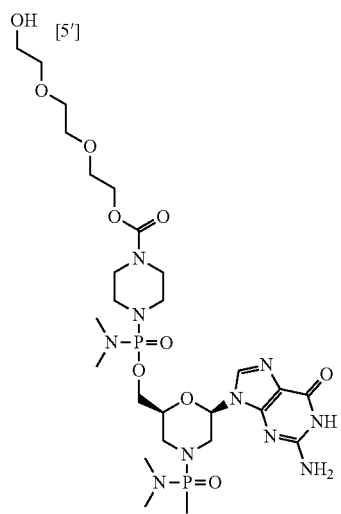
148
-continued
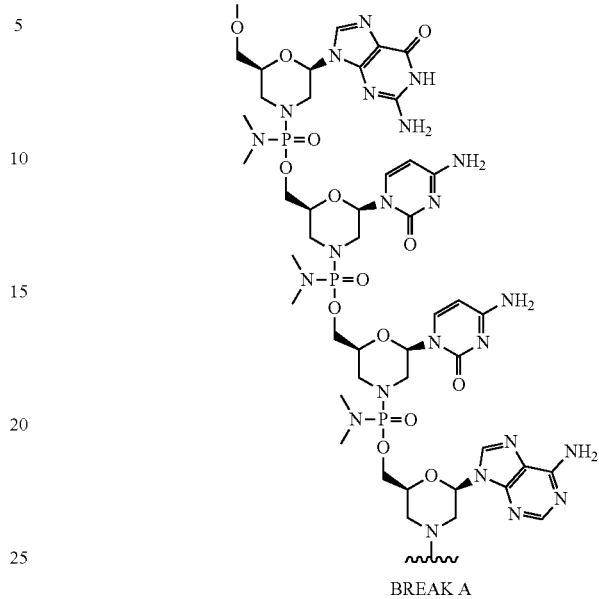
(XXIII e)

149
-continued
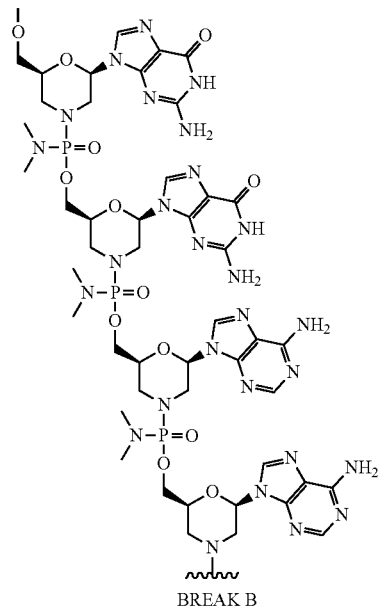
BREAK B
150
-continued
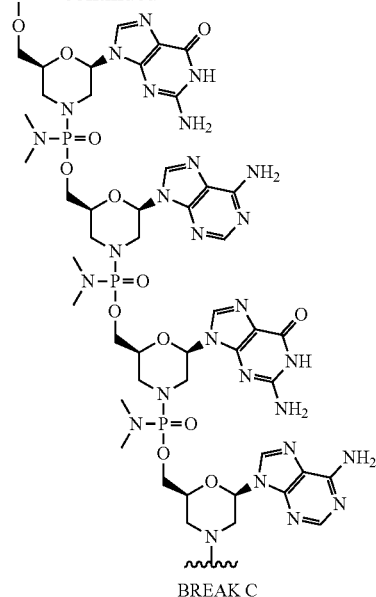
BREAK C
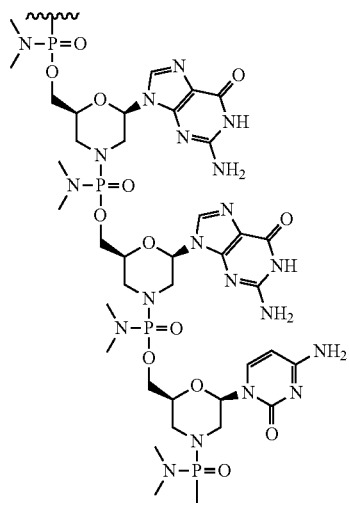
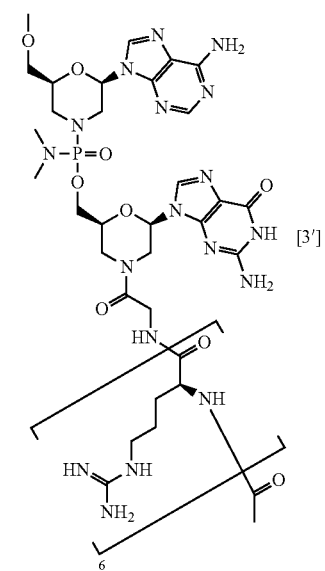

(XXIII f)
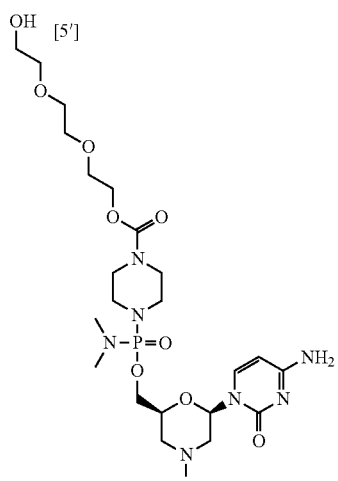
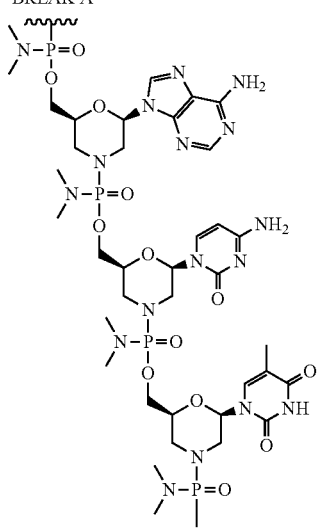
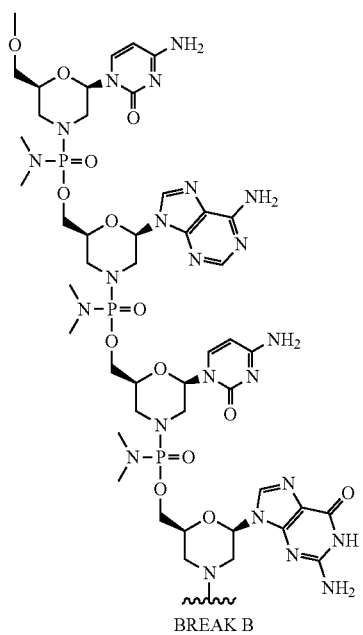
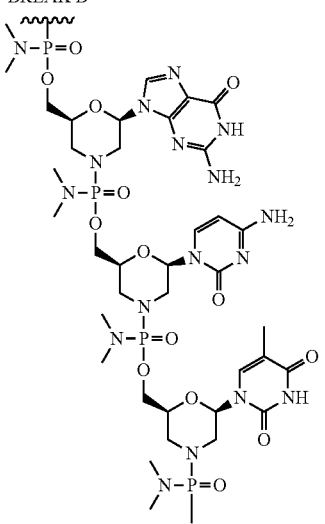

153
-continued
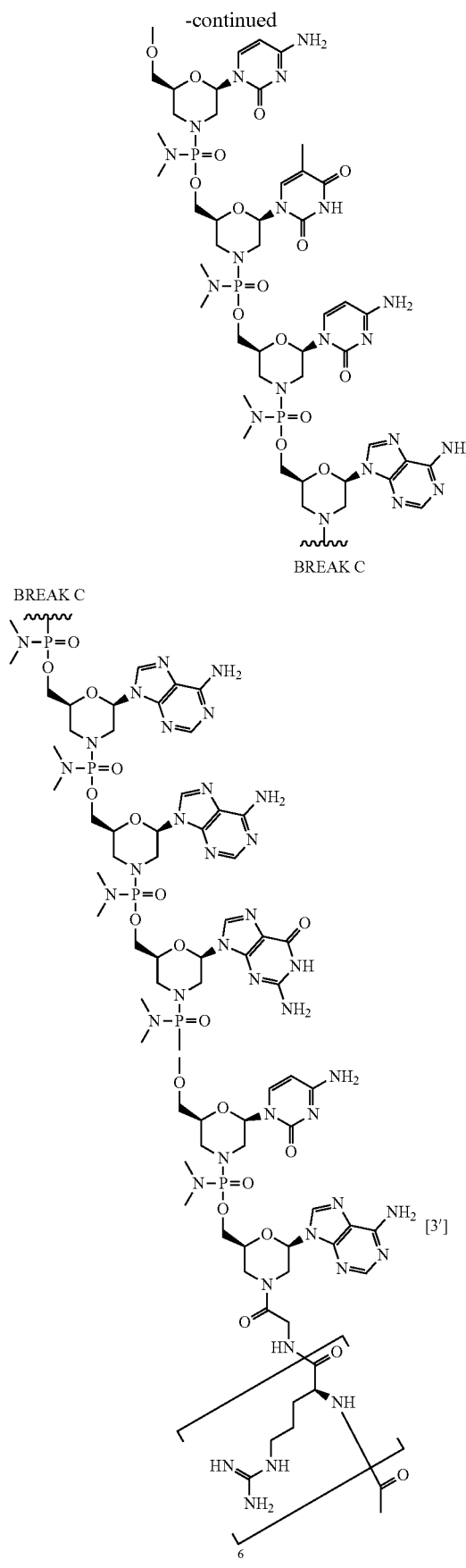
154
-continued
(XXIII g)
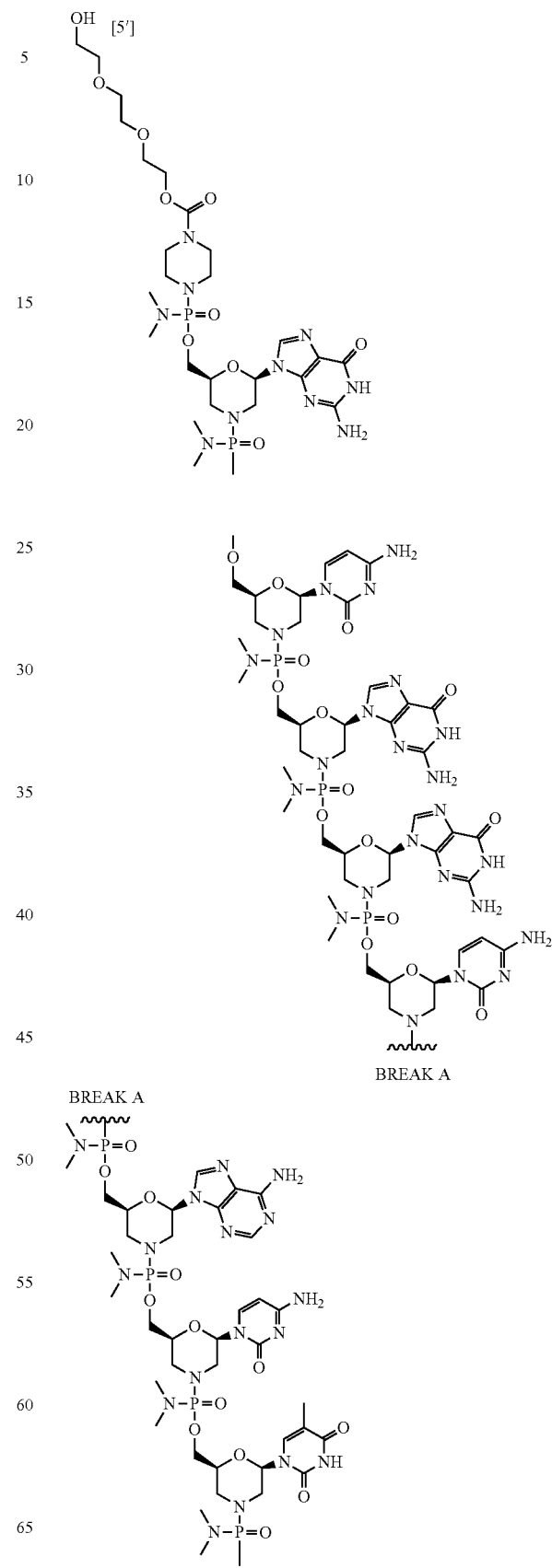

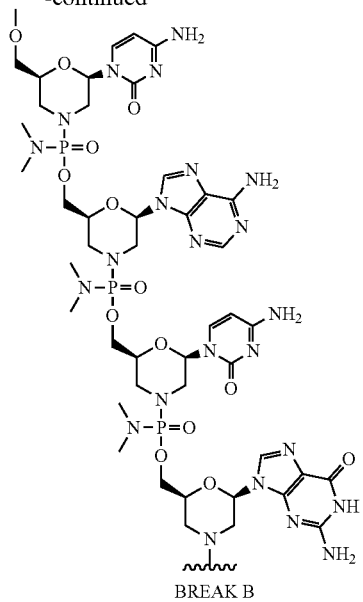
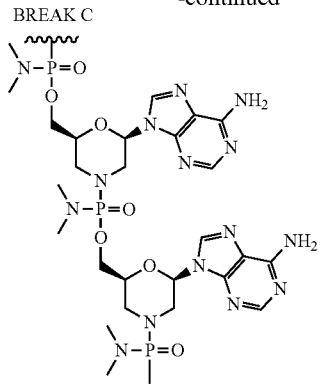
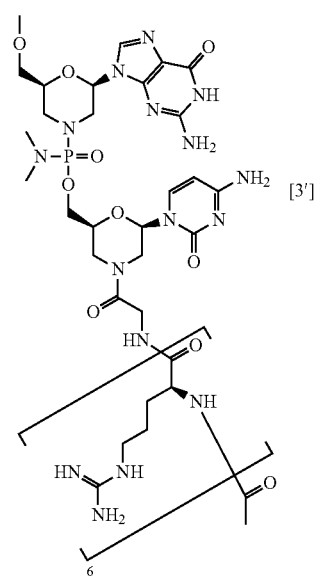
(XXIII h)

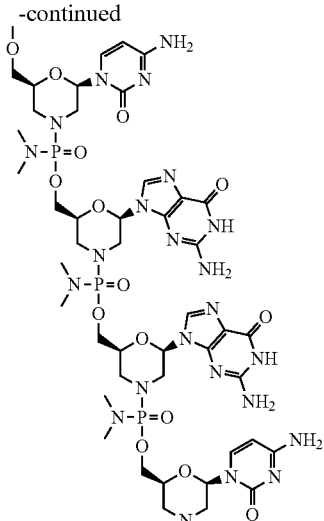
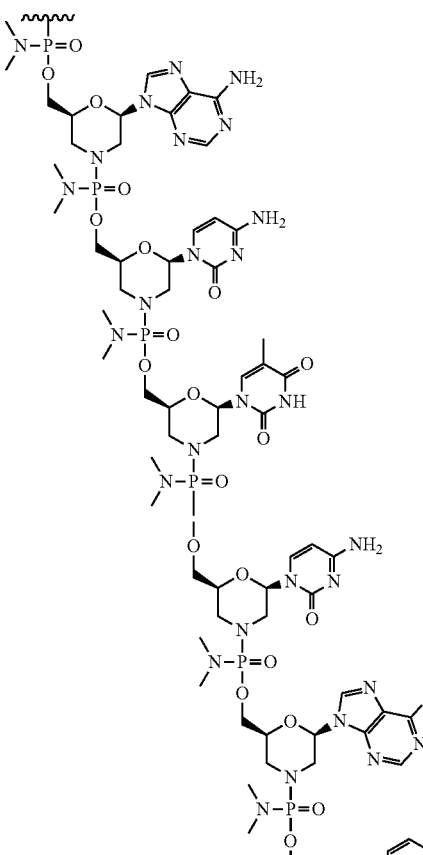
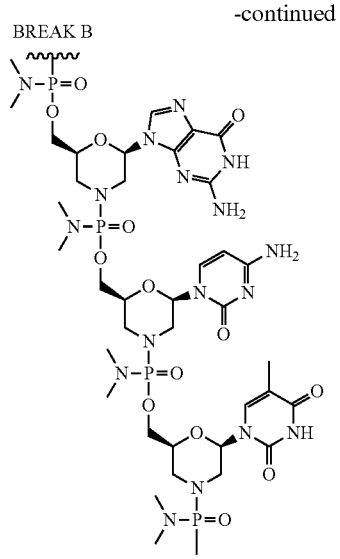
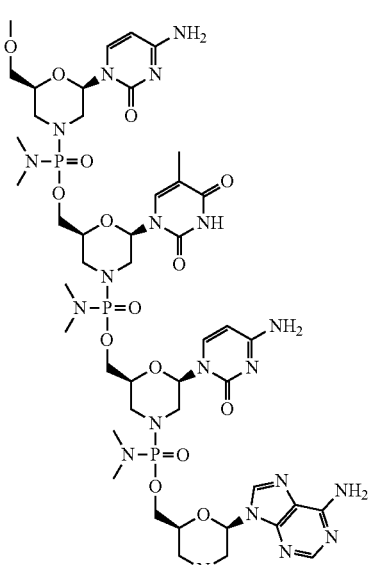
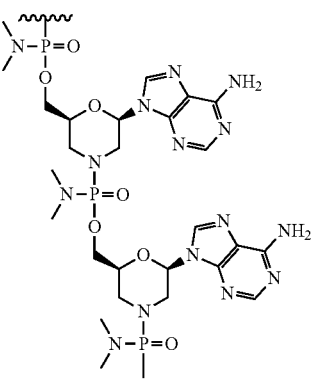

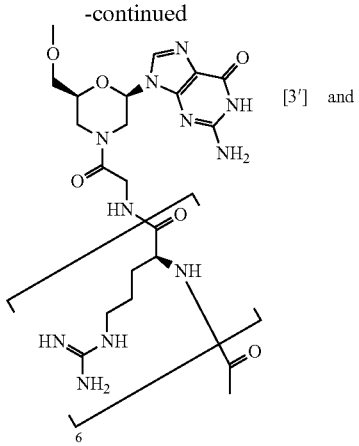 [3'] and
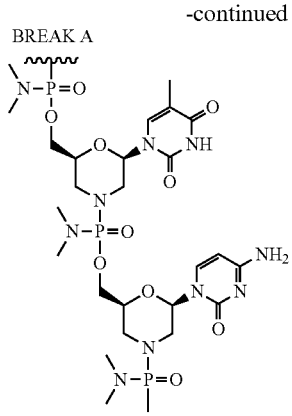
(XXIII i)
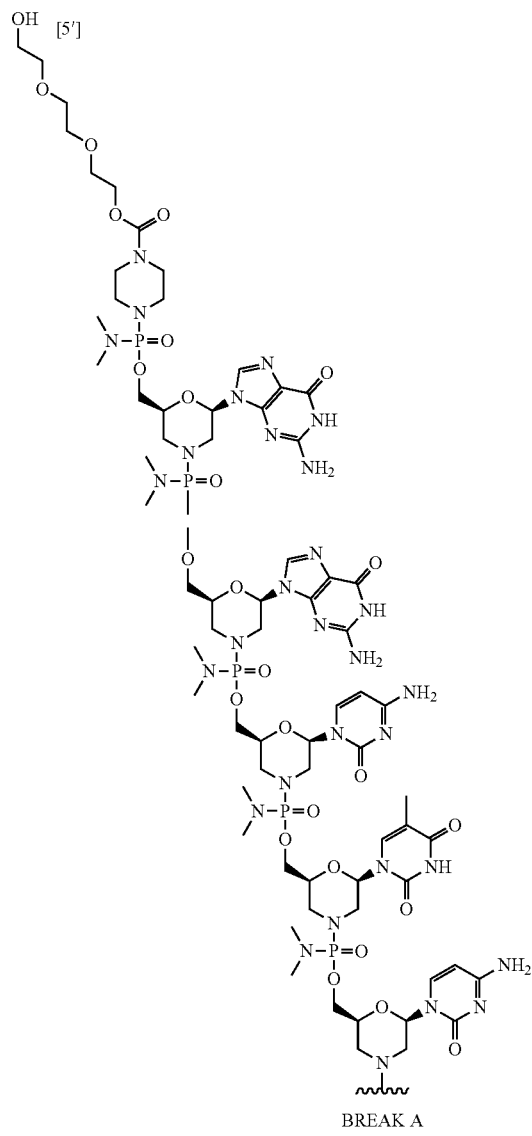
BREAK A
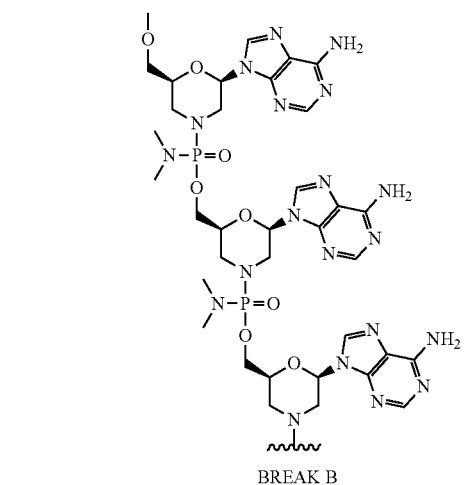
BREAK B
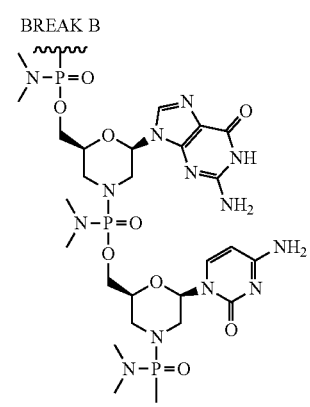

161
-continued

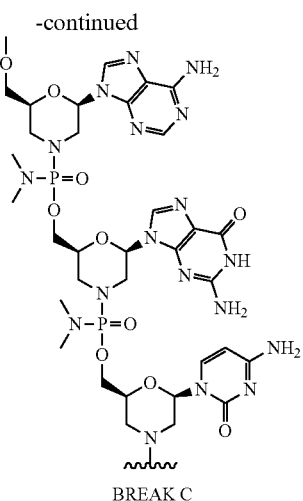

BREAK C

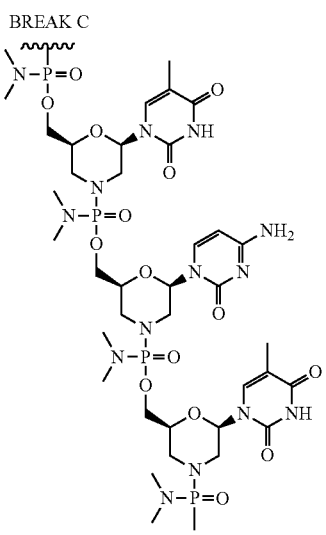

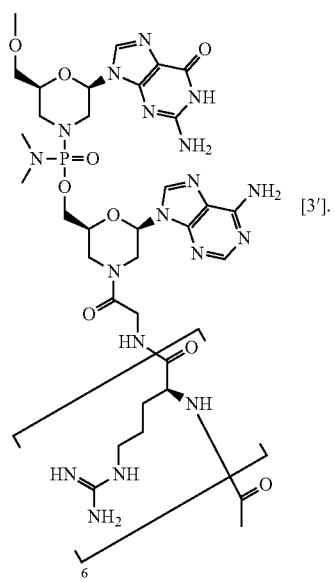

162

In some embodiments, the antisense oligomer of formula (XXIII) is of formula (XXIII a). In some embodiments, the antisense oligomer of formula (XXIII) is of formula (XXIII b). In some embodiments, the antisense oligomer of formula (XXIII) is of formula (XXIII c). In some embodiments, the antisense oligomer of formula (XXIII) is of formula (XXIII d). In some embodiments, the antisense oligomer of formula (XX) is of formula (XXIII e). In some embodiments, the antisense oligomer of formula (XXIII) is of formula (XXIII f). In some embodiments, the antisense oligomer of formula (XXIII) is of formula (XXIII g). In some embodiments, the antisense oligomer of formula (XXIII) is of formula (XXIII h). In some embodiments, the antisense oligomer of formula (XXIII) is of formula (XXIII i).

In another aspect, the disclosure features an antisense oligomer compound of any one of formulas (XXII a) to (XXII i), or a pharmaceutically acceptable salt thereof, wherein X at each occurrence is independently selected from

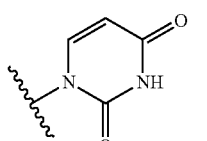
(U)

or

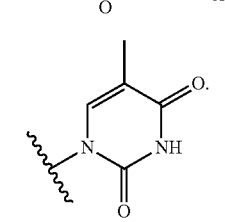
(T)

In some embodiments, each X is T.

In another aspect, the disclosure features an antisense oligomer compound of any one of formulas (XXIII a) to (XXIII i), or a pharmaceutically acceptable salt thereof.

D. The Preparation of PMO-X with Basic Nitrogen Internucleoside Linkers

Morpholino subunits, the modified intersubunit linkages, and oligomers comprising the same can be prepared as described, for example, in U.S. Pat. Nos. 5,185,444, and 7,943,762, which are incorporated by reference in their entireties. The morpholino subunits can be prepared according to the following general Reaction Scheme I.

Reaction Scheme 1. Preparation of Morpholino Subunit

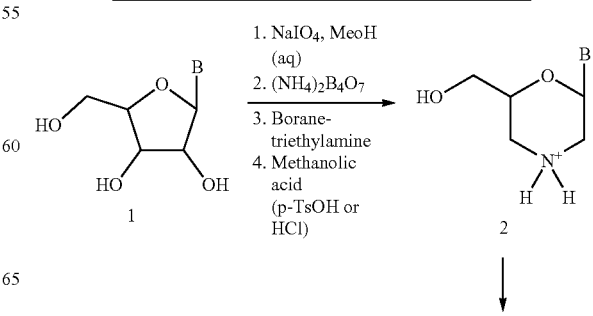

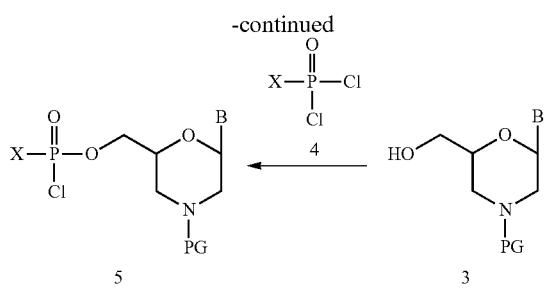

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunits having the desired linkage moiety 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762.

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$.

The preparation of modified morpholino subunits and morpholino oligomers are described in more detail in the Examples. The morpholino oligomers containing any number of modified linkages may be prepared using methods described herein, methods known in the art and/or described by reference herein. Also described in the examples are global modifications of morpholino oligomers prepared as previously described (see e.g., PCT publication WO2008036127).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

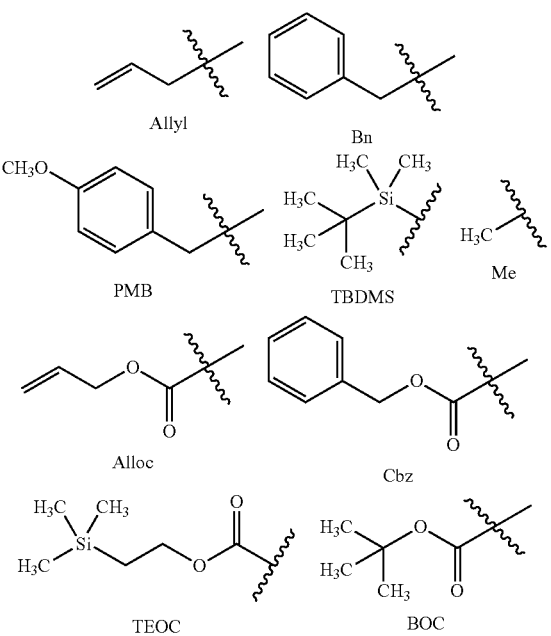

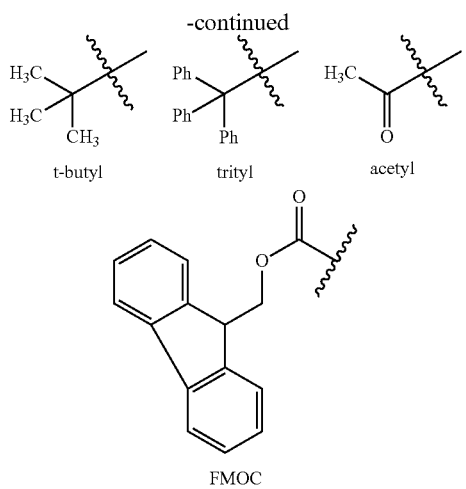

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO, and PMO-X containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

IV. Formulations

The compounds of the disclosure may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the disclosure encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the disclosure are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the disclosure: i.e., salts that retain the desired biological activity of the parent compound and do not impart undesired toxicological effects thereto. For oligomers, examples of pharmaceutically acceptable salts and their uses are further described in U.S. Pat. No. 6,287,860, which is incorporated herein in its entirety.

The present disclosure also includes pharmaceutical compositions and formulations which include the antisense compounds of the disclosure. The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present disclosure include, but are not limited to, solutions, emulsions, foams and liposome-containing formulations. The pharmaceutical compositions and formulations of the present disclosure may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is incorporated herein in its entirety.

Formulations of the present disclosure include liposomal formulations. As used in the present disclosure, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present disclosure may also include surfactants. The use of surfactants in drug products, formulations and in emulsions is well known in the art. Surfactants and their uses are further described in U.S. Pat. No. 6,287,860, which is incorporated herein in its entirety.

In some embodiments, the present disclosure employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers, surfactants and chelators. Surfactants include fatty acids and/or esters or salts thereof, bile acids and/or salts thereof. Bile acids/salts and fatty acids and their uses are further described in U.S. Pat. No. 6,287,860, which is incorporated herein in its entirety. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860, which is incorporated herein in its entirety. Oral formulations for oligomers and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the disclosure provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxyco-formycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the disclosure, such chemotherapeutic agents may be used individually (e.g., 5-FU and oligomer), sequentially (e.g., 5-FU and oligomer for a period of time followed by MTX and oligomer), or in combination with one or more other such chemotherapeutic agents (e.g., 5-FU, MTX and oligomer, or 5-FU, radiotherapy and oligomer). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the disclosure. Combinations of antisense compounds and other non-antisense drugs are also within the scope of this disclosure. Two or more combined compounds may be used together or sequentially.

In another related embodiment, compositions of the disclosure may contain one or more antisense compounds, particularly oligomers, targeted to a first nucleic acid and one or more additional antisense compounds targeted to a second nucleic acid target. Alternatively, compositions of the disclosure may contain two or more antisense compounds targeted to different regions of the same nucleic acid target. Numerous examples of antisense compounds are known in the art. Two or more combined compounds may be used together or sequentially.

V. Methods of Use

Certain embodiments relate to methods of increasing expression of exon 2-containing GAA mRNA and/or protein using the antisense oligomers of the present disclosure for therapeutic purposes (e.g., treating subjects with GSD-II). Accordingly, in some embodiments, the present disclosure provides methods of treating an individual afflicted with or at risk for developing GSD-II, comprising administering an effective amount of an antisense oligomer of the disclosure to the subject. In some embodiments, the antisense oligomer comprising a nucleotide sequence of sufficient length and complementarity to specifically hybridize to a region within the pre-mRNA of the acid alpha-glucosidase (GAA) gene, wherein binding of the antisense oligomer to the region increases the level of exon 2-containing GAA mRNA in a cell and/or tissue of the subject. Exemplary antisense targeting sequences are shown in Tables 2A-2C herein.

Also included are antisense oligomers for use in the preparation of a medicament for the treatment of glycogen storage disease type II (GSD-II; Pompe disease), comprising a nucleotide sequence of sufficient length and complementarity to specifically hybridize to a region within the pre-mRNA of the acid alpha-glucosidase (GAA) gene, wherein binding of the antisense oligomer to the region increases the level of exon 2-containing GAA mRNA.

In some embodiments of the method of treating GSD-II or the medicament for the treatment of GSD-II, the antisense oligomer compound comprises:
 a non-natural chemical backbone selected from a phosphoramidate or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing; and
 a targeting sequence complementary to a region within intron 1 (SEQ ID. NO: 1), intron 2 (SEQ ID. NO: 60), or exon 2 (SEQ ID. NO: 61) of a pre-mRNA of the human acid alpha-glucosidase (GAA) gene.

As noted above, "GSD-II" refers to glycogen storage disease type II (GSD-II or Pompe disease), a human autosomal recessive disease that is often characterized by under expression of GAA protein in affected individuals. Included are subjects having infantile GSD-II and those having late onset forms of the disease.

In certain embodiments, a subject has reduced expression and/or activity of GAA protein in one or more tissues (for example, relative to a healthy subject or an earlier point in time), including heart, skeletal muscle, liver, and nervous system tissues. In some embodiments, the subject has increased accumulation of glycogen in one or more tissues (for example, relative to a healthy subject or an earlier point in time), including heart, skeletal muscle, liver, and nervous system tissues. In specific embodiments, the subject has at least one IVS1-13T>G mutation (also referred to as c.336-13T>G), possibly in combination with other mutation(s) that leads to reduced expression of functional GAA protein. A summary of molecular genetic testing used in GSD-II is shown in Table 3 below.

TABLE 3

| Gene Symbol | Test Method | Mutations Detected | Mutation Detection Frequency by Test Method | Test Availability |
|---|---|---|---|---|
| GAA | Sequence analysis | p.Arg854* | ~50%-60% | Clinical |
| | | p.Asp645Glu | ~40%-80% | |
| | | IVS1-13T > G | ~50%-85% | |
| | | Other sequence variants in the gene | 83%-93% | |
| | Sequence analysis of select exons | Sequence variants in the select exons | 83%-93% | |
| | Targeted mutation analysis | Sequence variants in targeted sites | 100% of for variants among the targeted mutations | |
| | Deletion/ duplication analysis | Exonic and whole-gene deletions/duplications | 5%-13% | |

Certain embodiments relate to methods of increasing expression of exon 2-containing GAA mRNA or protein in a cell, tissue, and/or subject, as described herein. In some instances, exon-2 containing GAA mRNA or protein is increased by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject, a control composition without the antisense oligomer, the absence of treatment, and/or an earlier time-point. Also included are methods of maintaining the expression of containing GAA mRNA or protein relative to the levels of a healthy control.

Some embodiments relate to methods of increasing expression of functional/active GAA protein a cell, tissue, and/or subject, as described herein. In certain instances, the level of functional/active GAA protein is increased by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject, a control composition without the antisense oligomer, the absence of treatment, and/or an earlier time-point. Also included are methods of maintaining the expression of functional/active GAA protein relative to the levels of a healthy control.

Particular embodiments relate to methods of reducing the accumulation of glycogen in one or more cells, tissues, and/or subjects, as described herein. In certain instances, the accumulation of glycogen is reduced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject, a control composition without the antisense oligomer, the absence of treatment, and/or an earlier time-point. Also included are methods of maintaining normal or otherwise healthy glycogen levels in a cell, tissue, and/or subject (e.g., asymptomatic levels or levels associated with reduced symptoms of GSD-II).

Also included are methods of reducing one or more symptoms of GSD-II in a subject in need thereof. Particular examples include symptoms of infantile GSD-II such as cardiomegaly, hypotonia, cardiomyopathy, left ventricular outflow obstruction, respiratory distress, motor delay/muscle weakness, and feeding difficulties/failure to thrive. Additional examples include symptoms of late onset GSD-II such as muscle weakness (e.g., skeletal muscle weakness including progressive muscle weakness), impaired cough, recurrent chest infections, hypotonia, delayed motor milestones, difficulty swallowing or chewing, and reduced vital capacity or respiratory insufficiency.

The antisense oligomers of the disclosure can be administered to subjects to treat (prophylactically or therapeutically) GSD-II. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced. Direct CNS delivery may be employed, for instance, intracerebral ventribular or intrathecal administration may be used as routes of administration.

In particular embodiments, the antisense oligomer(s) are administered to the subject by intramuscular injection (IM), i.e., they are administered or delivered intramuscularly. Non-limiting examples of intramuscular injection sites include the deltoid muscle of the arm, the vastus lateralis muscle of the leg, and the ventrogluteal muscles of the hips, and dorsogluteal muscles of the buttocks. In specific embodiments, a PMO, PMO-X, or PPMO is administered by IM.

In certain embodiments, the subject in need thereof as glycogen accumulation in central nervous system tissues. Examples include instances where central nervous system pathology contributes to respiratory deficits in GSD-II (see, e.g., DeRuisseau et al., PNAS USA. 106:9419-24, 2009). Accordingly, the antisense oligomers described herein can be delivered to the nervous system of a subject by any art-recognized method, e.g., where the subject has GSD-II with involvement of the CNS. For example, peripheral blood injection of the antisense oligomers of the disclosure can be used to deliver said reagents to peripheral neurons via diffusive and/or active means. Alternatively, the antisense oligomers can be modified to promote crossing of the blood-brain-barrier (BBB) to achieve delivery of said reagents to neuronal cells of the central nervous system (CNS). Specific recent advancements in antisense oligomer technology and delivery strategies have broadened the scope of antisense oligomer usage for neuronal disorders (see, e.g., Forte, A., et al. 2005. Curr. Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the foregoing are incorporated herein in their entirety by reference). For example, the antisense oligomers of the disclosure can be generated as peptide nucleic acid (PNA) compounds. PNA reagents have each been identified to cross the BBB (Jaeger, L. B., and W. A. Banks. 2005. Methods Mol. Med. 106:237-251). Treatment of a subject with, e.g., a vasoactive agent, has also been described to promote transport across the BBB (Id). Tethering of the antisense oligomers of the disclosure to agents that are actively transported across the BBB may also be used as a delivery mechanism. Administration of antisense agents together with contrast agents such as iohexol (e.g., separately, concurrently, in the same formulation) can also facilitate delivery across the BBB, as described in PCT Publication No. WO/2013/086207, incorporated by reference in its entirety.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

The antisense oligomers described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compounds (e.g., antisense oligomers) of the present disclosure may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, the antisense oligomer is administered to a mammalian subject, e.g., human or domestic animal, exhibiting the symptoms of a lysosomal storage disorder, in a suitable pharmaceutical carrier. In one aspect of the method, the subject is a human subject, e.g., a patient diagnosed as having GSD-II (Pompe disease). In one preferred embodiment, the antisense oligomer is contained in a pharmaceutically acceptable carrier, and is delivered orally. In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer of the disclosure may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

In some embodiments, the antisense oligomer is actively taken up by mammalian cells. In further embodiments, the antisense oligomer may be conjugated to a transport moiety (e.g., transport peptide or CPP) as described herein to facilitate such uptake.

VI. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 μg to 100 g per kg of body weight, once or more daily, to once every 20 years.

While the present disclosure has been described with specificity in accordance with certain of its embodiments, the following examples serve only to illustrate the disclosure and are not intended to limit the same. Each of the references, patents, patent applications, GenBank accession numbers, and the like recited in the present application are incorporated herein by reference in its entirety.

VII. Examples

Example 1

Design of Antisense Targeting Sequences

Antisense oligomer targeting sequences were designed for therapeutic splice-switching applications related to the IVS1-13T>G mutation in the human GAA gene. Here, it is expected that splice-switching oligomers will suppress intronic and exonic splice silencer elements (ISS and ESS elements, respectively) and thereby promote exon 2 retention in the mature GAA mRNA. Restoration of normal or near-normal GAA expression would then allow functional enzyme to be synthesized, thereby providing a clinical benefit to GSD-II patients.

Certain antisense targeting sequences were thus designed to mask splice silencer elements, either within exon 2 of the GAA gene or within its flanking introns. Non-limiting examples of potential silencer element targets include hnRNPA1 motifs (TAGGGA), Tra2-β motifs, and 9G8 motifs. In silico secondary structure analysis (mFold) of introns 1 and 2 (IVS1 and IVS2, respectively) mRNAs was also employed to identify long distance interactions that could provide suitable antisense target sequences. The antisense targeting sequences resulting from this analysis are shown in Tables 2A-2C herein.

Exemplary oligomers comprising a targeting sequence as set forth in Tables 2A-2C were prepared as PMOs and/or PPMOs (oligomers conjugated to a CPP, such as an arginine-rich CPP). As described below, these antisense oligomers were introduced into GSD-II patient-derived fibroblasts using a nucleofection protocol as also described in Example 2 below.

Example 2

Materials and Methods

GSD-II cells. Patient-derived fibroblasts or lymphocytes from individuals with GSD-II (Coriell cell lines GM00443 and GM11661) were cultured according to standard protocols in Eagle's MEM with 10% FBS. Cells were passaged about 3-5 days before the experiments and are approximately 80% confluent at transfection or nucleofection.

GM00443 fibroblasts are from a 30 year old male. Adult form; onset in third decade; normal size and amount of mRNA for GAA, GAA protein detected by antibody, but only 9 to 26% of normal acid-alpha-1,4 glucosidase activity; passage 3 at CCR; donor subject is heterozygous with one allele carrying a T>G transversion at position −13 of the acceptor site of intron 1 of the GAA gene, resulting in alternatively spliced transcripts with deletion of the first coding exon [exon 2 (IVS1-13T>G)].

GM11661 fibroblasts are from a 38 year old male. Abnormal liver function tests; occasional charley-horse in legs during physical activity; morning headaches; intolerance to greasy foods; abdominal cyst; deficient fibroblast and WBC acid-alpha-1,4 glucosidase activity; donor subject is a compound heterozygote: allele one carries a T>G transversion at position −13 of the acceptor site of intron 1 of the GAA gene (IVS1-13T>G); the resulting alternatively spliced transcript has an in frame deletion of exon 2 which contains the initiation codon; allele two carries a deletion of exon 18.

Nucleofection Protocol. Antisense PMOs/PPMOs (PMOs conjugated to an arginine-rich peptide) are prepared as 1-2 mM stock solutions in nuclease-free water (not treated with DEPC) from which appropriate dilutions are made for nucleofection. GSD-II cells are trypsinized, counted, centrifuged at 90 g for 10 minutes, and $1-5\times10^5$ cells per well are resuspended in nucleofection Solution P2 (Lonza). Antisense PMO solution and cells are then added to each well of a Nucleocuvette 16-well strip, and pulsed with program EN-100. Cells are incubated at room temperature for 10 minutes and transferred to a 12-well plate in duplicate. Total RNA is isolated from treated cells after 48 hours using the GE Illustra 96 Spin kit following the manufacturer's recommended protocol. Recovered RNA is stored at −80° C. prior to analysis.

GAA RT-PCR. For PCR detection of exon 2-containing mRNAs, primer sequences are chosen from exon 1(forward) to exon 3(reverse). RT-PCR across exons 1-3 will generate a full length amplicon of around 1177 bases. The size difference between the intact amplicon (~1177 bases) and the ~600 base transcript that is missing exon 2 (exon 2 is ~578 bases) means there will be substantial preferential amplification of the shorter product. This will set a high benchmark in assaying the efficacy of antisense oligomers to induce splicing of the full-length transcript or exon2-containing transcript.

Reverse transcriptase PCR is performed to amplify the GAA allele using the SuperScript III One-Step RT-PCR system (Invitrogen). 400 ng total RNA isolated from nucleofected cells is reverse transcribed and amplified with the gene-specific primers.

The amplification solution provided in the One-Step kit is supplemented with Cy5-labeled dCTP (GE) to enable band visualization by fluorescence. Digested samples are run on a pre-cast 10% acrylamide/TBE gel (Invitrogen) and visualized on a Typhoon Trio (GE) using the 633 nm excitation laser and 670 nm BP 30 emission filter with the focal plane at the platen surface. Gels are analyzed with ImageQuant (GE) to determine the intensities of the bands. Intensities from all bands containing exon 2 are added together to represent the full exon 2 transcript levels in the inclusion analysis.

Alternatively, PCR amplification products (without the supplemented Cy5-labeled dCTP) are analyzed on a Caliper LabChip GX bioanalyzer or Agilent 2200 Tape Station for determination of % exon inclusion.

GAA Enzyme Assay & Protein Simple Wes. Untransformed patient-derived fibroblasts (GM00443) were nucleofected with PMO at various concentrations in Lonza's P3 nucleofector solution and incubated at 37° C. with 5% $C_{O2}$ for six days. Cells were washed twice with Hank's Balanced Salt Solution (HBSS), lysed with unbuffered $H_2O$, frozen/thawed three times, and then shaken at 1000 rpm for 1 minute. The Bio-Rad DC™ Assay Kit was used to quantify total protein concentration. For the enzyme assay, cell lysate was combined with 1.4 mM 4-methylumbelliferyl α-D-glucopyranoside in 0.2 M acetate buffer (pH 3.9 or 6.5), incubated at 37° C. for three hours, and then fluorescence was read at 360 nm excitation and 460 nm emission. A standard curve was generated using 4-methylumbelliferone.

A Western blot on GAA protein was performed using the ProteinSimple® Wes™ system (12-230 kDa Master Kit). Rabbit anti-GAA antibody [clone EPR4716(2)] from Abcam was diluted 1:100 and was duplexed with mouse anti-GAPDH [clone 6c5] from Santa Cruz Biotechnology diluted 1:5. Mouse and rabbit secondary antibodies from ProteinSimple® were combined 1:1 for duplexing. GAA was quantified using ProteinSimple® Compass software as area under the curve for all forms of GAA and normalized to GAPDH.

Example 3

Preparation of Antisense PMOS and PPMOS

Antisense PMOs were designed to target the human GAA pre-mRNA (e.g., intron 1 of the human GAA pre-mRNA) were synthesized as described herein and used to treat GSD-II patient-derived fibroblasts.

TABLE 4A

| Nucleofected PMO or PPMO Compounds (Internal Deletion Sequences) | | | | | |
|---|---|---|---|---|---|
| Name | Targeting Sequence (TS)* (5'-3') | TS SEQ ID NO | 5' Attachment** | 3' Attachment*** | CPP SEQ ID NO |
| GAA-IVS1.SA.(-189, -165)-G | GGC CAG AAG GAA GGC GAG AAA AGC | 13 | TEG | H | |
| GAA-IVS1.SA.(-190, -166)-G | GCC AGA AGG AAG GC GAG AAA AGC T | 87 | TEG | H | |
| GAA-IVS1.SA.(-191, -167)-G | CCA GAA GGA AGG CGA GAA AAG CTC | 88 | TEG | H | |
| GAA-IVS1.SA.(-192, -168)-G | CAG AAG GAA GGC GAG AAA AGC TCC | 89 | TEG | H | |
| GAA-IVS1.SA.(-193, -169)-G | AGA AGG AAG GCG AGA AAA GCT CCA | 90 | TEG | H | |
| GAA-IVS1.SA.(-194, -170)-G | GAA GGA AGG CGA GAA AAG CTC CAG | 91 | TEG | H | |
| GAA-IVS1.SA.(-195, -171)-G | AAG GAA GGC GAG AAA AGC TCC AGC | 92 | TEG | H | |
| GAA-IVS1.SA.(-196, -172)-G | AGG AAG GCG AGA AAA GCT CCA GCA | 93 | TEG | H | |
| GAA-IVS1(-76-52)-2G | CGG CTC TCA AAG CAG CTC TGA GA | 94 | TEG | H | |
| GAA-IVS1(-75-51)-2G | ACG GCT CTC AAA GCA GCT CTG AG | 95 | TEG | H | |
| GAA-IVS1(-74-50)-2G | CAC GGC TCT CAA AGC AGC TCT GA | 96 | TEG | H | |
| GAA-IVS1(-73-49)-2G | TCA CGG CTC TCA AAG CAG CTC TG | 97 | TEG | H | |
| GAA-IVS1(-72-48)-2G | CTC ACG GCT CTC AAA GCA GCT CT | 98 | TEG | H | |
| GAA-IVS1(-71-47)-2G | ACT CAC GGC TCT CAA AGC AGC TC | 99 | TEG | H | |
| GAA-IVS1(-66-42)-2G | GCG GCA CTC ACG GCT CTC AAA GC | 100 | TEG | H | |

TABLE 4A-continued

Nucleofected PMO or PPMO Compounds (Internal Deletion Sequences)

| Name | Targeting Sequence (TS)* (5'-3') | TS SEQ ID NO | 5' Attachment** | 3' Attachment*** | CPP SEQ ID NO |
|---|---|---|---|---|---|
| GAA-IVS1(-65-41)-2G | GGC GGC ACT CAC GGC TCT CAA AG | 101 | TEG | H | |
| GAA-IVS1(-67-43)-2G | CGG CAC TCA CGG CTC TCA AAG CA | 102 | TEG | H | |
| GAA-IVS1(-69-45)-2G | GCA CTC ACG GCT CTC AAA GCA GC | 103 | TEG | H | |
| GAA-IVS1(-68-44)-2G | GGC ACT CAC GGC TCT CAA AGC AG | 104 | TEG | H | |
| GAA-IVS1(-70-46)-2G | CAC TCA CGG CTC TCA AAG CAG CT | 105 | TEG | H | |
| GAA-IVS1.SA.(-189, -166)-G | GCC AGA AGG AAG GCG AGA AAA GC | 33 | TEG | H | |
| GAA-IVS1.SA.(-189, -167)-G | CCA GAA GGA AGG CGA GAA AAG C | 34 | TEG | H | |
| GAA-IVS1.SA.(-189, -168)-G | CAG AAG GAA GGC GAG AAA AGC | 35 | TEG | H | |
| GAA-IVS1.SA.(-188, -165)-G | GGC CAG AAG GAA GGC GAG AAA AG | 36 | TEG | H | |
| GAA-IVS1.SA.(-187, -165)-G | GGC CAG AAG GAA GGC GAG AAA A | 37 | TEG | H | |
| GAA-IVS1.SA.(-186, -165)-G | GGC CAG AAG GAA GGC GAG AAA | 38 | TEG | H | |
| GAA-IVS1(-67-43)-2G/R6 | CGG CAC TCA CGGC TCT CAA AGC A | 106 | TEG | R6G | 11 |
| GAA-IVS1(-66-42)-2G/R6 | GCG GCA CTC ACGG CTC TCA AAG C | 107 | TEG | R6G | 11 |
| GAA-IVS1(-65-41)-2G/R6 | GGC GGC ACT CAC G GCT CTC AAA G | 108 | TEG | R6G | 11 |
| GAA-IVS1.SA.(-189, -167)-G/R6 | CCA GAA GGA AGG CGA GAA AAG C | 34 | TEG | R6G | 11 |
| GAA-IVS1.SA.(-189, -168)-G/R6 | CAG AAG GAA GGC GAG AAA AGC | 35 | TEG | R6G | 11 |
| GAA-IVS1.SA.(-188, -165)-G/R6 | GGC CAG AAG GAA GGC GAG AAA AG | 36 | TEG | R6G | 11 |
| GAA-IVS1.SA.(-189, -165)-G/R6 | GGC CAG AAG GAA GGC GAG AAA AGC | 13 | TEG | R6G | 11 |
| GAA-IVS1.SA.(-180, -156)-G | TGG GGA GAG GGC CAG AAG GAA GGC | 109 | TEG | H | |
| GAA-IVS1.SA.(-180, -156)-2G | TGG GGA GAG GGC CAG AAG GAA GC | 110 | TEG | H | |
| GAA-IVS1.SA.(-180, -156)-3G | TGG GGA GAG GGC CAG AAG GAA C | 111 | TEG | H | |
| GAA-IVS1.SA.(-189, -165)-2G | GGC CAG AAG GAA GCG AGA AAA GC | 45 | TEG | H | |
| GAA-IVS1.SA.(-189, -165)-3G | GGC CAG AAG GAA CGA GAA AAG C | 46 | TEG | H | |
| GAA-IVS1.SA.(-196, -172)-2G | AGG AAG CGA GAA AAG CTC CAG CA | 112 | TEG | H | |
| GAA-IVS1.SA.(-196, -172)-3G | AGG AAC GAG AAA AGC TCC AGC A | 113 | TEG | H | |

TABLE 4A-continued

Nucleofected PMO or PPMO Compounds (Internal Deletion Sequences)

| Name | Targeting Sequence (TS)* (5'-3') | TS SEQ ID NO | 5' Attachment** | 3' Attachment*** | CPP SEQ ID NO |
|---|---|---|---|---|---|
| GAA-IVS1(-76-52)-G | CGG GCT CTC AAA GCA GCT CTG AGA | 114 | TEG | H | |
| GAA-IVS1(-76-52)-3G | CGC TCT CAA AGC AGC TCT GAG A | 115 | TEG | H | |
| GAA-IVS1(-76-52)-4G | CCT CTC AAA GCA GCT CTG AGA | 116 | TEG | H | |
| GAA-IVS1(-65-41)-G | GGC GGC ACT CAC GGG CTC TCA AAG | 117 | TEG | H | |
| GAA-IVS1(-65-41)-3G | GGC GGC ACT CAC GCT CTC AAA G | 118 | TEG | H | |
| GAA-IVS1(-65-41)-4G | GGC GGC ACT CAC CTC TCA AAG | 119 | TEG | H | |
| GAA-IVS1(-57-33)-G | GCG GGA GGG GCG GCA CTC ACG GGC | 120 | TEG | H | |
| GAA-IVS1(-57-33)-2G | GCG GGA GGG GCG GCA CTC ACG GC | 121 | TEG | H | |
| GAA-IVS1(-57-33)-3G | GCG GGA GGG GCG GCA CTC ACG C | 122 | TEG | H | |
| GAA-IVS1(-57-33)-4G | GCG GGA GGG GCG GCA CTC ACC | 123 | TEG | H | |

*Thymines (T) are optionally uracils (U).
**TEG is defined above.

TABLE 4B Nucleofected PMO or PPMO compounds

| Name | Targeting Sequence (TS)* (5'-3') | TS SEQ ID NO | 5' Attachment** | 3' Attachment*** | CPP SEQ ID NO |
|---|---|---|---|---|---|
| GAA-IVS1.SA.(-189, -165) | GGC CAG AAG GAA GGG CGA GAA AAG C | 59 | TEG | H | |
| GAA-IVS1.SA.(-191, -167) | CCA GAA GGA AGG GCG AGA AAA GCT C | 124 | TEG | H | |
| GAA-IVS1.SA.(-195, -171) | AAG GAA GGG CGA GAA AAG CTC CAG C | 125 | TEG | H | |
| GAA-IVS1(-57-33) | GCG GGA GGG GCG GCA CTC ACG GGG C | 126 | TEG | H | |
| GAA-IVS1.SA.(-180, -156) | TGG GGA GAG GGC CAG AAG GAA GGG C | 127 | TEG | H | |
| GAA-IVS1.SA.(-189, -165)-R6 | GGC CAG AAG GAA GGG CGA GAA AAG C | 59 | TEG | R6G | 11 |
| GAA-IVS1(-74-55)-R6 | GGC TCT CAA AGC AGC TCT GA | 128 | TEG | R6G | 11 |
| GAA-IVS1.SA.(-193, -169) | AGA AGG AAG GGC GAG AAA AGC TCC A | 129 | TEG | H | |
| GAA-IVS1(-80-56) | GCT CTC AAA GCA GCT CTG AGA CAT C | 130 | TEG | H | |
| GAA-IVS1(-81-57) | CTC TCA AAG CAG CTC TGA GAC ATC A | 131 | TEG | H | |

TABLE 4B Nucleofected PMO or PPMO compounds

| Name | Targeting Sequence (TS)* (5'-3') | TS SEQ ID NO | 5' Attachment** | 3' Attachment*** | CPP SEQ ID NO |
|---|---|---|---|---|---|
| GAA-IVS1(-82-58) | TCT CAA AGC AGC TCT GAG ACA TCA A | 132 | TEG | H | |
| GAA-IVS1(-83-59) | CTC AAA GCA GCT CTG AGA CAT CAA C | 133 | TEG | H | |
| GAA-IVS1(-84-60) | TCA AAG CAG CTC TGA GAC ATC AAC C | 134 | TEG | H | |
| GAA-IVS1(-85-61) | CAA AGC AGC TCT GAG ACA TCA ACC G | 135 | TEG | H | |
| GAA-IVS1(-86-62) | AAA GCA GCT CTG AGA CAT CAA CCG C | 136 | TEG | H | |
| GAA-IVS1(-87-63) | AAG CAG CTC TGA GAC ATC AAC CGC G | 137 | TEG | H | |
| GAA-IVS1(-88-64) | AGC AGC TCT GAG ACA TCA ACC GCG G | 138 | TEG | H | |
| GAA-IVS1(-89-65) | GCA GCT CTG AGA CAT CAA CCG CGG C | 139 | TEG | H | |
| GAA-IVS1(-90-66) | CAG CTC TGA GAC ATC AAC CGC GGC T | 140 | TEG | H | |

*Thymines (T) are optionally uracils (U).
**TEG is defined above.

TABLE 4C

Nucleofected PMO or PPMO compounds

| Name | Targeting Sequence (TS)* (5'-3') | TS SEQ ID NO | 5' Attachment** | 3' Attachment** |
|---|---|---|---|---|
| GAA-IVS1.SA.(-190, -166) | GCC AGA AGG AAG GGC GAG AAA AGC T | 141 | TEG | H |
| GAA-IVS1.SA.(-192, -168) | CAG AAG GAA GGG CGA GAA AAG CTC C | 142 | TEG | H |
| GAA-IVS1.SA.(-194, -170) | GAA GGA AGG GCG AGA AAA GCT CCA G | 143 | TEG | H |
| GAA-IVS1.SA.(-196, -172) | AGG AAG GGC GAG AAA AGC TCC AGC A | 144 | TEG | H |
| GAA-IVS1(-71-47) | ACT CAC GGG GCT CTC AAA GCA GCT C | 145 | TEG | H |
| GAA-IVS1(-79-55) | GGCTCTCAAAGCAGCT CTGAGACAT | 146 | TEG | H |
| GAA-IVS1(-74-55) | GGC TCT CAA AGC AGC TCT GA | 128 | TEG | H |
| GAA-IVS1(-179-160) | GAG AGG GCC AGA AGG AAG GG | 83 | TEG | H |
| GAA-IVS1.2178.20 | TTT GCC ATG TTA CCC AGG CT | 146 | TEG | H |
| GAA-IVS2.27.20 | GCG CAC CCT CTG CCC TGG CC | 147 | TEG | H |

TABLE 4C-continued

Nucleofected PMO or PPMO compounds

| Name | Targeting Sequence (TS)* (5'-3') | TS SEQ ID NO | 5' Attachment** | 3' Attachment** |
|---|---|---|---|---|
| GAAEx2A(+202+226) | GGC CCT GGT CTG CTG GCT CCC TGC T | 148 | TEG | H |

*Thymines (T) are optionally uracils (U).
**TEG is defined above.

Example 4

Antisense Oligomers Induce Elevated Expression Levels of Acid Alpha-Glucosidase in GSD-II Patient-Derived Fibroblasts The above-described antisense PMOs and PPMOs were delivered to GM00443 or GM11661 cells by nucleofection (see above, e.g., Materials and Methods). After six days of incubation at 37° C. with 5% $C_{O2}$, cells were lysed and GAA activity in the lysates or GAA protein expression was measured by immunoassay as described above. In general, protein expression of GAA enzyme in cells treated with antisense oligonucleotides of the disclosure was higher than the GAA expression level in untreated cells, (see specific experimental results below). These results indicate that oligonucleotides of the disclosure induce elevated protein expression levels of GAA enzyme in GSD-II patient-derived fibroblasts. While not being bound by any theory or mechanism of action, in view of the experimental results described herein, the inventors believe that the oligomers of the disclosure suppress ISS and/or ESS elements and thereby promote exon 2 retention in the mature GAA mRNA.

Figure 16:
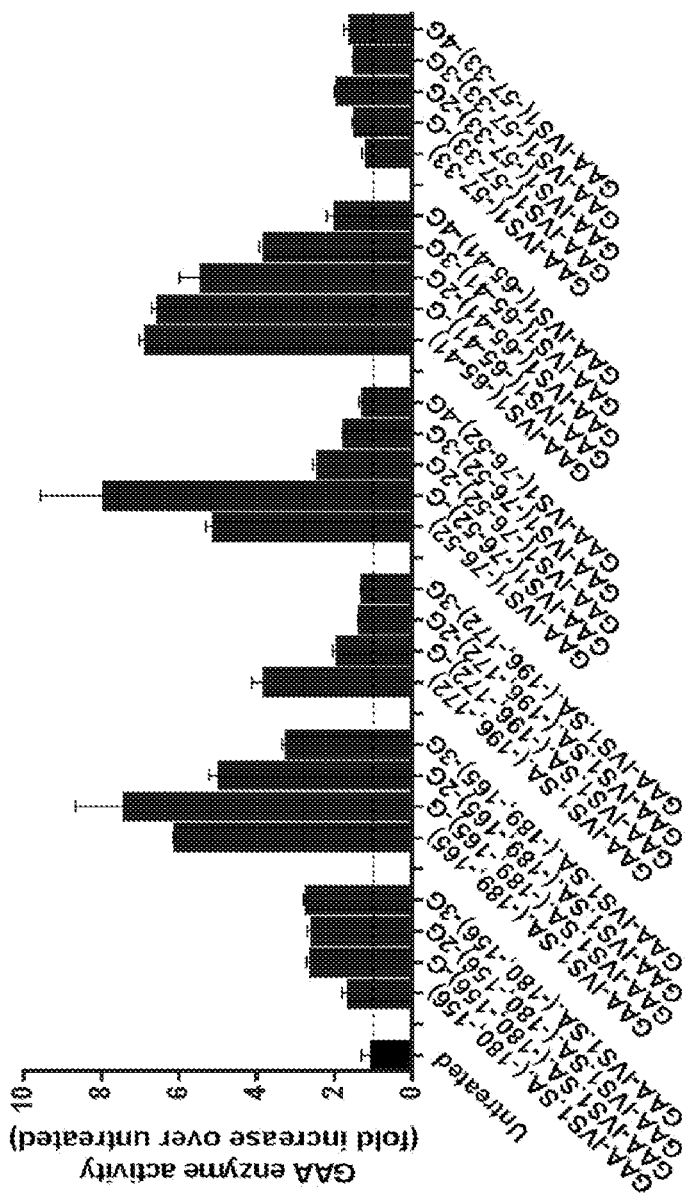
FIG. 16 is a bar graph depicting the the Enzyme Assay Dose Response found for various PMO compounds. The Y axis represents fold increase in GAA enzyme activity relative to untreated control. Individual compounds were dosed at 5 µM. The horizontal hashed line signifies the level of GAA activity in untreated cells.

As detailed in the following experiments, a series of variant PPMO and PMO oligonucleotides were evaluated for their ability to increase expression and/or activity of the GAA enzyme in cells from patients with Pompe disease. The targeting sequence of the variant oligonucleotides are complementary to a target region within intron 1 (SEQ ID NO: 1) of a pre-mRNA of the human alpha glucosidase (GAA) gene, wherein the target region comprises one, two, three, or four additional nucleobases compared to the targeting sequence, wherein those additional nucleobases are cytosines, and wherein the one, two, three, or four additional nucleobases have no corresponding complementary nucleobases in the targeting sequence (hence, the "-G" (guanine), "-2G", "-3G", or "-4G" annotations). The additional nucleobases are internal to the target region. Surprisingly it was discovered that many of these variant oligonucleotides had the same or similar activity to oligonucleotides having the corresponding non-variant targeting sequence (see, e.g., FIGS. 10b and 16). In some instances, oligonucleotides having variant targeting sequences were more active at increasing GAA enzyme activity in patient cells, as compared to oligonucleotides having the corresponding non-variant targeting sequence (see, e.g., FIG. 16). For example, as shown in FIG. 16, two different oligonucleotides having variant targeting sequences with one fewer G residue, as compared to oligonucleotides with targeting sequences that are 100% complementary to the GAA (non-variant), were more active at increasing GAA in fibroblasts derived from Pompe patients (FIG. 16).

Experiment 1

Figure 2:
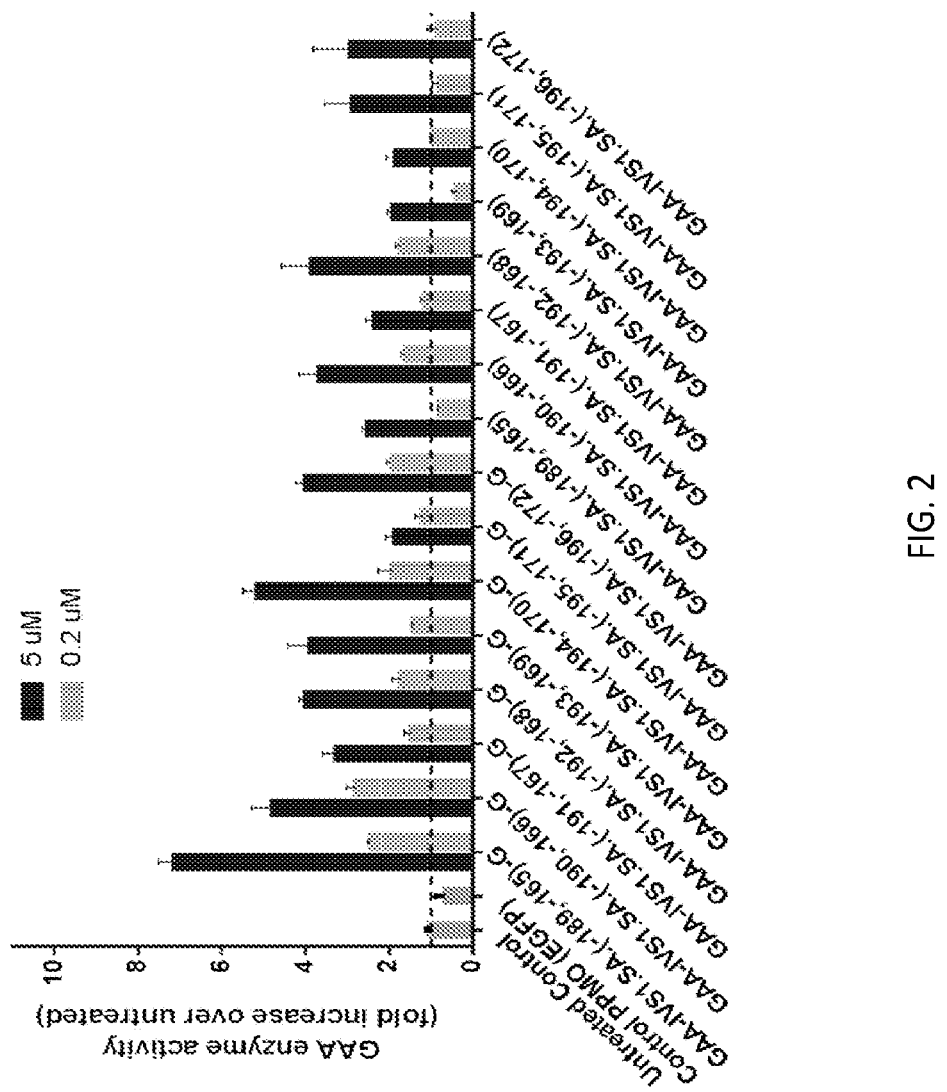

Selected oligonucleotides were evaluated in GM00443 cells at multiple doses (5 µM, and 0.2 µM). Following incubation of nucleofected cells for six days, lysates were prepared as above and the GAA enzyme activity was measured in the lysates. As shown in FIGS. 1 and 2, the lysates of cells treated with each of these compounds at all concentrations tested exhibited increased GAA enzyme activity as compared to the GAA enzyme activity level in lysates from untreated cells.

Experiment 2

Figure 3:
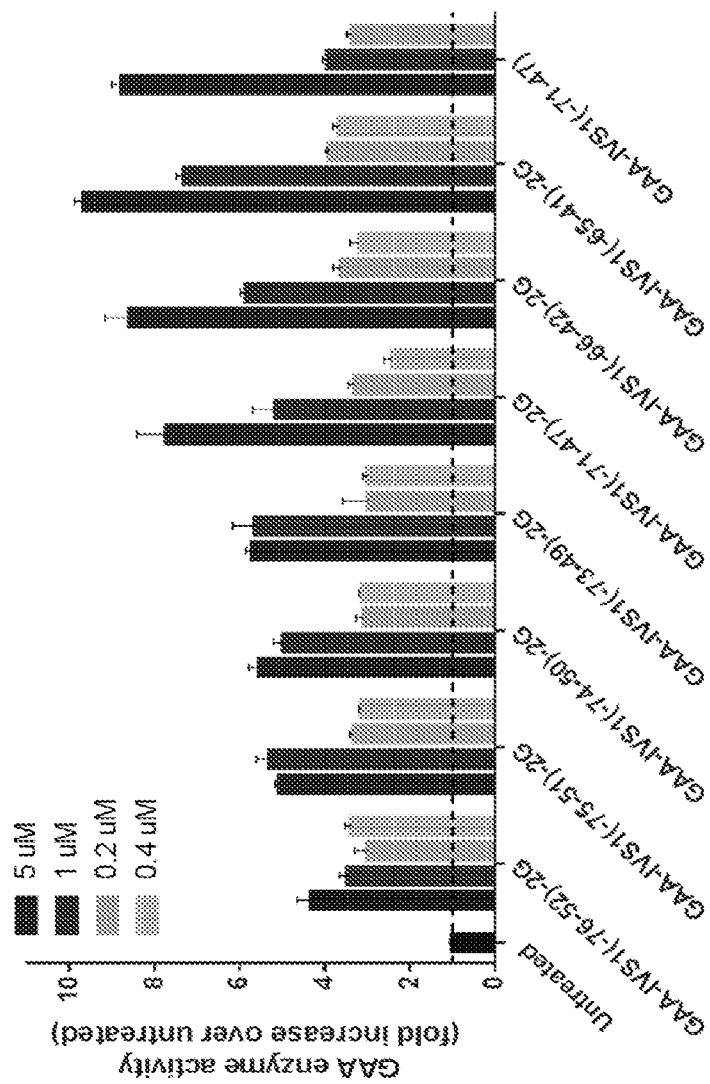
FIGS. 3 and 4 are bar graphs depicting the Enzyme Assay Dose Response found for various PMO compounds. The Y axis represents fold increase in GAA enzyme activity relative to untreated control. Individual compounds were dosed at 5 µM, 1 µM, 0.2 µM and 0.4 µM. The horizontal hashed line signifies the level of GAA activity in untreated cells.
Figure 4:
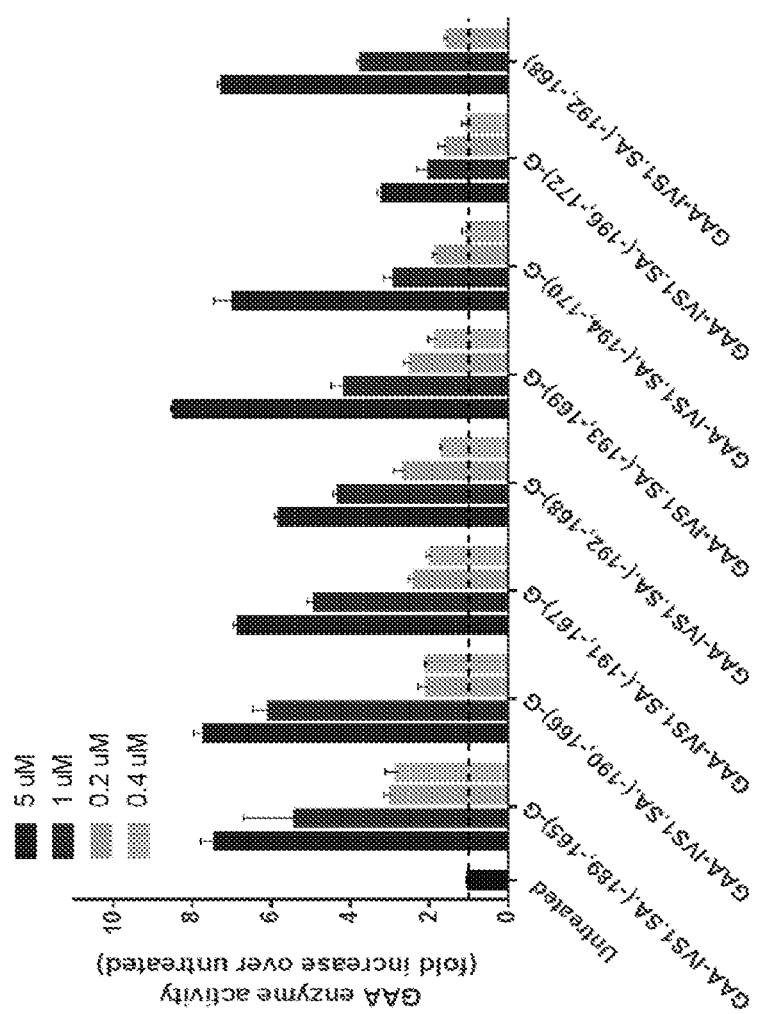
Figure 5:
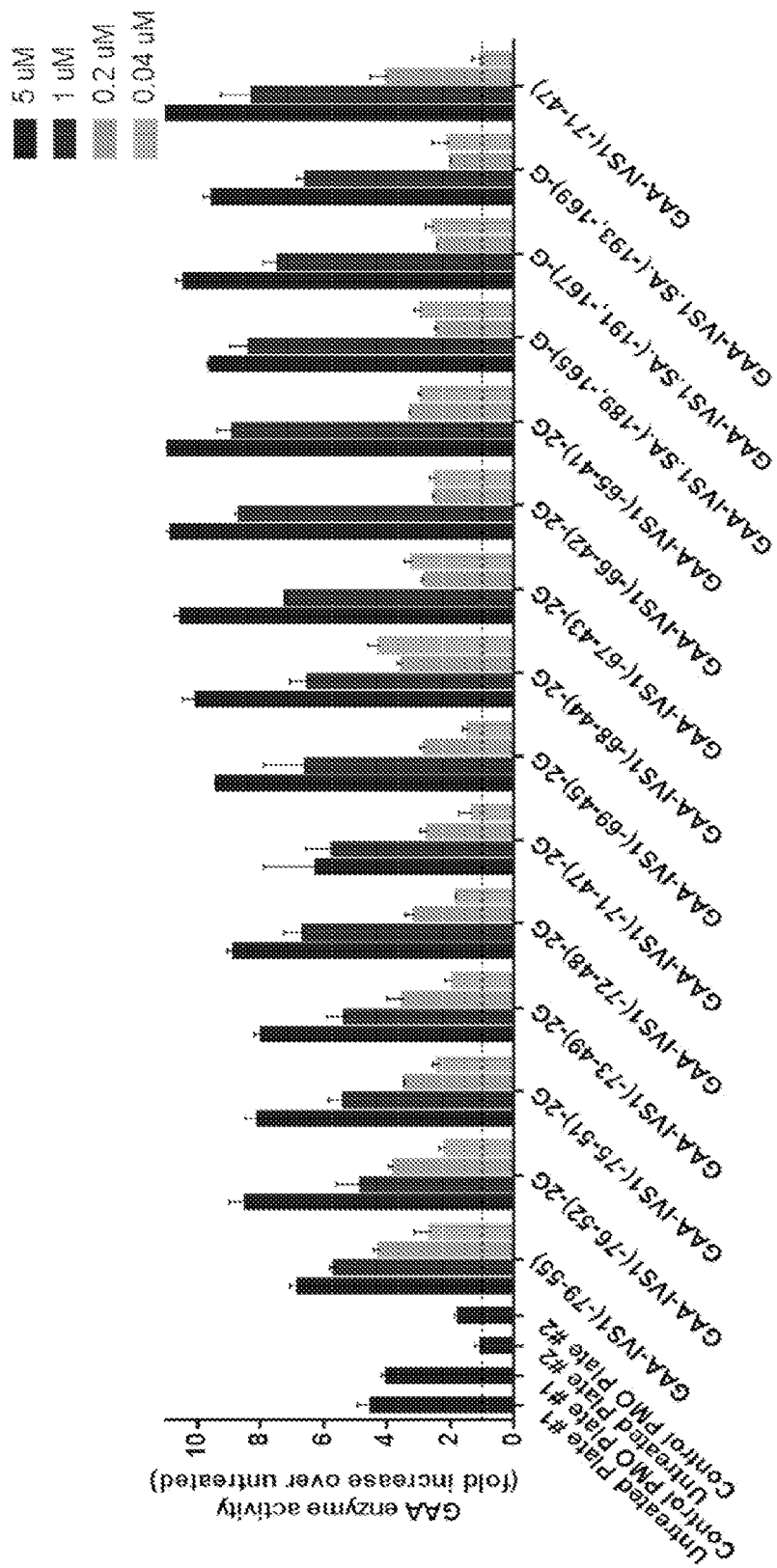
FIGS. 5-8 are bar graphs depicting the Enzyme Assay Dose Response found for various PMO compounds. The Y axis represents fold increase in GAA enzyme activity relative to untreated control. Individual compounds were dosed at 5 µM, 1 µM, 0.2 µM and 0.04 µM. The horizontal hashed line signifies the level of GAA activity in untreated cells.
Figure 6:
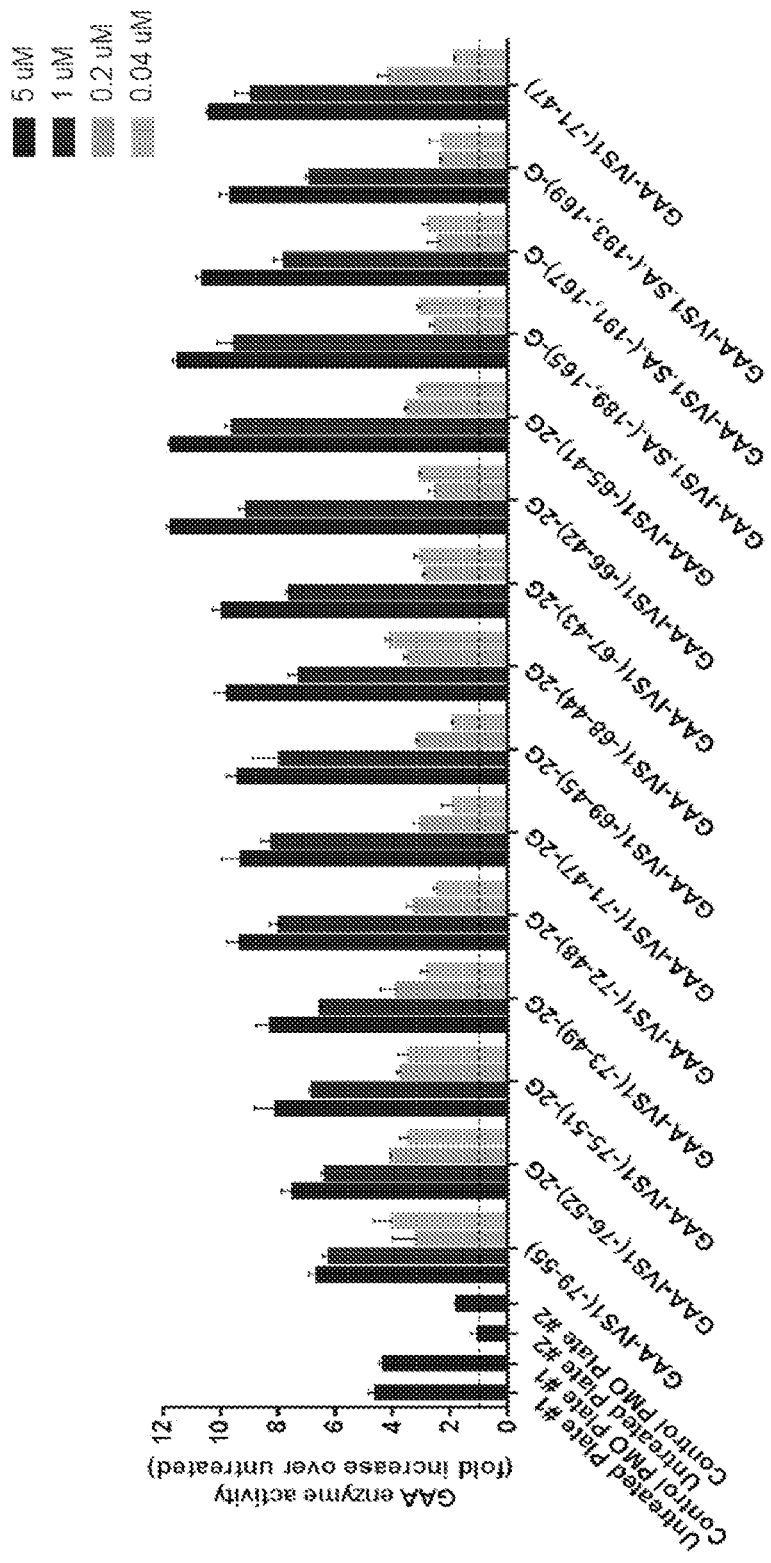
Figure 7:
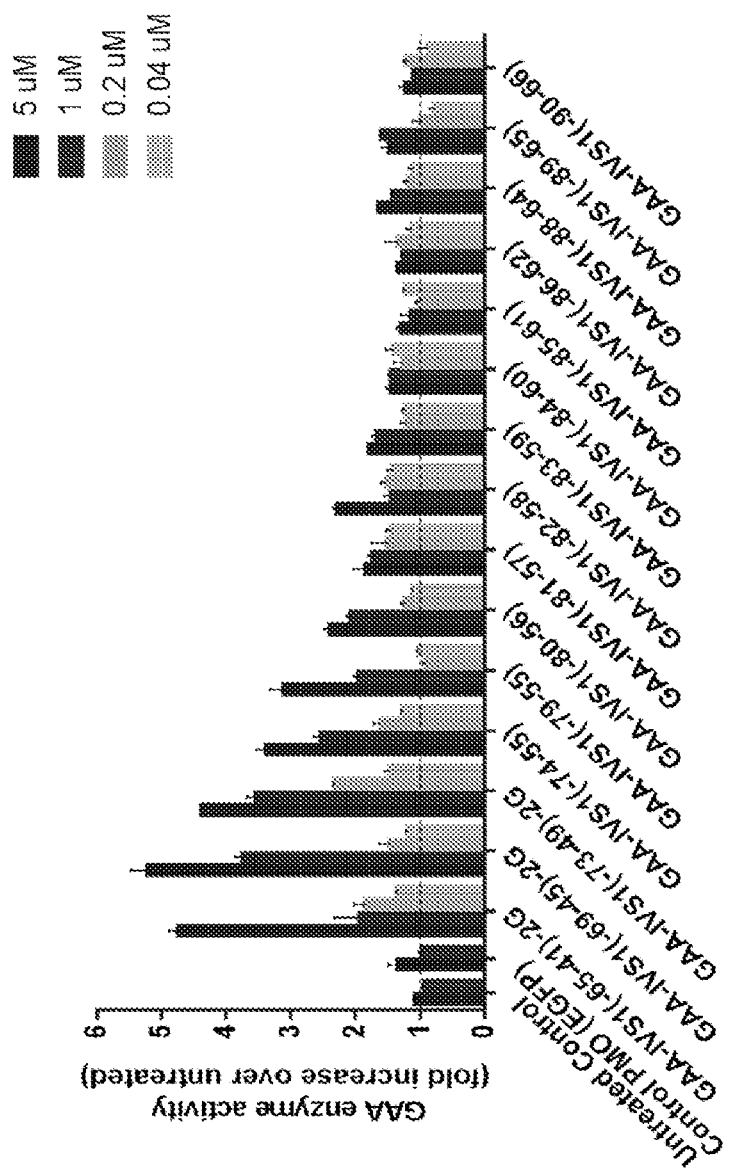
Figure 8:
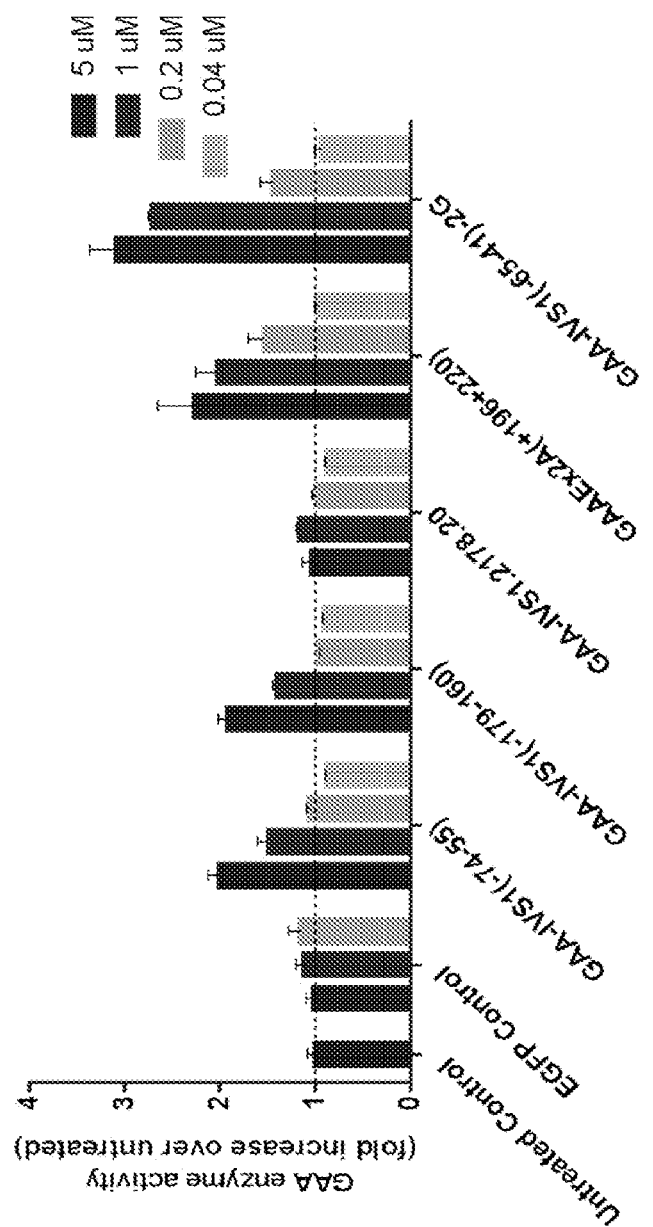

In another experiment, selected oligonucleotides were evaluated in GM00443 cells at multiple doses (5 µM, 1 µM, 0.2 µM, and 0.4 µM). As shown in FIGS. 3 and 4, the lysates of cells treated with each of these compounds at all concentrations tested exhibited increased GAA enzyme activity as compared to the GAA enzyme activity level in lysates from untreated cells.

Experiment 3

In another experiment, selected oligonucleotides were evaluated in GM00443 cells at multiple doses (5 µM, 1 µM, 0.2 µM, and 0.04 µM). As shown in FIGS. 5-8, the lysates of cells treated with each of these compounds at all concentrations tested exhibited increased GAA enzyme activity as compared to the GAA enzyme activity level in lysates from untreated cells.

Experiment 4

Figure 9:
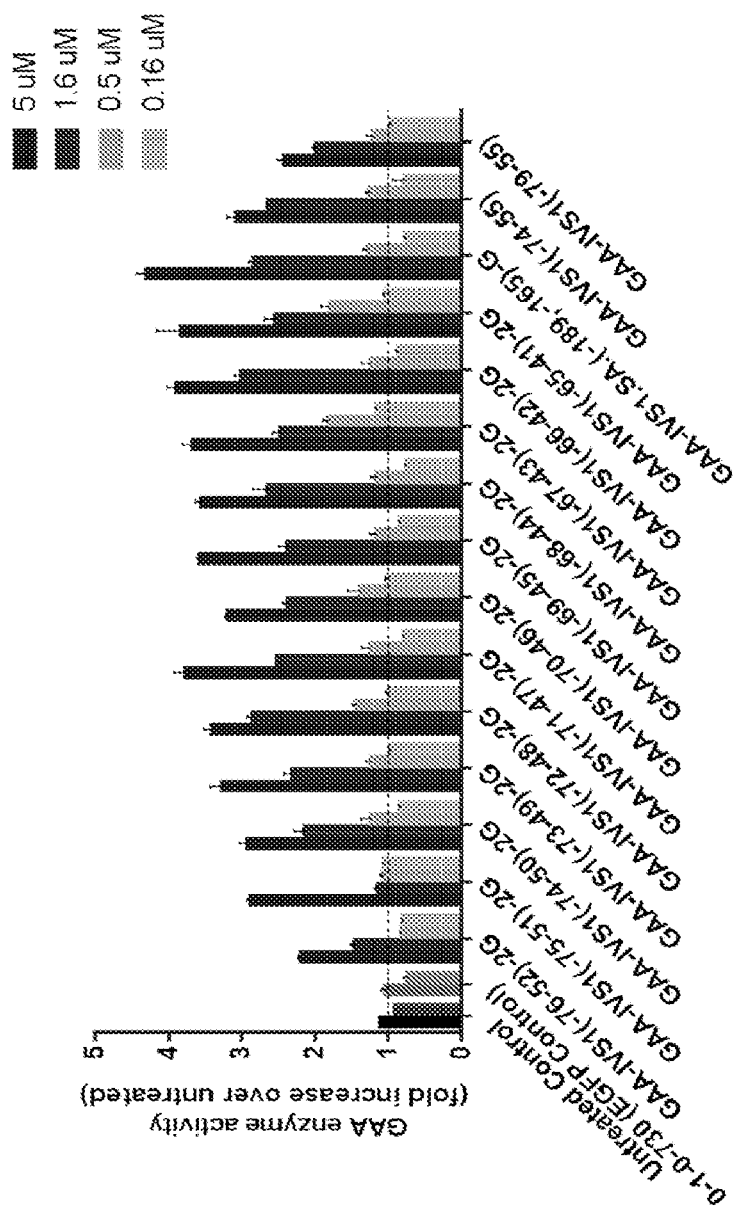
FIGS. 9-14 are bar graphs depicting the Enzyme Assay Dose Response found for various PMO compounds. The Y axis represents fold increase in GAA enzyme activity relative to untreated control. Individual compounds were dosed at 5 µM, 1.6 µM, 0.5 µM and 0.16 µM. The horizontal hashed line signifies the level of GAA activity in untreated cells.

In another experiment, selected oligonucleotides were evaluated in GM00443 cells at multiple doses (5 µM, 1.6 µM, 0.5 µM, and 0.16 µM). As shown in FIG. 9, the lysates of cells treated with each of these compounds at all concentrations tested exhibited increased GAA enzyme activity as compared to the GAA enzyme activity level in lysates from untreated cells.

Experiment 5

Figure 10A:
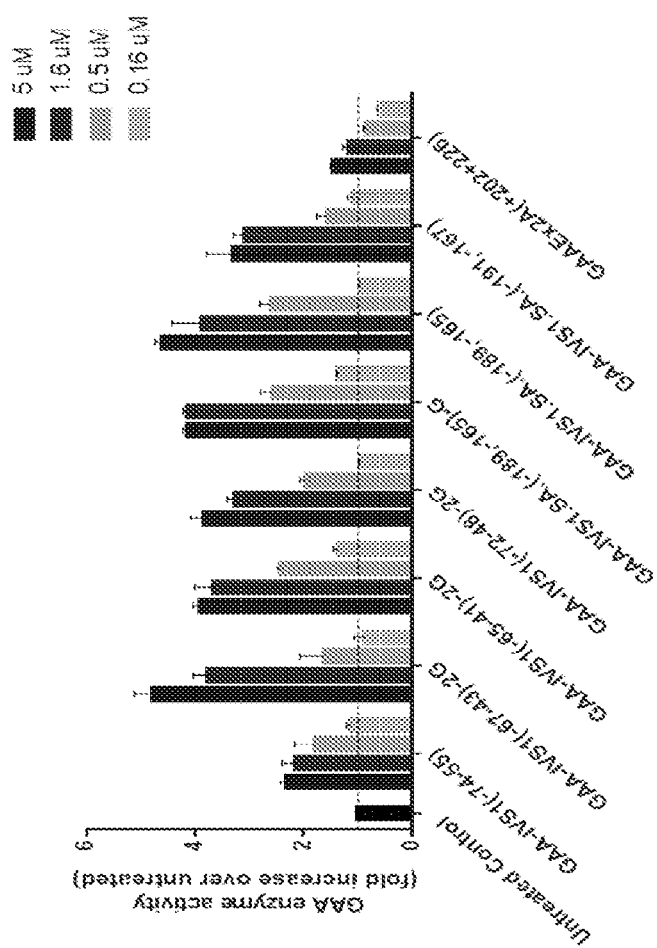

In another experiment, selected oligonucleotides were evaluated in GM00443 cells at multiple doses (5 µM, 1.6 µM, 0.5 µM, and 0.16 µM). As shown in FIG. 10a, the lysates of cells treated with each of these compounds at all concentrations tested exhibited increased GAA enzyme activity as compared to the GAA enzyme activity level in lysates from untreated cells.

Experiment 6

Figure 10B:
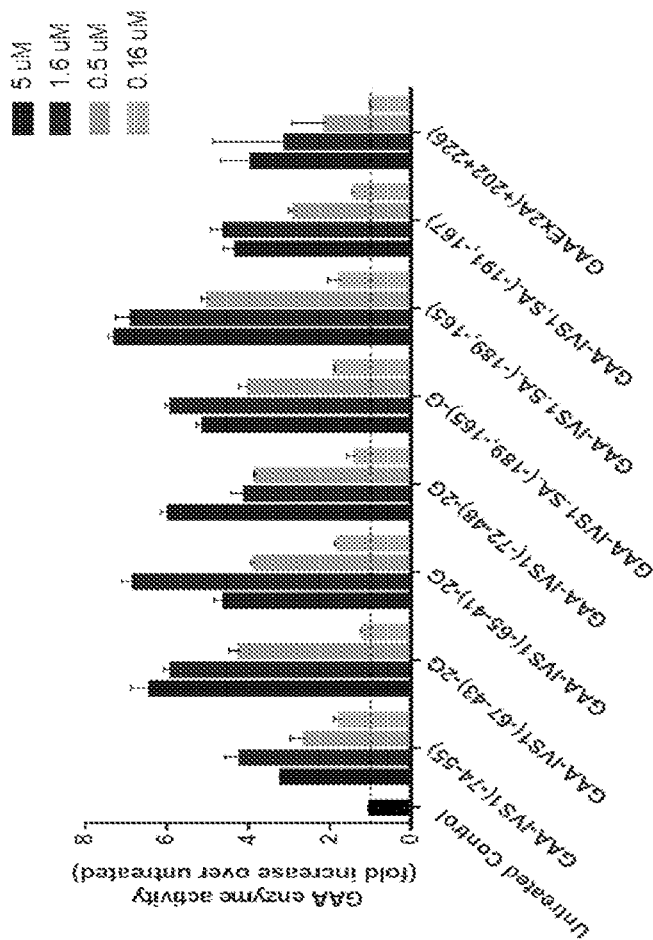

In another experiment, selected oligonucleotides were evaluated in GM11661 cells at multiple doses (5 µM, 1.6 µM, 0.5 µM, and 0.16 µM). As shown in FIG. 10b, the lysates of cells treated with each of these compounds at all concentrations tested exhibited increased GAA enzyme activity as compared to the GAA enzyme activity level in lysates from untreated cells.

Experiment 7

Figure 11:
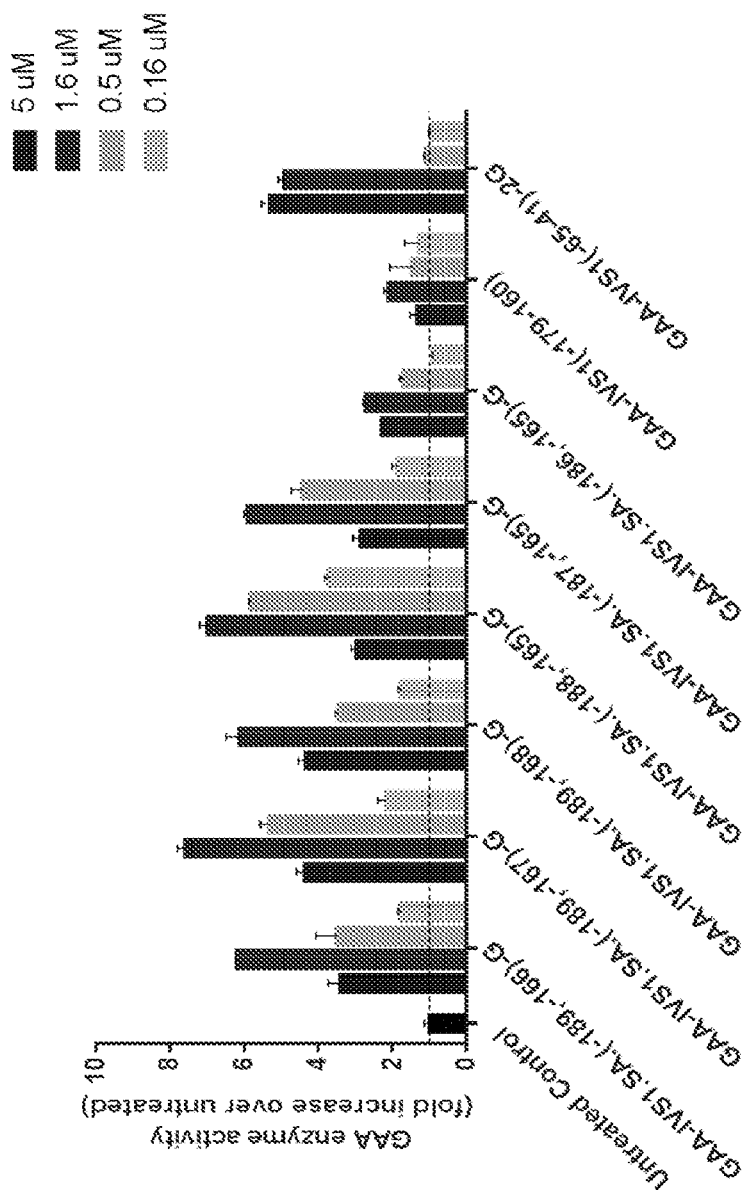
Figure 12:
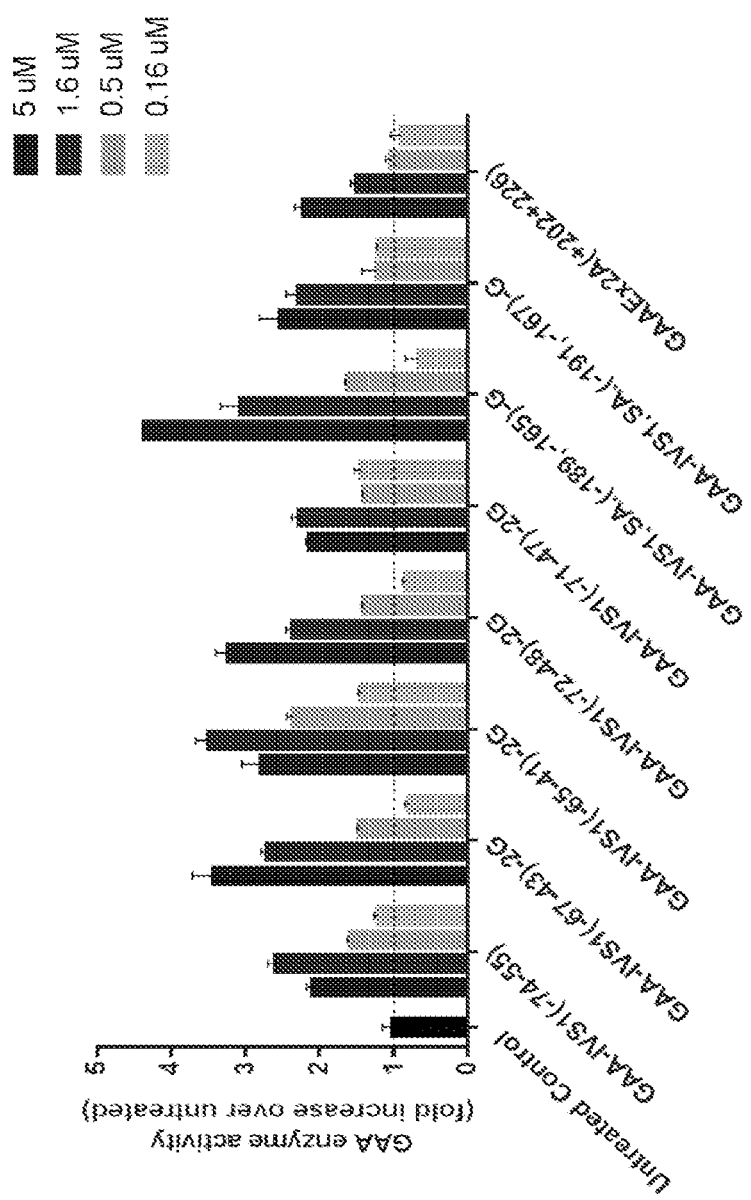

In another experiment, selected oligonucleotides were evaluated in GM00443 cells at multiple doses (5 µM, 1.6 µM, 0.5 µM, and 0.16 µM). As shown in FIGS. 11 and 12, the lysates of cells treated with each of these compounds at all concentrations tested exhibited increased GAA enzyme activity as compared to the GAA enzyme activity level in lysates from untreated cells.

Experiment 8

Figure 13A:
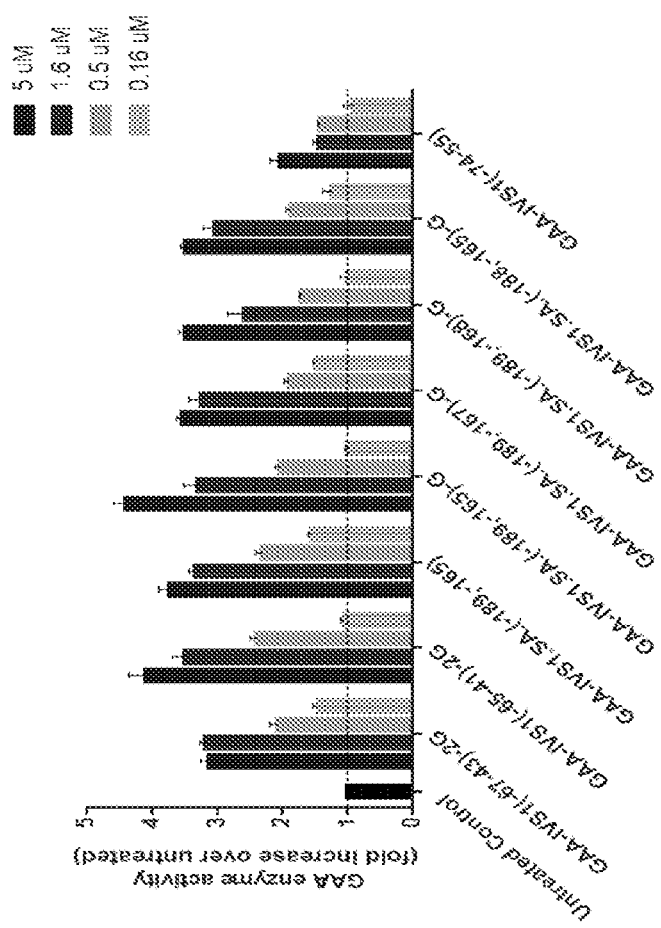

In another experiment, selected oligonucleotides were evaluated in GM00443 cells at multiple doses (5 µM, 1.6 µM, 0.5 µM, and 0.16 µM). As shown in FIG. 13a, the lysates of cells treated with each of these compounds at all concentrations tested exhibited increased GAA enzyme activity as compared to the GAA enzyme activity level in lysates from untreated cells.

Experiment 9

Figure 13B:
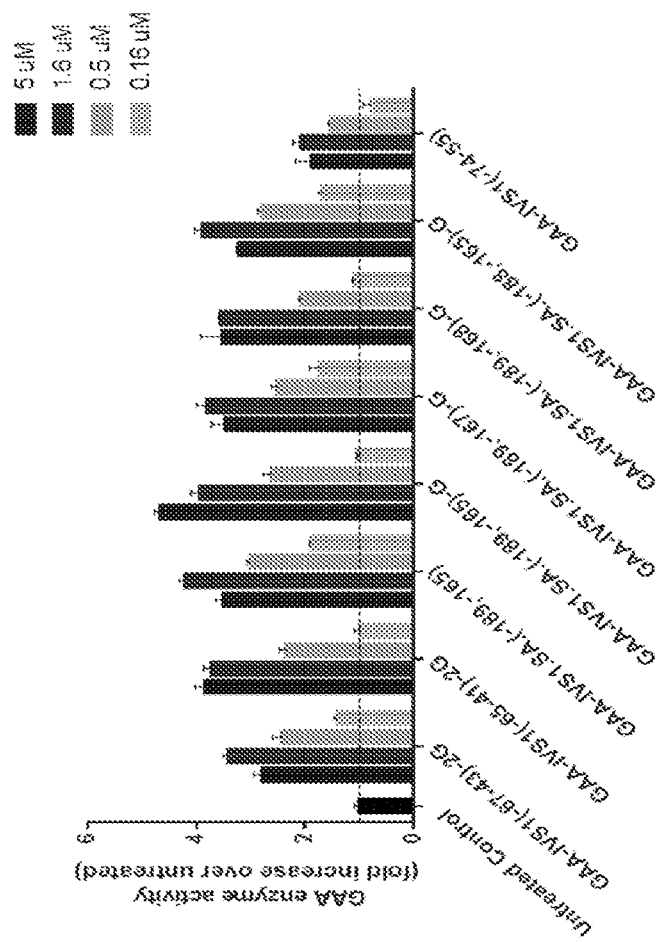

In another experiment, selected oligonucleotides were evaluated in GM11661 cells at multiple doses (5 µM, 1.6 µM, 0.5 µM, and 0.16 µM). As shown in FIG. 13b, the lysates of cells treated with each of these compounds at all concentrations tested exhibited increased GAA enzyme activity as compared to the GAA enzyme activity level in lysates from untreated cells.

Experiment 10

Figure 14:
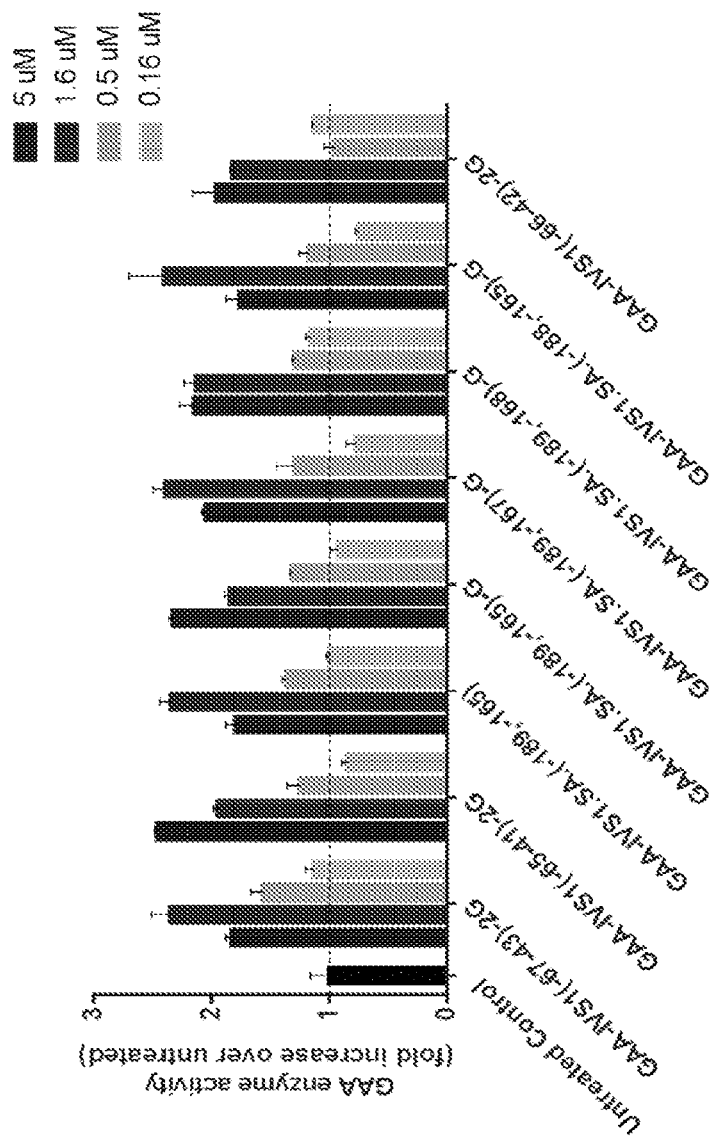

In another experiment, selected oligonucleotides were evaluated in GM00443 cells at multiple doses (5 µM, 1.6 µM, 0.5 µM, and 0.16 µM). As shown in FIG. 14, the lysates of cells treated with each of these compounds at all concentrations tested exhibited increased GAA enzyme activity as compared to the GAA enzyme activity level in lysates from untreated cells.

Experiment 11

Figure 15A:
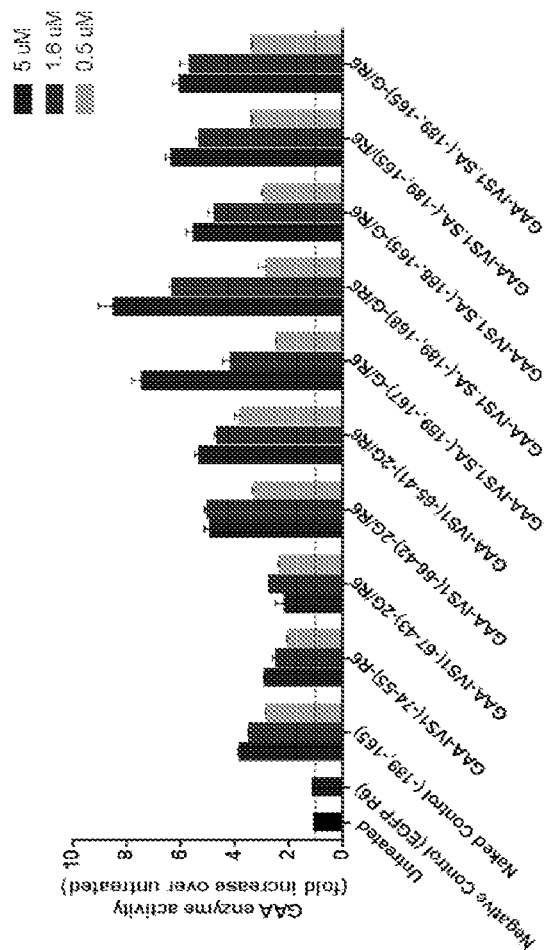
FIGS. 15a and 15b are bar graphs depicting the Enzyme Assay Dose Response found for various PPMO compounds. The Y axis represents fold increase in GAA enzyme activity relative to untreated control. Individual compounds were dosed at 5 µM, 1.6 µM, and 0.5 µM. The horizontal hashed line signifies the level of GAA activity in untreated cells.

In another experiment, selected PPMO oligonucleotides were evaluated in GM00443 cells at multiple doses (5 µM, 1.6 µM, 0.5 µM, and 0.16 µM). As shown in FIG. 15a, the lysates of cells treated with each of these compounds at all concentrations tested exhibited increased GAA enzyme activity as compared to the GAA enzyme activity level in lysates from untreated cells.

Experiment 12

Figure 15B:
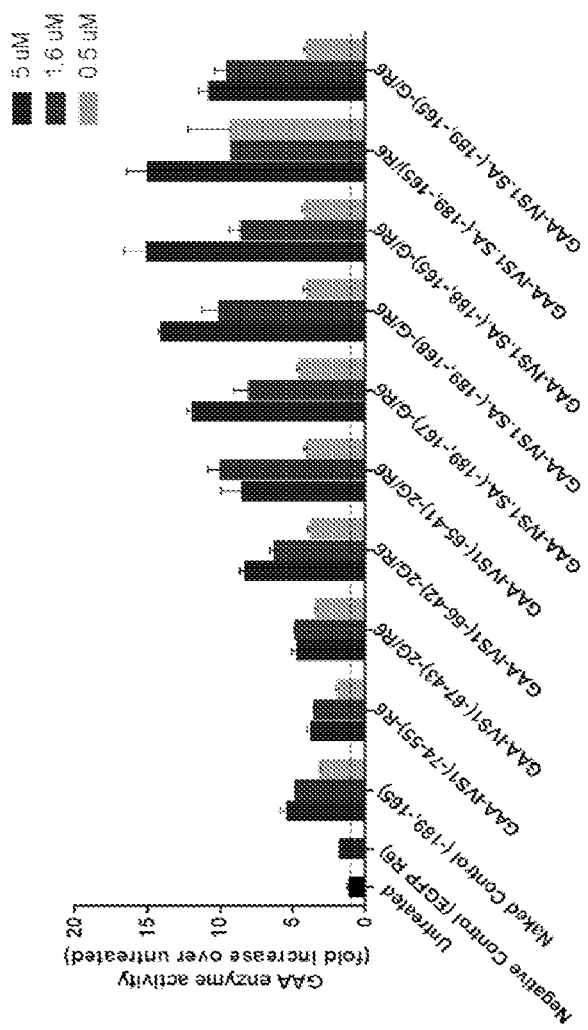

In another experiment, selected PPMO oligonucleotides were evaluated in GM11661 cells at multiple doses (5 µM, 1.6 µM, 0.5 µM, and 0.16 µM). As shown in FIG. 15b, the lysates of cells treated with each of these compounds at all concentrations tested exhibited increased GAA enzyme activity as compared to the GAA enzyme activity level in lysates from untreated cells.

Experiment 13

In another experiment, selected oligonucleotides were evaluated in GM00443 cells at the single dose of 5 µM. As shown in FIG. 16, the lysates of cells treated with each of these compounds at all concentrations tested exhibited increased GAA enzyme activity as compared to the GAA enzyme activity level in lysates from untreated cells.

Experiment 14

Figure 17:
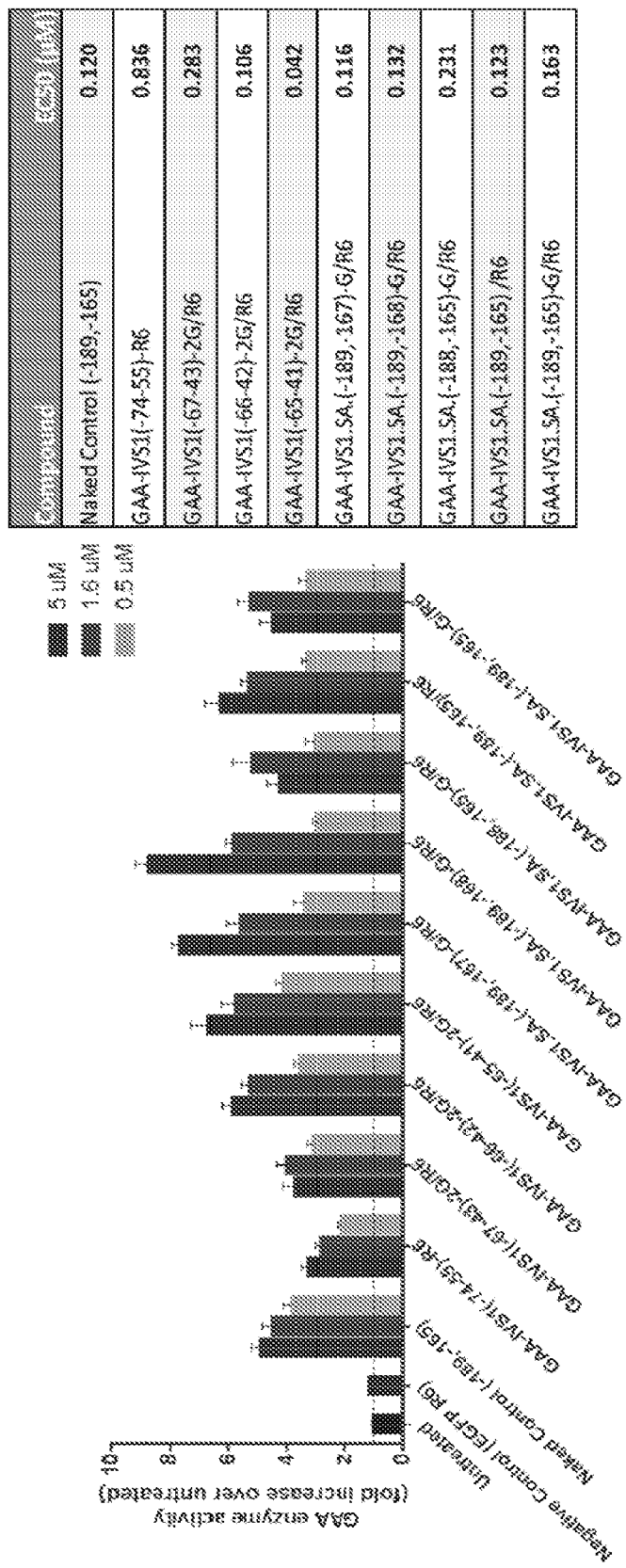
FIGS. 17 and 18 are bar graphs depicting GAA enzyme activity (Enzyme Assay) found for various PPMO compounds. The Y axis represents fold increase in GAA enzyme activity relative to untreated control. Individual compounds were dosed at 5 µM, 1.6 µM, and 0.5 µM. The horizontal hashed line signifies the level of GAA activity in untreated cells. "N=9" refers to the number of replicates evaluated in each study. The data summary tables show $EC_{50}$ in µM.

In another experiment, selected PPMO oligonucleotides were evaluated in GM00443 cells at multiple doses (5 µM, 1.6 µM, and 0.5 µM). As shown in FIG. 17, the lysates of cells treated with each of these compounds at all concentrations tested exhibited increased GAA enzyme activity as compared to the GAA enzyme activity level in lysates from untreated cells. Additionally, the $EC_{50}$ (µM) ranged from 0.042 to 0.836.

Experiment 15

Figure 18:
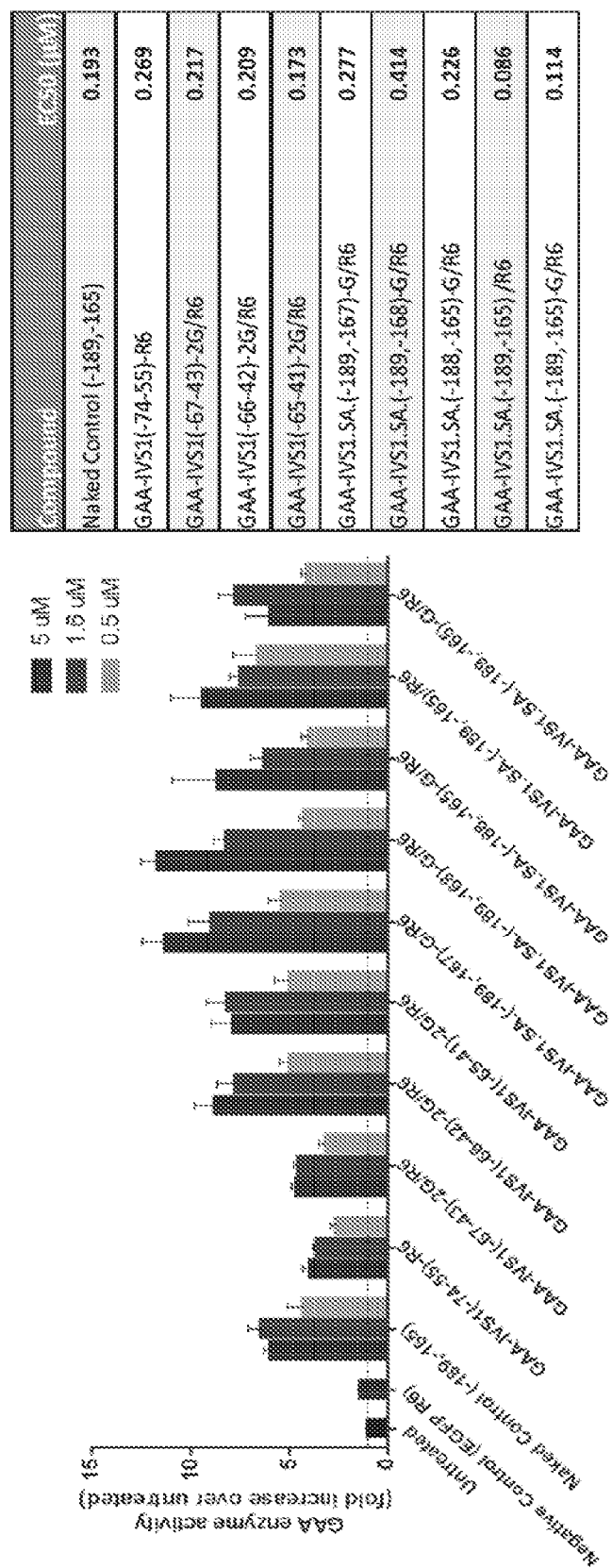

In another experiment, selected PPMO oligonucleotides were evaluated in GM11661 cells at multiple doses (5 µM, 1.6 µM, and 0.5 µM). As shown in FIG. 18, the lysates of cells treated with each of these compounds at all concentrations tested exhibited increased GAA enzyme activity as compared to the GAA enzyme activity level in lysates from untreated cells. Additionally, the $EC_{50}$ (µM) ranged from 0.086 to 0.414.

Experiment 16

FIG. 19 provides a tabular summary of the $EC_{50}$ (µM) values for selected PPMO oligonucleotides evaluated in both GM00443 and GM11661 cells, averaged over three experiments, N=9.

Experiment 17

Figure 20:
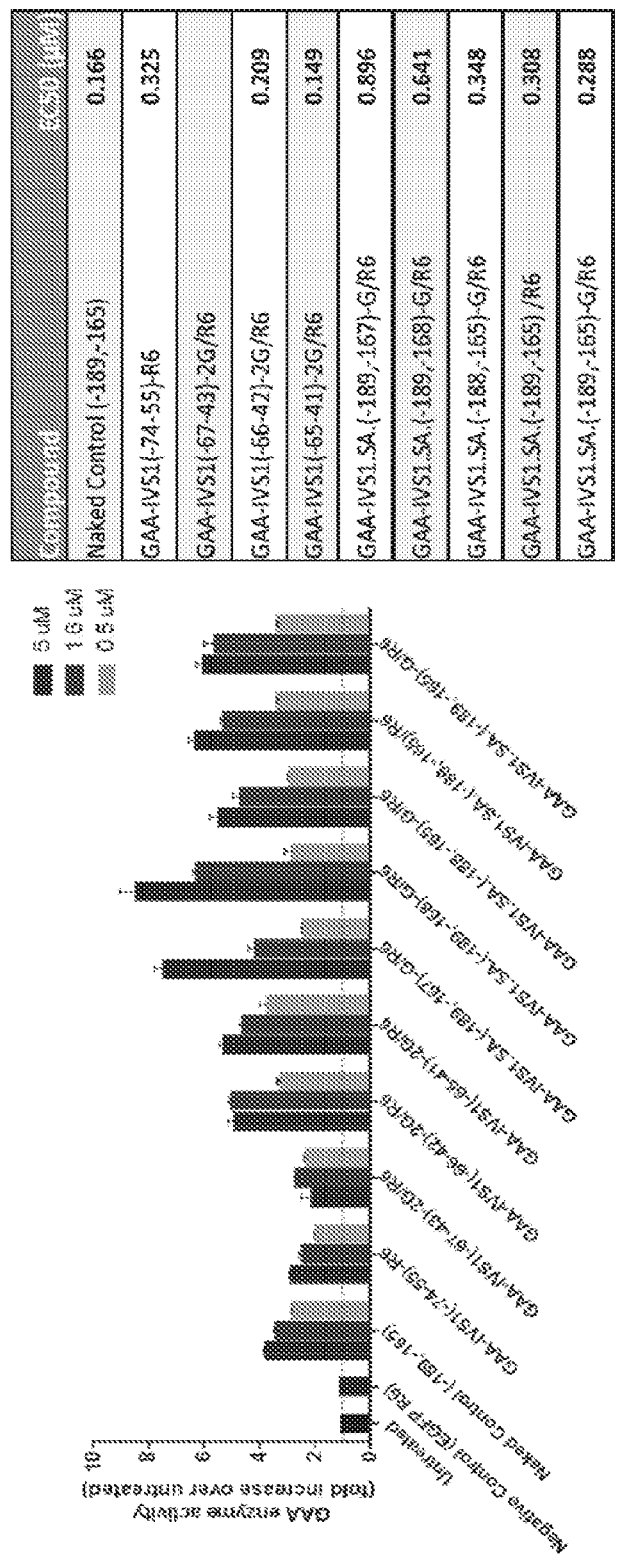
FIG. 20-22 are bar graphs depicting GAA enzyme activity (Enzyme Assay) found for various PPMO compounds. The Y axis represents fold increase in GAA enzyme activity relative to untreated control. Individual compounds were dosed at 5 µM, 1.6 µM, and 0.5 µM. The horizontal hashed line signifies the level of GAA activity in untreated cells. The data summary tables show $EC_{50}$ in µM

In another experiment, selected PPMO oligonucleotides were evaluated in GM00443 cells at multiple doses (5 µM, 1.6 µM, and 0.5 µM). As shown in FIG. 20, the lysates of cells treated with each of these compounds at all concentrations tested exhibited increased GAA enzyme activity as compared to the GAA enzyme activity level in lysates from untreated cells. Additionally, the $EC_{50}$ (µM) ranged from 0.149 to 0.896.

Experiment 18

Figure 21:
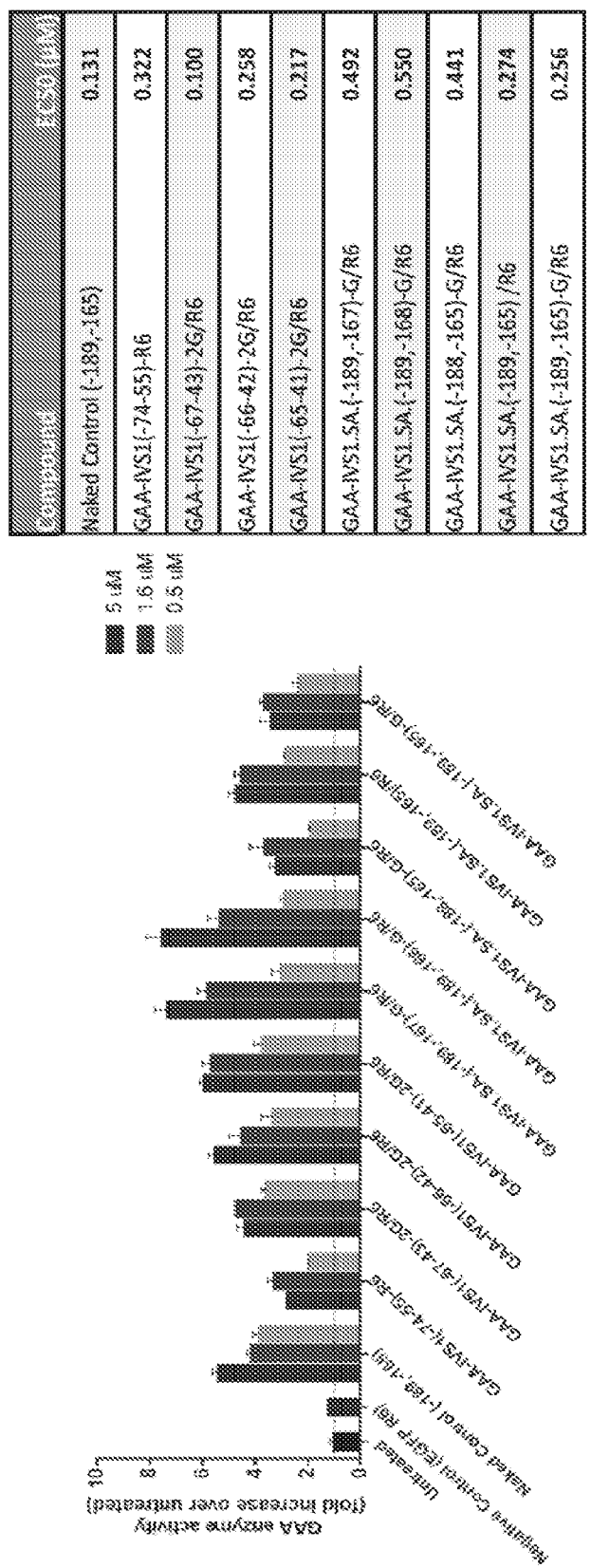

In another experiment, selected PPMO oligonucleotides were evaluated in GM00443 cells at multiple doses (5 µM, 1.6 µM, and 0.5 µM). As shown in FIG. 21, the lysates of cells treated with each of these compounds at all concentrations tested exhibited increased GAA enzyme activity as compared to the GAA enzyme activity level in lysates from untreated cells. Additionally, the $EC_{50}$ (µM) ranged from 0.100 to 0.550.

Experiment 19

Figure 22:
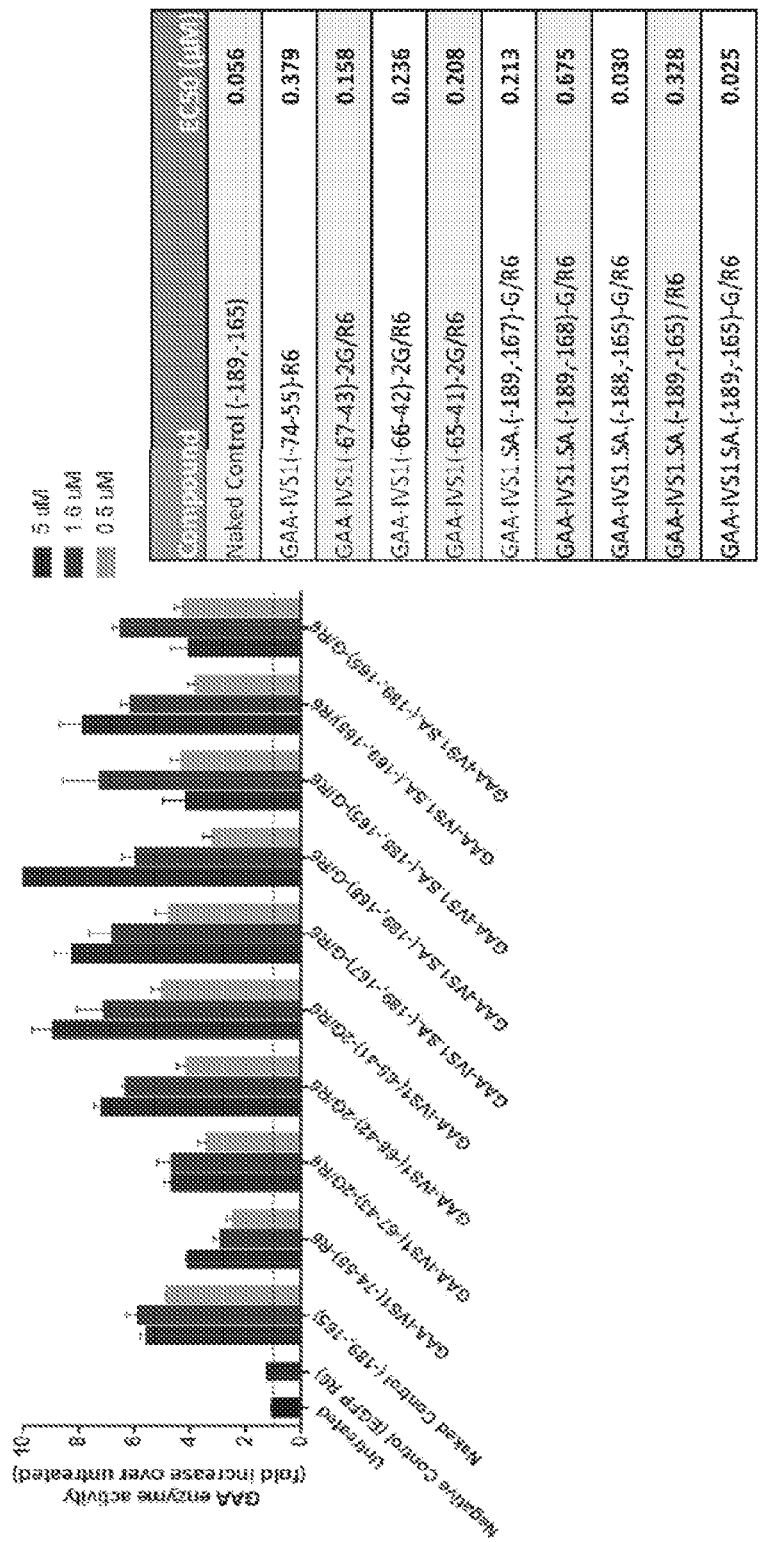

In another experiment, selected PPMO oligonucleotides were evaluated in GM00443 cells at multiple doses (5 µM, 1.6 µM, and 0.5 µM). As shown in FIG. 22, the lysates of cells treated with each of these compounds at all concentrations tested exhibited increased GAA enzyme activity as compared to the GAA enzyme activity level in lysates from untreated cells. Additionally, the $EC_{50}$ (µM) ranged from 0.025 to 0.675.

Experiment 20

FIG. 23 provides a tabular summary of the the $EC_{50}$ (µM) values for selected PPMO oligonucleotides evaluated in both GM00443 and GM11661 cells, averaged across all assays, N=9.

Experiment 21

Figure 24:
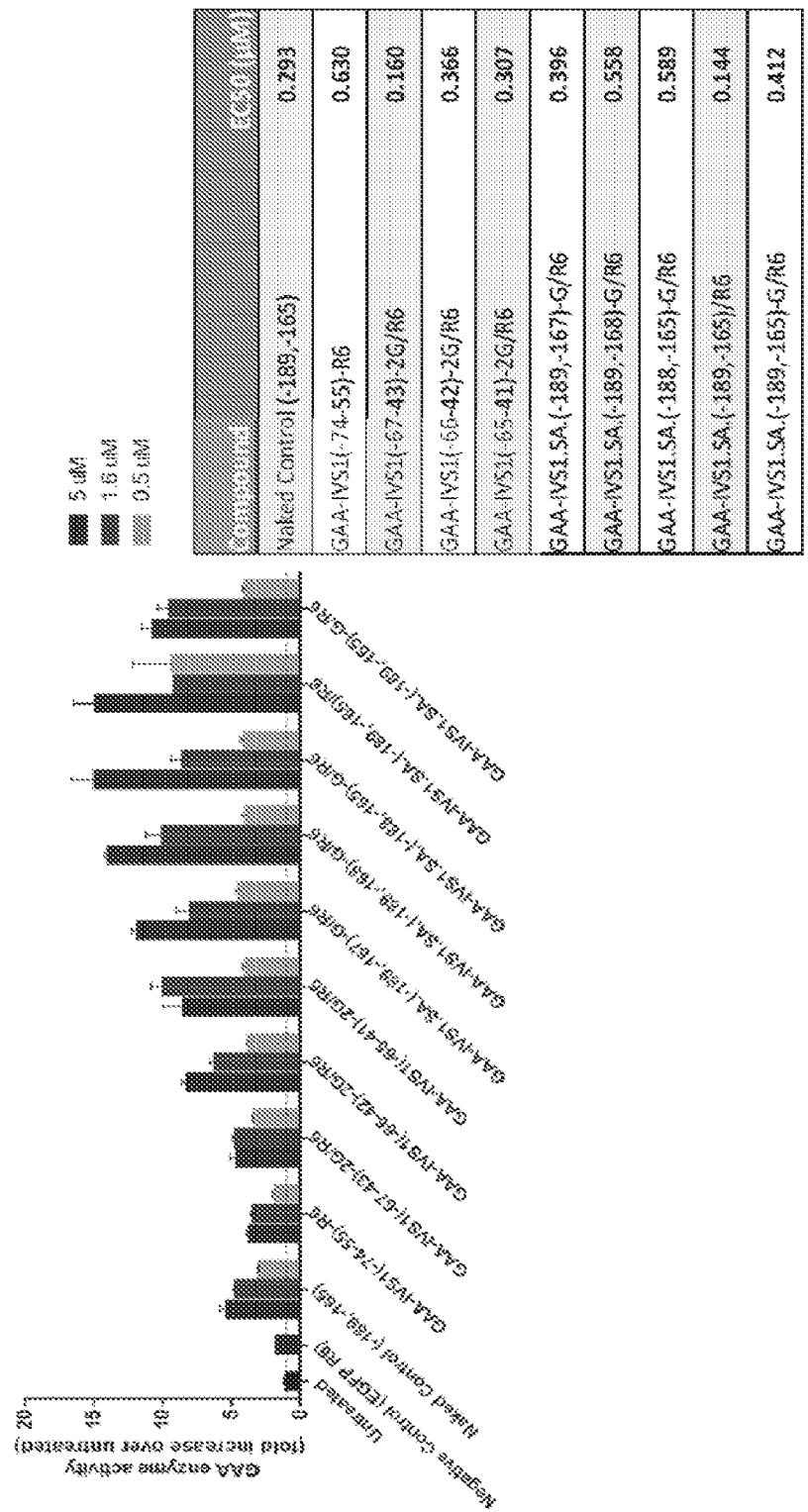
FIGS. 24-26 are bar graphs depicting GAA enzyme activity (Enzyme Assay) found for various PPMO compounds. The Y axis represents fold increase in GAA enzyme activity relative to untreated control. Individual compounds were dosed at 5 µM, 1.6 µM, and 0.5 µM. The horizontal hashed line signifies the level of GAA activity in untreated cells. The data summary tables show $EC_{50}$ in µM.

In another experiment, selected PPMO oligonucleotides were evaluated in GM11661 cells at multiple doses (5 µM, 1.6 µM, and 0.5 µM). As shown in FIG. 24, the lysates of cells treated with each of these compounds at all concentrations tested exhibited increased GAA enzyme activity as compared to the GAA enzyme activity level in lysates from untreated cells. Additionally, the $EC_{50}$ (μM) ranged from 0.144 to 0.630.

Experiment 22

Figure 25:
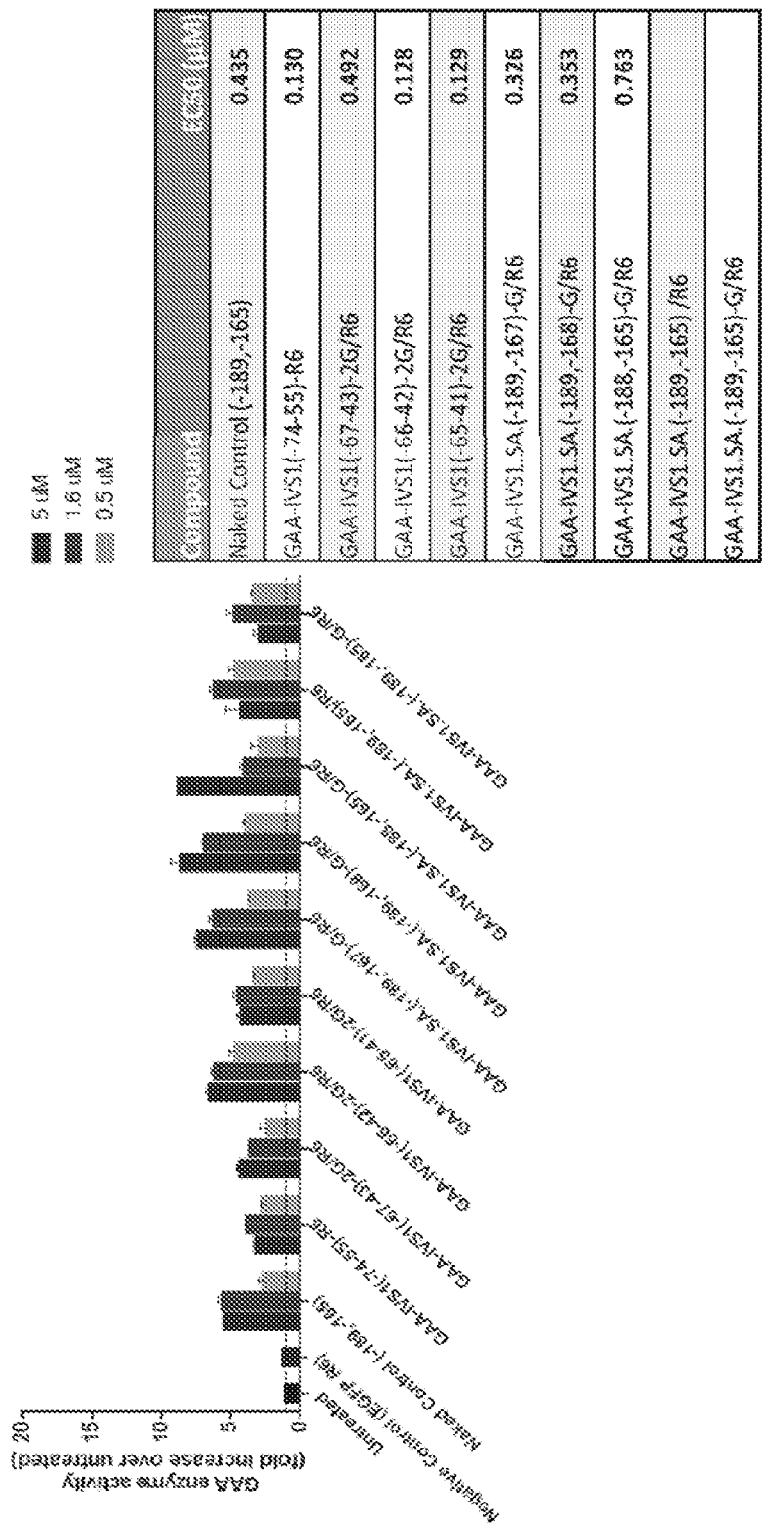

In another experiment, selected PPMO oligonucleotides were evaluated in GM11661 cells at multiple doses (5 μM, 1.6 μM, and 0.5 μM). As shown in FIG. 25, the lysates of cells treated with each of these compounds at all concentrations tested exhibited increased GAA enzyme activity as compared to the GAA enzyme activity level in lysates from untreated cells. Additionally, the $EC_{50}$ (μM) ranged from 0.128 to 0.763.

Experiment 23

Figure 26:
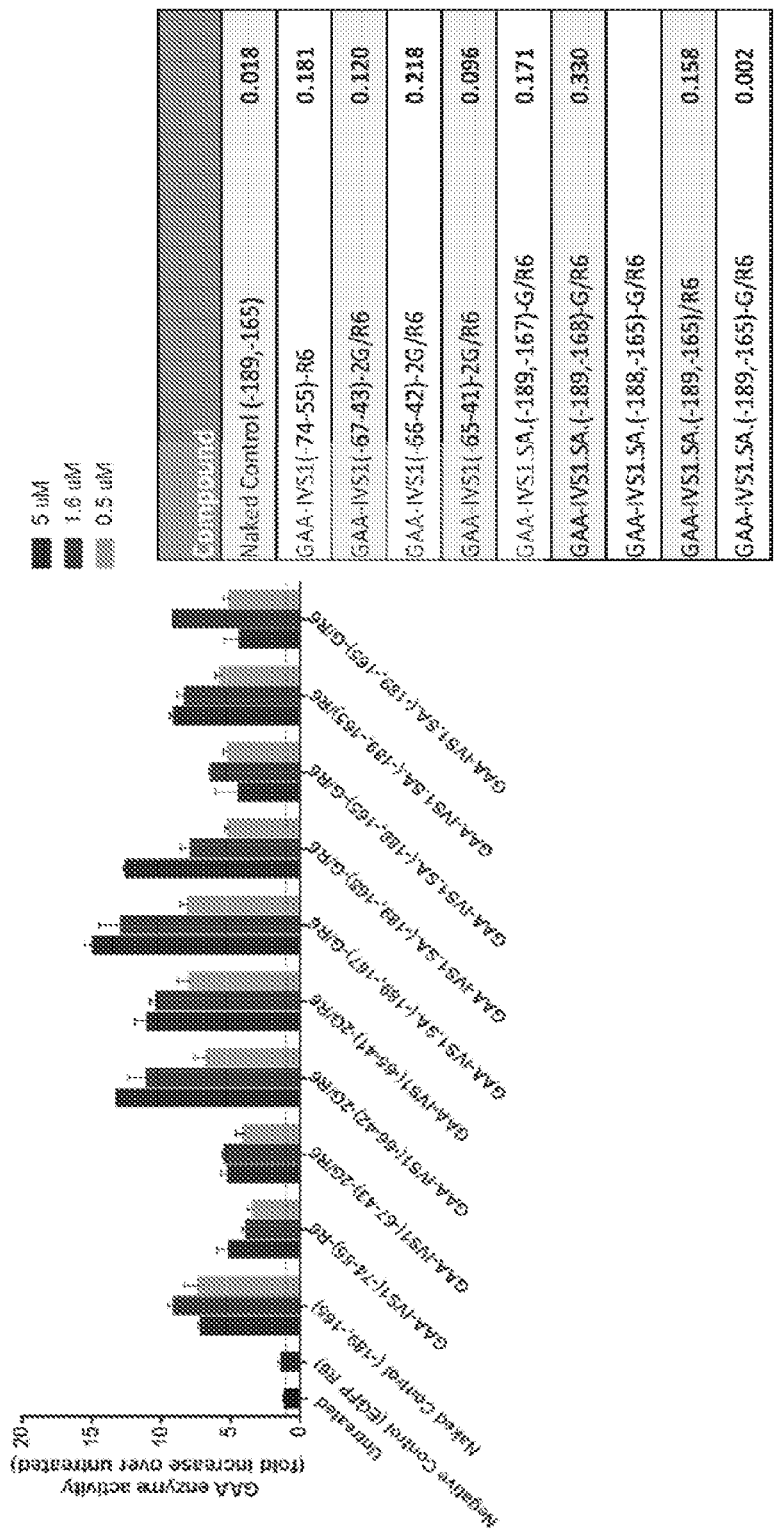

In another experiment, selected PPMO oligonucleotides were evaluated in GM11661 cells at multiple doses (5 μM, 1.6 μM, and 0.5 μM). As shown in FIG. 26, the lysates of cells treated with each of these compounds at all concentrations tested exhibited increased GAA enzyme activity as compared to the GAA enzyme activity level in lysates from untreated cells. Additionally, the $EC_{50}$ (μM) ranged from 0.002 to 0.218.

What is claimed is:

1. A modified antisense oligonucleotide of 10 to 40 nucleobases, or a pharmaceutically acceptable salt thereof, comprising a targeting sequence complementary to a target region within intron 1 of a pre-mRNA of the human alpha glucosidase (GAA) gene (SEQ ID NO: 1), wherein the target region comprises at least one additional nucleobase compared to the targeting sequence, and wherein the at least one additional nucleobase is internal to the target region.

2. The modified antisense oligonucleotide, or a pharmaceutically acceptable salt thereof, of claim 1, wherein the target region comprises at least one of SEQ ID NO: 2 or SEQ ID NO: 3.

3. The modified antisense oligonucleotide of claim 1, or a pharmaceutically acceptable salt thereof, wherein the antisense oligonucleotide promotes retention of exon 2 in the GAA mRNA upon binding of the targeting sequence to the target region.

4. The modified antisense oligonucleotide of claim 1, or a pharmaceutically acceptable salt thereof, wherein the target region comprises from one to three additional nucleobases compared to the targeting sequence.

5. The modified antisense oligonucleotide of claim 1, or a pharmaceutically acceptable salt thereof, wherein the antisense oligonucleotide induces GAA enzyme activity at least-two-fold according to an enzyme activity test as compared to a second antisense oligonucleotide that is fully complementary to the target region within SEQ ID NO: 1.

6. The modified antisense oligonucleotide of claim 1, or a pharmaceutically acceptable salt thereof, wherein the targeting sequence is selected from any one of SEQ ID NOs: 33-42.

7. A pharmaceutical composition comprising: (a) a pharmaceutically acceptable carrier and (b) a modified antisense oligonucleotide of 10 to 40 nucleobases, or a pharmaceutically acceptable salt thereof, comprising a targeting sequence complementary to a target region within intron 1 of a pre-mRNA of the human alpha glucosidase (GAA) gene (SEQ ID NO: 1), wherein the target region comprises at least one additional nucleobase compared to the targeting sequence, and wherein the at least one additional nucleobase is internal to the target region.

8. The modified antisense oligonucleotide of claim 1, or a pharmaceutically acceptable salt thereof, wherein the targeting sequence is SEQ ID NO: 33.

9. The modified antisense oligonucleotide of claim 1, or a pharmaceutically acceptable salt thereof, wherein the targeting sequence is SEQ ID NO: 34.

10. The modified antisense oligonucleotide of claim 1, or a pharmaceutically acceptable salt thereof, wherein the targeting sequence is SEQ ID NO: 35.

11. The modified antisense oligonucleotide of claim 1, or a pharmaceutically acceptable salt thereof, wherein the targeting sequence is SEQ ID NO: 36.

12. The modified antisense oligonucleotide of claim 1, or a pharmaceutically acceptable salt thereof, wherein the targeting sequence is SEQ ID NO: 37.

13. The modified antisense oligonucleotide of claim 1, or a pharmaceutically acceptable salt thereof, wherein the targeting sequence is SEQ ID NO: 38.

14. The modified antisense oligonucleotide of claim 1, or a pharmaceutically acceptable salt thereof, wherein the targeting sequence is SEQ ID NO: 45.

15. The modified antisense oligonucleotide of claim 1, or a pharmaceutically acceptable salt thereof, wherein the targeting sequence is SEQ ID NO: 46.

16. The modified antisense oligonucleotide of claim 1, or a pharmaceutically acceptable salt thereof, wherein the at least one additional nucleobase is cytosine.

* * * * *